(12) United States Patent
Siegel et al.

(10) Patent No.: US 11,339,157 B1
(45) Date of Patent: May 24, 2022

(54) 4H-PYRROLO[3,2-C]PYRIDIN-4-ONE DERIVATIVES

(71) Applicants: Bayer Aktiengesellschaft, Leverkusen (DE); Bayer Pharma Aktiengesellschaft, Berlin (DE); Dana-Farber Cancer Institute, Inc., Boston, MA (US); The Broad Institute, Inc., Cambridge, MA (US)

(72) Inventors: Stephan Siegel, Berlin (DE); Franziska Siegel, Berlin (DE); Volker Schulze, OT Bergf (DE); Markus Berger, Berlin (DE); Keith Graham, Berlin (DE); Ulrich Klar, Berlin (DE); Knut Eis, Berlin (DE); Detlev Sülzle, Berlin (DE); Ulf Bömer, Glienicke (DE); Daniel Korr, Berlin (DE); Kirstin Petersen, Berlin (DE); Ursula Mönning, Woltersdorf (DE); Uwe Eberspächer, Berlin (DE); Dieter Moosmayer, Berlin (DE); Matthew Meyerson, Boston, MA (US); Heidi Greulich, Cambridge, MA (US); Bethany Kaplan, Cambridge, MA (US); Hassan Youssef Harb, Cheshire (GB); Phi Manh Dinh, Staffordshire (GB)

(73) Assignees: Bayer Aktiengesellschaft, Leverkusen (DE); Bayer Pharma Aktiengesellschaft, Berlin (DE); Dana-Farber Cancer Institute, Inc., Boston, MA (US); The Broad Institute, Inc., Cambridge, MA (US)

( * ) Notice: Subject to any disclaimer, the term of this patent is extended or adjusted under 35 U.S.C. 154(b) by 34 days.

(21) Appl. No.: 16/758,018

(22) PCT Filed: Oct. 23, 2018

(86) PCT No.: PCT/EP2018/078995
§ 371 (c)(1),
(2) Date: Apr. 21, 2020

(87) PCT Pub. No.: WO2019/081486
PCT Pub. Date: May 2, 2019

Related U.S. Application Data

(60) Provisional application No. 62/576,166, filed on Oct. 24, 2017.

(51) Int. Cl.
*C07D 471/04* (2006.01)
*A61P 35/00* (2006.01)
*A61K 45/06* (2006.01)

(52) U.S. Cl.
CPC ............ *C07D 471/04* (2013.01); *A61P 35/00* (2018.01); *A61K 45/06* (2013.01)

(58) Field of Classification Search
CPC ........ C07D 471/04; A61P 35/00; A61K 45/06
See application file for complete search history.

(56) References Cited

FOREIGN PATENT DOCUMENTS

| WO | 2015193339 A1 | 12/2015 |
| WO | 2016120196 A1 | 8/2016 |
| WO | 2016185333 A1 | 11/2016 |
| WO | 2020216773 A1 | 10/2020 |
| WO | 2020216774 A1 | 10/2020 |
| WO | 2020216781 A1 | 10/2020 |

OTHER PUBLICATIONS

Yasuda, H., "Structural, biochemical, and clinical characterization of epidermal growth factor receptor (EGFR) exon 20 insertion mutations in lung cancer." Science translational medicine 5.216 (2013): 1-10.*
International Search Report and Written Opinion in corresponding PCT Patent Application No. PCT/EP2018/078995, dated Apr. 12, 2018 (10 pages).
Chen et al., "Clinical efficacy of first-generation EGFR-TKIs in patients with advanced non-small-cell lung cancer harboring EGFR exon 20 mutations," OncoTargets and Therapy, Jul. 8, 2016, vol. 9, pp. 4181-4186.

(Continued)

*Primary Examiner* — John M Mauro
(74) *Attorney, Agent, or Firm* — Melissa Hunter-Ensor; Scott Goncher; Greenberg Traurig, LLP

(57) ABSTRACT

Compounds of formula (I) processes for their production and their use as pharmaceuticals.

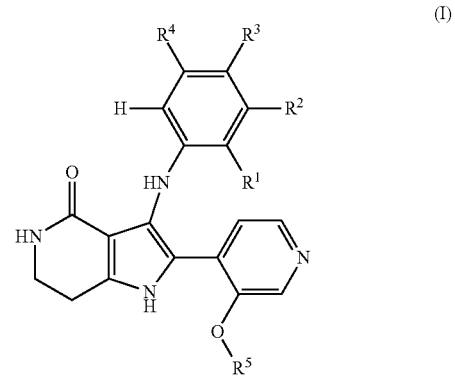

19 Claims, No Drawings
Specification includes a Sequence Listing.

(56) References Cited

OTHER PUBLICATIONS

Doebele et al., "First Report on Safety, Pharmacokinetics, and Preliminary Antitumor Activity of the Oral EGFR/HER2 Exon 20 Inhibitor TAK-788 (AP32788) in Non-Small Cell Lung Cancer," Poster 338, presented at the 54th Annual Meeting of the American Society of Clinical Oncology, Jun. 1-5, 2018, Chicago, Illinois.
Floc'h et al., "Antitumor Activity of Osimertinib, an Irreversible Mutant-Selective EGFR Tyrosine Kinase Inhibitor, in NSCLC Harboring EGFR Exon 20 Insertions," Molecular Cancer Therapeutics, May 2018, vol. 17, No. 5, pp. 885-896.
Hasako et al., "TAS6417, A Novel EGFR Inhibitor Targeting Exon 20 Insertion Mutations," Molecular Cancer Therapeutics, Aug. 2018, vol. 17, No. 8, pp. 1648-1658.
Jang et al., "Discovery of a Highly Potent and Broadly Effective Epidermal Growth Factor Receptor and HER2 Exon 20 Insertion Mutant Inhibitor," Angewandte Chemie International Edition, Sep. 3, 2018, vol. 57, No. 36, pp. 11629-11633.
Mok et al., "Gefitinib or Carboplatin-Paclitaxel in Pulmonary Adenocarcinoma," The New England Journal of Medicine, Sep. 3, 2009, vol. 361, No. 10, pp. 947-957.
Mok et al., "Osimertinib or Platinum-Pemetrexed in EGFR T790M-Positive Lung Cancer," The New England Journal of Medicine, Feb. 16, 2017, vol. 376, No. 7, pp. 629-640.
Oxnard et al., "Natural History and Molecular Characteristics of Lung Cancers Harboring EGFR Exon 20 Insertions," Journal of Thoracic Oncology, Feb. 2013, vol. 8, No. 2, pp. 179-184.
Paez et al., "EGFR Mutations in Lung Cancer: Correlation with Clinical Response to Gefitinib Therapy," Science, Jun. 4, 2004, vol. 304, No. 5676, pp. 1497-1500.
Pao et al., "Acquired Resistance of Lung Adenocarcinomas to Gefitinib or Erlotinib is Associated with a Second Mutation in the EGFR Kinase Domain," PLoS Medicine, Mar. 2005, vol. 2, No. 3, e73, pp. 0225-0235.
Pao et al., "Rational, biologically based treatment of EGFR-mutant non-small-cell lung cancer," Nature Reviews: Cancer, Nov. 2010, vol. 10, No. 11, pp. 760-774.
Robichaux et al., "Mechanisms and clinical activity of an EGFR and HER2 exon 20-selective kinase inhibitor in non-small cell lung cancer," Nature Medicine, May 2018, vol. 24, No. 5, pp. 638-646.
Sequist et al., "Phase III Study of Afatinib or Cisplatin Plus Pemetrexed in Patients With Metastatic Lung Adenocarcinoma With EGFR Mutations," Journal of Clinical Oncology, Sep. 20, 2013, vol. 31, No. 27, pp. 3327-3334.
Yang et al., "Clinical activity of afatinib in patients with advanced non-small-cell lung cancer harbouring uncommon EGFR mutations: a combined post-hoc analysis of LUX-Lung 2, LUX-Lung 3, and LUX-Lung 6," The Lancet Oncology, Jul. 2015, vol. 16, No. 7, pp. 830-838.

* cited by examiner

4H-PYRROLO[3,2-C]PYRIDIN-4-ONE DERIVATIVES

This application is the U.S. national phase application, pursuant to 35 U.S.C. § 371, of PCT International Application Serial No.: PCT/EP2018/078995, filed Oct. 23, 2018, designating the United States and published in English, which claims the benefit of the following U.S. Provisional Application No. 62/576,166, filed Oct. 24, 2017, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Oct. 12, 2020, is named 167741_016702_US_SL.txt and is 37,837 bytes in size.

FIELD OF APPLICATION OF THE INVENTION

The invention relates to substituted 4H-pyrrolo[3,2-c]pyridin-4-one compounds, a process for their production and uses thereof.

BACKGROUND OF THE INVENTION

The Epidermal Growth Factor Receptor (EGFR or EGF-receptor) receptor tyrosine kinase family consists of 4 members: EGFR (Erbb1, Her1), ERBB2 (Her2), ERBB3 (Her3), and ERBB4 (Her4). EGFR mediates activation of MAPK and PI3K signaling pathways and thereby regulates cell proliferation, differentiation, migration and survival. EGFR gene amplification, overexpression, and mutation are frequently observed in various cancer indications and are associated with a poor prognosis.

In lung adenocarcinoma, mutations of EGFR are prevalent in approximately 15% of Western patients and up to 50% of East Asian patients. These mutations typically occur in one of four exons, exons 18-21, in the kinase domain of EGFR. The FDA-approved inhibitors gefitinib, erlotinib, and afatinib, targeting mutations in exons 18, 19, and 21 of EGFR, are effective in patients but the response is often not durable. Resistance frequently occurs in these patients in response to acquisition of a second mutation, T790M. Second generation inhibitors, e.g. afatinib, irreversibly target this mutation but are still potent inhibitors of wild-type EGFR. A third-generation irreversible inhibitor, osimertinib, that maximizes activity towards T790M while minimizing activity towards wild-type EGFR, is also effective in T790M mutant patients and is currently the standard treatment for T790M positive patients.

By contrast, and with the exception of A763_Y764insFQEA, small in-frame insertions of EGFR exon 20 are resistant to available EGFR inhibitors at doses achievable in lung cancer patients and comprise an unmet medical need.

Patients with EGFR exon 20 insertions, such as V769_770ins ASV and D770_N771ins SVD, show particular low response rates to all currently approved EGFR-targeted therapies, resulting in significantly reduced progression-free survival as well as overall survival. This has been shown for the first-generation inhibitors erlotinib and gefitinib as well as for the second-generation inhibitor afatinib. Therefore, the standard treatment for EGFR exon 20 insertion patients is currently chemotherapy.

Mutant EGFR is a promising drug target for cancer therapy. In particular, patients with primary resistance to approved anti-EGFR therapies, due to EGFR exon 20 insertions, have only few treatment options to date and there is a great need for novel alternative and/or improved therapeutics to provide these patients with an efficacious, well-tolerable therapy.

Therefore, potent inhibitors of mutant EGFR, particularly of mutant EGFR with exon 20 insertion mutations that show improved selectivity versus wild-type EGFR, represent valuable compounds that should complement therapeutic options either as single agents or in combination with other drugs.

SUMMARY OF THE INVENTION

The invention provides compounds that inhibit a mutant EGFR (e.g., an EGFR comprising one or more exon 20 insertion mutations, etc.) and are selective for wild-type-EGFR.

It has now been found that the compounds of the present invention have surprising and advantageous properties.

In particular, said compounds of the present invention have surprisingly been found to effectively inhibit mutant EGFR with exon 20 insertion mutations, particularly those harboring a D770_N771ins SVD exon 20 insertion with an $IC_{50}$ below 5 nM. Furthermore it has been found that these compounds additionally show cellular potency below 1 µM in EGFR D770_N771ins SVD exon 20 insertion harboring BA/F3 cell lines. Surprisingly these compounds additionally show at least 5 fold selectivity in an antiproliferative assay of EGFR D770_N771ins SVD exon 20 insertion harboring BA/F3 cell lines versus wild-type EGFR harboring BA/F3 cells. and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses mediated by mutant EGFR with exon 20 insertion mutations and/or reduce (or block) proliferation in cells harboring EGFR exon 20 insertion mutations, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

DESCRIPTION OF THE INVENTION

In accordance with a first aspect, the invention relates to compounds of formula (I),

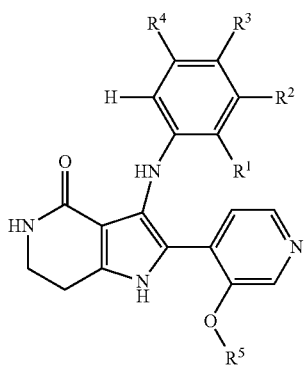

in which:
R¹ represents methyl, ethyl, trifluoromethyl, 2,2-difluoroethyl, cyano, bromo, methoxy, or difluoromethoxy, or with the proviso that when R¹ is chloro, then R² represents hydrogen or chloro and R³ and R⁴ represent hydrogen;
R² represents hydrogen, methyl, fluoro, chloro or bromo;
R³ represents hydrogen or fluoro;
R⁴ represents hydrogen or fluoro, wherein at least one of R³ and R⁴ represents hydrogen;
R⁵ represents C₂-C₅-alkyl,
which is substituted once with hydroxy, C₁-C₄-alkoxy, R⁷R⁸N—, or phenyl, or R⁶—CH₂—,
wherein said phenyl groups are optionally substituted one or more times, independently of each other, with R';
R' represents, independently of each other, hydroxy, halogen, cyano, C₁-C₄-alkyl, C₁-C₄-alkoxy, C₁-C₄-haloalkyl or C₁-C₄-haloalkoxy;
R⁶ represents a group selected from the group:

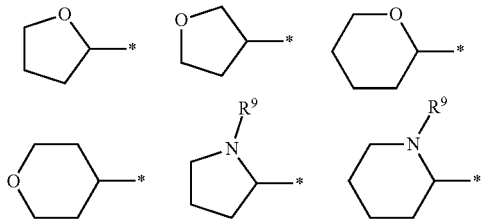

wherein * indicates the point of attachment of said group with the rest of the molecule;
R⁷, R⁸ represent, independently of each other, C₁-C₃-alkyl, C₁-C₃-haloalkyl or
R⁷ and R⁸ together with the nitrogen atom to which they are attached form a 5- to 6-membered nitrogen containing heterocyclic ring, optionally containing one additional heteroatom or heteroatom containing group selected from O and NR¹⁰;
R⁹ represents hydrogen, C₁-C₃-alkyl or C₁-C₃-haloalkyl;
R¹⁰ represents hydrogen or C₁-C₃-alkyl;
or an N-oxide, a salt, a tautomer or a stereoisomer of said compound, or a salt of said N-oxide, tautomer or stereoisomer.

In a second aspect, the invention relates to compounds of formula (I) as described supra, wherein
R¹ represents methyl, ethyl, trifluoromethyl, 2,2-difluoroethyl, cyano, bromo, methoxy, or difluoromethoxy, or with the proviso that when R¹ is chloro, then R² represents chloro;
R² represents fluoro or chloro;
R³ represents hydrogen;
R⁴ represents hydrogen;
R⁵ represents C₂-C₅-alkyl,
which is substituted once with hydroxy, C₁-C₂-alkoxy or R⁷R⁸N—, or R⁶—CH₂—;
R⁶ represents a group selected from the group:

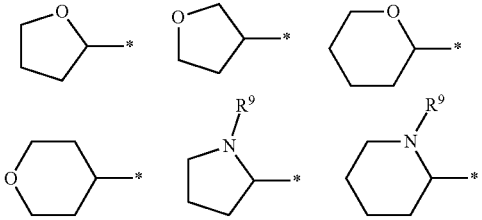

wherein * indicates the point of attachment of said group with the rest of the molecule;
R⁷, R⁸ represent, independently of each other, C₁-C₂-alkyl, or C₁-C₂-haloalkyl;
R⁹ represents hydrogen, C₁-C₂-alkyl or C₁-C₂-haloalkyl;
or an N-oxide, a salt, a tautomer or a stereoisomer of said compound, or a salt of said N-oxide, tautomer or stereoisomer.

In a third aspect, the invention relates to compounds of formula (I) as described supra, wherein:
R¹ represents methyl, ethyl, trifluoromethyl, 2,2-difluoroethyl, cyano, bromo, methoxy, or difluoromethoxy, or with the proviso that when R¹ is chloro, then R² represents chloro;
R² represents fluoro or chloro;
R³ represents hydrogen;
R⁴ represents hydrogen;
R⁵ represents C₄-C₅-alkyl,
which is substituted once with hydroxy, methoxy or R⁷R⁸N—, or R⁶—CH₂—;
R⁶ represents a group selected from the group:

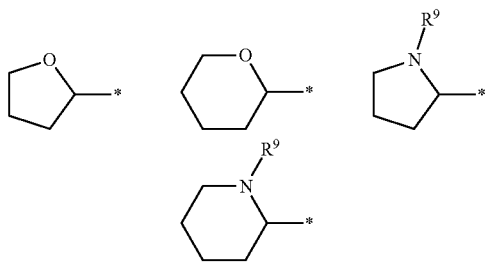

wherein * indicates the point of attachment of said group with the rest of the molecule;
is R⁷, R⁸ represent, independently of each other, methyl, or C₁-C₂-fluoroalkyl;
R⁹ represents C₁-C₂-alkyl or C₁-C₂-fluoroalkyl;
or an N-oxide, a salt, a tautomer or a stereoisomer of said compound, or a salt of said N-oxide, tautomer or stereoisomer.

In a fourth aspect, the invention relates to compounds of formula (I),

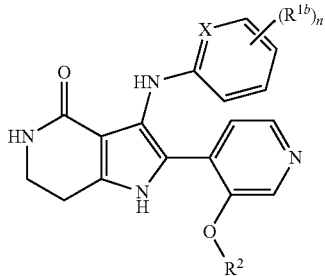

in which:

X represents CR$^{1a}$;

R$^{1a}$ represents, independently of each other, hydrogen, hydroxy, halogen, cyano, C$_1$-C$_4$-alkyl, C$_1$-C$_4$-alkoxy, C$_1$-C$_4$-haloalkyl or C$_1$-C$_4$-haloalkoxy;

R$^{1b}$ represents, independently of each other, hydroxy, halogen, cyano, C$_1$-C$_4$-alkyl, C$_1$-C$_4$-alkoxy, C$_1$-C$_4$-haloalkyl or C$_1$-C$_4$-haloalkoxy;

R$^{1c}$ represents, independently of each other, hydroxy, halogen, cyano, C$_1$-C$_4$-alkyl, C$_1$-C$_4$-alkoxy, C$_1$-C$_4$-haloalkyl or C$_1$-C$_4$-haloalkoxy;

R$^2$ represents C$_1$-C$_6$-alkyl
which is optionally substituted one, two or three times, independently of each other, with halogen and is optionally substituted one time with hydroxy, C$_1$-C$_4$-alkoxy, R$^3$R$^4$N—, C$_3$-C$_6$-cycloalkyl, 5- to 6-membered heterocycloalkyl or phenyl,
wherein C$_3$-C$_6$-cycloalkyl, 5- to 6-membered heterocycloalkyl and phenyl groups are optionally substituted one or more times, independently of each other, with R$^{1c}$;

R$^3$, R$^4$ represent, independently of each other, hydrogen or C$_1$-C$_4$-alkyl, or R$^3$ and R$^4$ together with the nitrogen atom to which they are attached form a 5- to 6-membered nitrogen containing heterocyclic ring, optionally containing one additional heteroatom or heteroatom containing group selected from O, NR$^5$ and S;

R$^5$ represents hydrogen, C$_1$-C$_4$-alkyl, C$_3$-C$_6$-cycloalkyl, C$_1$-C$_4$-haloalkyl;

n represents 0, 1, 2 or 3;

or an N-oxide, a salt, a tautomer or a stereoisomer of said compound, or a salt of said N-oxide, tautomer or stereoisomer.

In a fifth aspect, the invention relates to compounds of formula (I) as described supra, which is selected from the group consisting of:

2-[3-(2-methoxyethoxy)pyridin-4-yl]-3-(phenylamino)-1,5,6,7-tetrahydro-4H-pyrrolo[3,2-c]pyridin-4-one, 2-[3-(3,3-dimethylbutoxy)pyridin-4-yl]-3-[(3-fluorophenyl)amino]-1,5,6,7-tetrahydro-4H-pyrrolo[3,2-c]pyridin-4-one, 2-[3-(benzyloxy)pyridin-4-yl]-3-[(3-fluorophenyl)amino]-1,5,6,7-tetrahydro-4H-pyrrolo[3,2-c]pyridin-4-one, 3-[(3-fluorophenyl)amino]-2-[3-(2-hydroxy-2-methylpropoxy)pyridin-4-yl]-1,5,6,7-tetrahydro-4H-pyrrolo[3,2-c]pyridin-4-one, 2-{3-[2-(dimethylamino)ethoxy]pyridin-4-yl}-3-[(3-fluorophenyl)amino]-1,5,6,7-tetrahydro-4H-pyrrolo[3,2-c]pyridin-4-one, 3-[(3-fluorophenyl)amino]-2-[3-(2-methoxy-2-methylpropoxy)pyridin-4-yl]-1,5,6,7-tetrahydro-4H-pyrrolo[3,2-c]pyridin-4-one, 3-[(3-fluorophenyl)amino]-2-{3-[2-methyl-2-(morpholin-4-yl)propoxy]pyridin-4-yl}-1,5,6,7-tetrahydro-4H-pyrrolo[3,2-c]pyridin-4-one, 3-[(3-fluorophenyl)amino]-2-(3-{[(2S)-1-methylpyrrolidin-2-yl]methoxy}pyridin-4-yl)-1,5,6,7-tetrahydro-4H-pyrrolo[3,2-c]pyridin-4-one, 3-[(3,5-difluorophenyl)amino]-2-[3-(2-methoxyethoxy)pyridin-4-yl]-1,5,6,7-tetrahydro-4H-pyrrolo[3,2-c]pyridin-4-one, 3-[(3,5-difluorophenyl)amino]-2-[3-(2-methoxy-2-methylpropoxy)pyridin-4-yl]-1,5,6,7-tetrahydro-4H-pyrrolo[3,2-c]pyridin-4-one, 3-{[2-(difluoromethoxy)phenyl]amino}-2-[3-(2-methoxyethoxy)pyridin-4-yl]-1,5,6,7-tetrahydro-4H-pyrrolo[3,2-c]pyridin-4-one, 3-[(2-bromo-3-fluorophenyl)amino]-2-[3-(2-methoxyethoxy)pyridin-4-yl]-1,5,6,7-tetrahydro-4H-pyrrolo[3,2-c]pyridin-4-one, 2-[3-(2-methoxyethoxy)pyridin-4-yl]-3-[(2-methoxyphenyl)amino]-1,5,6,7-tetrahydro-4H-pyrrolo[3,2-c]pyridin-4-one, 2-[3-(2-methoxyethoxy)pyridin-4-yl]-3-{[2-(trifluoromethoxy)phenyl]amino}-1,5,6,7-tetrahydro-4H-pyrrolo[3,2-c]pyridin-4-one, 3-{[2-(2,2-difluoroethyl)phenyl]amino}-2-[3-(2-methoxyethoxy)pyridin-4-yl]-1,5,6,7-tetrahydro-4H-pyrrolo[3,2-c]pyridin-4-one, 3-[(3-fluoro-2-methoxyphenyl)amino]-2-[3-(2-methoxyethoxy)pyridin-4-yl]-1,5,6,7-tetrahydro-4H-pyrrolo[3,2-c]pyridin-4-one, 3-[(3-fluoro-2-methoxyphenyl)amino]-2-[3-(2-methoxy-2-methylpropoxy)pyridin-4-yl]-1,5,6,7-tetrahydro-4H-pyrrolo[3,2-c]pyridin-4-one, 3-{[2-(difluoromethoxy)-3-fluorophenyl]amino}-2-[3-(2-methoxyethoxy)pyridin-4-yl]-1,5,6,7-tetrahydro-4H-pyrrolo[3,2-c]pyridin-4-one, 3-{[2-(difluoromethoxy)-3-fluorophenyl]amino}-2-[3-(2-methoxy-2-methylpropoxy)pyridin-4-yl]-1,5,6,7-tetrahydro-4H-pyrrolo[3,2-c]pyridin-4-one, 3-[(3-fluoro-2-methylphenyl)amino]-2-[3-(2-methoxyethoxy)pyridin-4-yl]-1,5,6,7-tetrahydro-4H-pyrrolo[3,2-c]pyridin-4-one, 3-[(3-fluoro-2-methylphenyl)amino]-2-[3-(2-methoxy-2-methylpropoxy)pyridin-4-yl]-1,5,6,7-tetrahydro-4H-pyrrolo[3,2-c]pyridin-4-one, 3-{[2-(2,2-difluoroethyl)-3-fluorophenyl]amino}-2-[3-(2-methoxyethoxy)pyridin-4-yl]-1,5,6,7-tetrahydro-4H-pyrrolo[3,2-c]pyridin-4-one, 3-{[2-(2,2-difluoroethyl)-3-fluorophenyl]amino}-2-[3-(2-methoxy-2-methylpropoxy)pyridin-4-yl]-1,5,6,7-tetrahydro-4H-pyrrolo[3,2-c]pyridin-4-one, 3-[(3-fluoro-2-hydroxyphenyl)amino]-2-[3-(2-methoxy-2-methylpropoxy)pyridin-4-yl]-1,5,6,7-tetrahydro-4H-pyrrolo[3,2-c]pyridin-4-one, 3-[(2-ethoxy-3-fluorophenyl)amino]-2-[3-(2-methoxyethoxy)pyridin-4-yl]-1,5,6,7-tetrahydro-4H-pyrrolo[3,2-c]pyridin-4-one, 3-[(2-ethoxy-3-fluorophenyl)amino]-2-[3-(2-methoxy-2-methylpropoxy)pyridin-4-yl]-1,5,6,7-tetrahydro-4H-pyrrolo[3,2-c]pyridin-4-one, 3-{[2-(2,2-difluoroethoxy)-3-fluorophenyl]amino}-2-[3-(2-methoxy-2-methylpropoxy)pyridin-4-yl]-1,5,6,7-tetrahydro-4H-pyrrolo[3,2-c]pyridin-4-one, 3-[(3,4-difluoro-2-methoxyphenyl)amino]-2-[3-(2-methoxyethoxy)pyridin-4-yl]-1,5,6,7-tetrahydro-4H-pyrrolo[3,2-c]pyridin-4-one, 3-[(3,4-difluoro-2-methoxyphenyl)amino]-2-[3-(2-methoxy-2-methylpropoxy)pyridin-4-yl]-1,5,6,7-tetrahydro-4H-pyrrolo[3,2-c]pyridin-4-one, 3-[(3,5-difluoro-2-methoxyphenyl)amino]-2-[3-(2-methoxyethoxy)pyridin-4-yl]-1,5,6,7-tetrahydro-4H-pyrrolo[3,2-c]pyridin-4-one, and 3-[(3,5-difluoro-2-methoxyphenyl)amino]-2-[3-(2-methoxy-2-methylpropoxy)pyridin-4-yl]-1,5,6,7-tetrahydro-4H-pyrrolo[3,2-c]pyridin-4-one, or an N-oxide, a salt, a tautomer or a stereoisomer of said compound, or a salt of said N-oxide, tautomer or stereoisomer.

In a further embodiment of the above-mentioned aspects, the invention relates to compounds of formula (I), wherein:
$R^1$ represents methyl, trifluoromethyl, 2,2-difluoroethyl, cyano, bromo, methoxy, difluoromethoxy, or
with the proviso that when $R^1$ is chloro, then $R^2$ represents hydrogen or chloro and $R^3$ and $R^4$ represent hydrogen.

In a further embodiment of the above-mentioned aspects, the invention relates to compounds of formula (I), wherein:
$R^1$ represents methyl, trifluoromethyl, 2,2-difluoroethyl, cyano, bromo, methoxy, difluoromethoxy, or
with the proviso that when $R^1$ is chloro, then $R^2$ represents chloro.

In a further embodiment of the above-mentioned aspects, the invention relates to compounds of formula (I), wherein:
$R^2$ represents hydrogen, fluoro or chloro.

In a further embodiment of the above-mentioned aspects, the invention relates to compounds of formula (I), wherein:
$R^2$ represents fluoro or chloro.

In a further embodiment of the above-mentioned aspects, the invention relates to compounds of formula (I), wherein:
$R^3$ represents hydrogen or fluoro.

In a further embodiment of the above-mentioned aspects, the invention relates to compounds of formula (I), wherein:
$R^3$ represents hydrogen.

In a further embodiment of the above-mentioned aspects, the invention relates to compounds of formula (I), wherein:
$R^4$ represents hydrogen or fluoro, wherein at least one of $R^3$ and $R^4$ represents hydrogen.

In a further embodiment of the above-mentioned aspects, the invention relates to compounds of formula (I), wherein:
$R^4$ represents hydrogen.

In a further embodiment of the above-mentioned aspects, the invention relates to compounds of formula (I), wherein:
$R^5$ represents $C_2$-$C_5$-alkyl,
which is substituted once with hydroxy, $C_1$-$C_4$-alkoxy, $R^7R^8N-$ or phenyl, or $R^6$—$CH_2$—,
wherein said phenyl groups are optionally substituted one or more times, independently of each other, with R'.

In a further embodiment of the above-mentioned aspects, the invention relates to compounds of formula (I), wherein:
$R^5$ represents $C_2$-$C_5$-alkyl, which is substituted once with hydroxy, $C_1$-$C_4$-alkoxy, $R^7R^8N-$ or phenyl,
wherein said phenyl groups are optionally substituted one or more times, independently of each other, with R'.

In a further embodiment of the above-mentioned aspects, the invention relates to compounds of formula (I), wherein:
$R^5$ represents $C_2$-$C_5$-alkyl,
which is substituted once with hydroxy, $C_1$-$C_4$-alkoxy, $R^7R^8N-$ or phenyl, or $R^6$—$CH_2$—.

In a further embodiment of the above-mentioned aspects, the invention relates to compounds of formula (I), wherein:

$R^5$ represents $C_2$-$C_5$-alkyl,
which is substituted once with hydroxy, $C_1$-$C_2$-alkoxy or $R^7R^8N$—, or $R^6$—$CH_2$—.

In a further embodiment of the above-mentioned aspects, the invention relates to compounds of formula (I), wherein:
$R^5$ represents $C_4$-$C_5$-alkyl,
which is substituted once with hydroxy, methoxy or $R^7R^8N$—, or $R^6$—$CH_2$—.

In a further embodiment of the above-mentioned aspects, the invention relates to compounds of formula (I), wherein:
$R^5$ represents $C_4$-$C_5$-alkyl, which is substituted once with hydroxy, methoxy or $R^7R^8N$—.

In a further embodiment of the above-mentioned aspects, the invention relates to compounds of formula (I), wherein:
$R^5$ represents $R^6$—$CH_2$—.

In a further embodiment of the above-mentioned aspects, the invention relates to compounds of formula (I), wherein:
$R^6$ represents a group selected from the group:

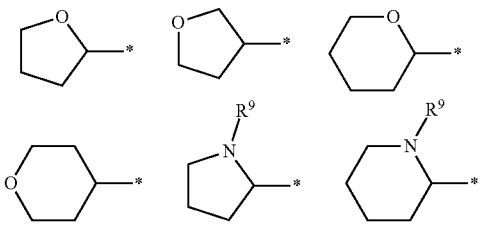

wherein * indicates the point of attachment of said group with the rest of the molecule.

In a further embodiment of the above-mentioned aspects, the invention relates to compounds of formula (I), wherein:
$R^6$ represents a group selected from the group:

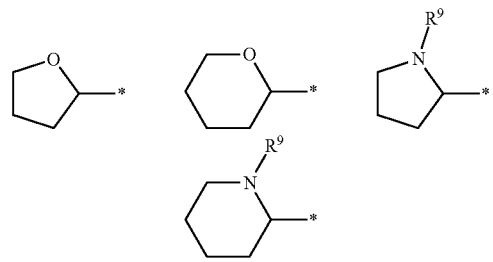

wherein * indicates the point of attachment of said group with the rest of the molecule.

In a further embodiment of the above-mentioned aspects, the invention relates to compounds of formula (I), wherein:
$R^7$, $R^8$ represent, independently of each other, $C_1$-$C_3$-alkyl, $C_1$-$C_3$-haloalkyl or
$R^7$ and $R^8$ together with the nitrogen atom to which they are attached form a 5- to 6-membered nitrogen containing heterocyclic ring, optionally containing one additional heteroatom or heteroatom containing group selected from O and $NR^{10}$.

In a further embodiment of the above-mentioned aspects, the invention relates to compounds of formula (I), wherein:
is $R^7$, $R^8$ represent, independently of each other, $C_1$-$C_2$-alkyl, or $C_1$-$C_2$-haloalkyl.

In a further embodiment of the above-mentioned aspects, the invention relates to compounds of formula (I), wherein:
$R^7$, $R^8$ represent, independently of each other, methyl, or $C_1$-$C_2$-fluoroalkyl.

In a further embodiment of the above-mentioned aspects, the invention relates to compounds of formula (I), wherein: $R^9$ represents hydrogen, $C_1$-$C_3$-alkyl or $C_1$-$C_3$-haloalkyl.

In a further embodiment of the above-mentioned aspects, the invention relates to compounds of formula (I), wherein: $R^9$ represents hydrogen, $C_1$-$C_2$-alkyl or $C_1$-$C_2$-haloalkyl.

In a further embodiment of the above-mentioned aspects, the invention relates to compounds of formula (I), wherein: $R^9$ represents $C_1$-$C_2$-alkyl or $C_1$-$C_2$-fluoroalkyl.

In a further embodiment of the above-mentioned aspects, the invention relates to compounds of formula (I), wherein: $R^{10}$ represents hydrogen or $C_1$-$C_3$-alkyl.

In a further embodiment of the above-mentioned aspects, the invention relates to compounds of formula (I), wherein: $R^{10}$ represents hydrogen or methyl.

In a further embodiment of the above-mentioned aspects, the invention relates to compounds of formula (I), wherein: R' represents, independently of each other, hydroxy, halogen, cyano, $C_1$-$C_4$-alkyl, $C_1$-$C_4$-alkoxy, $C_1$-$C_4$-haloalkyl or $C_1$-$C_4$-haloalkoxy.

In a further embodiment of the above-mentioned aspects, the invention relates to compounds of formula (I), wherein: R' represents, independently of each other, hydroxy, fluoro, chloro, cyano, methyl, methoxy, trifluoromethyl or trifluoromethoxy.

A further aspect of the invention relates to compounds of formula (I), which are present as their salts.

It is to be understood that the present invention relates to any sub-combination within any embodiment or aspect of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

Another embodiment of the invention are compounds according to the claims as disclosed in the Claims section wherein the definitions are defined according to the preferred or more preferred definitions as disclosed below or specifically disclosed residues of the exemplified compounds and subcombinations thereof.

Definitions

It is to be understood that embodiments disclosed herein are not meant to be understood as individual embodiments which would not relate to one another. Features discussed with one embodiment or aspect of the invention are meant to be disclosed also in connection with other embodiments or aspects of the invention shown herein. If, in one case, a specific feature is not disclosed with one embodiment or aspect of the invention, but with another, the skilled person would understand that does not necessarily mean that said feature is not meant to be disclosed with said other embodiment or aspect of the invention. The skilled person would understand that it is the gist of this application to disclose said feature also for the other embodiment or aspect of the invention, but that just for purposes of clarity and to keep the length of this specification manageable. For example, it is to be understood that all aspects, embodiments, pharmaceutical compositions, combinations, uses and/or methods of the present invention defined herein for the compounds of formula (I) also relate to more specific embodiments of the compounds of formula (I), such as, but not limited to, the compounds of formula (Ia) and vice-versa, for example.

It is further to be understood that the content of the prior art documents referred to herein is incorporated by reference in their entirety, e.g., for enablement purposes, namely when e.g. a method is discussed details of which are described in said prior art document. This approach serves to keep the length of this specification manageable.

Constituents which are optionally substituted as stated herein, may be substituted, unless otherwise noted, one or more times, independently of one another at any possible position. When any variable occurs more than one time in any constituent, each definition is independent. For example, when $R^1$, $R^{1a}$, $R^{1b}$, $R^{1c}$, $R^2$, $R^3$ and/or $R^4$ occur more than one time in any compound of formula (I) each definition of $R^1$, $R^{1a}$, $R^{1b}$, $R^{1c}$, $R^2$, $R^3$ and $R^4$ is independent.

Should a constituent be composed of more than one part, e.g. $C_1$-$C_4$-alkoxy-C2-$C_4$-alkyl, the position of a possible substituent can be at any of these parts at any suitable position.

A hyphen at the beginning or at the end of the constituent marks the point of attachment to the rest of the molecule. Should a ring be substituted the substitutent could be at any suitable position of the ring, also on a ring nitrogen atom, if suitable.

The term "comprising" when used in the specification includes "consisting of".

If it is referred to "as mentioned above" or "mentioned above", "supra" within the description it is referred to any of the disclosures made within the specification in any of the preceding pages.

If it is referred to "as mentioned herein", "described herein", "provided herein" or "stated herein" within the description it is referred to any of the disclosures made within the specification in any of the preceding or subsequent pages.

"Suitable" within the sense of the invention means chemically possible to be made by methods within the knowledge of a skilled person.

The terms as mentioned in the present text have preferably the following meanings:

The term "halogen atom", "halo-" or "Hal-" is to be understood as meaning a fluorine, chlorine, bromine or iodine atom.

The term "$C_1$-$C_6$-alkyl" is to be understood as meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl or iso-propyl group.

The term "$C_1$-$C_4$-haloalkyl" is to be understood as meaning a linear or branched, saturated, monovalent hydrocarbon group in which the term "$C_1$-$C_4$-alkyl" is defined supra, and in which one or more hydrogen atoms is replaced by a halogen atom, in identically or differently, i.e. one halogen atom being independent from another. Particularly, said halogen atom is F. Said $C_1$-$C_4$-haloalkyl group is, for example, —CF$_3$, —CHF$_2$, —CH$_2$F, —CF$_2$CF$_3$, —CH$_2$CH$_2$F, —CH$_2$CHF$_2$, —CH$_2$CF$_3$, —CH$_2$CH$_2$CF$_3$, or —CH(CH$_2$F)$_2$.

The term "C$_1$-C$_4$-alkoxy" is to be understood as meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy or sec-butoxy group, or an isomer thereof.

Unless defined otherwise, the term "5- to 6-membered heterocycloalkyl" or "5- to 6-membered heterocyclic ring", is to be understood as meaning a saturated, monovalent, monocyclic hydrocarbon ring which contains 4 or 5 carbon atoms, and one heteroatom-containing group selected from O and NR, wherein R means a hydrogen atom, a C$_1$-C$_3$-alkyl or a C$_1$-C$_3$-haloalkyl group, it being possible for said heterocycloalkyl group to be attached to the rest of the molecule via any one of the carbon atoms.

Particularly, without being limited thereto, said heterocycloalkyl can be a 5-membered ring, such as tetrahydrofuranyl, pyrazolidinyl, or a 6-membered ring, such as tetrahydropyranyl, piperidinyl, for example.

The term "C$_1$-C$_6$", as used throughout this text, e.g. in the context of the definition of "C$_1$-C$_6$-alkyl" or "C$_1$-C$_6$-haloalkyl" is to be understood as meaning an alkyl group having a finite number of carbon atoms of 1 to 6, i.e. 1, 2, 3, 4, 5 or 6 carbon atoms. It is to be understood further that said term "C$_1$-C$_6$" is to be interpreted as any sub-range comprised therein, e.g. C$_1$-C$_6$, C$_2$-C$_6$, C$_3$-C$_6$, C$_1$-C$_2$, C$_1$-C$_3$, particularly C$_1$-C$_2$, C$_1$-C$_3$, C$_1$-C$_4$.

The term "C$_1$-C$_4$", as used throughout this text, e.g. in the context of the definition of "C$_1$-C$_4$-alkyl", "C$_1$-C$_4$-haloalkyl", "C$_1$-C$_4$-alkoxy", or "C$_1$-C$_4$-haloalkoxy" is to be understood as meaning an alkyl group having a finite number of carbon atoms of 1 to 4, i.e. 1, 2, 3 or 4 carbon atoms. It is to be understood further that said term "C$_1$-C$_4$" is to be interpreted as any sub-range comprised therein, e.g. C$_1$-C$_4$, C$_2$-C$_4$, C$_3$-C$_4$, C$_1$-C$_2$, C$_1$-C$_3$, particularly C$_1$-C$_2$, C$_1$-C$_3$, C$_1$-C$_4$, in the case of "C$_1$-C$_6$-haloalkyl" or "C$_1$-C$_4$-haloalkoxy" even more particularly C$_1$-C$_2$.

Further, as used herein, the term "C$_3$-C$_6$", as used throughout this text, e.g. in the context of the definition of "C$_3$-C$_6$-cycloalkyl", is to be understood as meaning a cycloalkyl group having a finite number of carbon atoms of 3 to 6, i.e. 3, 4, 5 or 6 carbon atoms. It is to be understood further that said term "C$_3$-C$_6$" is to be interpreted as any sub-range comprised therein, e.g. C$_3$-C$_6$, C$_4$-C$_5$, C$_3$-C$_5$, C$_3$-C$_4$, C$_4$-C$_6$, C$_5$-C$_6$; particularly C$_3$-C$_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The compounds of general formula (I) may exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" is to be understood as meaning a proportion of such isotope which is higher than its natural abundance. The natural abundances of isotopes to be applied in this context are described in "Isotopic Compositions of the Elements 1997", Pure Appl. Chem., 70(1), 217-235, 1998. Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively.

With respect to the treatment and/or prophylaxis of the disorders specified herein the isotopic variant(s) of the compounds of general formula (I) in one embodiment contain deuterium ("deuterium-containing compounds of general formula (I)"). Isotopic variants of the compounds of general formula (I) in which one or more radioactive isotopes, such as $^3$H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses (H. J. Leis et al., Curr. Org. Chem., 1998, 2, 131) in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, in one embodiment for a deuterium-containing reagent. Depending on the desired sites of deuteration, in some cases deuterium from D$_2$O can be incorporated either directly into the compounds or into reagents that are useful for synthesizing such compounds (Esaki et al., Tetrahedron, 2006, 62, 10954; Esaki et al., Chem. Eur. J., 2007, 13, 4052). Deuterium gas is also a useful reagent for incorporating deuterium into molecules. Catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron, 2011, 52, 3865) is a rapid route for incorporation of deuterium. Metal catalysts (i.e. Pd, Pt, and Rh) in the presence of deuterium gas can be used to directly exchange deuterium for hydrogen in functional groups containing hydrocarbons (J. G. Atkinson et al., U.S. Pat. No. 3,966,781). A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA. Further information on the state of the art with respect to deuterium-hydrogen exchange is given for example in Hanzlik et al., J. Org. Chem. 55, 3992-3997, 1990; R. P. Hanzlik et al., Biochem. Biophys. Res. Commun. 160, 844, 1989; P. J. Reider et al., J. Org. Chem. 52, 3326-3334, 1987; M. Jarman et al., Carcinogenesis 16(4), 683-688, 1993; J. Atzrodt et al., Angew. Chem., Int. Ed. 2007, 46, 7744; K. Matoishi et al., J. Chem. Soc, Chem. Commun. 2000, 1519-1520; K. Kassahun et al., WO2012/112363.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, in one embodiment higher than 90%, 95%, 96% or 97%, in other embodiments higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [A. Streitwieser et al., *J. Am. Chem. Soc.*, 1963, 85, 2759; C. L. Perrin, et al., *J. Am. Chem. Soc.*, 2007, 129, 4490], basicity [C. L. Perrin, et al., J. Am. Chem. Soc., 2003, 125, 15008; C. L. Perrin in Advances in Physical Organic Chemistry, 44, 144; C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (D. J. Kushner et al., Can. J. Physiol. Pharmacol., 1999, 77, 79; A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Uetrecht et al., Chemical Research in Toxicology, 2008, 21, 9, 1862; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. Indiplon (A. J. Morales et al., Abstract 285, The 15$^{th}$ North American Meeting of the International Society of Xenobiotics, San Diego, Calif., Oct. 12-16, 2008), ML-337 (C. J. Wenthur et al., J. Med. Chem., 2013, 56, 5208), and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch. Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome P450.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

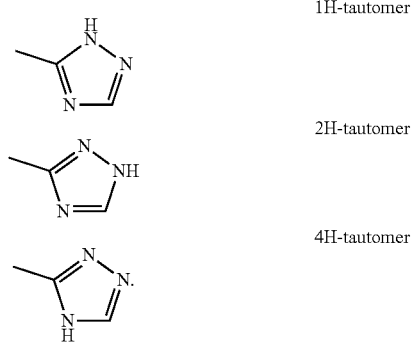

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric orthiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and stearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x CF$_3$COOH", "x Na$^+$", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

The salts include water-insoluble and, particularly, water-soluble salts.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl, 1,3-dioxolen-2-onylmethyl esters, e.g. 5-methyl-1,3-dioxolen-2-onylmethyl, and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or a may achieve a combination of both effects.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered. Any such combination of a compound of formula (I) of the present invention with an anti-cancer agent as defined below is an embodiment of the invention.

The term "(chemotherapeutic) anti-cancer agents" relates to any agent that reduces the survival or proliferation of a cancer cell, and includes but is not limited to 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, poziotinib, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

By "Epidermal Growth Factor Receptor (EGFR) Polypeptide" is meant a polypeptide having at least about 95% amino acid sequence identity to the sequence provided at UniProt Accession No. P00533-1 or a fragment thereof. Mutant EGFR polypeptides include those having an insertion between, for example, amino acids V769 and D770 or between D770 and N771. In other embodiments, the amino acid sequence identity is 96, 97, 98, 99, or 100% to UniProt Accession No. P00533-1.

An exemplary full length sequence of human EGFR, which indicates V769, D770, and N771 in bold, is provided at UniProt Accession No. P00533-1, which is reproduced below:

```
                                                    (SEQ ID NO: 6)
         10         20         30         40         50
     MRPSGTAGAA LLALLAALCP ASRALEEKKV CQGTSNKLTQ LGTFEDHFLS 60         70         80         90        100
     LQRMFNNCEV VLGNLEITYV QRNYDLSFLK TIQEVAGYVL IALNTVERIP 110        120        130        140        150
     LENLQIIRGN MYYENSYALA VLSNYDANKT GLKELPMRNL QEILHGAVRF 160        170        180        190        200
     SNNPALCNVE SIQWRDIVSS DFLSNMSMDF QNHLGSCQKC DPSCPNGSCW 210        220        230        240        250
     GAGEENCQKL TKIICAQQCS GRCRGKSPSD CCHNQCAAGC TGPRESDCLV 260        270        280        290        300
     CRKFRDEATC KDTCPPLMLY NPTTYQMDVN PEGKYSFGAT CVKKCPRNYV 310        320        330        340        350
     VTDHGSCVRA CGADSYEMEE DGVRKCKKCE GPCRKVCNGI GIGEFKDSLS 360        370        380        390        400
     INATNIKHFK NCTSISGDLH ILPVAFRGDS FTHTPPLDPQ ELDILKTVKE 410        420        430        440        450
     ITGFLLIQAW PENRTDLHAF ENLEIIRGRT KQHGQFSLAV VSLNITSLGL 460        470        480        490        500
     RSLKEISDGD VIISGNKNLC YANTINWKKL FGTSGQKTKI ISNRGENSCK 510        520        530        540        550
     ATGQVCHALC SPEGCWGPEP RDCVSCRNVS RGRECVDKCN LLEGEPREFV 560        570        580        590        600
     ENSECIQCHP ECLPQAMNIT CTGRGPDNCI QCAHYIDGPH CVKTCPAGVM 610        620        630        640        650
     GENNTLVWKY ADAGHVCHLC HPNCTYGCTG PGLEGCPTNG PKIPSIATGM
```

-continued

```
         660         670         680         690         700
    VGALLLLLVV  ALGIGLFMRR  RHIVRKRTLR  RLLQERELVE  PLTPSGEAPN 710         720         730         740         750
    QALLRILKET  EFKKIKVLGS  GAFGTVYKGL  WIPEGEKVKI  PVAIKELREA 760         770         780         790         800
    TSPKANKEIL  DEAYVMASVD  NPHVCRLLGI  CLTSTVQLIT  QLMPFGCLLD 810         820         830         840         850
    YVREHKDNIG  SQYLLNWCVQ  IAKGMNYLED  RRLVHRDLAA  RNVLVKTPQH 860         870         880         890         900
    VKITDFGLAK  LLGAEEKEYH  AEGGKVPIKW  MALESILHRI  YTHQSDVWSY 910         920         930         940         950
    GVTVWELMTF  GSKPYDGIPA  SEISSILEKG  ERLPQPPICT  IDVYMIMVKC 960         970         980         990        1000
    WMIDADSRPK  FRELIIEFSK  MARDPQRYLV  IQGDERMHLP  SPTDSNFYRA 1010        1020        1030        1040        1050
    LMDEEDMDDV  VDADEYLIPQ  QGFFSSPSTS  RTPLLSSLSA  TSNNSTVACI 1060        1070        1080        1090        1100
    DRNGLQSCPI  KEDSFLQRYS  SDPTGALTED  SIDDTFLPVP  EYINQSVPKR 1110        1120        1130        1140        1150
    PAGSVQNPVY  HNQPLNPAPS  RDPHYQDPHS  TAVGNPEYLN  TVQPTCVNST 1160        1170        1180        1190        1200
    FDSPAHWAQK  GSHQISLDNP  DYQQDFFPKE  AKPNGIFKGS  TAENAEYLRV

1210
    APQSSEFIGA
```

An exemplary polynucleotide encoding EGFR is provided at NCBI Reference Sequence: NM_001346897.1, which is reproduced below:

```
                                                         (SEQ ID NO: 7)
   1 gtccgggcag cccccggcgc agcgcggccg cagcagcctc cgccccccgc acggtgtgag 61 cgcccgacgc ggccgaggcg gccggagtcc cgagctagcc ccggcggccg ccgccgccca 121 gaccggacga caggccacct cgtcggcgtc cgcccgagtc cccgcctcgc cgccaacgcc 181 acaaccaccg cgcacggccc cctgactccg tccagtattg atcgggagag ccggagcgag 241 ctcttcgggg agcagcgatg cgaccctccg ggacggccgg ggcagcgctc ctggcgctgc 301 tggctgcgct ctgcccggcg agtcgggctc tggaggaaaa gaaagtttgc caaggcacga 361 gtaacaagct cacgcagttg gcacttttg aagatcattt tctcagcctc cagaggatgt 421 tcaataactg tgaggtggtc cttgggaatt tggaaattac ctatgtgcag aggaattatg 481 atctttcctt cttaaagacc atccaggagg tggctggtta tgtcctcatt gccctcaaca 541 cagtggagcg aattcctttg gaaaacctgc agatcatcag aggaaatatg tactacgaaa 601 attcctatgc cttagcagtc ttatctaact atgatgcaaa taaaaccgga ctgaaggagc 661 tgcccatgag aaatttacag ggccaaaagt gtgatccaag ctgtcccaat gggagctgct 721 ggggtgcagg agaggagaac tgccagaaac tgaccaaaat catctgtgcc cagcagtgct 781 ccgggcgctg ccgtggcaag tcccccagtg actgctgcca caaccagtgt gctgcaggct 841 gcacaggccc ccgggagagc gactgcctgg tctgccgcaa attccgagac gaagccacgt 901 gcaaggacac ctgcccccca ctcatgctct acaaccccac cacgtaccag atggatgtga 961 acccgagggg caaatacagc tttggtgcca cctgcgtgaa gaagtgtccc cgtaattatg 1021 tggtgacaga tcacggctcg tgcgtccgag cctgtgggc cgacagctat gagatggagg
```

-continued

```
1081  aagacggcgt ccgcaagtgt aagaagtgcg aagggccttg ccgcaaagtg tgtaacggaa
1141  taggtattgg tgaatttaaa gactcactct ccataaatgc tacgaatatt aaacacttca
1201  aaaactgcac ctccatcagt ggcgatctcc acatcctgcc ggtggcattt aggggtgact
1261  ccttcacaca tactcctcct ctggatccac aggaactgga tattctgaaa accgtaaagg
1321  aaatcacagg gtttttgctg attcaggctt ggcctgaaaa caggacggac ctccatgcct
1381  ttgagaacct agaaatcata cgcggcagga ccaagcaaca tggtcagttt tctcttgcag
1441  tcgtcagcct gaacataaca tccttgggat tacgctccct caaggagata agtgatggag
1501  atgtgataat ttcaggaaac aaaaatttgt gctatgcaaa tacaataaac tggaaaaaac
1561  tgtttgggac ctccggtcag aaaaccaaaa ttataagcaa cagaggtgaa aacagctgca
1621  aggccacagg ccaggtctgc catgccttgt gctcccccga gggctgctgg ggcccggagc
1681  ccagggactg cgtctcttgc cggaatgtca gccgaggcag ggaatgcgtg gacaagtgca
1741  accttctgga gggtgagcca agggagtttg tggagaactc tgagtgcata cagtgccacc
1801  cagagtgcct gcctcaggcc atgaacatca cctgcacagg acgggaccca gacaactgta
1861  tccagtgtgc ccactacatt gacggccccc actgcgtcaa gacctgcccg gcaggagtca
1921  tgggagaaaa caacaccctg gtctggaagt acgcagacgc cggccatgtg tgccacctgt
1981  gccatccaaa ctgcacctac ggatgcactg gccaggtctt tgaaggctgt ccaacgaatg
2041  ggcctaagat cccgtccatc gccactggga tggtgggggc cctcctcttg ctgctggtgg
2101  tggccctggg gatcggcctc ttcatgcgaa ggcgccacat cgttcggaag cgcacgctgc
2161  ggaggctgct gcaggagagg gagcttgtgg agcctcttac acccagtgga gaagctccca
2221  accaagctct cttgaggatc ttgaaggaaa ctgaattcaa aaagatcaaa gtgctgggct
2281  ccggtgcgtt cggcacggtg tataagggac tctggatccc agaaggtgag aaagttaaaa
2341  ttcccgtcgc tatcaaggaa ttaagagaag caacatctcc gaaagccaac aaggaaatcc
2401  tcgatgaagc ctacgtgatg gccagcgtgg acaacccca cgtgtgccgc ctgctgggca
2461  tctgcctcac ctccaccgtg cagctcatca cgcagctcat gcccttcggc tgcctcctgg
2521  actatgtccg ggaacacaaa gacaatattg gctcccagta cctgctcaac tggtgtgtgc
2581  agatcgcaaa gggcatgaac tacttggagg accgtcgctt ggtgcaccgc gacctggcag
2641  ccaggaacgt actggtgaaa acaccgcagc atgtcaagat cacagatttt gggctggcca
2701  aactgctggg tgcggaagag aaagaatacc atgcagaagg aggcaaagtg cctatcaagt
2761  ggatggcatt ggaatcaatt ttacacagaa tctatacccca ccagagtgat gtctggagct
2821  acggggtgac tgtttgggag ttgatgacct ttggatccaa gccatatgac ggaatccctg
2881  ccagcgagat ctcctccatc ctggagaaag gagaacgcct ccctcagcca cccatatgta
2941  ccatcgatgt ctacatgatc atggtcaagt gctggatgat agacgcagat agtcgcccaa
3001  agttccgtga gttgatcatc gaattctcca aaatggcccg agaccccag cgctaccttg
3061  tcattcaggg ggatgaaaga atgcatttgc caagtcctac agactccaac ttctaccgtg
3121  ccctgatgga tgaagaagac atggacgacg tggtggatgc cgacgagtac ctcatcccac
3181  agcagggctt cttcagcagc ccctccacgt cacggactcc cctcctgagc tctctgagtg
3241  caaccagcaa caattccacc gtggcttgca ttgatagaaa tgggctgcaa agctgtccca
3301  tcaaggaaga cagcttcttg cagcgataca gctcagaccc cacaggcgcc ttgactgagg
3361  acagcataga cgacaccttc ctcccagtgc ctggtgagtg gcttgtctgg aaacagtcct
3421  gctcctcaac ctcctcgacc cactcagcag cagccagtct ccagtgtcca agccaggtgc
3481  tccctccagc atctccagag ggggaaacag tggcagattt gcagacacag tgaagggcgt
```

```
3541 aaggagcaga taaacacatg accgagcctg cacaagctct ttgttgtgtc tggttgtttg 3601 ctgtacctct gttgtaagaa tgaatctgca aaatttctag cttatgaagc aaatcacgga 3661 catacacatc tgtgtgtgtg agtgttcatg atgtgtgtac atctgtgtat gtgtgtgtgt 3721 gtatgtgtgt gtttgtgaca gatttgatcc ctgttctctc tgctggctct atcttgacct 3781 gtgaaacgta tatttaacta attaaatatt agttaatatt aataaatttt aagctttatc 3841 cagaaaaaaa aaaaaaaaa
```

The intermediates used for the synthesis of the compounds of claims 1-6 as described below, as well as their use for the synthesis of the compounds of claims 1-6, are one further aspect of the present invention. Preferred intermediates are the Intermediate Examples as disclosed below.

General Procedures

The compounds according to the invention can be prepared according to the following schemes 1-4.

The schemes and procedures described below illustrate synthetic routes to the compounds of general formula (I) of the invention and are not intended to be limiting. It is obvious to the person skilled in the art that the order of transformations as exemplified in the schemes can be modified in various ways. The order of transformations exemplified in the schemes is therefore not intended to be limiting. In addition, interconversion of any of the substituents $R^1$, $R^2$, $R^3$, $R^4$, $R^5$ and PG can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art. Specific examples are described in the subsequent paragraphs.

Scheme 1

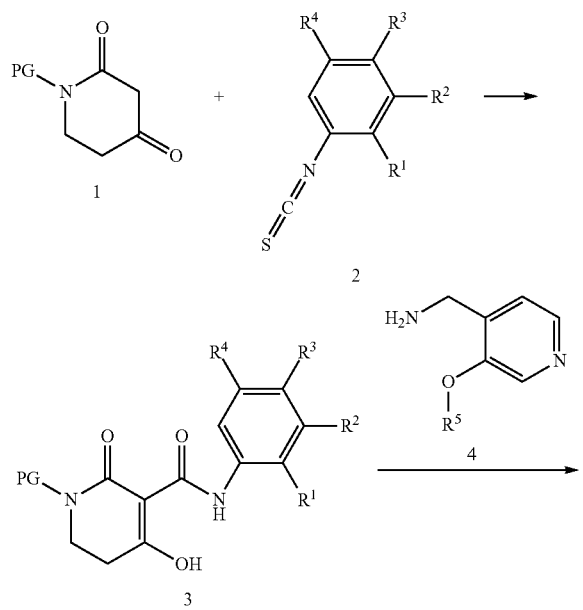

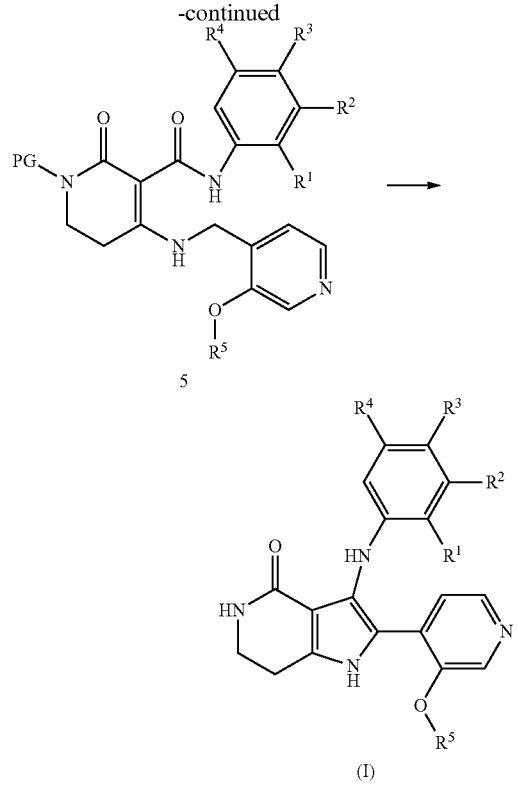

Scheme 1:

Route for the preparation of compounds of general formula (I), wherein $R^1$, $R^2$, $R^3$, $R^4$ and $R^5$ have the meaning as given for general formula (I) and PG can be hydrogen or optionally a suitable protecting group, e.g. tert-butoxycarbonyl (Boc). In addition, interconversion of any of the substituents $R^1$, $R^2$, $R^3$, $R^4$, $R^5$ and PG can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art. Specific examples are described in the subsequent paragraphs. Compound of formula 1, 2, and 4 are either commercially available or can be prepared according to procedures available from the public domain, as understandable to the person skilled in the art. Specific examples are described in the subsequent paragraphs.

A suitably substituted piperadine-2,4-diones of general formula (Compound of formula 1), such as, for example, 2,4-piperadinedione, can be reacted with a suitably substituted isothiocyanate (Compound of formula 2), such as, for example, 3-fluorophenylisothiocyanate, in a suitable solvent system, such as, for example, acetonitrile, in the presence of a suitable base, such as, for example, triethylamine or DBU, at temperatures ranging from −78° C. to +100° C., in some embodiments the reaction is carried out at 0° C. or +100° C., to furnish general formula (3). Similar reactions have been performed in the literature (D. E. Worrall, *J. Am. Chem. Soc.*, 1940, 62, 675).

Intermediates of general formula (3) can be converted to Intermediates of general formula (5) by reaction with a suitable amine (compounds of general formula 4), such as, for example 4-(aminomethyl)pyridine, in a suitable solvent system, such as, for example, ethanol and ethyl acetate, at a temperature between room temperature and the boiling point of the respective solvents, in some embodiments the reaction is carried out at the boiling point of the respective solvents, whereby the water formed in the reaction is removed from the reaction by methods known to those skilled in the art, such as, for example, azeotropic removal of water (Dean-Stark conditions) or with molecular sieves, to furnish general formula (5).

Intermediates of general formula (3) and intermediates of general formula (5) in which PG represents a protecting group can be converted to Intermediates in which PG represents a hydrogen atom using standard deprotection conditions known to those skilled in the art. When PG is a protecting group such as, for example, tert-butoxycarbonyl (Boc), the deprotection can be carried out using acids, such as, for example, hydrochloric acid and trifluoroacetic acid, in a suitable solvent system, such as, for example, dichloromethane and dioxane, at a temperature between 0° C. and the boiling point of the respective solvents, in one embodiment the reaction is carried out at the room temperature, to furnish compounds of general formula (3) and intermediates of general formula (5) whereby PG is hydrogen atom.

Intermediates of general formula (5) are reacted with a base and/or oxidizing reagent, in one embodiment an oxidizing agent, such as, for example hydrogen peroxide or SIBX (stabilized iodoxybenoic acid, in a suitable solvent system, such as, for example, methanol, in a temperature range from −30° C. to the boiling point of the respective solvent, in one embodiment the reaction is carried out at the boiling point of the respective solvent, to furnish compounds of general formula (I). Optionally, these types of reactions can be carried on with an additive, such as, for example, an acid or base, such as, for example, acetic acid or trifluoroacetic acid (not-limiting), and triethylamine or diisopropylethylamine (not-limiting).

Intermediates of general formula (5) could be converted to compounds of general formula (I) by thermal heating them in a suitable solvent at elevated temperatures, which could be above the boiling point of the said solvent, such as, for example, RT to +250° C. These reactions could optionally be carried out in vessel whereby the pressure can be increased, such as, for example, in an autoclave. Intermediates of general formula (5) can also be converted to compounds of general formula (I) by thermal heating in the presence of a metal catalyst, such as, for example, palladium on activated charcoal, in a suitable solvent, such as, for example, DMF, DMA, EtOH, MeOH, NMP (not-limiting) at elevated temperatures, such as, for example, RT to +150° C. Optionally, these types of reactions can be carried on with an additive, such as, for example, an acid or base, such as, for example, acetic acid or trifluoroacetic acid (not-limiting), and triethylamine or diispropylethylamine (not-limiting), to furnish compounds of general formula (I).

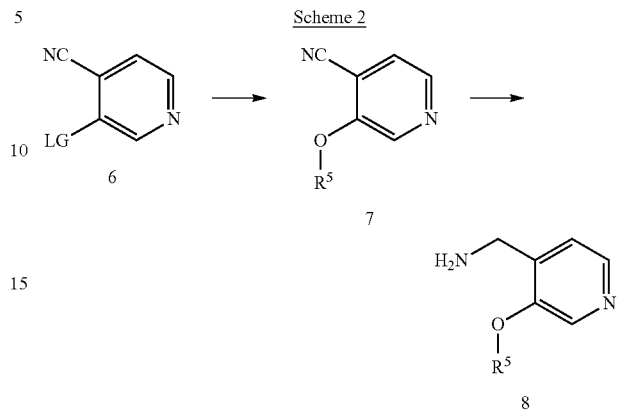

Scheme 2:

Process for the preparation of compounds of general formula (4), wherein $R^5$ has the meaning as given for general formula (I). In addition, interconversion of any of the substituents can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art. Compounds of general formula 6, whereby LG is a leaving group, such as, for example, F, Cl, Br, I or aryl sulfonate such as for example p-toluene sulfonate, or alkyl sulfonate such as for example methane sulfonate or trifluoromethane sulfonate, are commercially available or can be synthesized by those skilled in the art.

Compounds of general formula (6) can be converted to compounds of general formula (7) by treatment with a suitable nucleophile, such as for example, amines, alcohols, metal alkoxides, azides, thiols or metal thiolates, under either basic, neutral, acidic, catalytic conditions, in one embodiment basic conditions, in a suitable solvent or using the nucleophile as solvent, such as, for example, DMF, tetrahydrofuran (THF), in a temperature range from −78° C. to the boiling point of the respective solvent, in one embodiment the reaction is carried out −10° C. to the boiling point of the respective solvent, to furnish general formula (7). Such substitution reactions have been previously reported (Clark et al., *J. Med. Chem.*, 2008, 51, 6631-6634; Guo et al., *Tetrahedron Letts.*, 2013, 54, 3233-3237; Watterson et al., *J. Med. Chem.*, 2007, 50, 3730-3742; Bellale et al., *J. Med. Chem.*, 2014, 57, 6572-6582; Klimesova et al., *Eur. J. Med. Chem.*, 1996, 31, 389-395; Leroy et al., *Synth. Commun.*, 1997, 27, 2905-2916; LaMattina et al., *J. Org. Chem.*, 1981, 46, 4179-4182; Beugelmans et al., *Tetrahedron*, 1983, 39, 4153-4162).

Compounds of general formula (7) can be converted to compounds of general formula (4) by many reducing methods known to those skilled in the art, using numerous different reagents and reaction conditions; such methods and reagents can be carried out with metal hydrides, such as, for example, lithium aluminum hydride in THF (Bullock et al., J. Am. Chem. Soc., 1956, 78, 490, Wang et al., J. Org. Chem., 2006, 71, 4021-3160), or using zinc in acetic acid (Rabe, Chem. Ber., 1913, 46, 1024), or using diborane (De Munno et al., Heterocycles, 1996, 43, 1893-1900), or using catalytic hydrogenation methods, for example, hydrogen and palladium on carbon under acidic conditions (Stokker et al., J. Med. Chem., 1981, 24, 115-117; Bertini et al., J. Med. Chem., 2005, 48, 664-670), hydrogen and nickel under basic conditions (Walpole et al., J. Med. Chem., 1993, 36, 2362-2372, Kuramochi et al., Bioorg. Med. Chem., 2005, 13, 4022-4036.)

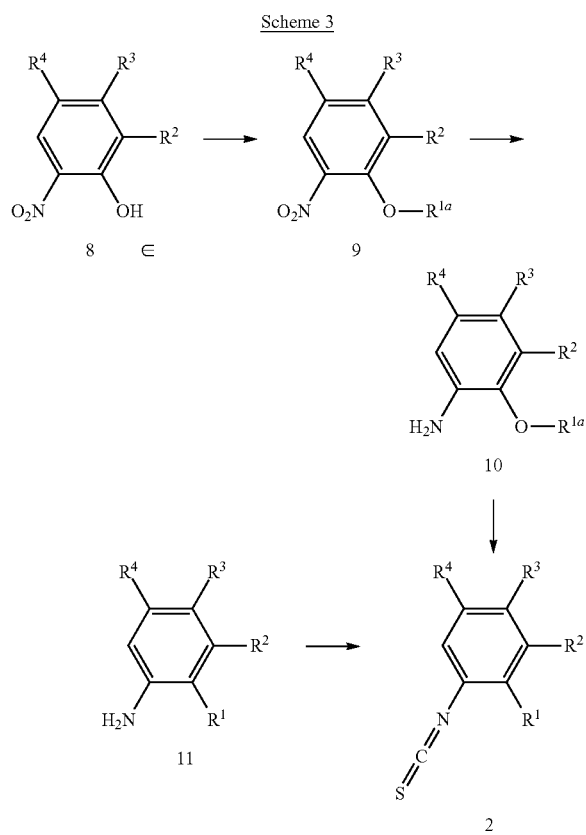

Scheme 3:

Process for the preparation of compounds of general formula 2, wherein $R^{1a}$ represents methyl or difluoromethyl corresponding to $R^1$ in the general formula (I) with the meaning of methoxy and difluoromethoxy. The synthesis of compounds 9 and 10 relates to alkoxy substitution of the phenyl ring. However, the isothiocyanate containing product 2 and the synthesis thereof (i.e., 10→2 or 11→2) is general to $R^1$ groups according to general formula (I). In addition, interconversion of any of the substituents can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art.

Compounds of general formula (8), can be converted to compounds of general formula (9), using various methods which are known to those skilled in the art. Such transformations could be, for example, to alkylate the phenolic alcohol with alkylating reagents, such as, for example, alkyl halides, alkyl sulfonates, in which these alkyl groups can optionally contain fluorides, alkoxyl groups. These alkylation reactions are known to those skilled in the art using a variety of methods: i) $K_2CO_3$ in a solvent such as, DMF, acetone, DMFA (see the teachings of Muro et al., J. Med. Chem., 2009, 52, 7974 and WO2009/20990 A1); ii) KOH in EtOH (see the teachings of Macias et al., J. Agric. Food Chem., 2006, 54, 9843); iii) Mitsunobu reaction (see the teachings of US2006/122168 A1 and EP2151431 A1) to furnish intermediates of general formula (9).

Compounds of general formula (9) can be converted to compounds of general formula (10) by reduction methods and these methods are known to those skilled in the art. These reductions can be carried using: i) hydrogen gas and a catalyst (for Pd/C as catalyst see the teachings of Chan et al., J. Am. Chem. Soc., 2011, 133, 2989; for platinum see the teachings of Niemann et al., J. Am. Chem Soc., 1941, 63, 2204; for Raney-Nickel see the teachings of US2009/253767 A1); ii) iron and ammonium chloride (see the teachings of Sweeney et al., Bioorg. Med. Chem. Lett., 2008, 18, 4348); iii) sodium dithionite (see the teachings of Chong et al., J. Med. Chem., 2012, 55, 10601); iv) zinc and ammonium chloride (see the teachings of WO2010/42699 A1) to furnish intermediates of general formula (10).

Compounds of general formula (10) can be converted to compounds of general formula (2) by using reagents such as, for example, thiophosgene, carbon disulphide, 1,1"-thiocarbonyldi-2(1H)-pyridone or 1,1'-thiocarbonyldiimidazole, in one embodiment thiophosgene, under basic conditions, in a suitable solvent, such as, for example, dichloromethane, chloroform, acetone, or biphasic mixtures, such as, for example, dichloromethane, chloroform with aqueous basic solutions, in another embodiment, dichloromethane with an aqueous saturated solution of sodium hydrogen carbonate or sodium carbonate, in a temperature range from −78° C. to the boiling point of the respective solvent, in another embodiment the reaction is carried out 0° C. to room temperature, to furnish compounds of general formula (2). Such transformations reactions have been previously reported (Harris et al., J. Med. Chem., 2005, 48, 1610; Degorce et al., Tetrahedron Lett., 2011, 52, 6719; WO2016/91845 A1; Fairhurst et al., Org. Lett., 2005, 7, 4697; Chaskar et al., Synth. Commun., 2008, 38, 16940; US2004/122237 A1).

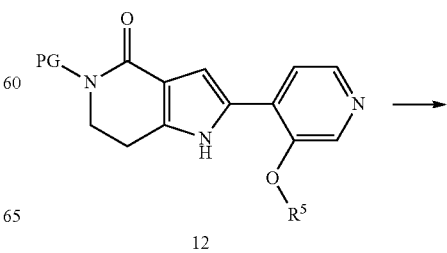

12

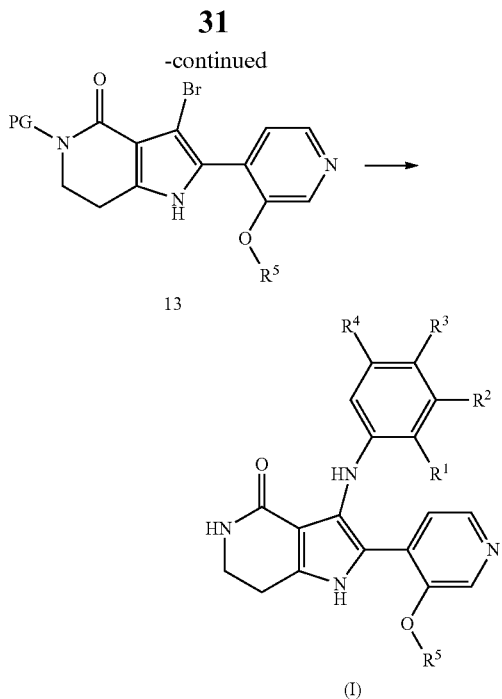

Scheme 4:

Route for the preparation of compounds of general formula (I), wherein $R^1$, $R^2$, $R^3$, $R^4$ and $R^5$ have the meaning as given for general formula (I) and PG can be hydrogen or optionally a suitable protecting group, e.g. tert-butoxycarbonyl (Boc). In addition, interconversion of any of the substituents $R^1$, $R^2$, $R^3$, $R^4$, $R^5$ and PG can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art. Specific examples are described in the subsequent paragraphs.

Compounds similar to those of general formula 12 are known to those skilled in the art and their syntheses have been reported in the literature (see the teachings of Voss et al., WO2015/22073 A1; Hart et al., WO2016/100166 A1; Anderson et al., J. Med. Chem., 2007, 50, 2647; Vanotti et al., J. Med. Chem., 2008, 51, 487).

Compounds of general formula (12) could be converted to compounds of general formula (13) using standard bromination methods which are known to those skilled in the art (WO2016/100166 A1). Such brominations could be carried out using a brominating agent, such as, for example, N-bromosuccinimide, in a suitable solvent, such as, for example, DMF, in a temperature range from −78° C. to the boiling point of said solvent, in one embodiment the temperature range is 0° C. to RT.

Intermediates of general formula (13) can be reacted with suitable anilines, such as, for example, 2-difluoromethoxyaniline, in the presence of a base, such as, for example, lithium bis(trimethylsilyl)amide (LHMDS), in the presence of a catalyst, such as, for example a suitable ligand, in one embodiment 2-(di-tert-butylphosphino)-2',4',6'-triisopropyl-3,6-dimethoxy-1,1'-biphenyl (tBuBrettPhos) and in the presence of a pre-catalyst, such as, for example a palladium pre-catalyst, in another embodiment chloro[2-(dicyclohexylphosphino)-3,6-dimethoxy-2',4',6'-triisopropyl-1,1'-biphenyl][2-(2-aminoethyl)phenyl]palladium(II) (BrettPhos-Pre-Cat MTBE ether adduct) in a suitable solvent system, such as, for example, tetrahydrofuran (THF), at a temperature range of 0° C. to 200° C. In one embodiment, the reaction is carried out at 80° C., to furnish compounds of general formula (I). Similar transformations have been carried out and have been reported (WO2015/193339 A1).

It is known to the person skilled in the art that, if there are a number of reactive centers on a starting or intermediate compound, it may be necessary to block one or more reactive centers temporarily by protective groups in order to allow a reaction to proceed specifically at the desired reaction center.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC may be applied. The compounds of the present invention which possess a sufficiently basic or acidic functionality, may result as a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of the compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, free acid, solvate, inclusion complex) of a compound of the present invention as isolated and described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art. Especially preferred are hydrochlorides and the process used in the example section.

Pure diastereomers and pure enantiomers of the compounds and salts according to the invention can be obtained e.g. by asymmetric synthesis, by using chiral starting compounds in synthesis or by splitting up enantiomeric and diasteriomeric mixtures obtained in synthesis.

Enantiomeric and diastereomeric mixtures can be split up into the pure enantiomers and pure diastereomers by methods known to the person skilled in the art. In one embodiment, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids by formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of claims 1-4 according to the examples as well as the intermediates used for their preparation.

Optionally, compounds of the formula (I) can be converted into their salts, or, optionally, salts of the compounds of the formula (I) can be converted into the free compounds. Corresponding processes are customary for the skilled person.

Commercial Utility

As mentioned supra, the compounds of the present invention have surprisingly been found to effectively inhibit mutant EGFR finally resulting in cell death (e.g., apoptosis) and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by mutant EGFR, such as, for example, benign and malignant neoplasia, more specifically haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof, especially haematological tumours, solid tumours, and/or metastases of breast, bladder, bone, brain, central and peripheral nervous system, cervix, colon, endocrine glands (e.g., thyroid and adrenal cortex), endocrine tumours, endometrium, esophagus, gastrointestinal tumours, germ cells, kidney, liver, lung, larynx and hypopharynx, mesothelioma, ovary, pancreas, prostate, rectum, renal, small intestine, soft tissue, stomach, skin, testis, ureter, vagina and vulva as well as malignant neoplasias including primary tumours in said organs and corresponding secondary tumours in distant organs ("tumour metastases"). Haematological tumours can e.g be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

A further aspect of the invention is the use of the compounds according to formula (I) for the treatment of lung cancer, particularly lung cancer harboring mutant EGFR with exon insertion mutations, more particularly lung cancer harboring V769_770ins ASV and/or D770_N771ins SVD exon 20 insertions, and/or metastases thereof, comprising administering an effective amount of a compound of formula (I).

In accordance with an aspect of the present invention therefore the invention relates to a compound of general formula I, or an N-oxide, a salt, a tautomer or a stereoisomer of said compound, or a salt of said N-oxide, tautomer or stereoisomer particularly a pharmaceutically acceptable salt thereof, or a mixture of same, as described and defined herein, for use in the treatment or prophylaxis of a disease, especially for use in the treatment of a disease.

Another particular aspect of the present invention is therefore the use of a compound of general formula I, described supra, or a stereoisomer, a tautomer, an N-oxide, a hydrate, a solvate, or a salt thereof, particularly a pharmaceutically acceptable salt thereof, or a mixture of same, for the prophylaxis or treatment of hyperproliferative disorders or disorders responsive to induction of cell death i.e apoptosis.

The term "inappropriate" within the context of the present invention, in particular in the context of "inappropriate cellular immune responses, or inappropriate cellular inflammatory responses", as used herein, is to be understood as generally meaning a response which is less than, or greater than normal, and which is associated with, responsible for, or results in, the pathology of said diseases.

In particular embodiments, the use is in the treatment or prophylaxis of diseases, especially the treatment, wherein the diseases are haematological tumours, solid tumours and/or metastases thereof.

Another aspect is the use of a compound of formula (I) for the prophylaxis and/or treatment of lung cancer, particularly lung cancer harboring mutant EGFR with exon 20 insertion mutations, more particularly lung cancer harboring V769_770ins ASV and/or D770_N771ins SVD exon 20 insertions, and/or metastases thereof, especially preferred for the treatment thereof.

Another aspect of the present invention is the use of a compound of formula (I) or a stereoisomer, a tautomer, an N-oxide, a hydrate, a solvate, or a salt thereof, particularly a pharmaceutically acceptable salt thereof, or a mixture of same, as described herein, in the manufacture of a medicament for the treatment or prophylaxis of a disease, wherein such disease is a hyperproliferative disorder or a disorder responsive to induction of cell death e.g., apoptosis. In an embodiment the disease is a haematological tumour, a solid tumour and/or metastases thereof. In another embodiment the disease is lung cancer, particularly lung cancer harboring mutant EGFR with exon 20 insertion mutations, more particularly lung cancer harboring V769_770ins ASV and/or D770_N771ins SVD exon 20 insertions, and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce cell death e.g. apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited to, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, inverted sinonasal papilloma, inverted sinonasal papilloma-associated sinonasal squamous cell carcinoma, Merkel cell skin cancer, and non-melanoma skin cancer.

Head-and-neck cancers include, but are not limited to laryngeal, hypopharyngeal, nasopharyngeal, oropharyngeal cancer, inverted sinonasal papilloma, inverted sinonasal papilloma-associated sinonasal squamous cell carcinoma, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, overexpression of the gene or polypeptide; gene amplification; mutations which produce constitutively-active or hyperactive kinase activity; gene mutations, deletions, substitutions, additions, etc.

The present invention also provides for methods of inhibiting kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Ophthalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death e.g. apoptosis of such cell types.

In various embodiments, the diseases of said method are haematological tumours, solid tumour and/or metastases thereof.

The compounds of the present invention can be used in particular in therapy and prevention i.e. prophylaxis, especially in therapy of tumour growth and metastases, especially in solid tumours of all indications and stages with or without pre-treatment of the tumour growth.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease.

Therefore, the present invention includes pharmaceutical compositions that are comprised of a pharmaceutically acceptable carrier or auxiliary and a pharmaceutically effective amount of a compound, or salt thereof, of the present invention.

Another aspect of the invention is a pharmaceutical composition comprising a pharmaceutically effective amount of a compound of formula (I) and a pharmaceutically acceptable auxiliary for the treatment of a disease mentioned supra, especially for the treatment of haematological tumours, solid tumours and/or metastases thereof.

A pharmaceutically acceptable carrier or auxiliary is preferably a carrier that is non-toxic and innocuous to a patient at concentrations consistent with effective activity of the active ingredient so that any side effects ascribable to the carrier do not vitiate the beneficial effects of the active ingredient. Carriers and auxiliaries are all kinds of additives assisting to the composition to be suitable for administration.

A pharmaceutically effective amount of compound is preferably that amount which produces a result or exerts the intended influence on the particular condition being treated.

The compounds of the present invention can be administered with pharmaceutically-acceptable carriers or auxiliaries well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing auxiliaries, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quaternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) in one embodiment of from about 12 to about 17. The quantity of surfactant in such formulation in one embodiment ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for administration, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$);

air displacement agents (examples include but are not limited to nitrogen and argon); antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate di hydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite); emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate);

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin); oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, crosslinked polyvinylpyrrolidone, sodium alginate, sodium starch glycollate and starch);

tablet qlidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide); tablet polishing agents (examples include but are not limited to carnuba wax and white wax); thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile i.v. Solution:

A 5 mg/ml solution of the desired compound of this invention can be made using sterile, injectable water, and the pH is adjusted if necessary. The solution is diluted for administration to 1-2 mg/ml with sterile 5% dextrose and is administered as an i.v. infusion over about 60 minutes.

Lyophilised Powder for i.v. Administration:

A sterile preparation can be prepared with (i) 100-1000 mg of the desired compound of this invention as a lyophilised powder, (ii) 32-327 mg/ml sodium citrate, and (iii) 300-3000 mg Dextran 40. The formulation is reconstituted with sterile, injectable saline or dextrose 5% to a concentration of 10 to 20 mg/ml, which is further diluted with saline or dextrose 5% to 0.2-0.4 mg/ml, and is administered either IV bolus or by IV infusion over 15-60 minutes.

Intramuscular Suspension:

The following solution or suspension can be prepared, for intramuscular injection:

50 mg/ml of the desired, water-insoluble compound of this invention 5 mg/ml sodium carboxymethylcellulose 4 mg/ml TWEEN 80

9 mg/ml sodium chloride 9 mg/ml benzyl alcohol

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:

A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules:

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and in particular embodiments from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will in other embodiments be from 0.01 to 200 mg/kg of total body weight. The average daily rectal dosage regimen will in particular embodiments be from 0.01 to 200 mg/kg of total body weight. The average daily vaginal dosage regimen will in other embodiments be from 0.01 to 200 mg/kg of total body weight. The average daily topical dosage regimen will in still other embodiments be from 0.1 to 200 mg administered between one to four times daily. The transdermal concentration will in other embodiments be that required to maintain a daily dose of from 0.01 to 200 mg/kg. The average daily inhalation dosage regimen will in other embodiments be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. Those combined pharmaceutical agents can be other agents having antiproliferative effects such as for example for the treatment of haematological tumours, solid tumours and/or metastases thereof and/or agents for the treatment of undesired side effects. The present invention relates also to such combinations.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, especially (chemotherapeutic) anti-cancer agents as defined supra. The combination can be a non-fixed combination or a fixed-dose combination as the case may be.

Methods of testing for a particular pharmacological or pharmaceutical property are well known to persons skilled in the art.

The example testing experiments described herein serve to illustrate the present invention and the invention is not limited to the examples given.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

EXPERIMENTAL SECTION

Chemical names were generated using the ACD/Name software from ACD/Labs. In some cases generally accepted names of commercially available reagents were used in place of ACD/Name generated names.

Table 1 lists the abbreviations used in this paragraph and in the Examples section as far as they are not explained within the text body. Other abbreviations have their meanings customary per se to the skilled person.

TABLE 1

Abbreviations

| Abbreviation | Meaning |
| --- | --- |
| AcOH | Acetic acid |
| br | broad signal (NMR) |
| d | doublet (NMR) |
| DAD | Diode Array Detector |
| DAST | Diethylaminosulfur trifluoride |
| DBU | 1,8-Diazabicyclo(5.4.0)undec-7-ene |
| DCM | Dichloromethane |
| dd | doublet of doublet (NMR) |
| DIPEA | Diisopropylethylamine |
| DMA | N,N-dimethylacetamide |
| DMAP | 4-Dimethylaminopyridine |
| DMF | N,N-dimethylformamide |
| DMSO | dimethylsulfoxide |
| EDC•HCl | N-(3-Dimethylaminopropyl)-N'-ethylcarbodiimide hydrochloride salt |
| ESI | electrospray (ES) ionization |
| EtOAc | Ethyl acetate |
| EtOH | Ethanol |
| h, hr (hrs) | hour(s) |
| HCl | hydrogen chloride, hydrochloric acid |
| HPLC | high performance liquid chromatography |
| LC-MS | liquid chromatography - mass spectrometry |
| m | multiplet (NMR) |
| MeCN | Acetonitrile |
| MeOH | Methanol |
| min | minute(s) |
| MS | mass spectrometry |
| MWD | Multiple wavelength detector |
| NMR | Nuclear Magnetic Resonance spectroscopy: chemical shifts ($\delta$) are given in ppm. The chemical shifts were corrected by setting the DMSO signal to 2.50 ppm using unless otherwise stated. |
| q | quartet (NMR) |
| Rt or RT | room temperature |
| $R_t$, Rt | retention time |
| s | singulet (NMR) |

TABLE 1-continued

Abbreviations

| Abbreviation | Meaning |
| --- | --- |
| SFC | Supercritical Fluid Chromatography |
| t | triplet (NMR) |
| td | triplet of doublet (NMR) |
| TEA | triethylamine |
| TFA | Trifluoroacetic acid |
| THF | tetrahydrofuran |
| $\delta$ | chemical shift |

Other abbreviations have their meanings customary per se to the skilled person.

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be removed by trituration using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or DCM/methanol. In flash column chromatography, unmodified ("regular") silica gel may be used as well as aminophase functionalized silica gel. If reference is made to flash column chromatography or to flash chromatography in the experimental section without specification of a stationary phase, regular silica gel was used.

In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Analytical LC-MS Methods:

Method 1:
Instrument: Waters Acquity UPLCMS SingleQuad; Column: Acquity UPLC BEH C18 1.7 µm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method 2:
Instrument: Waters Acquity UPLCMS SingleQuad; Column: Acquity UPLC BEH C18 1.7 µm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

Method 3:
Instrument: Waters Acquity UPLC H-Class system; Column: Acquity CSH C18 1.7 µm 2.1×50 mm; eluent A: water+0.1 vol % formic acid, eluent B: acetonitrile, eluent C: 2 vol % ammonia (28%) in water, eluent D: 2 vol % formic acid in water; gradient: 0-1.2 min 2-95% B with A and 5% D throughout, 1.2-1.4 min 95% B; flow 0.8 ml/min; temperature: 40° C.; PDA: 215-350 nm.

Method 4:
Instrument: Waters Acquity UPLC H-Class system; Column: XBridge BEH C18 2.5 µm 2.1×50 mm; eluent A: water+0.1 vol % formic acid, eluent B: acetonitrile, eluent C: 2 vol % ammonia (28%) in water, eluent D: 2 vol % formic acid in water; gradient: 0-1.2 min 2-95% B with A and 5% C throughout, 1.2-1.4 min 95% B; flow 0.8 ml/min; temperature: 40° C.; PDA: 215-350 nm.

Method 5:
MS instrument: SHIMADZU LCMS-2020; HPLC instrument: LabSolution Version 5.72; Column: Kinetex@5 um EVO C18 30×2.1 mm; eluent A: 0.0375% TFA in water (v/v), eluent B: 0.01875% TFA in acetonitrile: gradient: 0.0 min 0% B 3.00 min 60% B 3.50 min 60% B 3.51 min 0% B 4.00 min 0% B; flow rate: 0.8 mL/mix; oven temperature: 50° C.; UV detection: 220 nm & 254 nm.

Method 9:
Instrument: Agilent HPLC 1260; Column: Amylose SA 3µ 100×4.6 mm; Eluent A: Acetonitrile+0.1 Vol-% Diethylamine (99%); Eluent B: Ethanol; Isocratic: 90% A+10% B; Flow 1.4 ml/min; Temperature: 25° C.; DAD 220 nm Method 10:
Instrument: Agilent 1290 UPLCMS 6230 TOF; column: BEH C 18 1.7 µm, 50×2.1 mm; Eluent A: water+0.05% formic acid (99%); Eluent B: acetonitrile+0.05% formic acid (99%); gradient: 0-1.7 2-90% B, 1.7-2.0 90% B; flow 1.2 ml/min; temperature: 60° C.; DAD scan: 190-400 nm.

Method 11:
Column: CSH C18 1.7 µm 2.1×50 mm, Waters Acquity Quaternary pump (Flow 0.8 mL/min), Waters Acquity Autosampler, Waters Acquity QDA, Waters Acquity PDA, Waters Acquity ELSD, UV DAD: 215-350 nm, run time: 4.60 mins, solvents A) water B) acetonitrile D) 2% formic acid: the gradient runs with 5% D, Gradient: 2-95% B with A and 5% D 4.0 mins, hold at 95% B 5% D to 4.60 min @ 0.8 ml/min, 40° C.

Preparative LC-MS Methods:

Method 6:
Instrument: Waters Autopurification MS SingleQuad; Column: Waters XBrigde C18 5µ 100×30 mm; eluent A: water+0.2 vol % aqueous ammonia (32%), eluent B: acetonitrile; gradient: 0-5.5 min 5-100% B; flow 70 ml/min; temperature: 25° C.; DAD scan: 210-400 nm Method 7:
Instrument: pump: Labomatic HD-5000 or HD-3000, head HDK 280, lowpressure gradient module ND-B1000; manual injection valve: Rheodyne 3725i038; detector: Knauer Azura UVD 2.15; collector: Labomatic Labocol Vario-4000; column: Chromatorex RP C-18 10 µm, 125×30 mm; solvent A: water+0.1 vol-% formic acid, solvent B: acetonitrile; gradient: 0.00-0.50 min 30% B (150 ml/min), 0.50-6.00 min 30-70% B (150 ml/min), 6.00-6.10 min 70-100% B (150 ml/min), 6.10-8.00 min 100% B (150 ml/min); UV-Detection.

Method 8:
Instrument: Labomatic HD5000, Labocord-5000; Gilson GX-241, Labcol Vario 4000, Column: Amylose SA 5p 250×30 mm; Eluent A: Acetonitrile+0.1 Vol-% Diethylamine (99%); Eluent B: Ethanol; Isocratic: 90% A+10% B; Flow 50.0 ml/min; UV 220 nm NMR Spectra:

The multiplicities of proton signals in $^1$H NMR spectra given in the following paragraphs reflect the observed signal form and do not take into account any higher-order signal phenomena. As a rule, the chemical shift data refers to the center of the signal in question. In the case of wide multiplets, a range is specified. Signals hidden by solvent or water were either assigned tentatively or are not listed. Strongly broadened signals—e.g. caused by rapid rotation of molecular moieties or by interchanging protons—have also been assigned tentatively (often referred to as a broad multiplet or broad singlet) or are not shown.

The $^1$H-NMR data of selected compounds are listed in the form of $^1$H-NMR peaklists. Therein, for each signal peak the δ value in ppm is given, followed by the signal intensity, reported in round brackets. The δ value-signal intensity pairs from different peaks are separated by commas. Therefore, a peaklist is described by the general form: $δ_1$ (intensity$_1$), $δ_2$ (intensity$_2$), . . . , $δ_i$ (intensity$_i$), . . . , $δ_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of the particular target compound, peaks of impurities, $^{13}$C satellite peaks, and/or spinning sidebands. The peaks of stereoisomers, and/or peaks of impurities are typically displayed with a lower intensity compared to the peaks of the target compound (e.g., with a purity of >90%). Such stereoisomers and/or impurities may be typical for the particular manufacturing process, and therefore their peaks may help to identify a reproduction of the manufacturing process on the basis of "by-product fingerprints". An expert who calculates the peaks of the target compound by known methods (MestReC, ACD simulation, or by use of empirically evaluated expectation values), can isolate the peaks of the target compound as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. http://

Syntheses of Intermediates

Syntheses of Intermediate 1 Compounds

Intermediate 1-1

3-(2-hydroxy-2-methylpropoxy)pyridine-4-carbonitrile

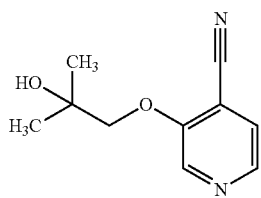

To an ice-cooled solution of 2-methylpropane-1,2-diol (3.20 g, 35.5 mmol) in DMF (62 ml) under an argon atmosphere was added NaH 60% dispersion on mineral oil (1.36 g, 34.0 mmol) slowly portionwise. The reaction mixture was stirred with ice-cooling for 30 min and 3-chloropyridine-4-carbonitrile (4.10 g, 29.6 mmol) was added. The reaction was allowed to warm slowly to RT and stirred at this temperature for 2 h. The reaction mixture was poured on an ice-water mixture and extracted with EtOAc. The organics were combined and washed with water, filtered through a hydrophobic filter and concentrated. The residue was purified by silica chromatography (hexane:EtOAc) to give the title compound (2 g, 35% yield).

$^1$H-NMR (400 MHz, DMSO-d$_6$): δ [ppm]=8.72 (s, 1H), 8.38 (d, 1H), 7.78 (d, 1H), 4.77 (s, 1H), 4.04-4.11 (m, 2H), 1.16-1.25 (m, 6H).

Intermediate 1-2

3-(2-methoxy-2-methylpropoxy)pyridine-4-carbonitrile

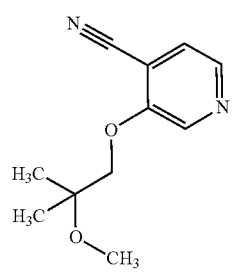

According to the method described for Intermediate 1-1 and using 2-methoxy-2-methylpropan-1-ol as a starting material, the title compound was prepared (18.77 g, 88% yield).

$^1$H-NMR (500 MHz, DMSO-d$_6$): δ [ppm]=8.72 (s, 1H), 8.38 (d, 1H), 7.78 (d, 1H), 4.19 (s, 2H), 3.15-3.22 (m, 3H), 1.24 (s, 6H).

Intermediate 1-3

3-[2-methyl-2-(morpholin-4-yl)propoxy]pyridine-4-carbonitrile

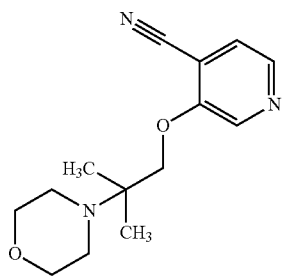 [SMILES: CC(C)(COc1cnccc1C#N)N1CCOCC1]

To an ice-cooled solution of 2-methyl-2-(morpholin-4-yl)propan-1-ol (4.00 g, 25.1 mmol) in THF (12.5 ml) under an argon atmosphere was added NaH 60% dispersion on mineral oil (1.1 g, 27.4 mmol) slowly portionwise. The reaction mixture was stirred with ice-cooling for 1 h and a solution of 3-chloropyridine-4-carbonitrile (4.10 g, 29.6 mmol) in THF (64.5 ml) was added. The reaction was allowed to warm slowly to RT and stirred at this temperature for 16 h. The reaction was then heated under reflux conditions for 2 h. The reaction mixture was quenched with a sat. NH4Cl solution and extracted with EtOAc. The organics were combined and washed with sat. NaCl, filtered through a hydrophobic filter and concentrated. The residue was crystallized with MTBE and collected by filtration to give the title compound (2 g, 35% yield) which was used without further purification.

$^1$H-NMR (400 MHz, DMSO-d$_6$): δ [ppm]=8.75 (s, 1H), 8.38 (d, 1H), 7.78 (d, 1H), 4.19 (s, 2H), 3.44-3.52 (m, 4H), 2.57-2.62 (m, 4H), 1.10-1.23 (m, 6H).

Intermediate 1-4

3-{[(2S)-1-methylpyrrolidin-2-yl]methoxy}pyridine-4-carbonitrile

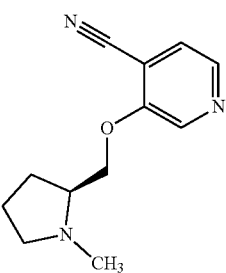 [SMILES: CN1CCC[C@H]1COc1cnccc1C#N]

According to the method described for Intermediate 1-3 and using [(2S)-1-methylpyrrolidin-2-yl]methanol (3.50 g, 30.4 mmol) as a starting material, the title compound was prepared (4.03 g, 67% yield).

¹H-NMR (400 MHz, DMSO-d₆): δ [ppm]=8.71 (s, 1H), 8.38 (d, 1H), 7.77 (d, 1H), 4.23 (d, 2H), 2.93-2.99 (m, 1H), 2.60-2.70 (m, 1H), 2.39 (s, 3H), 2.22 (q, 1H), 1.92-2.02 (m, 1H), 1.60-1.78 (m, 3H).

Intermediate 1-57

3-(3-methoxy-3-methylbutoxy)pyridine-4-carbonitrile

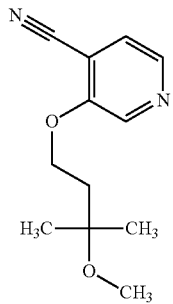 [SMILES: COC(C)(C)CCOc1cnccc1C#N]

To a solution of 3-methoxy-3-methylbutan-1-ol (4.00 g, 33.8 mmol) in 39 ml. THF sodium hydride (1.30 g, 60% purity, 32.4 mmol) was added portionswise at 0° C. and the suspension was stirred for 39 minutes at rt. Then 3-chloropyridine-4-carbonitrile (3.91 g, 28.2 mmol) solved in 78 ml. THF was added dropwise and the reaction mixture was stirred overnight at rt. The solution was diluted carefully with water and extracted with a mixture of dichloromethane and of methanol (9:1) three times. The combined organic layers were filtered through a waterresistant filter and the filtrate was concentrated under reduced pressure. The residue was purified by flash chromatography to give 4.30 g of the title compound (97% purity, 67% yield).

¹H-NMR (400 MHz, DMSO-d6) δ [ppm]: 1.074 (2.43), 1.188 (16.00), 1.960 (0.99), 1.978 (2.12), 1.995 (1.02), 3.056 (1.64), 3.121 (11.50), 4.330 (1.11), 4.347 (2.36), 4.364 (1.10), 7.766 (1.21), 7.768 (1.30), 7.778 (1.25), 7.780 (1.37), 8.370 (1.60), 8.382 (1.54), 8.720 (2.00).

LC-MS (method 2): R,=0.97 min; MS (ESIpos): m/z=221 [M+H]⁺

Intermediate 1-58

3-(2-ethoxy-2-methylpropoxy)pyridine-4-carbonitrile

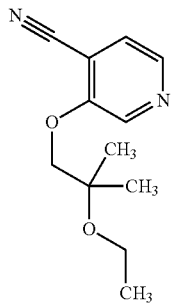

According to the method described for Intermediate 1-57 and using 2-ethoxy-2-methylpropan-1-ol (1.00 g, 8.46 mmol) as a starting material, the title compound was prepared 770 mg (98% purity, 49% yield).

¹H-NMR (400 MHz, DMSO-d6) δ [ppm]: 0.994 (2.41), 1.011 (5.70), 1.029 (2.49), 1.041 (0.53), 1.249 (16.00), 3.410 (0.79), 3.427 (2.60), 3.445 (2.54), 3.462 (0.75), 4.192 (4.92), 7.766 (1.29), 7.768 (1.32), 7.778 (1.30), 7.780 (1.37), 8.372 (1.71), 8.384 (1.64), 8.732 (2.12).

LC-MS (method 2): R,=0.99 min; MS (ESIpos): m/z=221 [M+H]⁺

Intermediate 1-60

3-[2-(dimethylamino)-2-methylpropoxy]pyridine-4-carbonitrile

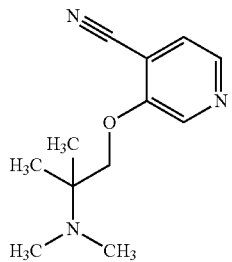 [SMILES: CN(C)C(C)(C)COc1cnccc1C#N]

According to the method described for Intermediate 1-57 and using 2-(dimethylamino)-2-methylpropan-1-ol (4.00 g, 34.1 mmol) as a starting material, the title compound was prepared 6.30 g (93% yield).

¹H-NMR (400 MHz, DMSO-d6) δ [ppm]: 1.035 (1.39), 1.052 (2.99), 1.070 (1.46), 1.119 (15.82), 2.240 (16.00), 2.518 (1.42), 2.522 (0.99), 3.422 (0.71), 3.435 (0.74), 3.440 (0.68), 3.452 (0.69), 4.157 (4.81), 4.342 (0.50), 4.355 (0.95), 4.368 (0.47), 5.758 (0.40), 7.767 (1.21), 7.779 (1.27), 8.373 (1.68), 8.385 (1.63), 8.738 (2.31). LC-MS (method 2): R,=0.90 min; MS (ESIpos): m/z=220 [M+H]⁺

Intermediate 1-63

3-{[1-methylpiperidin-2-yl]methoxy}pyridine-4-carbonitrile

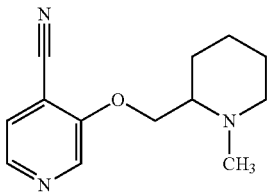 [SMILES: CN1CCCCC1COc1cnccc1C#N]

According to the method described for Intermediate 1-57 and using (1-methylpiperidin-2-yl)methanol (11 ml, 87 mmol) as a starting material, the title compound was prepared 11.5 g (95% purity, 65% yield).

¹H-NMR (400 MHz, DMSO-d6) δ [ppm]: 1.239 (0.49), 1.270 (0.60), 1.345 (0.53), 1.348 (0.52), 1.353 (0.51), 1.371 (0.50), 1.380 (0.57), 1.432 (0.43), 1.461 (0.61), 1.531 (0.59), 1.537 (0.45), 1.689 (0.49), 1.717 (0.44), 1.720 (0.44), 1.768 (0.52), 1.772 (0.53), 1.775 (0.49), 1.779 (0.45), 1.800 (0.43), 1.807 (0.41), 2.014 (0.52), 2.022 (0.59), 2.043 (1.06), 2.050 (1.07), 2.071 (0.56), 2.079 (0.51), 2.254 (16.00), 2.268 (0.58), 2.273 (0.61), 2.280 (0.51), 2.743 (0.64), 2.746 (0.64), 2.772 (0.60), 2.774 (0.59), 4.194 (0.98), 4.207 (0.98), 4.219 (1.31), 4.232 (1.24), 4.356 (1.28), 4.368 (1.31), 4.381 (0.98), 4.394 (0.96), 7.768 (2.20), 7.780 (2.36), 8.375 (3.15), 8.387 (3.05), 8.729 (3.99).

LC-MS (method 2): $R_t$=0.92 min; MS (ESIpos): m/z=232 [M+H]$^+$

Intermediate 1-65

3-[(oxolan-3-yl)methoxy]pyridine-4-carbonitrile

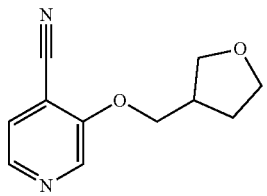 [SMILES: N#Cc1ccncc1OCC1CCOC1]

To a solution of 3-chloroisonicotinonitrile (1.23 g, 8.90 mmol) and (oxolan-3-yl)methanol (1.00 g, 9.79 mmol) in 40 ml. 2-methyltetrahydrofurane was added potassium tert-butoxide (1.20 g, 10.7 mmol) and the mixture was stirred for 4 h at rt. The reaction mixture was diluted slowly with a aqueous solution of ammonium chloride and extracted with ethyl acetate three times. The combined organic layer was washed with brine, dried over sodium sulfate, filtered and the filtrate was concentrated under reduced pressure. The residue was purified by flash chromatography to give 1.34 g of the title compound (74% yield, 90% purity).

1H NMR (400 MHz, CDCl3): d [ppm]=1.75-1.87 (m, 1H), 2.13-2.30 (m, 1H), 2.78-2.95 (m, 1H), 3.74-3.87 (m, 2H), 3.90-4.00 (m, 2H), 4.11-4.21 (m, 2H), 7.48 (d, 1H), 8.40 (d, 1H), 8.50 (s, 1H).

UPLC-MS (method 4): Rt=0.57 min., 94%. MS (ESIpos): m/z=(M+H)+222

Intermediate 1-66

3-{[(2S)-oxolan-2-yl]methoxy}pyridine-4-carbonitrile

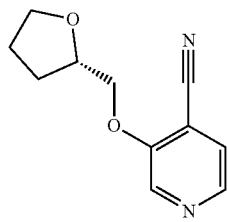 [SMILES: N#Cc1ccncc1OC[C@@H]1CCCO1]

According to the method described for Intermediate 1-57 and using [(2S)-oxolan-2-yl]methanol (1.00 g, 9.79 mmol) as a starting material, the title compound was prepared 1.71 g (99% purity, 85% yield).

$^1$H-NMR (400 MHz, DMSO-d6) δ [ppm]: 1.154 (2.31), 1.172 (4.65), 1.190 (2.40), 1.700 (0.67), 1.716 (1.62), 1.720 (1.19), 1.729 (1.38), 1.731 (1.35), 1.736 (2.07), 1.745 (2.56), 1.749 (1.39), 1.753 (1.52), 1.761 (1.81), 1.765 (2.68), 1.782 (1.96), 1.788 (0.78), 1.805 (1.06), 1.817 (1.15), 1.824 (1.48), 1.833 (1.88), 1.838 (1.69), 1.841 (1.45), 1.854 (2.48), 1.871 (2.12), 1.888 (1.38), 1.902 (1.61), 1.909 (0.84), 1.919 (2.04), 1.934 (1.89), 1.938 (1.69), 1.949 (1.19), 1.952 (1.13), 1.955 (1.41), 1.964 (0.76), 1.969 (1.02), 1.983 (2.72), 1.987 (9.66), 2.000 (2.04), 2.010 (1.89), 2.015 (1.57), 2.020 (1.52), 2.024 (1.46), 2.031 (1.86), 2.043 (1.46), 2.049 (1.19), 2.062 (0.82), 2.331 (0.56), 2.518 (3.41), 2.522 (2.11), 2.673 (0.58), 3.664 (1.92), 3.684 (3.84), 3.700 (4.51), 3.702 (3.81), 3.718 (2.78), 3.769 (2.68), 3.785 (5.28), 3.789 (2.72), 3.802 (3.67), 3.806 (3.47), 3.822 (1.96), 3.999 (0.68), 4.017 (2.07), 4.035 (2.07), 4.053 (0.70), 4.189 (0.87), 4.198 (1.10), 4.204 (1.82), 4.213 (2.20), 4.220 (2.49), 4.229 (2.98), 4.238 (1.78), 4.244 (6.81), 4.257 (1.50), 4.269 (8.40), 4.283 (5.50), 4.319 (6.52), 4.327 (6.36), 4.344 (3.74), 4.353 (2.58), 7.770 (8.92), 7.782 (9.31), 8.373 (11.59), 8.385 (11.19), 8.708 (16.00).

LC-MS (method 2): $R_t$=0.80 min; MS (ESIpos): m/z=205 [M+H]$^+$

Intermediate 1-67

3-{[(2R)-oxolan-2-yl]methoxy}pyridine-4-carbonitrile

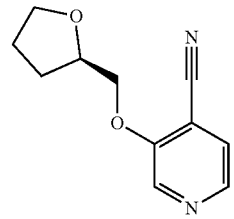 [SMILES: N#Cc1ccncc1OC[C@H]1CCCO1]

According to the method described for Intermediate 1-57 and using [(2R)-oxolan-2-yl]methanol (1.00 g, 9.79 mmol) as a starting material, the title compound was prepared 1.57 g (99% purity, 78% yield).

$^1$H-NMR (400 MHz, DMSO-d6) δ [ppm]: 1.154 (2.06), 1.172 (4.29), 1.189 (2.16), 1.700 (0.68), 1.716 (1.63), 1.720 (1.21), 1.729 (1.40), 1.731 (1.39), 1.736 (2.09), 1.745 (2.55), 1.749 (1.45), 1.753 (1.52), 1.761 (1.81), 1.765 (2.68), 1.782 (1.91), 1.788 (0.78), 1.805 (1.07), 1.817 (1.15), 1.823 (1.49), 1.833 (1.91), 1.837 (1.74), 1.841 (1.48), 1.853 (2.53), 1.871 (2.12), 1.887 (1.32), 1.902 (1.65), 1.909 (0.86), 1.918 (2.12), 1.934 (1.92), 1.938 (1.73), 1.949 (1.23), 1.954 (1.39), 1.964 (0.79), 1.968 (1.07), 1.983 (2.84), 1.986 (8.32), 2.000 (2.06), 2.010 (1.92), 2.020 (1.54), 2.024 (1.49), 2.031 (1.93), 2.043 (1.49), 2.049 (1.18), 2.062 (0.77), 2.518 (1.73), 2.522 (1.06), 3.664 (1.87), 3.684 (3.92), 3.700 (4.46), 3.718 (2.71), 3.769 (2.70), 3.785 (5.37), 3.802 (3.64), 3.806 (3.51), 3.822 (1.94), 3.999 (0.62), 4.016 (1.88), 4.034 (1.86), 4.052 (0.74), 4.189 (0.86), 4.198 (1.12), 4.205 (1.89), 4.213 (2.25), 4.220 (2.57), 4.229 (3.07), 4.238 (1.83), 4.243 (6.71), 4.257 (1.42), 4.269 (8.22), 4.283 (5.52), 4.318 (6.39), 4.327 (6.34), 4.344 (3.72), 4.352 (2.60), 7.770 (8.53), 7.783 (8.91), 8.372 (11.38), 8.384 (10.95), 8.708 (16.00).

LC-MS (method 2): $R_t$=0.80 min; MS (ESIpos): m/z=205 [M+H]$^+$

Intermediate 1-68

3-[(oxan-2-yl)methoxy]pyridine-4-carbonitrile

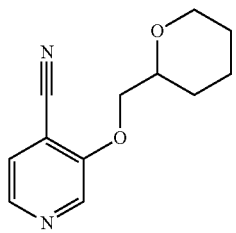 [SMILES: N#Cc1ccncc1OCC1CCCCO1]

According to the method described for Intermediate 1-57 and using (oxan-2-yl)methanol (4.00 g, 98% purity, 33.7 mmol) as a starting material, the title compound was prepared 4.44 g (99% purity, 60% yield).

$^1$H-NMR (400 MHz, DMSO-d6) δ [ppm]: 1.317 (0.67), 1.327 (0.58), 1.347 (2.01), 1.357 (1.66), 1.376 (2.31), 1.379 (2.27), 1.385 (2.15), 1.399 (0.91), 1.407 (2.07), 1.416 (2.07), 1.422 (2.00), 1.432 (2.43), 1.438 (1.54), 1.454 (2.00), 1.463 (2.87), 1.473 (3.60), 1.481 (6.00), 1.488 (6.43), 1.503 (2.42), 1.512 (3.34), 1.521 (1.76), 1.533 (1.58), 1.543 (1.96), 1.553 (1.37), 1.573 (0.60), 1.643 (2.27), 1.649 (2.31), 1.678 (1.99), 1.757 (0.58), 1.773 (0.43), 1.813 (2.16), 1.842 (1.42), 1.907 (1.48), 2.331 (0.61), 2.518 (4.00), 2.522 (2.49), 3.200 (0.40), 3.209 (0.63), 3.214 (0.94), 3.222 (0.73), 3.228 (0.72), 3.233 (0.84), 3.241 (1.31), 3.253 (0.75), 3.256 (1.12), 3.268 (0.84), 3.278 (0.43), 3.299 (1.01), 3.306 (1.13), 3.317 (1.96), 3.343 (1.42), 3.364 (1.69), 3.374 (1.87), 3.392 (2.78), 3.400 (3.57), 3.419 (1.76), 3.428 (1.88), 3.651 (1.04), 3.656 (1.19), 3.665 (1.97), 3.669 (1.70), 3.680 (1.96), 3.693 (1.87), 3.703 (1.19), 3.709 (1.06), 3.821 (0.66), 3.830 (0.58), 3.849 (0.51), 3.854 (0.58), 3.875 (2.31), 3.879 (2.81), 3.884 (2.03), 3.903 (2.12), 3.907 (2.13), 3.913 (1.94), 4.241 (0.79), 4.257 (16.00), 4.267 (9.01), 4.272 (8.57), 4.298 (0.64), 4.522 (1.30), 4.537 (2.06), 4.551 (0.91), 7.766 (8.21), 7.778 (8.57), 8.370 (10.48), 8.382 (10.13), 8.710 (15.12).

LC-MS (method 2): R$_t$=0.94 min; MS (ESIpos): m/z=219 [M+H]$^+$

Intermediate 1-80 tert-butyl (2S)-2-{[(4-cyanopyridin-3-yl)oxy]methyl}pyrrolidine-1-carboxylate

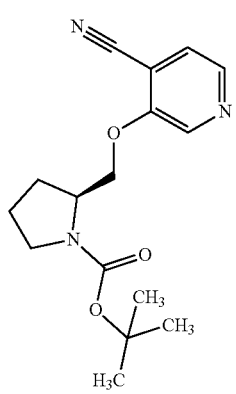 [SMILES: CC(C)(C)OC(=O)N1CCC[C@H]1COc1cnccc1C#N]

According to the method described for Intermediate 1-57 and using tert-butyl (2S)-2-(hydroxymethyl)pyrrolidine-1-carboxylate (4.00 g, 19.9 mmol) as a starting material, the title compound was prepared 4.02 g (74% yield).

$^1$H-NMR (400 MHz, DMSO-d6) δ [ppm]: 1.154 (1.08), 1.172 (2.07), 1.190 (0.95), 1.376 (14.20), 1.383 (16.00), 1.808 (0.85), 1.816 (0.68), 1.834 (0.40), 1.839 (0.40), 1.921 (0.85), 1.928 (0.98), 1.941 (0.57), 1.948 (0.53), 1.956 (0.52), 1.988 (4.17), 2.024 (1.33), 2.332 (0.67), 2.518 (3.50), 2.523 (2.43), 2.673 (0.68), 3.273 (1.02), 3.282 (1.48), 3.292 (1.80), 3.300 (1.93), 4.017 (0.85), 4.035 (0.87), 4.053 (0.62), 4.067 (0.93), 4.073 (1.02), 4.079 (0.97), 4.285 (0.43), 4.302 (0.53), 4.337 (1.67), 4.353 (0.82), 4.420 (0.42), 4.440 (0.40), 7.775 (0.85), 7.787 (1.48), 8.390 (1.52), 8.748 (7.37).

LC-MS (method 2): R, =1.17 min; MS (ESIpos): m/z=304 [M+H]$^+$

Intermediate 1-81

3-[2-(morpholin-4-yl)ethoxy]pyridine-4-carbonitrile

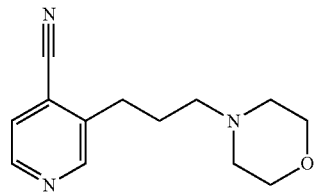 [SMILES: N#Cc1ccncc1CCCN1CCOCC1]

To a solution of 2-(morpholin-4-yl)ethan-1-ol, 500 mg (3.81 mmol), in tetrahydrofuran, 4.40 mL, was added sodium hydride (60% in oil), 191 mg (4.76 mmol). After stirring at room temperature for 1 hour, 3-chloropyridine-4-carbonitrile, 440 mg (3.18 mmol), in tetrahydrofuran, 4.40 mL, was added. After stirring at room temperature for 18 hours, the reaction was quenched with water, extracted with ethyl acetate, the organic layers were dried over magnesium sulfate, filtered and concentrated in vacuo. Trituration with heptane gave 3-[2-(morpholin-4-yl)ethoxy]pyridine-4-carbonitrile, 695 mg (94%). $^1$H NMR (400 MHz, CDCl$_3$): δ [ppm]=2.58-2.66 (m, 4H), 2.89 (t, 2H), 3.67-3.75 (m, 4H), 4.35 (t, 2H), 7.44 (d, 1H), 8.37 (d, 1H), 8.49 (s, 1H);

LC-MS (method 3): R, =0.50 min., 88%. MS (ESIpos): m/z=(M+H)+234.

Intermediate 1-82

3-[(oxan-4-yl)methoxy]pyridine-4-carbonitrile

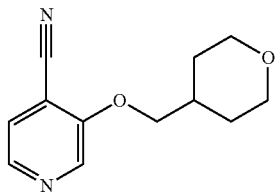 [SMILES: N#Cc1ccncc1OCC1CCOCC1]

To a solution of 3-chloroisonicotinonitrile (618 mg, 4.46 mmol) and tetrahydro-2H-pyran-4-ylmethanol (570 mg, 4.91 mmol) in 2-MeTHF (25 mL) was added KOtBu (601 mg, 5.35 mmol) and the mixture stirred at room temperature for 4 h. TLC showed mostly product. The mixture was diluted slowly with water and extracted with EtOAc, washed with brine, dried over sodium sulfate, filtered and concentrated under reduced pressure to give the title compound (960 mg (99% yield) as a pale yellow oil.

1H NMR (400 MHz, CDCl$_3$): d [ppm]=1.44-1.56 (m, 2H), 1.78-1.88 (m, 2H), 2.14-2.39 (m, 1H), 3.36-3.57 (m, 4H), 4.08 (d, 2H), 7.46 (d, 1H), 8.40 (d, 1H), 8.50 (s, 1H).

LC-MS (Method 4): Rt=0.63 min., 86%. MS (ESIpos): m/z=(M+H)+218

Intermediate 1-96 tert-butyl {2-[(4-cyanopyridin-3-yl)oxy]ethyl}methylcarbamate

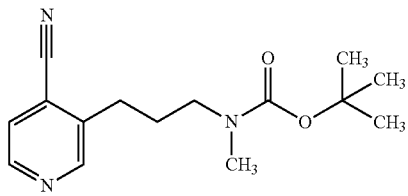 [SMILES: CN(CCCc1cnccc1C#N)C(=O)OC(C)(C)C]

According to the method described for Intermediate 1-57 and using [tert-butyl (2-hydroxyethyl)methylcarbamate (15.2 g, 86.6 mmol) as a starting material, the title compound was prepared 19.1 g (95% yield).

LC-MS (method 2): R$_t$=1.07 min; MS (ESIpos): m/z=278 [M+H]$^+$

Syntheses of Intermediate 2 Compounds

Intermediate 2-1

1-{[4-(aminomethyl)pyridin-3-yl]oxy}-2-methylpropan-2-ol

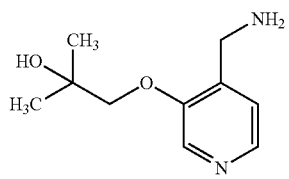

An autoclave was charged with 3-(2-hydroxy-2-methylpropoxy)pyridine-4-carbonitrile (2.00 g, 10.4 mmol), ammonia (36 ml, 7.0 M in methanol) and Raney-Nickel (1.53 g, 50% wet) and the mixture was stirred under 25 bar hydrogen atmosphere at RT for 20 h. For the work-up, the mixture was filtered through a pad of celite, eluted with methanol and the combined filtrates were concentrated under reduced pressure. The residue was used directly in the next step without further purification (2 g, 98% yield).

$^1$H-NMR (400 MHz, DMSO-d$_6$): δ [ppm]=8.12-8.25 (m, 2H), 7.38 (d, 1H), 4.52-5.06 (m, 1H), 3.84 (s, 2H), 3.66-3.81 (m, 2H), 1.84 (brs, 1H), 1.17-1.26 (m, 6H).

Intermediate 2-2

1-[3-(2-methoxy-2-methylpropoxy)pyridin-4-yl]methanamine

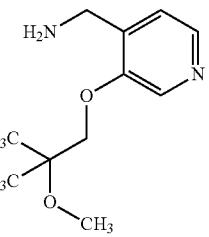

According to the method described for Intermediate 2-1 and using 3-(2-methoxy-2-methylpropoxy)pyridine-4-carbonitrile as a starting material, the title compound was prepared (18.3 g, 99% yield)

$^1$H-NMR (400 MHz, DMSO-d$_6$): δ [ppm]=8.24 (br s, 1H), 8.17 (br d, 1H), 7.33-7.44 (m, 1H), 3.97 (s, 2H), 3.71 (brs, 2H), 3.16 (s, 3H), 1.80 (brs, 2H), 1.22 (s, 6H).

Intermediate 2-3

1-{3-[2-methyl-2-(morpholin-4-yl)propoxy]pyridin-4-yl}methanamine

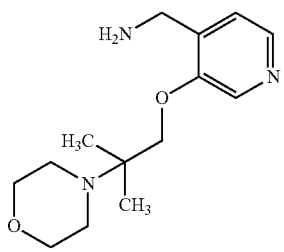 [SMILES: CC(C)(COc1cnccc1CN)N1CCOCC1]

According to the method described for Intermediate 2-1 and using 3-[2-methyl-2-(morpholin-4-yl)propoxy]pyridine-4-carbonitrile as a starting material, the title compound was prepared (3.07 g, 89% yield)

$^1$H-NMR (400 MHz, DMSO-d$_6$): δ [ppm]=8.24 (s, 1H), 8.16 (d, 1H), 7.37 (d, 1H), 3.97 (s, 2H), 3.72 (s, 2H), 3.50-3.56 (m, 4H), 2.55-2.61 (m, 4H), 1.87 (brs, 2H), 1.05-1.15 (m, 6H).

Intermediate 2-4

1-(3-{[(2S)-1-methylpyrrolidin-2-yl]methoxy}pyridin-4-yl)methanamine

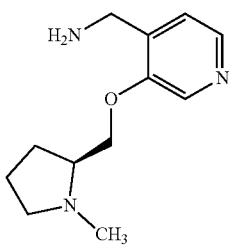 [SMILES: CN1CCC[C@H]1COc1cnccc1CN]

According to the method described for Intermediate 2-1 and using 3-{[(2S)-1-methylpyrrolidin-2-yl]methoxy}pyridine-4-carbonitrile (4.71 g, 21.7 mmol) as a starting material, the title compound was prepared (4.60 g, 96% yield)

¹H-NMR (400 MHz, DMSO-d₆): δ [ppm]=8.24 (s, 1H), 8.16 (d, 1H), 7.38 (d, 1H), 4.08 (m, 1H), 3.95 (m, 1H), 3.62-3.78 (m, 2H), 2.91-3.00 (m, 1H), 2.58 (dq, 1H), 2.34-2.39 (m, 3H), 2.20 (q, 1H), 1.56-2.08 (m, 6H).

Intermediate 2-58

1-[3-(2-ethoxy-2-methylpropoxy)pyridin-4-yl]methanamine

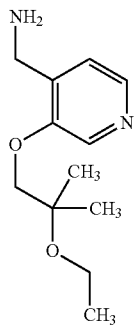

According to the method described for intermediate 2-57 and using 3-(2-ethoxy-2-methylpropoxy)pyridine-4-carbonitrile (intermediate 1-58, 770 mg, 3.50 mmol) as a starting material, the title compound was prepared 250 mg (99% purity, 60% yield).

¹H-NMR (400 MHz, DMSO-d6) δ [ppm]: 0.970 (0.66), 1.013 (0.72), 1.026 (3.44), 1.031 (0.73), 1.035 (0.55), 1.043 (7.38), 1.061 (3.55), 1.206 (3.67), 1.222 (7.65), 1.236 (16.00), 1.258 (0.80), 1.264 (0.54), 1.295 (0.44), 1.352 (0.48), 2.518 (1.02), 2.522 (0.63), 3.384 (0.46), 3.388 (0.46), 3.399 (1.15), 3.406 (0.47), 3.417 (3.18), 3.434 (3.31), 3.452 (1.08), 3.713 (2.29), 3.958 (2.52), 3.963 (4.45), 3.985 (0.56), 4.061 (0.49), 4.543 (0.52), 4.554 (0.53), 7.367 (0.80), 7.380 (1.09), 8.156 (1.08), 8.167 (1.08), 8.190 (0.69), 8.202 (0.67), 8.234 (1.85), 8.247 (0.94).

LC-MS (method 2): R,=0.75 min; MS (ESIpos): m/z=225 [M+H]⁺

Intermediate 2-60

1-{[4-(aminomethyl)pyridin-3-yl]oxy}-N,N,2-trimethylpropan-2-amine

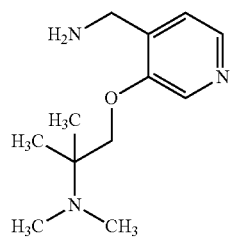 [SMILES: CN(C)C(C)(C)COc1cnccc1CN]

According to the method described for intermediate 2-57 and using 3-[2-(dimethylamino)-2-methylpropoxy]pyridine-4-carbonitrile (intermediate 1-60, 6.30 g, 28.7 mmol) as a starting material, the title compound was prepared (additional a flash chromatography) 5.12 g (80% yield).

¹H-NMR (400 MHz, DMSO-d6) δ [ppm]: 1.020 (1.05), 1.099 (14.49), 2.133 (1.17), 2.225 (16.00), 2.518 (1.04), 2.523 (0.73), 3.712 (1.47), 3.943 (4.03), 7.370 (0.51), 7.382 (0.53), 8.153 (1.27), 8.164 (1.27), 8.243 (2.05).

LC-MS (method 2): R₁=0.69 min; MS (ESIpos): m/z=224 [M+H]⁺

Intermediate 2-63

1-{3-[(1-methylpiperidin-2-yl)methoxy}pyridin-4-yl}methanamine

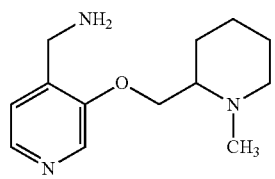 [SMILES: CN1CCCCC1COc1cnccc1CN]

According to the method described for intermediate 2-57 and using 3-[(1-methylpiperidin-2-yl)methoxy]pyridine-4-carbonitrile (Intermediate 1-63, 12.8 g, 55.4 mmol) as a starting material, the title compound was prepared 12.9 g (95% purity, 94% yield).

LC-MS (method 2): R₁=0.72 min; MS (ESIpos): m/z=236 [M+H]⁺

¹H-NMR (400 MHz, DMSO-d6) δ [ppm]: 1.223 (0.41), 1.233 (0.72), 1.242 (0.49), 1.254 (0.53), 1.263 (0.77), 1.272 (0.52), 1.293 (0.43), 1.355 (0.73), 1.381 (0.62), 1.389 (0.73), 1.411 (0.44), 1.422 (0.52), 1.433 (0.63), 1.454 (0.47), 1.463 (0.74), 1.473 (0.47), 1.528 (0.94), 1.560 (0.49), 1.684 (0.88), 1.744 (1.78), 1.768 (1.16), 1.998 (0.64), 2.006 (0.72), 2.027 (1.25), 2.035 (1.25), 2.055 (0.68), 2.062 (0.64), 2.123 (0.45), 2.128 (0.47), 2.186 (0.75), 2.193 (0.81), 2.209 (1.16), 2.228 (16.00), 2.518 (0.92), 2.522 (0.58), 2.744 (0.95), 2.773 (0.88), 3.333 (10.42), 3.766 (0.57), 3.987 (0.80), 3.998 (0.89), 4.012 (1.10), 4.024 (1.06), 4.159 (1.02), 4.171 (1.09), 4.185 (0.86), 4.195 (0.83), 7.370 (0.95), 7.378 (0.98), 8.165 (0.98), 8.245 (1.23).

LC-MS (method 2): R, =0.72 min; MS (ESIpos): m/z=236 [M+H]⁺

Intermediate 2-65

1-{3-[(oxolan-3-yl)methoxy]pyridin-4-yl}methanamine

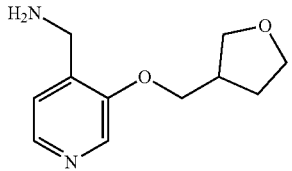 [SMILES: NCc1ccncc1OCC1CCOC1]

To a solution of 3-[(oxolan-3-yl)methoxy]pyridine-4-carbonitrile (intermediate 1-65, 500 mg, 2.45 mmol) in 30 mL methanol was added palladium on carbon (10%, slurried in 0.1 ml. toluene) and the mixture placed under an atmosphere of hydrogen and stirred 4 days at room temperature. Filtered through a plug of celite, washing with methanol. The filtrate was concentrated under reduced pressure to give the desired product 530 mg LC-MS (method 4): Rt=0.43 min., >66%. MS (ESIpos): m/z=(M+H)+209.

Intermediate 2-66

1-(3-{[(2S)-oxolan-2-yl]methoxy}pyridin-4-yl)methanamine

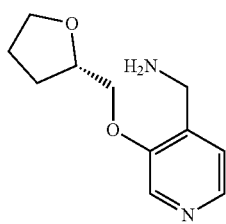 [SMILES: NCc1ccncc1OC[C@@H]1CCCO1]

According to the method described for Intermediate 2-57 and using 3-{[(2S)-oxolan-2-yl]methoxy}pyridine-4-carbonitrile (intermediate 1-66, 1.71 g, 8.37 mmol) as a starting material, the title compound was prepared 1.51 g (93% purity, 81% yield).

$^1$H-NMR (400 MHz, DMSO-d6) δ [ppm]: 1.676 (1.30), 1.692 (2.52), 1.713 (3.36), 1.721 (3.46), 1.726 (2.85), 1.729 (2.81), 1.737 (2.99), 1.742 (3.99), 1.759 (3.23), 1.783 (2.99), 1.801 (3.62), 1.813 (3.49), 1.819 (3.58), 1.829 (4.08), 1.850 (4.83), 1.867 (5.48), 1.883 (4.41), 1.898 (2.94), 1.903 (2.89), 1.919 (2.07), 1.933 (1.32), 1.948 (0.92), 1.962 (2.14), 1.981 (2.86), 1.993 (2.94), 2.002 (2.40), 2.005 (2.30), 2.011 (2.71), 2.024 (2.06), 2.044 (1.06), 2.323 (0.56), 2.327 (0.75), 2.332 (0.56), 2.665 (0.56), 2.669 (0.75), 2.673 (0.54), 3.634 (0.62), 3.661 (3.32), 3.681 (16.00), 3.697 (7.84), 3.715 (3.51), 3.742 (0.76), 3.760 (3.36), 3.770 (2.03), 3.777 (6.40), 3.796 (4.67), 3.814 (2.14), 4.014 (2.86), 4.028 (3.51), 4.039 (5.48), 4.053 (6.30), 4.090 (5.63), 4.099 (6.81), 4.116 (3.25), 4.124 (4.01), 4.152 (2.09), 4.168 (3.44), 4.178 (3.29), 4.183 (3.37), 4.193 (2.77), 4.209 (1.42), 4.220 (0.73), 4.228 (0.70), 4.244 (0.77), 4.269 (0.62), 4.283 (0.52), 4.296 (0.47), 4.304 (0.43), 4.319 (0.71), 4.327 (0.62), 7.373 (4.73), 7.384 (4.89), 7.407 (0.52), 7.419 (0.41), 7.605 (0.45), 7.617 (0.47), 7.771 (0.47), 7.784 (0.46), 8.158 (5.39), 8.169 (5.59), 8.235 (8.50), 8.272 (1.00), 8.297 (0.64), 8.309 (0.63), 8.373 (0.55), 8.385 (0.54), 8.472 (0.45), 8.549 (0.84), 8.709 (0.76).

LC-MS (method 1): R$_t$=0.27 min; MS (ESIpos): m/z=209 [M+H]$^+$

Intermediate 2-67

1-(3-{[(2R)-oxolan-2-yl]methoxy}pyridin-4-yl)methanamine

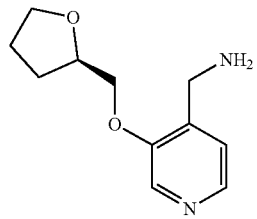 [SMILES: NCc1ccncc1OC[C@H]1CCCO1]

According to the method described for intermediate 2-57 and using 3-{[(2R)-oxolan-2-yl]methoxy}pyridine-4-carbonitrile (intermediate 1-67, 1.57 g, 7.69 mmol) as a starting material, the title compound was prepared 1.52 g (95% purity, 90% yield).

$^1$H-NMR (400 MHz, DMSO-d6) δ [ppm]: 1.675 (0.81), 1.693 (1.68), 1.713 (2.32), 1.721 (2.34), 1.742 (2.49), 1.759 (1.86), 1.803 (2.43), 1.820 (3.01), 1.830 (3.53), 1.849 (3.93), 1.867 (4.10), 1.883 (3.45), 1.900 (2.47), 1.931 (1.13), 1.949 (0.80), 1.963 (1.45), 1.982 (2.09), 1.994 (2.23), 2.011 (2.07), 2.024 (1.52), 2.043 (0.70), 2.327 (0.65), 2.669 (0.69), 3.166 (2.08), 3.681 (16.00), 3.696 (5.57), 3.714 (2.28), 3.760 (2.02), 3.776 (4.01), 3.795 (3.20), 3.813 (1.26), 4.013 (1.80), 4.028 (2.40), 4.038 (3.50), 4.053 (3.90), 4.090 (3.87), 4.099 (4.61), 4.115 (2.46), 4.124 (2.70), 4.151 (1.31), 4.168 (2.60), 4.183 (2.73), 4.193 (2.20), 7.373 (4.28), 7.384 (4.37), 8.156 (4.90), 8.168 (4.93), 8.234 (7.87), 8.271 (0.67).

LC-MS (method 2): R$_t$=0.61 min; MS (ESIpos): m/z=209 [M+H]$^+$

Intermediate 2-68

1-{3-[(oxan-2-yl)methoxy]pyridin-4-yl}methanamine

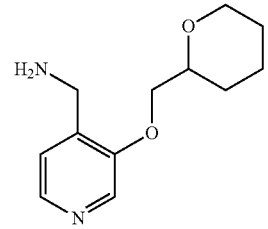 [SMILES: NCc1ccncc1OCC1CCCCO1]

According to the method described for Intermediate 2-57 and using 3-[(oxan-2-yl)methoxy]pyridine-4-carbonitrile (intermediate 1-68, 4.44 g, 20.3 mmol) as a starting material, the title compound was prepared 3.53 g (62% purity, 48% yield).

$^1$H-NMR (400 MHz, DMSO-d6) δ [ppm]: 1.297 (1.12), 1.307 (0.98), 1.327 (2.67), 1.337 (2.14), 1.356 (3.24), 1.365 (2.48), 1.387 (2.48), 1.396 (1.71), 1.424 (2.14), 1.434 (2.83), 1.444 (2.39), 1.457 (3.78), 1.481 (10.83), 1.489 (10.17), 1.501 (5.95), 1.522 (2.21), 1.532 (2.67), 1.541 (1.66), 1.552 (0.91), 1.561 (1.07), 1.572 (0.87), 1.643 (3.51), 1.674 (3.10), 1.810 (5.45), 1.832 (3.99), 2.322 (0.96), 2.327 (1.30), 2.331 (0.98), 2.665 (1.03), 2.669 (1.39), 2.673 (1.05), 3.160 (0.66), 3.171 (0.71), 3.214 (0.55), 3.234 (0.59), 3.242 (0.55), 3.255 (0.59), 3.269 (0.59), 3.359 (3.33), 3.367 (3.28), 3.387 (3.65), 3.395 (4.42), 3.413 (2.32), 3.422 (2.51), 3.604 (1.34), 3.609 (1.53), 3.616 (2.62), 3.621 (2.87), 3.633 (2.74), 3.643 (3.19), 3.648 (3.33), 3.656 (2.92), 3.677 (13.49), 3.773 (1.00), 3.829 (0.71), 3.880 (4.22), 3.903 (3.30), 3.908 (3.67), 4.019 (1.94), 4.034 (16.00), 4.046 (15.70), 4.084 (0.71), 4.099 (0.71), 4.130 (0.73), 4.146 (0.64), 4.209 (0.41), 4.257 (2.03), 4.267 (1.30), 4.272 (1.32), 4.540 (0.43), 7.364 (5.04), 7.376 (5.29), 7.396 (0.93), 7.407 (0.77), 7.766 (0.80), 7.778 (0.80), 8.151 (5.97), 8.163 (6.22), 8.179 (1.28), 8.227 (9.25), 8.248 (1.19), 8.268 (1.87), 8.370 (0.96), 8.382 (0.91), 8.474 (1.62), 8.710 (1.34).

LC-MS (method 2): $R_t$=0.71 min; MS (ESIpos): m/z=223 [M+H]$^+$

Intermediate 2-80 tert-butyl (2S)-2-({[4-(aminomethyl)pyridin-3-yl]oxy}methyl)pyrrolidine-1-carboxylate

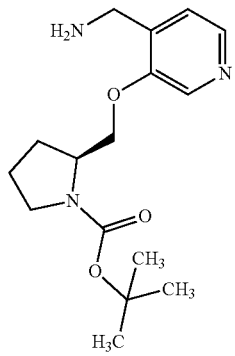 [SMILES: CC(C)(C)OC(=O)N1CCC[C@H]1COc1cnccc1CN]

According to the method described for intermediate 2-57 and using tert-butyl (2S)-2-{[(4-cyanopyridin-3-yl)oxy]methyl}pyrrolidine-1-carboxylate (Intermediate 1-80, 5.00 g, 16.5 mmol) as a starting material, the title compound was prepared 5.05 g (100% yield).

$^1$H-NMR (400 MHz, DMSO-d6) δ [ppm]: 1.145 (0.40), 1.380 (13.73), 1.387 (11.86), 1.396 (16.00), 1.817 (0.94), 1.921 (1.30), 1.928 (1.57), 1.936 (1.50), 1.942 (1.57), 1.956 (1.64), 2.336 (0.77), 2.518 (8.18), 2.523 (5.61), 2.678 (0.63), 3.159 (3.17), 3.172 (3.31), 3.296 (2.77), 3.381 (0.47), 3.696 (6.08), 4.037 (1.27), 4.054 (1.64), 4.096 (0.87), 4.110 (0.77), 4.123 (0.57), 4.135 (0.94), 4.144 (1.14), 4.157 (1.40), 4.166 (1.17), 4.420 (0.57), 4.440 (0.57), 4.443 (0.53), 4.462 (0.43), 7.396 (1.40), 8.172 (1.74), 8.182 (1.70), 8.274 (2.87).

LC-MS (method 2): $R_t$=0.85 min; MS (ESIpos): m/z=308 [M+H]$^+$

Intermediate 2-81

1-{3-[2-(morpholin-4-yl)ethoxy]pyridin-4-yl}methanamine

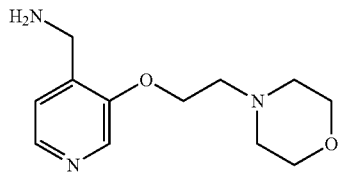 [SMILES: NCc1ccncc1OCCN1CCOCC1]

To a solution of 3-[2-(morpholin-4-yl)ethoxy]pyridine-4-carbonitrile, (intermediate 1-81; 690 mg 2.96 mmol), in methanol, 45.0 mL, was added palladium on carbon (10% wt) under a nitrogen atmosphere. After stirring at room temperature for 2 days under an atmosphere of hydrogen, the suspension was filtered through a pad of celite, washed with methanol and the filtrate was concentrated in vacuo to give 1-{3-[2-(morpholin-4-yl)ethoxy]pyridin-4-yl}methanamine, 687 mg (99%).

$^1$H NMR (400 MHz, DMSO-d6): δ [ppm]=2.43-2.49 (m, 4H), 2.71 (t, 2H), 3.52-3.61 (m, 4H), 3.71 (s, 2H), 4.22 (t, 2H), 7.37 (d, 1H), 8.17 (d, 1H), 8.27 (s, 1H); UPLC-MS (method 4): $R_t$=0.37 min., 75%. MS (ESIpos): m/z=(M+H)+250.

Intermediate 2-82

1-{3-[(oxan-4-yl)methoxy]pyridin-4-yl}methanamine

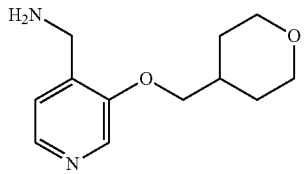 [SMILES: NCc1ccncc1OCC1CCOCC1]

To a solution of 3-[(oxan-4-yl)methoxy]pyridine-4-carbonitrile (500 mg, 2.29 mmol) in methanol (30 mL) was added 10% Pd/C (97.5 mg, 916 μmol) under a nitrogen atmosphere as a toluene (83 μl) slurry. After stirring at room temperature for 2 days under an atmosphere of hydrogen, the suspension was filtered through a pad of celite and washed with ethanol. The filtrate was concentrated under reduced pressure to give the desired title compound (490 mg, 96% yield).

$^1$H NMR (400 MHz, CDCl$_3$): δ [ppm]=1.41-1.59 (m, 2H), 1.71-1.82 (m, 2H), 2.06-2.23 (m, 1H), 3.36-3.56 (m, 4H), 3.88 (s, 2H), 3.97 (d, 2H), 4.00-4.11 (m, 2H), 7.26 (d, 1H), 8.21 (s, 1H), 8.25 (d, 1H).

UPLC-MS (method 4): Rt=0.44 min., 68%. MS (ESIpos): m/z=(M+H)+223.

Intermediate 2-96 tert-butyl (2-{[4-(aminomethyl)pyridin-3-yl]oxy}ethyl)methylcarbamate

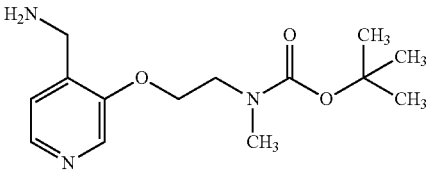 [SMILES: CN(CCOc1cnccc1CN)C(=O)OC(C)(C)C]

According to the method described for intermediate 2-57 and using tert-butyl {2-[(4-cyanopyridin-3-yl)oxy]ethyl}methylcarbamate (intermediate 1-96, 19.1 g, 68.9 mmol) as a starting material, the title compound was prepared 18.72 g (90% purity, 97% yield).

LC-MS (method 2): $R_t$=0.84 min; MS (ESIpos): m/z=282 [M+H]$^+$ $^1$H-NMR (400 MHz, DMSO-d6) δ [ppm]: 1.233 (0.76), 1.349 (16.00), 1.398 (9.05), 1.889 (0.77), 2.518 (2.35), 2.523 (1.57), 2.739 (0.66), 2.863 (4.11), 2.888 (3.51), 3.558 (2.60), 3.571 (5.32), 3.585 (2.84), 3.678 (3.07), 4.198 (1.79), 4.212 (1.58), 7.394 (1.11), 8.169 (1.53), 8.180 (1.54), 8.255 (1.29).

Syntheses of Intermediate 3 Compounds

Intermediate 3-1

1-(difluoromethoxy)-2-isothiocyanatobenzene

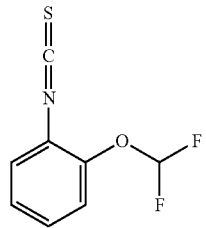 [SMILES: FC(F)Oc1ccccc1N=C=S]

To a ice-cooled biphasic system of 2-(difluoromethoxy) aniline (25.0 g, 157 mmol) in DCM (20 ml) and sat. NaHCO$_3$ (20 ml) was added slowly dropwise thiophosgene (13 ml, 160 mmol). The reaction was stirred at 0° C. for 2 h. TLC (EtOAc:Hexane) showed complete conversion. The DCM layer was separated and washed with sat. NaHCO$_3$, brine, filtered through a hydrophobic filter and concentrated to give the title compound (29.95 g, 95%) which was used directly in the next step.

$^1$H-NMR (400 MHz, DMSO-d$_6$): δ [ppm]=7.09-7.64 (m, 1H).

Intermediate 3-2-1

3-(2-nitrophenyl)propan-1-ol

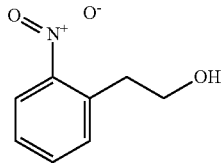

Into a 10-L 4-necked round-bottom flask purged and maintained with an inert atmosphere of nitrogen, was placed a solution of 3-(2-nitrophenyl)propanoic acid (300 g, 1.54 mol, 1.00 equiv) in tetrahydrofuran (1500 mL). This was followed by the addition of BH$_3$-THF (3315 mL, 2.00 equiv, 1 M) dropwise with stirring at 0° C. in 60 min. The resulting solution was stirred overnight at room temperature. The resulting solution was extracted with 3×2 L of ethyl acetate and the organic layers combined. The resulting mixture was washed with 3×1 L of brine. The mixture was dried over anhydrous sodium sulfate and concentrated under vacuum. This resulted in 300 g of 3-(2-nitrophenyl)propan-1-ol as yellow oil.

Intermediate 3-2-2

2-(2-nitrophenyl)acetaldehyde

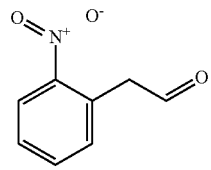

Into a 500-L 4-necked round-bottom flask purged and maintained with an inert atmosphere of nitrogen, was placed a solution of 2-(2-nitrophenyl)ethan-1-ol (300 g, 1.79 mol, 1.00 equiv) in dichloromethane (3000 mL), Dess-Martin (837.8 g, 1.10 equiv). The resulting solution was stirred overnight at room temperature. The reaction was then quenched by the addition of 2 L of water/ice. The pH value of the solution was adjusted to 8 with sodium carbonate. The resulting solution was extracted with 3×2 L of dichloromethane and the organic layers combined. The resulting mixture was washed with 3×1 L of sodium chloride. The mixture was dried over anhydrous sodium sulfate and concentrated under vacuum. The residue was applied onto a silica gel column with ethyl acetate/petroleum ether (1:1). This resulted in 150 g (51%) of 2-(2-nitrophenyl)acetaldehyde as yellow oil.

Intermediate 3-2-3

1-(2,2-difluoroethyl)-2-nitrobenzene

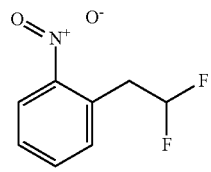

Into a 5-L 4-necked round-bottom flask purged and maintained with an inert atmosphere of nitrogen, was placed a solution of 2-(2-nitrophenyl)acetaldehyde (150 g, 908.29 mmol, 1.00 equiv) in dichloromethane (2000 mL). This was followed by the addition of DAST (366 g, 2.50 equiv) dropwise with stirring at −30° C. in 20 min. The resulting solution was stirred overnight at room temperature. The reaction was then quenched by the addition of 300 mL of methanol. The pH value of the solution was adjusted to 7 with sodium carbonate. The resulting solution was extracted with 3×1 L of dichloromethane and the organic layers combined. The resulting mixture was washed with 3×1 L of brine. The mixture was dried over anhydrous sodium sulfate and concentrated under vacuum. The residue was applied onto a silica gel column with ethyl acetate/petroleum ether (1:10). This resulted in 35 g (21%) of 1-(2,2-difluoroethyl)-2-nitrobenzene as yellow oil.

Intermediate 3-2-4

2-(2,2-difluoroethyl)aniline; oxalic acid salt

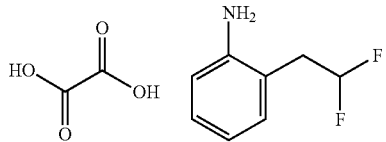

Into a 1000-mL 3-necked round-bottom flask purged and maintained with an inert atmosphere of nitrogen, was placed a solution of 1-(2,2-difluoroethyl)-2-nitrobenzene (35 g, 187.02 mmol, 1.00 equiv) in methanol (350 mL), Palladium carbon (20 g). To the above hydrogen (enough, gas) was introduced in. The resulting solution was stirred overnight at room temperature. The solids were filtered out. The resulting mixture was concentrated under vacuum. The resulting solution was diluted with 300 ml. of EtOAc. This was followed by the addition of oxalic acid (16 g, 0.95 equiv) in several batches. The resulting solution was stirred for 30 min at room temperature. The solids were collected by filtration. This resulted in 33.8 g (73%) of 2-(2,2-difluoroethyl)aniline; oxalic acid as an off-white solid.

$^1$H-NMR (300 MHz, DMSO-$d_6$): δ [ppm]=2.92-3.12 (2H, m), 5.94-6.35 (1H, m), 6.50-6.55 (1H, m), 6.64-6.67 (1H, m), 6.95-6.99 (2H, m).

Intermediate 3-2

2-(2,2-difluoroethyl)aniline; oxalic acid salt

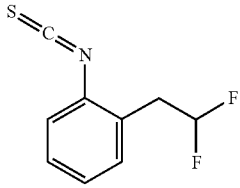 [SMILES: FC(F)Cc1ccccc1N=C=S]

Into a 500-mL 3-necked round-bottom flask purged and maintained with an inert atmosphere of nitrogen, was placed a solution of 2-(2,2-difluoroethyl)aniline (18 g, 114.53 mmol, 1.00 equiv) in dichloromethane (180 mL), CaCO$_3$ (35.5 g, 3.10 equiv), water (180 mL). This was followed by the addition of CsCl$_2$ (18.3 g, 1.40 equiv) dropwise with stirring at 0° C. in 30 min. The resulting solution was stirred overnight at room temperature. The reaction was then quenched by the addition of 1000 ml. of water/ice. The solids were filtered out. The resulting solution was extracted with 2×500 ml. of dichloromethane and the organic layers combined. The resulting mixture was washed with 1×500 ml. of brine. The mixture was dried over anhydrous sodium sulfate and concentrated under vacuum. The residue was applied onto a silica gel column with ethyl acetate/petroleum ether (1:20). This resulted in 10.5 g (46%) of 1-(2,2-difluoroethyl)-2-isothiocyanatobenzene as yellow oil.

$^1$H-NMR (300 MHz, CDCl$_3$): δ [ppm]=3.21-3.33 (2H, m), 5.81-6.21 (1H, m), 7.23-7.36 (4H, m).

Intermediate 3-3

1-fluoro-3-isothiocyanato-2-methoxybenzene

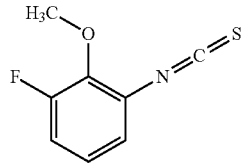

Using an analogous method as described for Intermediate 3-1,3-fluoro-2-methoxyaniline (5.00 g, 35.4 mmol) as the starting material, the title compound was prepared 6.24 g (96% yield).

$^1$H-NMR (400 MHz, DMSO-$d_6$): δ [ppm]=7.32 (m, 1H), 7.10-7.19 (m, 2H), 3.96 (d, 3H).

Intermediate 3-4

2-(difluoromethoxy)-1-fluoro-3-isothiocyanatobenzene

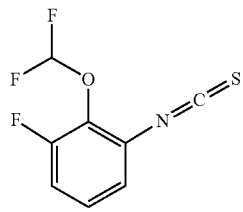 [SMILES: Fc1cccc(N=C=S)c1OC(F)F]

Using an analogous method as described for Intermediate 3-1,2-(difluoromethoxy)-3-fluoroaniline (5.00 g, 28.2 mmol—Apollo) as the starting material, the title compound was prepared 5.96 g (96% yield).

$^1$H-NMR (400 MHz, DMSO-$d_6$): δ [ppm]=7.30-7.49 (m, 4H).

Intermediate 3-5

1-fluoro-3-isothiocyanato-2-methylbenzene

Using an analogous method as described for Intermediate 3-1,3-fluoro-2-methylaniline (5.00 g, 40.0 mmol) as the starting material, the title compound was prepared 6.42 g (96% yield).

$^1$H-NMR (400 MHz, DMSO-$d_6$): δ [ppm]=7.19-7.34 (m, 3H), 2.25 (d, 3H).

Intermediate 3-5-1

2-(2-fluoro-6-nitrophenyl)ethan-1-ol

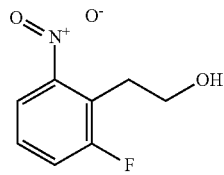

Into a 2000-mL 4-necked round-bottom flask purged and maintained with an inert atmosphere of nitrogen, was placed a solution of 1-fluoro-2-methyl-3-nitrobenzene (400 g, 2.58 mol, 1.00 equiv) in DMSO (1000 mL), Potassium tert-butoxide (46.3 g, 0.16 equiv), polyoxymethylene (77.3 g, 1.00 equiv). The resulting solution was stirred for 1 h at 70° C. in an oil bath. The reaction mixture was cooled with a water bath. The pH value of the solution was adjusted to 7 with hydrogen chloride (12 mol/L). The resulting solution was diluted with 1000 ml. of H$_2$O. The resulting solution was extracted with 4×500 ml. of ethyl acetate and the organic layers combined. The resulting mixture was washed with 2×500 ml. of brine. The mixture was dried over anhydrous sodium sulfate and concentrated under vacuum. The residue was applied onto a silica gel column with ethyl acetate/petroleum ether (1:10). This resulted in 330 g (69%) of 2-(2-fluoro-6-nitrophenyl)ethan-1-ol as yellow oil.

Intermediate 3-6-2

2-(2-fluoro-6-nitrophenyl)acetaldehyde

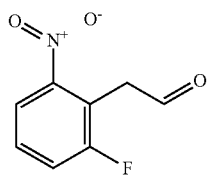

Into a 5000-mL 4-necked round-bottom flask purged and maintained with an inert atmosphere of nitrogen, was placed a solution of 2-(2-fluoro-6-nitrophenyl)ethan-1-ol (330 g, 1.78 mol, 1.00 equiv) in dichloromethane (3500 mL), Dess-Martin reagent (794 g, 1.05 equiv). The resulting solution was stirred overnight at room temperature. The reaction was then quenched by the addition of 5 L of saturated aqueous sodium carbonate. The resulting solution was extracted with 2×3 L of dichloromethane and the organic layers combined. The resulting mixture was washed with 2×2 L of brine. The mixture was dried over anhydrous sodium sulfate and concentrated under vacuum. The residue was applied onto a silica gel column with ethyl acetate/petroleum ether (1:3). This resulted in 180 g (55%) of 2-(2-fluoro-6-nitrophenyl)acetaldehyde as yellow oil.

Intermediate 3-6-3

2-(2,2-difluoroethyl)-1-fluoro-3-nitrobenzene

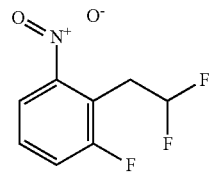

Into a 5000-mL 4-necked round-bottom flask purged and maintained with an inert atmosphere of nitrogen, was placed a solution of 2-(2-fluoro-6-nitrophenyl)acetaldehyde (180 g, 982.87 mmol, 1.00 equiv) in dichloromethane (2500 mL). This was followed by the addition of DAST (405 g) drop-wise with stirring at −30° C. in 30 min. The resulting solution was stirred overnight at room temperature. The reaction mixture was cooled to −30° C. The reaction was then quenched by the addition of 300 mL of methanol. The pH value of the solution was adjusted to 8 with saturated aqueous sodium carbonate. The resulting solution was extracted with 3×2 L of dichloromethane and the organic layers combined. The resulting mixture was washed with 3×2 L of brine. The mixture was dried over anhydrous sodium sulfate and concentrated under vacuum. The residue was applied onto a silica gel column with ethyl acetate/petroleum ether (1:10). This resulted in 34 g (17%) of 2-(2,2-difluoroethyl)-1-fluoro-3-nitrobenzene as yellow oil.

Intermediate 3-6-4

2-(2,2-difluoroethyl)-3-fluoroaniline; oxalic acid salt

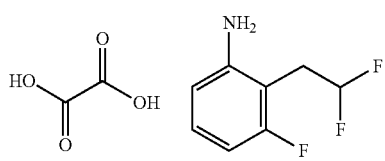

Into a 1000-mL 4-necked round-bottom flask purged and maintained with an inert atmosphere of nitrogen, was placed a solution of 2-(2,2-difluoroethyl)-1-fluoro-3-nitrobenzene (34 g, 165.75 mmol, 1.00 equiv) in methanol (500 mL), Palladium carbon (17 g). To the above hydrogen (enough, gas) was introduced in. The resulting solution was stirred overnight at room temperature. The solids were filtered out. The resulting mixture was concentrated under vacuum. The resulting solution was diluted with 300 ml. of EtOAc. This was followed by the addition of oxalic acid (16 g, 0.95 equiv) in several batches. The resulting solution was stirred for 30 min at room temperature. The solids were collected by filtration. This resulted in 33.2 g (76%) of 2-(2,2-difluoroethyl)-3-fluoroaniline; oxalic acid as an off-white solid.

$^1$H-NMR (300 MHz, CDCl3): δ [ppm]=3.04-3.17 (2H, m), 5.89-6.27 (1H, m), 6.29-6.35 (1H, m), 6.45-6.48 (1H, m), 6.93-7.00 (1H, m), 9.65 (1H, s).

Intermediate 3-6

1-fluoro-3-isothiocyanato-2-methylbenzene

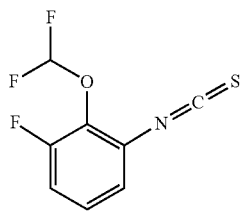

Into a 500-mL 4-necked round-bottom flask purged and maintained with an inert atmosphere of nitrogen, was placed a solution of 2-(2,2-difluoroethyl)-3-fluoroaniline; oxalic acid (18 g, 67.88 mmol, 1.00 equiv) in dichloromethane (180 mL), a solution of $CaCO_3$ (52 g, 5.10 equiv) in water (180 mL). This was followed by the addition of $CSCl_2$ (17.6 g, 15.00 equiv) dropwise with stirring at 0° C. The resulting solution was stirred overnight at room temperature. The reaction was then quenched by the addition of 500 ml. of saturated aqueous sodium bicarbonate. The solids were filtered out. The resulting solution was extracted with 3×500 ml. of dichloromethane and the organic layers combined. The resulting mixture was washed with 2×300 ml. of brine. The mixture was dried over anhydrous sodium sulfate and concentrated under vacuum. The residue was applied onto a silica gel column with ethyl acetate/petroleum ether (1:20). This resulted in 10.2 g (69%) of 2-(2,2-difluoroethyl)-1-fluoro-3-isothiocyanatobenzene as a yellow liquid.

$^1$H-NMR (300 MHz, CDCl3): δ [ppm]=3.26-3.39 (2H, m), 5.83-6.23 (1H, m), 7.02-7.08 (1H, m), 7.14-7.18 (1H, m), 7.25-7.34 (1H, m).

Intermediate 3-7-1

2-fluoro-6-nitrophenyl prop-2-en-1-yl ether

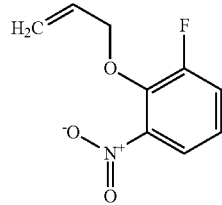

A mixture of 2-fluoro-6-nitrophenol (5.00 g, 31.8 mmol), 3-bromoprop-1-ene (3.4 ml, 40 mmol) and K2CO3 (8.80 g, 63.7 mmol) in DMF (50 ml) was heated at 100° C. for 6 h. The reaction mixture was allowed to cool and diluted with EtOAc (400 ml) and washed with water (3×50 ml), sat. NaCl(aq) and filtered through a hydrophobic filter and concentrated to give the titled compound (5.47 g, 83% yield).

$^1$H-NMR (400 MHz, DMSO-$d_6$): δ [ppm]=7.76 (d, 1H), 7.65-7.71 (m, 1H), 7.34 (m, 1H), 5.95-6.05 (m, 1H), 5.38 (dq, 1H), 5.28 (dq, 1H), 4.71 (dq, 2H).

Intermediate 3-7-2

3-fluoro-2-(prop-2-en-1-yloxy)aniline

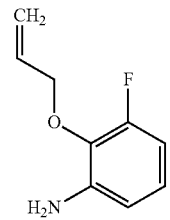

To a mixture of 2-fluoro-6-nitrophenyl prop-2-en-1-yl ether (5.47 g, 27.7 mmol) and ZnCl2 (31.3 g, 139 mmol) in EtOH (300 ml) was added TEA (77 ml, 550 mmol). The reaction was heated at 70° C. for 4 h. The reaction mixture was filtered and the solid washed with EtOAc (500 ml) and the filtrate was concentrated. The residue was purified by silica chromatography (Hexane:EtOAc) to give the titled compound (1.12 g, 23% yield).

$^1$H-NMR (400 MHz, DMSO-$d_6$): δ [ppm]=6.75 (m, 1H), 6.47 (dt, 1H), 6.33 (m, 1H), 6.01-6.13 (m, 1H), 5.32 (dq, 1H), 5.20 (ddt, 1H), 5.13 (s, 2H), 4.42 (d, 2H).

Intermediate 3-7

2-fluoro-6-isothiocyanatophenyl prop-2-en-1-yl ether

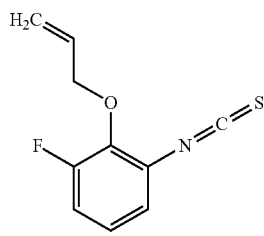

Using an analogous method as described for Intermediate 3-1,3-fluoro-2-(prop-2-en-1-yloxy)aniline (1.12 g, 6.70 mmol) as the starting material, the title compound was prepared 1.29 g (87% yield).

$^1$H-NMR (500 MHz, DMSO-$d_6$): δ [ppm]=7.32 (m, 1H), 7.12-7.20 (m, 2H), 6.00-6.09 (m, 1H), 5.41 (dq, 1H), 5.30 (dq, 1H), 4.68 (dq, 2H).

Intermediate 3-8-1

2-ethoxy-1-fluoro-3-nitrobenzene

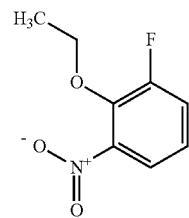

Using an analogous method as described for Intermediate 3-12-1,2-fluoro-6-nitrophenol (5.00 g, 31.8 mmol) as the starting material, the title compound was prepared 5.40 g (87% yield).

$^1$H-NMR (400 MHz, DMSO-d$_6$): δ [ppm]=7.75 (d, 1H), 7.65-7.71 (m, 1H), 7.32 (m, 1H), 4.23 (qd, 2H), 1.31 (t, 3H).

Intermediate 3-8-2

2-ethoxy-3-fluoroaniline

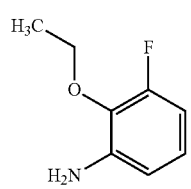

An autoclave was charged with 2-ethoxy-1-fluoro-3-nitrobenzene (5.40 g, 29.2 mmol), and Platinum/Vanadium (1%/2%) on activated charcoal (1.42 g, 50% wet) in MeOH (160 ml) and THF (17 ml) was stirred under a hydrogen atmosphere at RT for 2.5 h. For the work-up, the mixture was filtered through a pad of celite, eluted with methanol and the combined filtrates were concentrated under reduced pressure. The residue was used directly in the next step without further purification (4.13 g, 91% yield).

$^1$H-NMR (400 MHz, DMSO-d$_6$): δ [ppm]=6.74 (m, 1H), 6.47 (dt, 1H), 6.32 (m, 1H), 5.12 (s, 2H), 3.92 (q, 2H), 1.29 (t, 3H).

Intermediate 3-8

2-ethoxy-1-fluoro-3-isothiocyanatobenzene

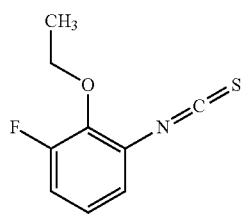

Using an analogous method as described for Intermediate 3-1,2-ethoxy-3-fluoroaniline (4.13 g, 26.6 mmol) as the starting material, the title compound was prepared 4.61 g (83% yield).

$^1$H-NMR (400 MHz, DMSO-d$_6$): δ [ppm]=7.31 (m, 1H), 7.09-7.18 (m, 2H), 4.20 (qd, 2H), 1.36 (t, 3H).

Intermediate 3-9-1

2-(2,2-difluoroethoxy)-1-fluoro-3-nitrobenzene

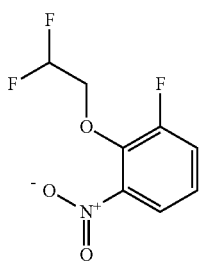

Using an analogous method as described for Intermediate 3-7-1,2-fluoro-6-nitrophenol (2.91 g, 18.5 mmol) as the starting material, the title compound was prepared 4.71 g (98% yield).

$^1$H-NMR (400 MHz, DMSO-d$_6$): δ [ppm]=7.82 (dt, 1H), 7.74 (m, 1H), 7.39 (m, 1H), 6.12-6.54 (m, 1H), 4.49 (tm, 2H).

Intermediate 3-9-2

2-(2,2-difluoroethoxy)-3-fluoroaniline

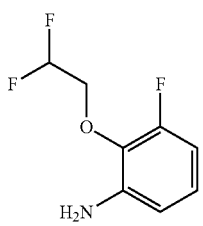 [SMILES: Nc1cccc(F)c1OCC(F)F]

Using an analogous method as described for Intermediate 3-8-2, 2-(2,2-difluoroethoxy)-1-fluoro-3-nitrobenzene (4.10 g, 18.5 mmol) as the starting material, the title compound was prepared 3.95 g (quantitative).

$^1$H-NMR (400 MHz, DMSO-d$_6$): δ [ppm]=6.80 (m, 1H), 6.18-6.52 (m, 3H), 5.24 (br s, 2H), 4.14 (m, 2H).

Intermediate 3-9

2-(2,2-difluoroethoxy)-1-fluoro-3-isothiocyanatobenzene

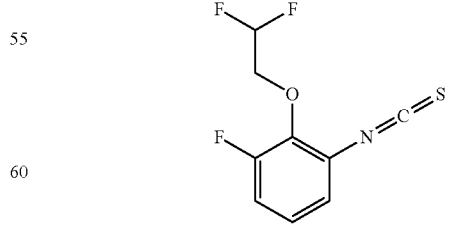

Using an analogous method as described for Intermediate 3-9-2, 2-(2,2-difluoroethoxy)-3-fluoroaniline (3.95 g, 20.7 mmol) as the starting material, the title compound was prepared 3.89 g (77% yield).

¹H-NMR (500 MHz, DMSO-d₆): δ [ppm]=7.35 (m, 1H), 7.15-7.24 (m, 2H), 6.34 (brd, 1H), 6.34 (t, 1H), 4.48 (tm, 2H).

Intermediate 3-10

1,2-difluoro-4-isothiocyanato-3-methoxybenzene

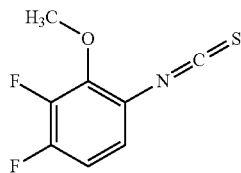

Using an analogous method as described for Intermediate 3-1,3,4-difluoro-2-methoxyaniline (5.00 g, 31.4 mmol) as the starting material, the title compound was prepared 6.18 g (93% yield).
¹H-NMR (400 MHz, DMSO-d₆): δ [ppm]=7.18-7.26 (m, 2H), 4.04 (d, 3H).

Intermediate 3-11

1,5-difluoro-3-isothiocyanato-2-methoxybenzene

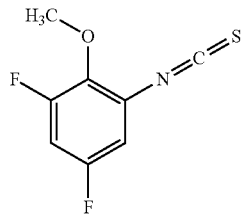

Using an analogous method as described for Intermediate 3-1,3,5-difluoro-2-methoxyaniline (5.00 g, 31.4 mmol) as the starting material, the title compound was prepared 6.18 g (89% yield).
¹H-NMR (400 MHz, DMSO-d₆): δ [ppm]=7.44 (m, 1H), 7.18-7.23 (m, 1H), 3.92 (d, 3H).

Intermediate 3-32

1-chloro-3-isothiocyanato-2-methoxybenzene

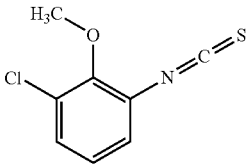

According to the method described for intermediate 3-1 and using 3-chloro-2-methoxyaniline (4.2 ml, 32 mmol) as a starting material, the title compound was prepared 6.58 g (99% purity, 103% yield).
¹H-NMR (400 MHz, DMSO-d6) δ [ppm]: 2.518 (1.69), 2.522 (1.08), 3.380 (11.66), 3.701 (0.51), 3.908 (0.45), 4.067 (0.47), 7.179 (6.92), 7.199 (16.00), 7.219 (9.82), 7.337 (9.53), 7.341 (10.67), 7.357 (7.25), 7.361 (7.55), 7.498 (8.95), 7.502 (9.32), 7.518 (8.68), 7.522 (8.33).
LC-MS (method 2): $R_t$=1.31 min; MS (ESIpos): m/z=200 [M+H]⁺

Intermediate 3-35

2-ethyl-1-fluoro-3-isothiocyanatobenzene

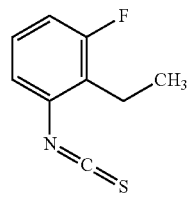

According to the method described for intermediate 3-1 and using 2-ethyl-3-fluoroaniline (2.50 g, 18.0 mmol) as a starting material, the title compound was prepared 3.00 g (90% purity, 83% yield).
¹H-NMR (400 MHz, DMSO-d6) δ [ppm]: 1.108 (7.13), 1.127 (16.00), 1.146 (7.13), 2.462 (0.95), 2.483 (1.27), 2.517 (0.79), 2.522 (0.48), 2.637 (0.95), 2.641 (1.11), 2.655 (3.17), 2.659 (3.17), 2.674 (3.17), 2.678 (3.17), 2.693 (0.95), 2.697 (0.95), 3.461 (0.48), 3.477 (0.63), 3.484 (0.63), 3.506 (1.11), 3.528 (2.06), 3.537 (2.69), 3.625 (3.01), 3.648 (1.11), 3.663 (0.63), 3.669 (0.63), 7.185 (1.11), 7.189 (1.11), 7.205 (1.58), 7.209 (2.53), 7.212 (1.27), 7.229 (1.43), 7.233 (1.74), 7.243 (1.27), 7.246 (1.43), 7.263 (3.80), 7.266 (2.38), 7.282 (2.53), 7.296 (2.38), 7.301 (2.38), 7.317 (2.53), 7.322 (0.79), 7.337 (0.79).
LC-MS (method 2): $R_t$=1.46 min; MS (ESIpos): m/z=226 [M+H]⁺

Intermediate 3-38

1-chloro-2-(difluoromethoxy)-3-isothiocyanatobenzene

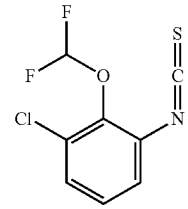 [SMILES: FC(F)Oc1c(Cl)cccc1N=C=S]

According to the method described for intermediate 3-1 and using 3-chloro-2-(difluoromethoxy)aniline (2.00 g, 95% purity, 9.81 mmol) as a starting material, the title compound was prepared 2.40 g (80% purity, 83% yield).
¹H-NMR (400 MHz, DMSO-d6) δ [ppm]: 1.912 (0.72), 2.326 (0.43), 2.517 (1.73), 2.522 (1.15), 3.158 (0.58), 3.396 (0.43), 3.418 (0.58), 3.715 (0.72), 6.639 (1.30), 6.643 (1.44), 6.659 (1.59), 6.663 (1.59), 6.690 (1.44), 6.713 (1.30), 6.717 (1.30), 6.734 (1.73), 6.737 (1.44), 6.876 (2.74), 6.934 (0.72), 6.947 (1.87), 6.967 (2.45), 6.987 (1.15), 7.030 (7.21), 7.060 (1.30), 7.211 (15.14), 7.327 (0.43), 7.347 (1.01), 7.367 (7.50), 7.388 (16.00), 7.391 (8.22), 7.409 (11.39), 7.488

(0.72), 7.494 (9.80), 7.497 (10.52), 7.508 (0.86), 7.514 (7.35), 7.518 (6.63), 7.597 (10.09), 7.601 (9.80), 7.618 (8.79), 7.622 (7.78), 9.798 (0.58).

LC-MS (method 2): R$_t$=1.31 min; MS (ESIpos): m/z=236 [M+H]$^+$

Intermediate 3-39

1-chloro-3-isothiocyanato-2-methoxybenzene

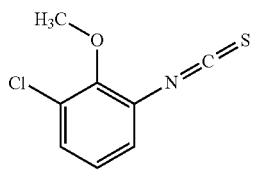

According to the method described for intermediate 3-1 and using 3-chloro-2-methoxyaniline (8.4 ml, 63 mmol) as a starting material, the title compound was prepared 12.97 g (95% purity, 100% yield).

$^1$H-NMR (400 MHz, DMSO-d6) δ [ppm]: 2.518 (1.79), 2.523 (1.10), 3.395 (8.24), 3.701 (0.51), 4.067 (0.50), 7.179 (7.00), 7.200 (16.00), 7.220 (9.88), 7.338 (9.39), 7.341 (10.13), 7.358 (7.31), 7.362 (7.40), 7.498 (8.97), 7.502 (9.26), 7.519 (8.57), 7.523 (7.92).

Intermediate 3-40

1,5-difluoro-3-isothiocyanato-2-methylbenzene

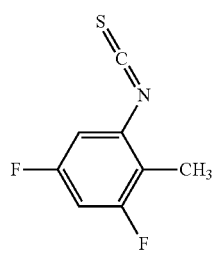

According to the method described for Intermediate 3-38 and using 3,5-difluoro-2-methylaniline hydrogen chloride (1/1) (3.13 g, 17.4 mmol) as a starting material, the title compound was prepared 3.10 g (95% purity, 91% yield).

$^1$H-NMR (400 MHz, DMSO-d6) δ [ppm]: 2.197 (13.69), 2.199 (16.00), 2.204 (13.66), 2.518 (0.46), 7.287 (1.15), 7.294 (2.26), 7.302 (1.13), 7.308 (5.47), 7.314 (4.39), 7.325 (1.21), 7.331 (5.10), 7.337 (3.84), 7.343 (0.92).

Intermediate 3-41

1-fluoro-3-isothiocyanato-2-(trifluoromethyl)benzene

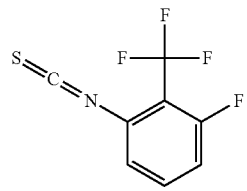 [SMILES: Fc1cccc(N=C=S)c1C(F)(F)F]

According to the method described for intermediate 3-1 and using 3-fluoro-2-(trifluoromethyl)aniline (1.00 g, 5.58 mmol) as a starting material, the title compound was prepared 1.35 g (75% purity, 82% yield).

$^1$H-NMR (400 MHz, DMSO-d6) δ [ppm]: 1.231 (0.73), 2.331 (1.42), 2.518 (7.57), 2.523 (4.91), 5.933 (1.83), 6.385 (2.00), 6.405 (2.21), 6.415 (2.04), 6.435 (2.07), 6.609 (3.59), 6.611 (3.42), 6.630 (3.84), 6.632 (3.80), 7.202 (1.38), 7.224 (2.66), 7.240 (2.70), 7.260 (1.28), 7.488 (5.74), 7.491 (7.57), 7.493 (5.84), 7.510 (6.98), 7.512 (9.54), 7.514 (8.78), 7.517 (7.81), 7.519 (8.43), 7.538 (6.67), 7.540 (9.23), 7.542 (6.53), 7.599 (12.89), 7.600 (12.86), 7.619 (16.00), 7.621 (15.55), 7.779 (6.32), 7.781 (5.94), 7.794 (6.70), 7.795 (6.81), 7.800 (10.40), 7.815 (10.30), 7.821 (5.32), 7.835 (4.60), 7.837 (4.39).

LC-MS (method 2): R, =1.40 min; MS (ESIpos): m/z=222 [M+H]$^+$

Intermediate 3-42

1-isothiocyanato-2-(trifluoromethyl)benzene

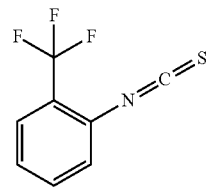

According to the method described for intermediate 3-1 and using 2-(trifluoromethyl)aniline (4.6 ml, 97% purity, 36 mmol) as a starting material, the title compound was prepared 6.80 g (60% purity, 57% yield).

$^1$H-NMR (400 MHz, DMSO-d6) δ [ppm]: 2.518 (1.74), 2.523 (1.08), 5.017 (3.83), 6.605 (0.97), 6.623 (1.74), 6.625 (1.80), 6.641 (0.80), 6.642 (1.10), 6.829 (1.95), 6.850 (2.10), 7.248 (0.87), 7.250 (0.98), 7.252 (0.88), 7.268 (1.62), 7.287 (0.81), 7.289 (0.92), 7.290 (0.91), 7.301 (1.85), 7.305 (1.74), 7.314 (0.74), 7.321 (1.82), 7.324 (1.69), 7.553 (3.39), 7.554 (4.45), 7.556 (4.89), 7.559 (3.66), 7.572 (9.30), 7.574 (10.37), 7.576 (9.50), 7.591 (4.79), 7.594 (6.18), 7.596 (4.97), 7.636 (0.53), 7.655 (0.54), 7.668 (0.40), 7.683 (0.90), 7.700 (0.87), 7.724 (4.80), 7.727 (5.42), 7.744 (16.00), 7.748 (13.39), 7.758 (9.49), 7.760 (10.01), 7.777 (8.71), 7.778 (9.85), 7.796 (3.72), 7.798 (3.85), 7.817 (0.60), 7.834 (11.34), 7.837 (10.84), 7.853 (9.62), 7.856 (9.30), 8.758 (0.89), 9.729 (0.40).

Intermediate 3-44

2-chloro-1-fluoro-4-isothiocyanato-3-methoxybenzene

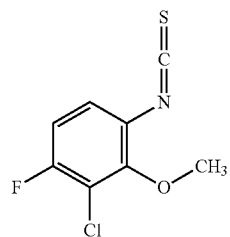

According to the method described for intermediate 3-1 and using 3-chloro-4-fluoro-2-methoxyaniline (4.59 g, 26.1 mmol) as a starting material, the title compound was prepared 5.42 g (95% purity, 91% yield).

$^1$H-NMR (400 MHz, DMSO-d6) δ [ppm]: 3.934 (16.00), 7.287 (1.04), 7.309 (1.91), 7.331 (1.55), 7.423 (1.37), 7.437 (1.54), 7.445 (0.99), 7.460 (1.12).

Intermediate 3-78

2-bromo-1-chloro-3-isothiocyanatobenzene

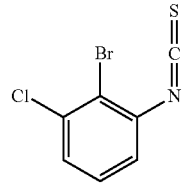 [SMILES: S=C=Nc1cccc(Cl)c1Br]

According to the method described for intermediate 3-1 and using 2-bromo-3-chloroaniline (5.00 g, 24.2 mmol) as a starting material, the title compound was prepared 6.08 g (99% purity, 100% yield).

$^1$H-NMR (400 MHz, DMSO-d6) δ [ppm]: 2.518 (1.86), 2.522 (1.27), 7.443 (6.36), 7.463 (16.00), 7.483 (12.28), 7.530 (9.89), 7.533 (12.44), 7.550 (6.35), 7.554 (6.25), 7.616 (10.66), 7.620 (9.74), 7.636 (7.63), 7.640 (7.42).

LC-MS (method 2): R$_t$=1.51 min; MS (ESIpos): m/z=249 [M+H]$^+$

Syntheses of Intermediate 4 Compounds

Intermediate 4-1 tert-butyl 5-[(3,5-difluorophenyl)carbamothioyl]-4-hydroxy-6-oxo-3,6-dihydropyridine-1(2H)-carboxylate

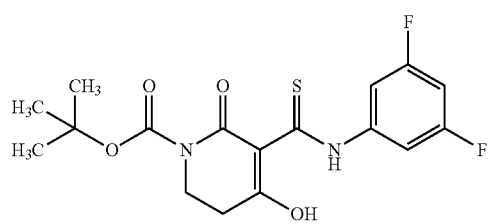 [SMILES: CC(C)(C)OC(=O)N1CCC(O)=C(C(=S)Nc2cc(F)cc(F)c2)C1=O]

To an ice-cooled solution of tert-butyl 2,4-dioxopiperidine-1-carboxylate (5.93 g, 27.8 mmol) and 1,3-difluoro-5-isothiocyanatobenzene (4.76 g, 27.8 mmol) in MeCN (40 ml) was added dropwise DBU (6.2 ml, 42 mmol). The reaction mixture solidified and was sonicated to allow stirring. The reaction was stirred at 0° C. for 16 h. The reaction mixture was added to ice-water (200 ml.) containing conc. HCl (5 mL). The resulting solid was collected by filtration, washed with water and dried in vacuo at 60° C. for 5 h to give the titled compound 10.4 g (97% yield).

$^1$H-NMR (400 MHz, DMSO-d$_6$): δ [ppm]=13.68 (br s, 1H), 12.53 (br s, 1H), 7.64 (brd, 2H), 7.14-7.31 (m, 1H), 3.75 (brt, 2H), 2.74 (brt, 2H), 1.46 (s, 9H).

Intermediate 4-2 tert-butyl 5-{[2-(difluoromethoxy)phenyl]carbamothioyl}-4-hydroxy-6-oxo-3,6-dihydropyridine-1(2H)-carboxylate

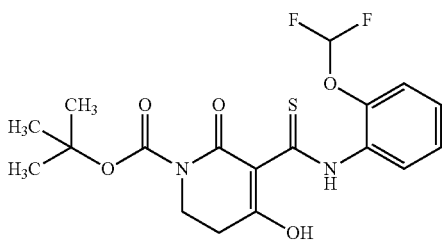 [SMILES: CC(C)(C)OC(=O)N1CCC(O)=C(C(=S)Nc2ccccc2OC(F)F)C1=O]

To an ice-cooled mixture of tert-butyl 2,4-dioxopiperidine-1-carboxylate (10.6 g, 49.7 mmol) and 1-(difluoromethoxy)-2-isothiocyanatobenzene (Intermediate 3-1, 10.0 g, 49.7 mmol) in MeCN (100 ml) was added DBU (11 ml, 75 mmol) slowly. The reaction was stirred at 0° C. for 16 h. The reaction mixture was concentrated to ½ volume and the reaction mixture added to 1M HCl (500 ml) and extracted with EtOAc. The organics were combined and concentrated in vacuo. The residue was purified by silica chromatography (EtOAc:Hexane), to give the title compound 16.4 g (80% yield).

$^1$H-NMR (400 MHz, DMSO-d6): Shift [ppm]=13.32 (br s, 1H), 7.67 (d, 1H), 6.99-7.47 (m, 4H), 3.75-3.77 (m, 1H), 3.72-3.88 (m, 1H), 2.89 (br t, 2H), 1.48 (s, 9H).

Intermediate 4-3 tert-butyl 5-[(2-bromo-3-fluorophenyl)carbamothioyl]-4-hydroxy-6-oxo-3,6-dihydropyridine-1(2H)-carboxylate

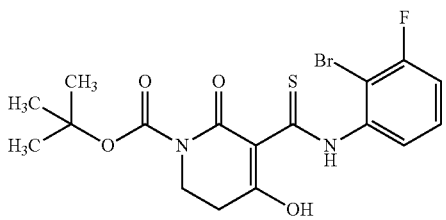 [SMILES: CC(C)(C)OC(=O)N1CCC(O)=C(C(=S)Nc2cccc(F)c2Br)C1=O]

Using an analogous method as described for Intermediate 4-1, 2 tert-butyl 2,4-dioxopiperidine-1-carboxylate (5.12 g, 24.0 mmol) and 2-bromo-1-fluoro-3-isothiocyanatobenzene (5.57 g, 24.0 mmol—Ellanova Laboratories) as the starting materials, the title compound was prepared 10.3 g (87% yield).

Intermediate 4-4 tert-butyl 4-hydroxy-5-[(2-methoxyphenyl)carbamothioyl]-6-oxo-3,6-dihydropyridine-1(2H)-carboxylate

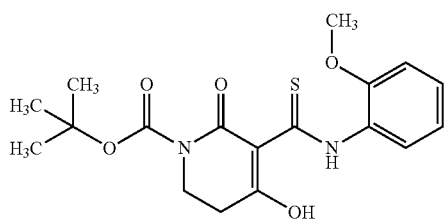 [SMILES: COc1ccccc1NC(=S)C1=C(O)CCN(C(=O)OC(C)(C)C)C1=O]

Using an analogous method as described for Intermediate 4-1, 2 tert-butyl 2,4-dioxopiperidine-1-carboxylate (1.81 g, 8.47 mmol) and 1-isothiocyanato-2-methoxybenzene (1.40 g, 8.47 mmol) as the starting materials, the title compound was prepared 952 mg (28% yield) after silica chromatography (Hexane:EtOAc).

$^1$H-NMR (400 MHz, DMSO-$d_6$): δ [ppm]=13.33 (brs, 1H), 7.69 (brd, 1H), 7.32 (t, 1H), 7.15 (d, 1H), 7.00 (t, 1H), 3.75-3.85 (m, 5H), 2.87 (br t, 2H), 1.48 (s, 9H).

Intermediate 4-5 tert-butyl 4-hydroxy-6-oxo-5-{[2-(trifluoromethoxy)phenyl]carbamothioyl}-3,6-dihydropyridine-1(2H)-carboxylate

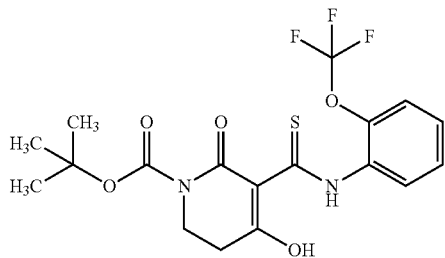 [SMILES: CC(C)(C)OC(=O)N1CCC(O)=C(C(=S)Nc2ccccc2OC(F)(F)F)C1=O]

Using an analogous method as described for Intermediate 4-1, 2 tert-butyl 2,4-dioxopiperidine-1-carboxylate (920 mg, 4.32 mmol) and 2-isothiocyanatophenyl trifluoromethyl ether (946 mg, 4.32 mmol) as the starting materials, the title compound was prepared 1.09 g (56% yield) after silica chromatography (Hexane:EtOAc).

$^1$H-NMR (400 MHz, DMSO-$d_6$): δ [ppm]=16.42 (br s, 1H), 13.50 (br s, 1H), 7.76-7.83 (m, 1H), 7.44-7.55 (m, 3H), 3.78 (t, 2H), 2.90 (t, 2H), 1.46-1.54 (m, 9H).

Intermediate 4-6 tert-butyl 5-{[2-(2,2-difluoroethyl)phenyl]carbamothioyl}-4-hydroxy-6-oxo-3,6-dihydropyridine-1(2H)-carboxylate

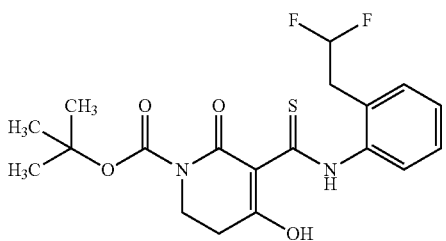 [SMILES: CC(C)(C)OC(=O)N1CCC(O)=C(C(=S)Nc2ccccc2CC(F)F)C1=O]

Using an analogous method as described for Intermediate 4-1, 2 tert-butyl 2,4-dioxopiperidine-1-carboxylate (2.14 g, 10.0 mmol) and 1-(2,2-difluoroethyl)-2-isothiocyanatobenzene (2.00 g, 10.0 mmol) as the starting materials, the title compound was prepared 3.78 g (87% yield).

$^1$H-NMR (400 MHz, DMSO-$d_6$): δ [ppm]=15.43 (br s, 1H), 12.70 (br s, 1H), 7.34-7.47 (m, 3H), 7.26 (m, 1H), 6.23 (tt, 1H), 3.78 (t, 2H), 3.13 (m, 2H), 2.83 (t, 2H), 1.47 (s, 9H).

Intermediate 4-7 tert-butyl 5-[(3-fluoro-2-methoxyphenyl)carbamothioyl]-4-hydroxy-6-oxo-3,6-dihydropyridine-1(2H)-carboxylate

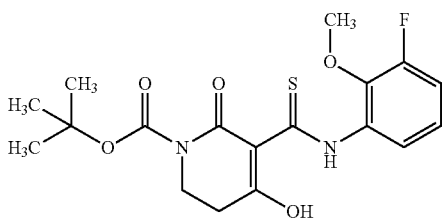 [SMILES: COc1c(F)cccc1NC(=S)C1=C(O)CCN(C(=O)OC(C)(C)C)C1=O]

Using an analogous method as described for Intermediate 4-1, 2 tert-butyl 2,4-dioxopiperidine-1-carboxylate (7.26 g, 34.1 mmol) and 1-fluoro-3-isothiocyanato-2-methoxybenzene (6.24 g, 34.1 mmol) as the starting materials, the title compound was prepared 9.49 g (67% yield) after slurring the product in MeOH and filtering the solid and drying in vacuo.

$^1$H-NMR (400 MHz, DMSO-$d_6$): δ [ppm]=13.37 (br s, 1H), 7.58 (br d, 1H), 7.23-7.30 (m, 1H), 7.09-7.20 (m, 1H), 3.84-3.88 (m, 3H), 3.78 (t, 2H), 3.17 (s, 3H), 2.88 (br t, 2H), 1.42-1.51 (m, 9H).

Intermediate 4-8 tert-butyl 5-{[2-(difluoromethoxy)-3-fluorophenyl]carbamothioyl}-4-hydroxy-6-oxo-3,6-dihydropyridine-1(2H)-carboxylate

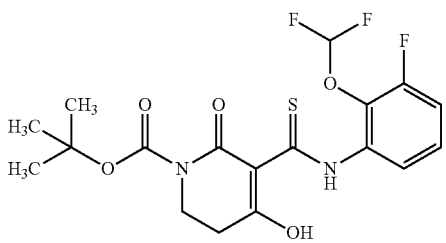 [SMILES: CC(C)(C)OC(=O)N1CCC(O)=C(C(=S)Nc2cccc(F)c2OC(F)F)C1=O]

Using an analogous method as described for Intermediate 4-1, 2 tert-butyl 2,4-dioxopiperidine-1-carboxylate (5.80 g, 27.2 mmol) and 2-(difluoromethoxy)-1-fluoro-3-isothiocyanatobenzene (5.96 g, 27.2 mmol) as the starting materials, the title compound was prepared 10.7 g (82% yield).

¹H-NMR (400 MHz, DMSO-d₆): δ [ppm]=12.95-13.73 (m, 1H), 7.52 (br s, 1H), 7.36-7.48 (m, 2H), 6.87-7.32 (m, 1H), 3.76 (br t, 2H), 2.85 (br s, 2H), 1.42-1.51 (m, 9H).

Intermediate 4-9 tert-butyl 5-[(3-fluoro-2-methylphenyl)carbamothioyl]-4-hydroxy-6-oxo-3,6-dihydropyridine-1(2H)-carboxylate

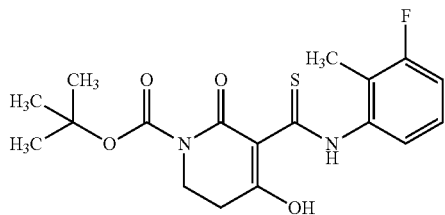 [SMILES: Cc1c(F)cccc1NC(=S)C1=C(O)CCN(C(=O)OC(C)(C)C)C1=O]

Using an analogous method as described for Intermediate 4-1, 2 tert-butyl 2,4-dioxopiperidine-1-carboxylate (8.19 g, 38.4 mmol) and 1-fluoro-3-isothiocyanato-2-methylbenzene (6.42 g, 38.4 mmol)) as the starting materials, the title compound was prepared 11.1 g (72% yield) after slurring the product in MeOH and filtering the solid and drying in vacuo.

¹H-NMR (400 MHz, DMSO-d₆): δ [ppm]=15.81 (br s, 1H), 12.78 (br s, 1H), 7.27-7.34 (m, 1H), 7.19 (t, 1H), 7.08 (d, 1H), 3.78 (t, 2H), 2.85 (t, 2H), 2.07-2.11 (m, 3H), 1.48 (s, 9H).

Intermediate 4-10 tert-butyl 5-{[2-(2,2-difluoroethyl)-3-fluorophenyl]carbamothioyl}-4-hydroxy-6-oxo-3,6-dihydropyridine-1(2H)-carboxylate

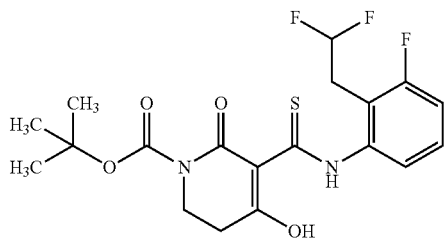 [SMILES: CC(C)(C)OC(=O)N1CCC(O)=C(C(=S)Nc2cccc(F)c2CC(F)F)C1=O]

Using an analogous method as described for Intermediate 4-1, 2 tert-butyl 2,4-dioxopiperidine-1-carboxylate (7.85 g, 36.8 mmol) and 2-(2,2-difluoroethyl)-1-fluoro-3-isothiocyanatobenzene (8 g, 36.8 mmol) as the starting materials, the title compound was prepared 12.1 g (76% yield) after slurring the product in MeOH and filtering the solid and drying in vacuo.

¹H-NMR (400 MHz, DMSO-d₆): δ [ppm]=15.12 (br s, 1H), 12.74 (br s, 1H), 7.41-7.49 (m, 1H), 7.27 (t, 1H), 7.16 (d, 1H), 6.22 (br t, 1H), 6.21 (brt, 1H), 4.10 (br s, 1H), 3.77 (t, 2H), 3.11-3.25 (m, 5H), 2.80 (brt, 2H), 1.47 (s, 9H).

Intermediate 4-11 tert-butyl 5-{[3-fluoro-2-(prop-2-en-1-yloxy)phenyl]carbamothioyl}-4-hydroxy-6-oxo-3,6-dihydropyridine-1(2H)-carboxylate

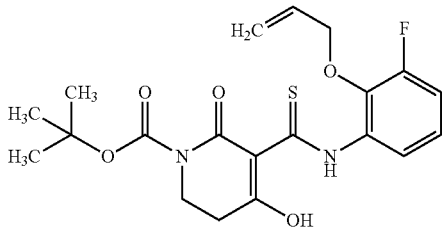 [SMILES: C=CCOc1c(F)cccc1NC(=S)C1=C(O)CCN(C(=O)OC(C)(C)C)C1=O]

Using an analogous method as described for Intermediate 4-1, 2 tert-butyl 2,4-dioxopiperidine-1-carboxylate (1.31 g, 6.17 mmol) and 2-fluoro-6-isothiocyanatophenyl prop-2-en-1-yl ether (1.29 g, 6.17 mmol) as the starting materials, the title compound was prepared 1.59 g (58% yield) after slurring the product in MeOH and filtering the solid and drying in vacuo.

¹H-NMR (400 MHz, DMSO-d₆): δ [ppm]=13.41 (br s, 1H), 7.61 (br d, 1H), 7.08-7.29 (m, 2H), 5.99-6.09 (m, 1H), 5.30-5.39 (m, 1H), 5.18-5.25 (m, 1H), 4.57 (d, 2H), 3.77 (t, 2H), 2.82-2.93 (m, 2H), 1.44-1.51 (m, 9H).

Intermediate 4-12 tert-butyl 5-[(2-ethoxy-3-fluorophenyl)carbamothioyl]-4-hydroxy-6-oxo-3,6-dihydropyridine-1(2H)-carboxylate

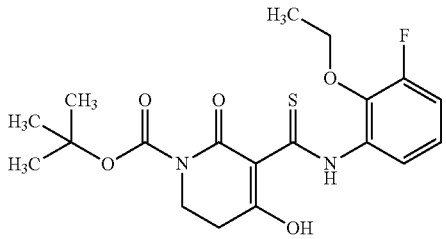 [SMILES: CCOc1c(F)cccc1NC(=S)C1=C(O)CCN(C(=O)OC(C)(C)C)C1=O]

Using an analogous method as described for Intermediate 4-1, 2 tert-butyl 2,4-dioxopiperidine-1-carboxylate (4.97 g, 23.3 mmol) and 2-ethoxy-1-fluoro-3-isothiocyanatobenzene (4.60 g, 23.3 mmol) as the starting materials, the title compound was prepared 6.74 g (67% yield) after slurring the product in MeOH and filtering the solid and drying in vacuo.

¹H-NMR (400 MHz, DMSO-d₆): δ [ppm]=13.54 (brs, 1H), 7.73 (d, 1H), 7.07-7.28 (m, 2H), 4.05-4.14 (m, 2H), 3.78 (t, 2H), 3.33 (br s, 2H), 2.82-2.94 (m, 2H), 1.43-1.51 (m, 9H), 1.31 (t, 3H).

Intermediate 4-13 tert-butyl 5-{[2-(2,2-difluoroethoxy)-3-fluorophenyl]carbamothioyl}-4-hydroxy-6-oxo-3,6-dihydropyridine-1(2H)-carboxylate

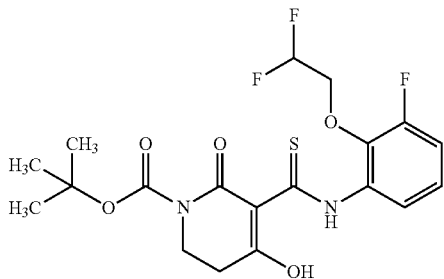 [SMILES: CC(C)(C)OC(=O)N1CCC(O)=C(C(=S)Nc2cccc(F)c2OCC(F)F)C1=O]

Using an analogous method as described for Intermediate 4-1, 2 tert-butyl 2,4-dioxopiperidine-1-carboxylate (3.56 g, 16.7 mmol) and 2-(2,2-difluoroethoxy)-1-fluoro-3-isothiocyanatobenzene (3.89 g, 16.7 mmol) as the starting materials, the title compound was prepared 5.48 g (70% yield) after slurring the product in MeOH and filtering the solid and drying in vacuo.

$^1$H-NMR (400 MHz, DMSO-d$_6$): δ [ppm]=16.08 (br s, 1H), 13.20 (br s, 1H), 7.57 (brd, 1H), 7.12-7.34 (m, 2H), 6.34 (tt, 1H), 4.28-4.46 (m, 2H), 3.77 (t, 2H), 2.87 (br t, 2H), 1.42-1.51 (m, 9H).

Intermediate 4-14 tert-butyl 5-[(3,4-difluoro-2-methoxyphenyl)carbamothioyl]-4-hydroxy-6-oxo-3,6-dihydropyridine-1(2H)-carboxylate

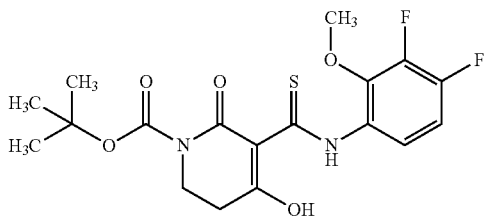 [SMILES: COc1c(NC(=S)C2=C(O)CCN(C(=O)OC(C)(C)C)C2=O)ccc(F)c1F]

Using an analogous method as described for Intermediate 4-1, 2 tert-butyl 2,4-dioxopiperidine-1-carboxylate (6.55 g, 30.7 mmol) and 1,2-difluoro-4-isothiocyanato-3-methoxybenzene (6.18 g, 30.7 mmol) as the starting materials, the title compound was prepared 9.03 g (67% yield) after slurring the product in MeOH and filtering the solid and drying in vacuo.

$^1$H-NMR (400 MHz, DMSO-d$_6$): δ [ppm]=16.28 (br s, 1H), 13.15 (br s, 1H), 7.42-7.48 (m, 1H), 7.20-7.29 (m, 1H), 3.92 (d, 3H), 3.73-3.83 (m, 2H), 2.88 (t, 2H), 1.44-1.53 (m, 9H).

Intermediate 4-15 tert-butyl 5-[(3,5-difluoro-2-methoxyphenyl)carbamothioyl]-4-hydroxy-6-oxo-3,6-dihydropyridine-1(2H)-carboxylate

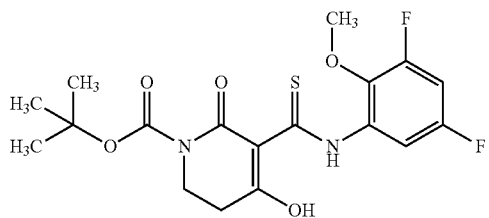 [SMILES: COc1c(F)cc(F)cc1NC(=S)C1=C(O)CCN(C(=O)OC(C)(C)C)C1=O]

Using an analogous method as described for Intermediate 4-1, 2 tert-butyl 2,4-dioxopiperidine-1-carboxylate (6.27 g, 29.4 mmol) and 1,5-difluoro-3-isothiocyanato-2-methoxybenzene (5.92 g, 29.4 mmol) as the starting materials, the title compound was prepared 9.50 g (74% yield) after slurring the product in MeOH and filtering the solid and drying in vacuo.

$^1$H-NMR (400 MHz, DMSO-d$_6$): δ [ppm]=16.19 (br s, 1H), 13.49 (br s, 1H), 7.69 (brd, 1H), 7.36 (m, 1H), 3.83 (s, 3H), 3.78 (t, 2H), 2.89 (t, 2H), 1.48 (s, 9H).

Intermediate 4-34 tert-butyl 5-[(2,3-dichlorophenyl)carbamothioyl]-4-hydroxy-6-oxo-3,6-dihydropyridine-1(2H)-carboxylate

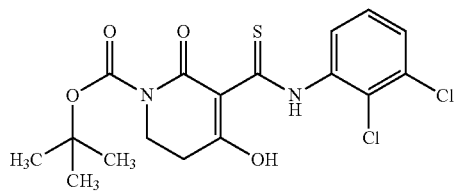

1,2-dichloro-3-isothiocyanatobenzene (5.00 g, 24.5 mmol) and tert-butyl 2,4-dioxopiperidine-1-carboxylate (5.22 g, 24.5 mmol) were solubilised in 55 ml. acetonitrile, 1,8-diazabicyclo(5.4.0)undec-7-en (5.5 ml, 37 mmol) was added carefully at 0° C. under argon atmosphere and the mixture was stirred overnight at rt. The reaction mixture was diluted with hydrogen chloride solution (1N in water) and stirred for 30 min at rt. The resulting solid was filtered off, the filter-cake was washed with water and dried at 50° C. in vacuo oven overnight to give 9.40 g of the title compound (92% yield).

$^1$H-NMR (400 MHz, DMSO-d6) δ [ppm]: 1.467 (16.00), 1.484 (0.56), 1.622 (0.34), 1.644 (0.25), 1.661 (0.20), 1.674 (0.17), 1.898 (0.19), 1.913 (0.31), 1.927 (0.19), 2.075 (0.20), 2.327 (0.18), 2.518 (0.60), 2.523 (0.39), 2.621 (0.30), 2.647 (0.32), 2.665 (0.24), 2.669 (0.29), 2.673 (0.25), 3.249 (0.25), 3.459 (0.23), 3.473 (0.39), 3.487 (0.22), 3.538 (0.28), 3.561 (0.29), 3.727 (0.50), 7.357 (0.17), 7.377 (0.36), 7.383 (0.28), 7.397 (0.28), 7.544 (0.27), 7.547 (0.33), 7.560 (0.29), 7.564 (0.31), 7.568 (0.25), 7.580 (0.18).

LC-MS (method 2): R$_t$=0.70 min; MS (ESIpos): m/z=416 [M−H]$^-$

Intermediate 4-32 tert-butyl 5-[(3-chloro-2-methoxyphenyl)carbamothioyl]-4-hydroxy-6-oxo-3,6-dihydropyridine-1(2H)-carboxylate

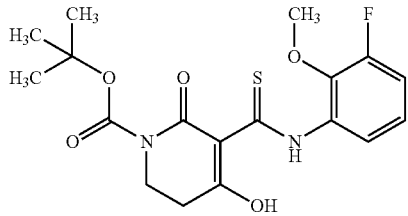 [SMILES: COc1c(F)cccc1NC(=S)C1=C(O)CCN(C(=O)OC(C)(C)C)C1=O]

According to the method described for Intermediate 4-34 and using 1-chloro-3-isothiocyanato-2-methoxybenzene (intermediate 3-32, 4.00 g, 20.0 mmol) as a starting material, the title compound was prepared (additional flash chromatography) 6.54 g (90% purity, 71% yield).

$^1$H-NMR (400 MHz, DMSO-d6) δ [ppm]: 1.154 (1.09), 1.172 (2.39), 1.190 (1.20), 1.484 (16.00), 1.496 (0.78), 1.987 (4.14), 2.867 (0.45), 2.883 (0.85), 2.900 (0.48), 3.336 (0.71), 3.669 (0.68), 3.774 (8.05), 3.787 (1.07), 3.799 (0.50), 3.803 (0.56), 4.017 (0.90), 4.035 (0.89), 7.201 (0.52), 7.221 (1.13), 7.241 (0.64), 7.453 (0.62), 7.457 (0.67), 7.474 (0.55), 7.478 (0.54), 7.716 (0.46), 7.718 (0.46), 7.736 (0.43), 7.738 (0.41).

LC-MS (method 2): $R_t$=1.49 min; MS (ESIpos): m/z=413 [M+H]$^+$

Intermediate 4-35 tert-butyl 5-[(2-ethyl-3-fluorophenyl)carbamothioyl]-4-hydroxy-6-oxo-3,6-dihydropyridine-1(2H)-carboxylate

According to the method described for Intermediate 4-34 and using 2-ethyl-1-fluoro-3-isothiocyanatobenzene (intermediate 3-35, 3.00 g, 16.6 mmol) as a starting material, the title compound was prepared 5.46 g (95% purity, 79% yield).

$^1$H-NMR (400 MHz, DMSO-d6) δ [ppm]: 1.066 (1.02), 1.085 (2.41), 1.104 (1.06), 1.477 (16.00), 1.486 (1.04), 2.074 (0.65), 2.518 (1.12), 2.522 (0.92), 2.538 (0.61), 2.858 (0.69), 3.771 (0.55), 3.787 (0.98), 3.803 (0.50), 7.092 (0.50), 7.112 (0.55), 7.186 (0.45), 7.311 (0.44), 7.327 (0.41).

LC-MS (method 2): $R_t$=0.72 min; MS (ESIpos): m/z=395 [M+H]$^+$

Intermediate 4-36 tert-butyl 5-[(3-chloro-2-methylphenyl)carbamothioyl]-4-hydroxy-6-oxo-3,6-dihydropyridine-1(2H)-carboxylate

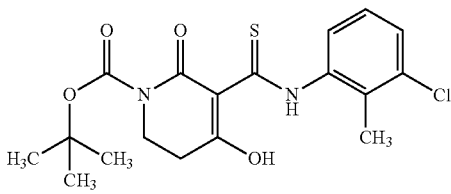 [SMILES: Cc1c(Cl)cccc1NC(=S)C1=C(O)CCN(C(=O)OC(C)(C)C)C1=O]

According to the method described for intermediate 4-34 and using 1-chloro-3-isothiocyanato-2-methylbenzene (CAS: 19241-35-1; 2.50 g, 13.6 mmol) as a starting material, the title compound was prepared 4.68 g (90% purity, 78% yield).

$^1$H-NMR (400 MHz, DMSO-d6) δ [ppm]: 1.478 (16.00), 2.198 (4.35), 2.832 (0.48), 2.848 (0.92), 2.864 (0.51), 3.769 (0.53), 3.785 (0.95), 3.801 (0.50), 7.180 (0.46), 7.199 (0.63), 7.283 (0.42), 7.304 (0.76), 7.447 (0.62), 7.466 (0.48).

LC-MS (method 2): $R_t$=0.72 min; MS (ESIpos): m/z=397 [M+H]$^+$

Intermediate 4-37 tert-butyl 5-[(2-bromo-3-fluorophenyl)carbamothioyl]-4-hydroxy-6-oxo-3,6-dihydropyridine-1(2H)-carboxylate

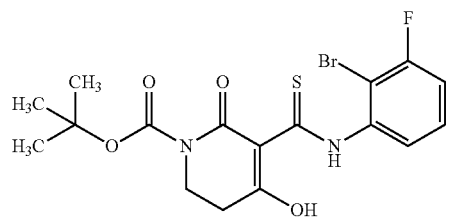 [SMILES: CC(C)(C)OC(=O)N1CCC(O)=C(C(=S)Nc2cccc(F)c2Br)C1=O]

According to the method described for intermediate 4-34 and using 2-bromo-1-fluoro-3-isothiocyanatobenzene (CAS: 364364-00-1, 5.57 g, 24.0 mmol) as a starting material, the title compound was prepared 10.3 g (90% purity, 87% yield).

$^1$H-NMR (400 MHz, DMSO-d6) δ [ppm]: 1.424 (0.24), 1.474 (16.00), 1.486 (0.76), 1.505 (0.17), 1.600 (0.20), 1.621 (0.23), 1.630 (0.22), 1.643 (0.19), 1.912 (0.23), 2.518 (0.34), 2.523 (0.23), 2.624 (0.19), 2.650 (0.20), 2.779 (0.22), 3.245 (0.19), 3.249 (0.19), 3.459 (0.17), 3.473 (0.29), 3.537 (0.20), 3.561 (0.21), 3.737 (0.38), 3.752 (0.61), 3.768 (0.35), 7.323 (0.21), 7.426 (0.20), 7.432 (0.25), 7.455 (0.41), 7.472 (0.27).

LC-MS (method 1): $R_t$=1.48 min; MS (ESIpos): m/z=446 [M+H]$^+$

Intermediate 4-38 tert-butyl 5-{[3-chloro-2-(difluoromethoxy)phenyl]carbamothioyl}-4-hydroxy-6-oxo-3,6-dihydropyridine-1(2H)-carboxylate

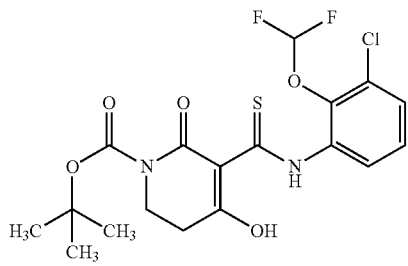 [SMILES: CC(C)(C)OC(=O)N1CCC(O)=C(C(=S)Nc2cccc(Cl)c2OC(F)F)C1=O]

According to the method described for Intermediate 4-34 and using 1-chloro-2-(difluoromethoxy)-3-isothiocyanatobenzene (2.44 g, 94% purity, 9.73 mmol) as a starting material, (additional flash chromatography) the title compound was prepared 2.11 g (82% purity, 38% yield).

$^1$H-NMR (400 MHz, DMSO-d6) δ [ppm]: 1.475 (16.00), 1.486 (2.52), 2.083 (3.92), 2.518 (3.00), 2.522 (1.89), 3.749 (0.52), 3.764 (0.85), 3.780 (0.52), 7.036 (0.76), 7.411 (0.52), 7.599 (0.44).

LC-MS (method 2): R, =0.75 min; MS (ESIpos): m/z=449 [M+H]$^+$

Intermediate 4-39 2 tert-butyl 5-[(2-chlorophenyl)carbamothioyl]-4-hydroxy-6-oxo-3,6-dihydropyridine-1(2H)-carboxylate

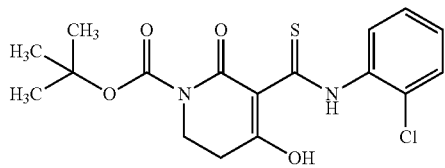 [SMILES: CC(C)(C)OC(=O)N1CCC(O)=C(C(=S)Nc2ccccc2Cl)C1=O]

According to the method described for Intermediate 4-34 and using 1-chloro-2-isothiocyanatobenzene (CAS: 2740-81-0, 6.4 ml, 49 mmol) as a starting material, the title compound was prepared 12.5 g (70% purity, 49% yield).

LC-MS (method 2): R$_f$=0.64 min; MS (ESIneg): m/z=381 [M−H]$^-$ $^1$H-NMR (400 MHz, DMSO-d6) δ [ppm]: 1.442 (16.00), 1.598 (0.47), 1.608 (0.46), 1.618 (0.46), 1.909 (0.59), 2.261 (0.47), 2.275 (0.74), 2.290 (0.49), 2.627 (0.42), 2.653 (0.44), 3.246 (0.60), 3.471 (0.66), 3.535 (0.46), 3.558 (0.50), 3.582 (0.49), 3.597 (0.72), 3.612 (0.45), 7.072 (0.42), 7.076 (0.41), 7.221 (0.40), 7.400 (0.64), 7.404 (0.66), 7.421 (0.60), 7.424 (0.55), 8.177 (0.48), 8.181 (0.48), 8.197 (0.47), 8.201 (0.44), 14.352 (0.78).

Intermediate 4-40 tert-butyl 5-[(3,5-difluoro-2-methylphenyl)carbamothioyl]-4-hydroxy-6-oxo-3,6-dihydropyridine-1(2H)-carboxylate

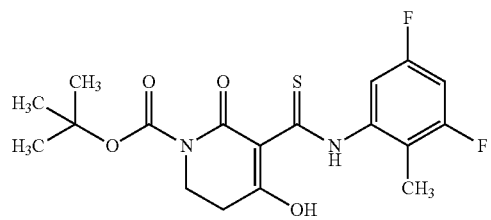 [SMILES: Cc1c(F)cc(F)cc1NC(=S)C1=C(O)CCN(C(=O)OC(C)(C)C)C1=O]

According to the method described for Intermediate 4-34 and using 1,5-difluoro-3-isothiocyanato-2-methylbenzene (intermediate 3-40, 3.10 g, 16.7 mmol) as a starting material, (additional flash chromatography) the title compound was prepared 5.24 g (95% purity, 75% yield).

$^1$H-NMR (400 MHz, DMSO-d6) δ [ppm]: 1.477 (16.00), 2.048 (2.23), 2.074 (0.72), 2.518 (0.65), 2.523 (0.41), 2.832 (0.48), 2.848 (0.91), 2.865 (0.50), 3.345 (0.39), 3.763 (0.57), 3.779 (1.02), 3.795 (0.52), 7.060 (0.30), 7.084 (0.30), 7.234 (0.19), 7.240 (0.20), 7.258 (0.34), 7.264 (0.34), 7.282 (0.19), 7.288 (0.19), 12.773 (0.22), 15.600 (0.21).

LC-MS (method 2): R$_f$=0.67 min; MS (ESIpos): m/z=399 [M+H]$^+$

Intermediate 4-41 tert-butyl 5-{[3-fluoro-2-(trifluoromethyl)phenyl]carbamothioyl}-4-hydroxy-6-oxo-3,6-dihydropyridine-1(2H)-carboxylate

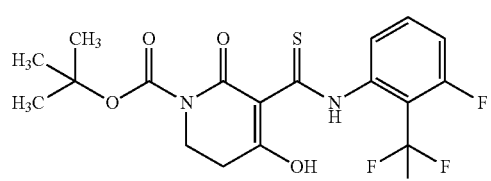

According to the method described for Intermediate 4-34 and using 1-fluoro-3-isothiocyanato-2-(trifluoromethyl)benzene (intermediate 3-41, 1.35 g, 91% purity, 5.55 mmol) as a starting material, the title compound was prepared 1.98 g (95% purity, 78% yield).

$^1$H-NMR (400 MHz, DMSO-d6) δ [ppm]: 1.479 (16.00), 2.518 (0.63), 2.895 (0.53), 3.769 (0.55), 3.785 (0.98), 3.802 (0.50), 7.287 (0.46), 7.306 (0.50).

LC-MS (method 2): R, =0.77 min; MS (ESIpos): m/z=435 [M+H]$^+$

Intermediate 4-42 tert-butyl 4-hydroxy-6-oxo-5-{[2-(trifluoromethyl)phenyl]carbamothioyl}-3,6-dihydropyridine-1(2H)-carboxylate

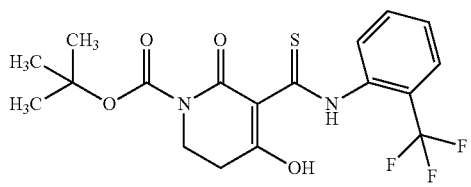 [SMILES: CC(C)(C)OC(=O)N1CCC(O)=C(C(=S)Nc2ccccc2C(F)(F)F)C1=O]

According to the method described for Intermediate 4-34 and using 1-isothiocyanato-2-(trifluoromethyl)benzene (intermediate 3-42, 6.80 g, 33.5 mmol) as a starting material, (additional flash chromatography) the title compound was prepared 5.01 g (76% purity, 28% yield).

$^1$H-NMR (400 MHz, DMSO-d6) δ [ppm]: 1.477 (16.00), 2.518 (0.45), 2.523 (0.30), 2.915 (0.41), 3.779 (0.50), 3.795 (0.91), 3.812 (0.47), 7.570 (0.57), 7.589 (0.85), 7.608 (0.24), 7.753 (0.26), 7.772 (0.39), 7.791 (0.18), 7.838 (0.44), 7.857 (0.38), 13.585 (0.19).

LC-MS (method 2): R, =0.67 min; MS (ESIneg): m/z=415 [M−H]$^-$

Intermediate 4-43 tert-butyl 5-{[3,5-difluoro-2-(difluoromethoxy)phenyl]carbamothioyl}-4-hydroxy-6-oxo-3,6-dihydropyridine-1(2H)-carboxylate

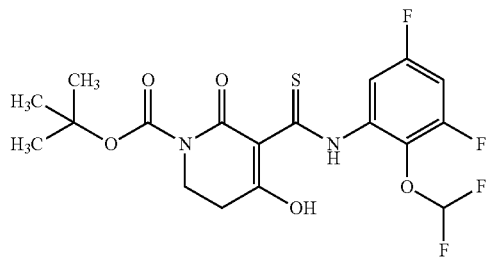 [SMILES: CC(C)(C)OC(=O)N1CCC(O)=C(C(=S)Nc2cc(F)cc(F)c2OC(F)F)C1=O]

To a solution of 1,5-difluoro-3-isothiocyanato-2-difluoromethoxybenzene (30.0 g, 149 mmol, 1.00 eq) in DCM (120 mL) was added DBU (45.4 g, 298 mmol, 45.0 mL, 2.00 eq) and compound tert-butyl 2,4-dioxopiperidine-1-carboxylate (32.0 g, 150 mmol, 1.01 eq). The mixture was stirred at 15° C. for 12 hrs. The reaction mixture was poured into 1 M HCl aqueous solution (250 mL) and extracted with DCM (150 mL*3). The combined organic layer was washed with brine (150 mL), dried over Na$_2$SO$_4$, filtered and concentrated. The yellow residue was purified by column chromatography (SiO$_2$, Petroleum ether: Ethyl acetate=10:1-5:1)). The title compound (25.0 g, 60.3 mmol, 40.5% yield) was obtained as yellow oil.

$^1$H-NMR (400 MHz, CDCl$_3$) δ [ppm]: 13.45-13.34 (m, 1H), 7.42-7.39 (m, 1H), 6.95-6.88 (m, 1H), 4.02-4.01 (m, 3H), 3.88-3.83 (m, 2H), 2.84-2.75 (m, 2H), 1.64-1.54 (m, 9H)

Intermediate 4-44 tert-butyl 5-[(3-chloro-4-fluoro-2-methoxyphenyl)carbamothioyl]-4-hydroxy-6-oxo-3,6-dihydropyridine-1(2H)-carboxylate

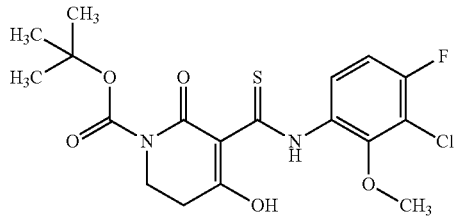 [SMILES: COc1c(NC(=S)C2=C(O)CCN(C(=O)OC(C)(C)C)C2=O)ccc(F)c1Cl]

According to the method described for Intermediate 4-34 and using 2-chloro-1-fluoro-4-isothiocyanato-3-methoxybenzene (intermediate 3-44, 5.42 g, 24.9 mmol) as a starting material, (additional flash chromatography) the title compound was prepared 5.96 g (95% purity, 53% yield).

LC-MS (method 1): R$_t$=1.50 min; MS (ESIpos): m/z=431 [M+H]$^+$ $^1$H-NMR (400 MHz, DMSO-d6) δ [ppm]: 1.154 (2.03), 1.172 (4.39), 1.190 (2.24), 1.482 (16.00), 1.987 (8.02), 2.518 (0.60), 2.876 (0.74), 2.893 (0.41), 3.769 (0.54), 3.785 (0.98), 3.801 (0.56), 3.813 (7.96), 3.999 (0.59), 4.017 (1.78), 4.035 (1.76), 4.053 (0.57), 7.280 (0.49), 7.303 (0.92), 7.325 (0.54).

Intermediate 4-45 tert-butyl 5-[(5-fluoro-2-methylphenyl)carbamothioyl]-4-hydroxy-6-oxo-3,6-dihydropyridine-1(2H)-carboxylate

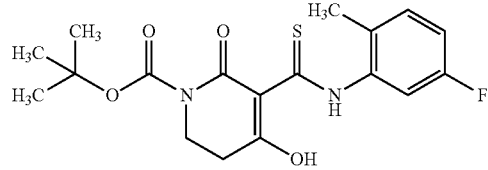 [SMILES: Cc1ccc(F)cc1NC(=S)C1=C(O)CCN(C(=O)OC(C)(C)C)C1=O]

According to the method described for Intermediate 4-34 and using 4-fluoro-2-isothiocyanato-1-methylbenzene (CAS: 175205-39-7, 1.00 g, 5.98 mmol) as a starting material, the title compound was prepared 2.10 g (94% purity, 92% yield).

$^1$H-NMR (400 MHz, DMSO-d6) δ [ppm]: 1.478 (16.00), 2.154 (3.37), 2.518 (0.39), 2.523 (0.27), 2.840 (0.43), 2.857 (0.83), 2.872 (0.46), 3.765 (0.54), 3.781 (0.97), 3.797 (0.50), 7.104 (0.16), 7.111 (0.22), 7.126 (0.35), 7.133 (0.48), 7.147 (0.20), 7.154 (0.30), 7.162 (0.32), 7.169 (0.27), 7.186 (0.31), 7.193 (0.26), 7.344 (0.34), 7.361 (0.38), 7.365 (0.35), 7.381 (0.29), 12.876 (0.21), 15.970 (0.31).

LC-MS (method 2): R, =0.64 min; MS (ESIpos): m/z=381 [M+H]$^+$

Intermediate 4-78 tert-butyl 5-[(2-bromo-3-chlorophenyl)carbamothioyl]-4-hydroxy-6-oxo-3,6-dihydropyridine-1(2H)-carboxylate

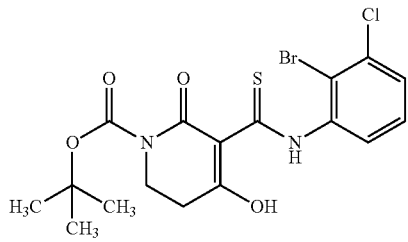 [SMILES: CC(C)(C)OC(=O)N1CCC(O)=C(C(=S)Nc2cccc(Cl)c2Br)C1=O]

According to the method described for Intermediate 4-34 and using 2-bromo-1-chloro-3-isothiocyanatobenzene (intermediate 3-78, 6.08 g, 24.5 mmol) as a starting material, (additional flash chromatography) the title compound was prepared 4.04 g (99% purity, 35% yield).

$^1$H-NMR (400 MHz, DMSO-d6) δ [ppm]: 1.155 (0.55), 1.172 (1.25), 1.190 (0.49), 1.483 (16.00), 1.987 (1.98), 2.518 (0.71), 2.522 (0.48), 2.907 (0.67), 3.778 (0.53), 3.794 (0.95), 3.811 (0.49), 4.017 (0.48), 4.034 (0.43), 7.431 (0.56), 7.434 (0.55), 7.471 (0.65), 7.491 (1.05), 7.511 (0.47), 7.628 (0.58), 7.631 (0.56), 7.648 (0.45), 7.652 (0.42).

LC-MS (method 2): R$_t$=0.71 min; MS (ESIpos): m/z=461 [M+H]$^+$

Syntheses of Intermediate 5 Compounds

Intermediate 5-1

N-(3,5-difluorophenyl)-4-hydroxy-2-oxo-1,2,5,6-tetrahydropyridine-3-carbothioamide

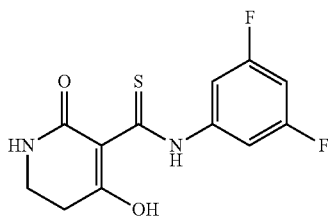 [SMILES: O=C1NCCC(O)=C1C(=S)Nc1cc(F)cc(F)c1]

To an-ice-cooled solution of tert-butyl 5-[(3,5-difluorophenyl)carbamothioyl]-4-hydroxy-6-oxo-3,6-dihydropyridine-1(2H)-carboxylate (Intermediate 4-1; 10.3 g, 26.9 mmol) in DCM (100 ml) was added TFA (10 ml). The reaction mixture was stirred at 0° C. for 4 h and concentrated. The residue was redissolved in DCM and washed with sat. NaHCO3, filtered through a hydrophobic filter and concentrated to give the titled compound 6.04 g (79% yield).

$^1$H-NMR (400 MHz, DMSO-d$_6$): δ [ppm]=16.33 (s, 1H), 14.45 (br s, 1H), 14.29-15.04 (m, 1H), 8.01-9.79 (m, 1H), 7.29 (br s, 2H), 7.18 (br s, 1H), 3.22-3.50 (m, 2H), 2.56-2.87 (m, 2H).

Intermediate 5-2

N-[2-(difluoromethoxy)phenyl]-4-hydroxy-2-oxo-1,2,5,6-tetrahydropyridine-3-carbothioamide

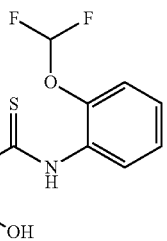

To an ice-cooled solution of tert-butyl 5-{[2-(difluoromethoxy)phenyl]carbamothioyl}-4-hydroxy-6-oxo-3,6-dihydropyridine-1(2H)-carboxylate (Intermediate 4-2, 16.4 g, 39.6 mmol) in DCM (30 ml) was added TFA (30 ml) and stirred for 15 min and allowed to warm to RT. The reaction mixture was poured onto a sat. NaHCO$_3$ solution and extracted with DCM. The organics were combined and filtered through hydrophobic filter and concentrated to give the title compound (12.43 g, 95%).

$^1$H-NMR (400 MHz, DMSO-d$_6$): δ [ppm]=14.04-14.82 (m, 1H), 8.05-9.60 (m, 1H), 7.74 (t, 1H), 6.88-7.50 (m, 5H), 3.43 (m, 1H), 3.26-3.32 (m, 1H), 2.78 (t, 1H), 2.58-2.68 (m, 1H).

Intermediate 5-3

N-(2-bromo-3-fluorophenyl)-4-hydroxy-2-oxo-1,2,5,6-tetrahydropyridine-3-carbothioamide

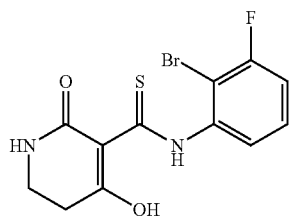 [SMILES: O=C1NCCC(O)=C1C(=S)Nc1cccc(F)c1Br]

Using an analogous method as described for Intermediate 5-2, intermediate 4-3 (10.0 g, 22.5 mmol) as the starting material, the title compound was prepared 4.66 g (54% yield).

$^1$H-NMR (400 MHz, DMSO-d$_6$): δ [ppm]=14.03-14.77 (m, 1H), 8.09-9.49 (m, 1H), 7.26-7.52 (m, 3H), 3.35-3.48 (m, 1H), 3.23-3.32 (m, 1H), 2.80 (brt, 1H), 2.59-2.70 (m, 1H).

Intermediate 5-4

4-hydroxy-N-(2-methoxyphenyl)-2-oxo-1,2,5,6-tetrahydropyridine-3-carbothioamide

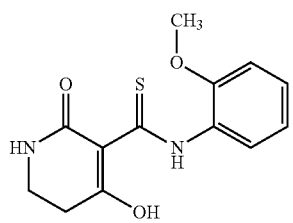

Using an analogous method as described for Intermediate 5-2, intermediate 4-4 (940 mg, 2.48 mmol) as the starting material, the title compound was prepared 680 mg (93% yield).

$^1$H-NMR (400 MHz, DMSO-d$_6$): δ [ppm]=14.35 (br s, 1H), 8.05 (br s, 1H), 7.72 (br d, 1H), 7.26 (dt, 1H), 7.08-7.16 (m, 1H), 6.92-7.02 (m, 1H), 3.80 (s, 3H), 3.37-3.45 (m, 1H), 3.25-3.32 (m, 1H), 2.75 (br t, 1H), 2.56-2.68 (m, 1H).

Intermediate 5-5

4-hydroxy-2-oxo-N-[2-(trifluoromethoxy)phenyl]-1,2,5,6-tetrahydropyridine-3-carbothioamide

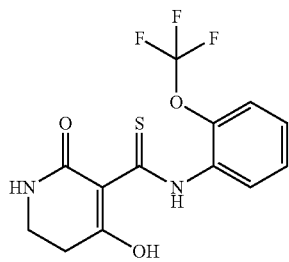 [SMILES: O=C1NCCC(O)=C1C(=S)Nc1ccccc1OC(F)(F)F]

Using an analogous method as described for Intermediate 5-2, intermediate 4-5 (1.02 g, 2.36 mmol) as the starting material, the title compound was prepared 785 mg (95% yield).

$^1$H-NMR (400 MHz, DMSO-d$_6$): δ [ppm]=16.40 (br d, 1H), 14.20-14.99 (m, 1H), 8.10-9.53 (m, 1H), 7.77-7.90 (m, 1H), 7.33-7.53 (m, 3H), 3.35-3.47 (m, 1H), 3.26-3.32 (m, 1H), 2.80 (br t, 1H), 2.64 (br t, 1H).

Intermediate 5-6

N-[2-(2,2-difluoroethyl)phenyl]-4-hydroxy-2-oxo-1,2,5,6-tetrahydropyridine-3-carbothioamide

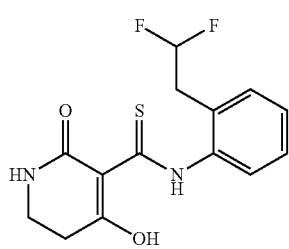 [SMILES: O=C1NCCC(O)=C1C(=S)Nc1ccccc1CC(F)F]

Using an analogous method as described for Intermediate 5-2, intermediate 4-6 (13.77 g, 9.13 mmol) as the starting material, the title compound was prepared 2.79 g (93% yield).

$^1$H-NMR (400 MHz, DMSO-d$_6$): δ [ppm]=13.82-14.53 (m, 1H), 7.93-9.50 (m, 1H), 7.25-7.47 (m, 4H), 6.20 (tt, 1H), 3.36-3.48 (m, 1H), 3.28-3.32 (m, 1H), 3.08 (m, 2H), 2.78 (br s, 1H), 2.59-2.72 (m, 1H).

Intermediate 5-7

N-(3-fluoro-2-methoxyphenyl)-4-hydroxy-2-oxo-1,2,5,6-tetrahydropyridine-3-carbothioamide

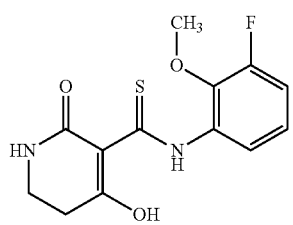 [SMILES: COc1c(F)cccc1NC(=S)C1=C(O)CCNC1=O]

Using an analogous method as described for Intermediate 5-2, intermediate 4-7 (9.49 g, 23.9 mmol) as the starting material, the title compound was prepared 6.98 g (89% yield).

$^1$H-NMR (400 MHz, DMSO-d$_6$): δ [ppm]=14.15-14.78 (m, 1H), 8.04-9.55 (m, 1H), 7.65 (t, 1H), 6.99-7.26 (m, 2H), 3.79-3.85 (m, 3H), 3.43 (m, 1H), 3.24-3.32 (m, 1H), 2.61-2.81 (m, 2H).

Intermediate 5-8

N-[2-(difluoromethoxy)-3-fluorophenyl]-4-hydroxy-2-oxo-1,2,5,6-tetrahydropyridine-3-carbothioamide

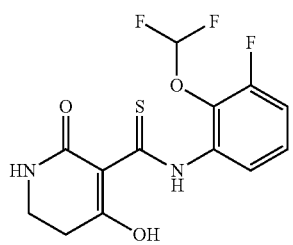 [SMILES: O=C1NCCC(O)=C1C(=S)Nc1cccc(F)c1OC(F)F]

Using an analogous method as described for Intermediate 5-2, intermediate 4-8 (10.7 g, 24.8 mmol) as the starting material, the title compound was prepared 7.38 g (89% yield).

$^1$H-NMR (400 MHz, DMSO-d$_6$): δ [ppm]=14.10-14.82 (m, 1H), 8.06-9.71 (m, 1H), 7.57 (br d, 1H), 7.32-7.43 (m, 2H), 6.89-7.31 (m, 1H), 3.35-3.46 (m, 1H), 3.26-3.32 (m, 1H), 2.79 (br t, 1H), 2.59-2.68 (m, 1H).

Intermediate 5-9

N-(3-fluoro-2-methylphenyl)-4-hydroxy-2-oxo-1,2,5,6-tetrahydropyridine-3-carbothioamide

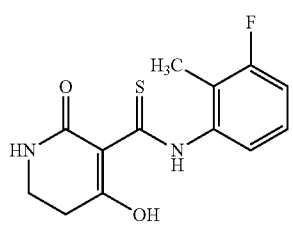 [SMILES: Cc1c(F)cccc1NC(=S)C1=C(O)CCNC1=O]

Using an analogous method as described for Intermediate 5-2, intermediate 4-9 (11.1 g, 29.1 mmol) as the starting material, the title compound was prepared 7.25 g (84% yield).

$^1$H-NMR (400 MHz, DMSO-d$_6$): δ [ppm]=13.89-14.53 (m, 1H), 7.88-9.66 (m, 1H), 7.24-7.33 (m, 1H), 7.11-7.20 (m, 2H), 3.40-3.46 (m, 1H), 3.27-3.33 (m, 1H), 2.78 (t, 1H), 2.59-2.68 (m, 1H), 2.06 (s, 3H).

Intermediate 5-10

N-[2-(2,2-difluoroethyl)-3-fluorophenyl]-4-hydroxy-2-oxo-1,2,5,6-tetrahydropyridine-3-carbothioamide

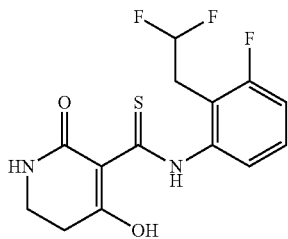

Using an analogous method as described for Intermediate 5-2, intermediate 4-10 (12.1 g, 28.0 mmol) as the starting material, the title compound was prepared 8.81 g (90% yield).

$^1$H-NMR (400 MHz, DMSO-d$_6$): δ [ppm]=13.77-14.57 (m, 1H), 7.98-9.51 (m, 1H), 7.38-7.49 (m, 1H), 7.15-7.30 (m, 2H), 6.21 (tt, 1H), 3.35-3.47 (m, 1H), 3.26-3.32 (m, 1H), 3.11 (m, 2H), 2.79 (brt, 1H), 2.60-2.69 (m, 1H).

Intermediate 5-11

N-[3-fluoro-2-(prop-2-en-1-yloxy)phenyl]-4-hydroxy-2-oxo-1,2,5,6-tetrahydropyridine-3-carbothioamide

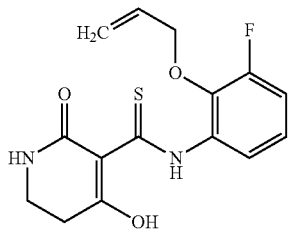 [SMILES: C=CCOc1c(F)cccc1NC(=S)C1=C(O)CCNC1=O]

Using an analogous method as described for Intermediate 5-2, intermediate 4-11 (1.58 g, 3.74 mmol) as the starting material, the title compound was prepared 1.17 g (87% yield).

$^1$H-NMR (400 MHz, DMSO-d$_6$): δ [ppm]=14.10-14.77 (m, 1H), 8.06-9.51 (m, 1H), 7.62 (br m, 1H), 6.99-7.25 (m, 2H), 5.95-6.17 (m, 1H), 5.18-5.39 (m, 2H), 4.51-4.61 (m, 2H), 3.36-3.46 (m, 1H), 3.26-3.32 (m, 1H), 2.73-2.84 (m, 1H), 2.58-2.66 (m, 1H).

Intermediate 5-12

N-(2-ethoxy-3-fluorophenyl)-4-hydroxy-2-oxo-1,2,5,6-tetrahydropyridine-3-carbothioamide

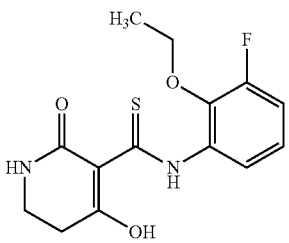 [SMILES: CCOc1c(F)cccc1NC(=S)C1=C(O)CCNC1=O]

Using an analogous method as described for Intermediate 5-2, intermediate 4-12 (6.97 g, 17.0 mmol) as the starting material, the title compound was prepared 5.20 g (94% yield).

$^1$H-NMR (400 MHz, DMSO-d$_6$): δ [ppm]=14.09-14.93 (m, 1H), 8.08-9.65 (m, 1H), 7.71 (m, 1H), 6.95-7.24 (m, 2H), 4.00-4.12 (m, 2H), 3.42 (m, 1H), 3.26-3.32 (m, 1H), 2.78 (t, 1H), 2.60-2.71 (m, 1H), 1.21-1.32 (m, 3H).

Intermediate 5-13

N-[2-(2,2-difluoroethoxy)-3-fluorophenyl]-4-hydroxy-2-oxo-1,2,5,6-tetrahydropyridine-3-carbothioamide

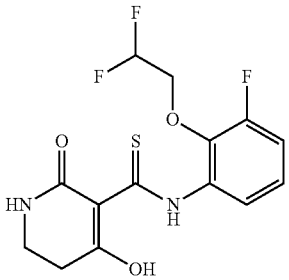 [SMILES: O=C1NCCC(O)=C1C(=S)Nc1cccc(F)c1OCC(F)F]

Using an analogous method as described for Intermediate 5-2, intermediate 4-13 (5.48 g, 12.3 mmol) as the starting material, the title compound was prepared 3.95 g (84% yield).

$^1$H-NMR (400 MHz, DMSO-d$_6$): δ [ppm]=14.07-14.80 (m, 1H), 8.09-9.53 (m, 1H), 7.54-7.66 (m, 1H), 7.06-7.31 (m, 2H), 6.07-6.60 (m, 1H), 4.22-4.39 (m, 2H), 3.35-3.46 (m, 1H), 3.25-3.32 (m, 1H), 2.79 (brt, 1H), 2.60-2.73 (m, 1H).

Intermediate 5-14

N-(3,4-difluoro-2-methoxyphenyl)-4-hydroxy-2-oxo-1,2,5,6-tetrahydropyridine-3-carbothioamide

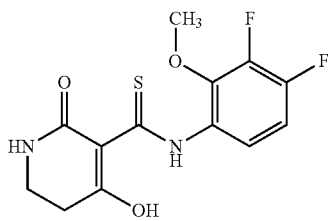 [SMILES: COc1c(NC(=S)C2=C(O)CCNC2=O)ccc(F)c1F]

Using an analogous method as described for Intermediate 5-2, intermediate 4-14 (9.03 g, 21.8 mmol) as the starting material, the title compound was prepared 6.69 g (93% yield).

$^1$H-NMR (400 MHz, DMSO-$d_6$): δ [ppm]=13.92-14.65 (m, 1H), 8.04-9.61 (m, 1H), 7.48-7.58 (m, 1H), 7.16-7.27 (m, 1H), 3.89 (s, 2H), 3.82-3.95 (m, 1H), 3.39-3.48 (m, 1H), 3.25-3.32 (m, 1H), 2.78 (brt, 1H), 2.63 (brt, 1H).

Intermediate 5-15

N-(3,5-difluoro-2-methoxyphenyl)-4-hydroxy-2-oxo-1,2,5,6-tetrahydropyridine-3-carbothioamide

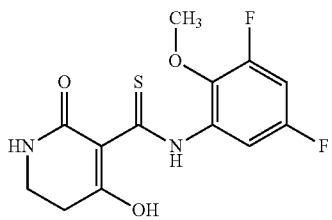 [SMILES: COc1c(F)cc(F)cc1NC(=S)C1=C(O)CCNC1=O]

Using an analogous method as described for Intermediate 5-2, intermediate 4-15 (9.50 g, 22.9 mmol) as the starting material, the title compound was prepared 6.99 g (92% yield).

$^1$H-NMR (400 MHz, DMSO-$d_6$): δ [ppm]=14.34-15.11 (m, 1H), 8.11-9.63 (m, 1H), 7.81 (br d, 1H), 7.23-7.36 (m, 1H), 3.81 (s, 3H), 3.43 (br t, 1H), 3.23-3.33 (m, 1H), 2.80 (br t, 1H), 2.60-2.70 (m, 1H).

Intermediate 5-32

N-(3-chloro-2-methoxyphenyl)-4-hydroxy-2-oxo-1,2,5,6-tetrahydropyridine-3-carbothioamide

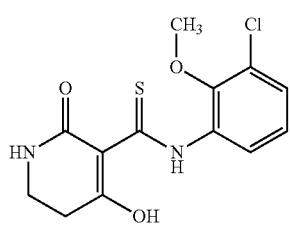

To a solution of tert-butyl 5-[(3-chloro-2-methoxyphenyl)carbamothioyl]-4-hydroxy-6-oxo-3,6-dihydropyridine-1(2H)-carboxylate (intermediate 4-32, 6.54 g, 15.8 mmol) in 94 ml. dichloromethane was added trifluoroacetic acid (12 ml, 160 mmol) and the mixture was stirred 1.5 h at rt. The reaction mixture was concentrated under reduced pressure and the residue was solved in ethyl acetate and washed with saturated aqueous solution and sodium bicarbonate and brine. The organic layer was filtered through a waterresistant filter and the filtrate was dried to dryness. The residue was purified by flash chromatography to give 4.06 g of the title compound (95% purity, 78% yield).

$^1$H-NMR (400 MHz, DMSO-d6) δ [ppm]: 1.172 (0.45), 1.987 (0.74), 2.518 (1.27), 2.523 (0.87), 2.625 (1.12), 2.643 (2.13), 2.661 (1.30), 2.669 (0.53), 2.773 (1.04), 2.791 (2.17), 2.808 (1.17), 3.279 (0.75), 3.286 (0.85), 3.297 (1.43), 3.304 (1.46), 3.314 (0.82), 3.411 (0.76), 3.418 (0.86), 3.430 (1.37), 3.437 (1.35), 3.447 (0.76), 3.455 (0.67), 3.742 (16.00), 3.744 (15.67), 7.154 (0.75), 7.174 (1.70), 7.187 (0.86), 7.194 (1.08), 7.207 (1.62), 7.228 (0.90), 7.379 (1.09), 7.382 (1.16), 7.399 (0.97), 7.402 (0.97), 7.422 (1.10), 7.425 (1.11), 7.442 (0.92), 7.445 (0.87), 7.779 (0.93), 7.798 (0.91), 7.815 (1.08), 7.836 (0.98), 8.184 (0.86), 9.368 (0.71), 14.326 (1.64), 14.693 (1.39), 16.447 (3.78), 16.457 (3.62).

LC-MS (method 2): $R_t$=1.50 min; MS (ESIpos): m/z=431 [M+H]$^+$

Intermediate 5-34

N-(2,3-dichlorophenyl)-4-hydroxy-2-oxo-1,2,5,6-tetrahydropyridine-3-carbothioamide

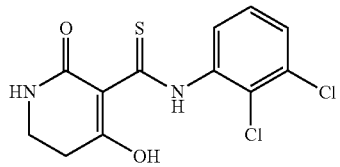 [SMILES: O=C1NCCC(O)=C1C(=S)Nc1cccc(Cl)c1Cl]

Using an analogous method as described for intermediate 5-32 and using tert-butyl 5-[(2,3-dichlorophenyl)carbamothioyl]-4-hydroxy-6-oxo-3,6-dihydropyridine-1(2H)-carboxylate (intermediate 4-34, 9.40 g, 22.5 mmol) as the starting material, the title compound was prepared 5.71 g (62% yield).

$^1$H-NMR (400 MHz, DMSO-d6) δ [ppm]: 1.018 (1.18), 1.050 (1.33), 1.072 (0.81), 1.102 (0.59), 1.132 (0.81), 1.154 (1.84), 1.172 (3.17), 1.189 (1.84), 1.199 (0.88), 1.231 (1.92), 1.259 (1.40), 1.486 (0.66), 1.593 (1.33), 1.626 (1.18), 1.695 (1.25), 1.727 (1.18), 1.907 (2.14), 1.987 (5.97), 2.322 (3.17), 2.326 (4.28), 2.331 (3.17), 2.518 (15.85), 2.522 (9.44), 2.638 (11.06), 2.664 (7.82), 2.669 (7.52), 2.673 (5.53), 2.798 (8.11), 3.436 (9.81), 4.017 (1.18), 4.035 (1.11), 5.560 (1.33), 5.579 (1.25), 7.392 (4.42), 7.410 (10.03), 7.430 (9.22), 7.565 (12.24), 7.585 (16.00), 7.605 (9.51), 8.134 (0.74), 8.197 (4.35), 9.418 (3.91), 14.273 (6.93), 14.665 (6.64), 16.114 (1.03), 16.295 (9.95), 16.352 (5.82), 16.503 (1.11).

LC-MS (method 2): $R_t$=0.55 min; MS (ESIpos): m/z=316 [M−H]$^-$

Intermediate 5-35

N-(2-ethyl-3-fluorophenyl)-4-hydroxy-2-oxo-1,2,5,6-tetrahydropyridine-3-carbothioamide

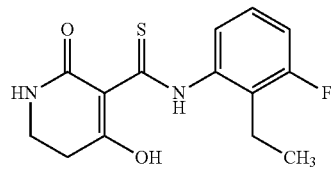 [SMILES: CCc1c(F)cccc1NC(=S)C1=C(O)CCNC1=O]

Using an analogous method as described for intermediate 5-32 and using tert-butyl 5-[(2-ethyl-3-fluorophenyl)carbamothioyl]-4-hydroxy-6-oxo-3,6-dihydropyridine-1(2H)-carboxylate (intermediate 4-35, 5.46 g, 71% purity, 9.83 mmol) as the starting material, the title compound was prepared 4.00 g (70% purity, 97% yield).

$^1$H-NMR (400 MHz, DMSO-d6) δ [ppm]: 1.052 (6.61), 1.071 (16.00), 1.089 (6.75), 1.116 (0.56), 1.224 (4.60), 1.734 (1.58), 2.326 (0.43), 2.472 (1.56), 2.518 (2.10), 2.523 (1.69), 2.647 (0.85), 2.659 (0.85), 2.664 (0.98), 2.668 (1.03), 2.673 (0.80), 2.782 (0.89), 3.423 (0.82), 4.037 (0.62), 7.160 (2.35), 7.288 (0.98), 8.170 (0.48), 14.073 (0.46), 14.414 (0.52).

LC-MS (method 2): $R_t$=0.55 min; MS (ESIpos): m/z=295 [M+H]$^+$

Intermediate 5-36

N-(3-chloro-2-methylphenyl)-4-hydroxy-2-oxo-1,2,5,6-tetrahydropyridine-3-carbothioamide

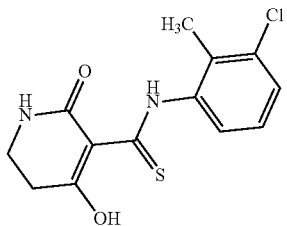 [SMILES: Cc1c(Cl)cccc1NC(=S)C1=C(O)CCNC1=O]

Using an analogous method as described for Intermediate 5-32 and using tert-butyl 5-[(3-chloro-2-methylphenyl)carbamothioyl]-4-hydroxy-6-oxo-3,6-dihydropyridine-1(2H)-carboxylate (intermediate 4-36, 4.67 g, 11.8 mmol) as the starting material, the title compound was prepared 3.54 g (90% purity, 91% yield).

$^1$H-NMR (400 MHz, DMSO-d6) δ [ppm]: 2.175 (16.00), 2.298 (0.54), 2.323 (0.48), 2.327 (0.70), 2.332 (0.72), 2.518 (3.34), 2.523 (2.06), 2.612 (0.74), 2.630 (1.44), 2.649 (0.84), 2.665 (0.56), 2.669 (0.71), 2.673 (0.51), 2.762 (0.82), 2.780 (1.64), 2.798 (0.90), 3.288 (0.73), 3.299 (1.17), 3.306 (1.19), 3.316 (0.73), 3.429 (1.24), 3.435 (1.17), 3.447 (0.69), 7.204 (0.51), 7.225 (1.19), 7.250 (1.77), 7.270 (1.07), 7.276 (0.90), 7.297 (1.04), 7.316 (0.40), 7.407 (0.84), 7.431 (1.24), 7.452 (0.72), 8.148 (0.76), 9.321 (0.63), 14.011 (1.08), 14.323 (1.03), 16.402 (1.62), 16.429 (1.40).

LC-MS (method 2): $R_t$=0.57 min; MS (ESIpos): m/z=297 [M+H]$^+$

Intermediate 5-37

N-(2-bromo-3-fluorophenyl)-4-hydroxy-2-oxo-1,2,5,6-tetrahydropyridine-3-carbothioamide

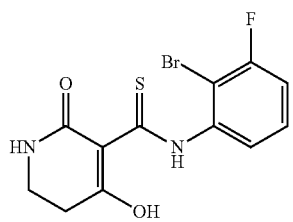 [SMILES: O=C1NCCC(O)=C1C(=S)Nc1cccc(F)c1Br]

Using an analogous method as described for intermediate 5-32 and using tert-butyl 5-[(2-bromo-3-fluorophenyl)carbamothioyl]-4-hydroxy-6-oxo-3,6-dihydropyridine-1(2H)-carboxylate (intermediate 4-37, 10.0 g, 22.5 mmol) as the starting material, the title compound was prepared 3.54 g (90% purity, 91% yield).

$^1$H-NMR (400 MHz, DMSO-d6) δ [ppm]: 1.224 (0.94), 1.416 (0.88), 1.446 (0.83), 1.456 (2.59), 1.530 (0.59), 1.540 (1.12), 1.625 (0.47), 1.907 (0.44), 2.322 (1.50), 2.327 (1.97), 2.332 (1.59), 2.518 (7.96), 2.523 (5.22), 2.535 (1.74), 2.551 (1.33), 2.625 (8.90), 2.643 (16.00), 2.661 (9.61), 2.786 (7.13), 2.803 (13.17), 2.821 (7.16), 3.296 (7.72), 3.308 (11.73), 3.314 (12.61), 3.422 (6.90), 3.429 (7.66), 3.441 (11.29), 3.446 (10.84), 3.457 (6.36), 5.757 (3.06), 7.169 (0.50), 7.190 (0.56), 7.283 (1.09), 7.309 (4.24), 7.329 (8.69), 7.347 (7.84), 7.366 (8.22), 7.386 (12.46), 7.405 (14.14), 7.426 (2.92), 7.436 (5.57), 7.456 (7.25), 7.471 (8.34), 7.489 (6.54), 7.504 (4.54), 7.524 (1.56), 7.801 (0.41), 8.017 (0.56), 8.038 (0.56), 8.196 (5.95), 9.411 (5.57), 9.748 (0.59), 14.210 (11.93), 14.613 (8.99), 16.337 (14.44), 16.388 (11.23).

LC-MS (method 2): $R_t$=1.16 min; MS (ESIpos): m/z=346 [M+H]$^+$

Intermediate 5-38

N-[3-chloro-2-(difluoromethoxy)phenyl]-4-hydroxy-2-oxo-1,2,5,6-tetrahydropyridine-3-carbothioamide

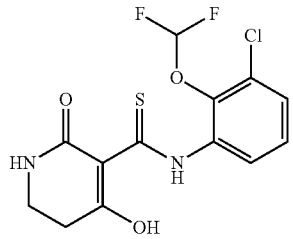 [SMILES: O=C1NCCC(O)=C1C(=S)Nc1cccc(Cl)c1OC(F)F]

Using an analogous method as described for Intermediate 5-32 and using tert-butyl 5-{[3-chloro-2-(difluoromethoxy)phenyl]carbamothioyl}-6-hydroxy-4-oxo-3,4-dihydropyridine-1(2H)-carboxylate (intermediate 4-38, 1.10 g, 88% purity, 2.16 mmol) as the starting material, the title compound was prepared 989 mg (76% purity, 100% yield).

$^1$H-NMR (400 MHz, DMSO-d6) δ [ppm]: 1.390 (0.59), 2.084 (0.44), 2.331 (3.08), 2.336 (1.39), 2.518 (16.00), 2.523 (10.94), 2.541 (0.95), 2.612 (2.35), 2.629 (4.40), 2.647 (2.64), 2.673 (3.30), 2.678 (1.54), 2.694 (0.44), 2.713

(0.81), 2.730 (0.51), 2.775 (2.06), 2.793 (3.74), 2.810 (2.13), 3.300 (3.30), 3.426 (6.09), 3.433 (6.02), 6.825 (1.47), 6.839 (1.25), 7.006 (3.08), 7.020 (2.50), 7.115 (0.51), 7.134 (0.73), 7.188 (1.54), 7.201 (1.25), 7.296 (0.44), 7.318 (0.81), 7.327 (0.81), 7.335 (1.76), 7.357 (1.39), 7.377 (3.01), 7.397 (2.42), 7.409 (2.57), 7.429 (1.39), 7.549 (2.50), 7.569 (2.42), 7.585 (2.42), 7.605 (4.26), 7.626 (4.33), 7.646 (1.91), 8.132 (0.37), 8.166 (2.06), 8.183 (0.66), 8.192 (0.59), 8.202 (0.44), 9.392 (2.13), 12.389 (0.66), 12.678 (0.44), 14.169 (3.60), 14.610 (2.72), 16.074 (0.44), 16.326 (4.40), 16.361 (3.30).

LC-MS (method 2): $R_t$=0.57 min; MS (ESIpos): m/z=349 [M+H]$^+$

Intermediate 5-39

N-(2-chlorophenyl)-4-hydroxy-2-oxo-1,2,5,6-tetra-hydropyridine-3-carbothioamide

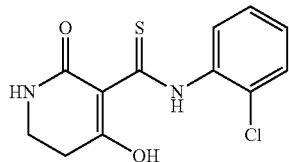 [SMILES: O=C1NCCC(O)=C1C(=S)Nc1ccccc1Cl]

Tert-butyl 5-[(2-chlorophenyl)carbamothioyl]-4-hydroxy-6-oxo-3,6-dihydropyridine-1(2H)-carboxylate (intermediate 4-39, 12.4 g, 32.4 mmol) was dissolved in a mixture of 250 ml. dichloromethane and of 105 ml. methanol, treated with hydrogen chloride (81 ml, 4.0 M in 1,4-dioxane, 320 mmol) and stirred overnight at rt. The reaction mixture was diluted with ice-water and the aqueous phase was extracted with a mixture of dichloromethane/methanol (9:1) two times. The combined organic layer was dried over sodium sulfate, filtered and the filtrate was concentrated under reduced pressure to give 6.05 g of the title compound (95% purity, 66% yield).

LC-MS (method 2): $R_t$=1.15 min; MS (ESIpos): m/z=283 [M+H]$^+$ $^1$H-NMR (400 MHz, DMSO-d6) δ [ppm]: 2.322 (0.70), 2.326 (0.98), 2.331 (0.70), 2.518 (3.98), 2.522 (2.49), 2.617 (4.53), 2.636 (8.51), 2.654 (5.01), 2.664 (0.95), 2.669 (1.08), 2.673 (0.79), 2.775 (4.04), 2.793 (8.70), 2.810 (4.63), 3.283 (2.80), 3.290 (2.93), 3.301 (5.28), 3.308 (5.17), 3.319 (2.83), 3.415 (2.93), 3.422 (3.21), 3.433 (5.10), 3.441 (4.97), 3.451 (2.81), 3.459 (2.65), 3.565 (1.00), 7.306 (1.37), 7.310 (1.59), 7.325 (3.65), 7.329 (3.63), 7.344 (4.38), 7.348 (4.20), 7.363 (4.09), 7.366 (5.27), 7.369 (4.16), 7.382 (3.99), so 7.386 (6.05), 7.389 (5.09), 7.397 (2.88), 7.401 (3.35), 7.403 (2.52), 7.408 (2.04), 7.416 (3.57), 7.420 (3.98), 7.435 (1.75), 7.439 (1.57), 7.562 (4.89), 7.566 (5.17), 7.582 (4.63), 7.587 (7.38), 7.590 (8.75), 7.594 (9.60), 7.610 (7.00), 7.614 (7.87), 8.168 (2.75), 9.365 (2.45), 14.209 (5.81), 14.572 (4.47), 16.420 (16.00), 16.440 (12.66).

Intermediate 5-40

N-(3,5-difluoro-2-methylphenyl)-4-hydroxy-2-oxo-1,2,5,6-tetrahydropyridine-3-carbothioamide

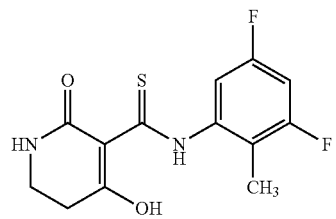 [SMILES: Cc1c(F)cc(F)cc1NC(=S)C1=C(O)CCNC1=O]

Using an analogous method as described for Intermediate 5-32 and using tert-butyl 5-[(3,5-difluoro-2-methylphenyl)carbamothioyl]-4-hydroxy-6-oxo-3,6-dihydropyridine-1(2H)-carboxylate (intermediate 4-40, 5.15 g, 12.9 mmol) as the starting material, the title compound was prepared 3.93 g (95% purity, 97% yield).

$^1$H-NMR (400 MHz, DMSO-d6) δ [ppm]: 1.224 (0.49), 2.028 (16.00), 2.297 (1.29), 2.326 (0.54), 2.518 (2.09), 2.522 (1.34), 2.618 (1.01), 2.635 (1.82), 2.652 (1.16), 2.664 (0.80), 2.669 (0.81), 2.673 (0.60), 2.771 (1.01), 2.789 (1.71), 2.805 (1.01), 3.431 (1.58), 3.603 (0.45), 7.141 (0.95), 7.162 (1.86), 7.181 (1.39), 7.211 (1.11), 7.230 (1.19), 7.235 (1.14), 7.266 (0.46), 8.190 (0.92), 9.388 (0.92), 14.078 (1.39), 14.436 (1.16), 16.343 (1.84), 16.357 (1.63).

LC-MS (method 2): $R_t$=0.52 min; MS (ESIpos): m/z=299 [M+H]$^+$

Intermediate 5-41

N-[3-fluoro-2-(trifluoromethyl)phenyl]-4-hydroxy-2-oxo-1,2,5,6-tetrahydropyridine-3-carbothioamide

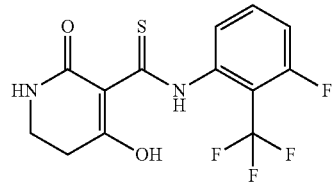 [SMILES: O=C1NCCC(O)=C1C(=S)Nc1cccc(F)c1C(F)(F)F]

Using an analogous method as described for intermediate 5-32 and using tert-butyl 5-{[3-fluoro-2-(trifluoromethyl)phenyl]carbamothioyl}-4-hydroxy-6-oxo-3,6-dihydropyridine-1(2H)-carboxylate (intermediate 4-41, 1.96 g, 4.51 mmol) as the starting material, the title compound was prepared 770 mg (95% purity, 48% yield).

$^1$H-NMR (400 MHz, DMSO-d6) δ [ppm]: 1.102 (0.57), 1.171 (0.45), 1.907 (0.90), 1.986 (0.73), 2.322 (1.06), 2.326 (1.55), 2.332 (1.06), 2.518 (6.80), 2.522 (4.48), 2.620 (4.40), 2.638 (8.47), 2.656 (4.89), 2.664 (1.79), 2.668 (1.83), 2.673 (1.30), 2.786 (3.38), 2.803 (7.29), 2.821 (3.95), 3.285 (2.36), 3.292 (3.09), 3.303 (4.97), 3.310 (5.13), 3.417 (2.93), 3.424 (3.18), 3.435 (5.21), 3.442 (5.17), 3.454 (2.93), 3.461 (2.61), 7.328 (4.60), 7.347 (5.13), 7.440 (1.79), 7.462 (2.52), 7.478 (1.83), 7.489 (2.44), 7.499 (2.20), 7.527 (1.67), 7.725 (1.47), 7.746 (2.73), 7.762 (3.38), 7.783 (2.97), 7.799 (2.12), 7.820 (0.90), 8.192 (2.77), 9.421 (2.81), 14.230 (5.86), 14.690 (4.44), 16.227 (16.00), 16.292 (11.85).

LC-MS (method 2): $R_t$=0.53 min; MS (ESIpos): m/z=335 [M+H]$^+$

Intermediate 5-42

4-hydroxy-2-oxo-N-[2-(trifluoromethyl)phenyl]-1,2,5,6-tetrahydropyridine-3-carbothioamide

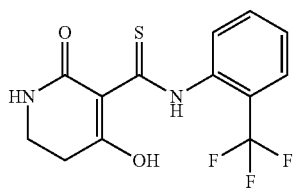 [SMILES: O=C1NCCC(O)=C1C(=S)Nc1ccccc1C(F)(F)F]

Using an analogous method as described for intermediate 5-32 and using tert-butyl 4-hydroxy-6-oxo-5-{[2-(trifluoromethyl)phenyl]carbamothioyl}-3,6-dihydropyridine-1(2H)-carboxylate (intermediate 4-42, 5.01 g, 76% purity, 9.14 mmol) as the starting material, the title compound was prepared 3.92 g (71% purity, 96% yield).

$^1$H-NMR (400 MHz, DMSO-d6) δ [ppm]: 1.430 (11.28), 2.323 (0.79), 2.327 (1.16), 2.331 (0.87), 2.518 (11.48), 2.523 (9.51), 2.623 (4.91), 2.641 (8.53), 2.659 (5.55), 2.669 (1.87), 2.673 (1.39), 2.713 (0.46), 2.785 (3.60), 2.803 (7.70), 2.821 (4.27), 3.288 (2.48), 3.295 (2.73), 3.306 (4.91), 3.314 (5.14), 3.324 (3.74), 3.419 (3.08), 3.426 (3.33), 3.438 (5.10), 3.445 (5.03), 3.455 (3.00), 3.463 (2.91), 7.469 (0.52), 7.488 (1.06), 7.504 (2.06), 7.523 (3.39), 7.542 (3.43), 7.560 (3.75), 7.580 (2.71), 7.592 (5.78), 7.611 (7.66), 7.641 (0.89), 7.660 (0.54), 7.674 (0.75), 7.700 (2.75), 7.720 (3.68), 7.736 (3.75), 7.755 (3.50), 7.774 (1.46), 7.790 (3.58), 7.808 (3.41), 7.823 (3.52), 7.841 (2.93), 8.176 (2.50), 8.209 (0.56), 8.725 (0.44), 9.392 (2.45), 9.580 (0.71), 14.316 (5.33), 14.768 (3.89), 16.371 (16.00), 16.414 (12.28).

LC-MS (method 2): $R_t$=0.48 min; MS (ESIpos): m/z=317 [M+H]$^+$

Intermediate 5-43

N-[3,5-difluoro-2-(difluoromethoxy)phenyl]-4-hydroxy-2-oxo-1,2,5,6-tetrahydropyridine-3-carbothioamide

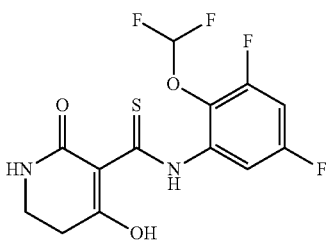 [SMILES: O=C1NCCC(O)=C1C(=S)Nc1cc(F)cc(F)c1OC(F)F]

To a solution of tert-butyl 5-{[3,5-difluoro-2-(difluoromethoxy)phenyl]carbamothioyl}-4-hydroxy-6-oxo-3,6-dihydropyridine-1(2H)-carboxylate (intermediate 4-43, 29.0 g, 64.4 mmol) in EtOAc (50 mL) was added HCl/EtOAc (4 M, 200 mL, 12.4 eq). The mixture was stirred at 25° C. for 20 min. The reaction mixture was concentrated under reduced pressure to remove solvent. The title compound was obtained as a yellow solid (22.36 g, 63.1 mmol, 98.1% yield, 98.9% purity).

$^1$H-NMR (400 MHz, DMSO-d6) δ [ppm]: 14.88-14.41 (m, 1H), 9.48-8.22 (m, 1H), 7.68-7.66 (m, 1H), 7.51-7.43 (m, 1H), 7.29-6.93 (m, 1H), 3.45-3.42 (m, 1H), 3.41-3.34 (m, 1H), 2.81 (s, 1H), 2.66-2.62 (m, 1H)

Intermediate 5-44

N-(3-chloro-4-fluoro-2-methoxyphenyl)-4-hydroxy-2-oxo-1,2,5,6-tetrahydropyridine-3-carbothioamide

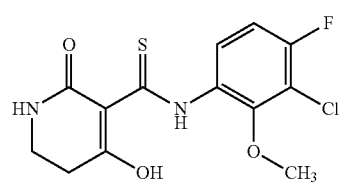

Using an analogous method as described for intermediate 5-32 and using tert-butyl 5-[(3-chloro-4-fluoro-2-methoxyphenyl)carbamothioyl]-4-hydroxy-6-oxo-3,6-dihydropyridine-1(2H)-carboxylate (Intermediate 4-44, 5.96 g, 13.8 mmol) as the starting material, the title compound was prepared 2.59 g (95% purity, 54% yield).

$^1$H-NMR (400 MHz, DMSO-d6) δ [ppm]: 1.154 (1.05), 1.172 (2.14), 1.190 (1.15), 1.987 (4.42), 2.322 (0.75), 2.327 (1.01), 2.331 (0.73), 2.518 (4.34), 2.523 (2.70), 2.639 (1.37), 2.659 (1.11), 2.664 (1.27), 2.669 (1.35), 2.673 (0.97), 2.790 (1.23), 3.302 (1.39), 3.429 (1.19), 3.778 (16.00), 3.849 (0.59), 4.017 (0.91), 4.035 (0.91), 7.240 (0.50), 7.261 (1.13), 7.285 (0.89), 7.699 (0.52), 7.738 (0.52), 7.754 (0.61), 8.187 (0.65), 9.386 (0.56), 14.191 (1.01), 14.577 (1.07), 16.369 (2.04), 16.389 (1.78).

LC-MS (method 2): $R_t$=1.22 min; MS (ESIpos): m/z=331 [M+H]$^+$

Intermediate 5-45

N-(5-fluoro-2-methylphenyl)-4-hydroxy-2-oxo-1,2,5,6-tetrahydropyridine-3-carbothioamide

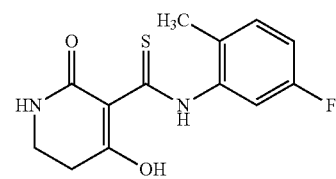

Using an analogous method as described for Intermediate 5-32 and using tert-butyl 5-[(5-fluoro-2-methylphenyl)carbamothioyl]-4-hydroxy-6-oxo-3,6-dihydropyridine-1(2H)-carboxylate (intermediate 4-45, 2.00 g, 5.26 mmol) as the starting material, the title compound was prepared 1.03 g (75% purity, 52% yield).

$^1$H-NMR (400 MHz, DMSO-d6) δ [ppm]: 1.574 (0.91), 1.600 (4.08), 1.611 (4.36), 1.621 (4.40), 1.644 (3.70), 1.660 (3.04), 1.673 (2.64), 1.884 (1.16), 1.898 (2.98), 1.913 (5.12), 1.927 (3.09), 1.942 (1.26), 2.138 (16.00), 2.322 (0.51), 2.327 (0.75), 2.332 (0.55), 2.518 (3.14), 2.523 (2.13), 2.625

(4.35), 2.635 (3.17), 2.651 (4.44), 2.665 (1.01), 2.669 (1.16), 2.673 (0.89), 2.765 (0.50), 3.230 (1.99), 3.238 (2.74), 3.245 (3.82), 3.250 (3.83), 3.256 (2.77), 3.265 (2.08), 3.308 (0.54), 3.416 (0.48), 3.459 (3.64), 3.474 (6.28), 3.488 (3.47), 3.537 (4.28), 3.547 (3.17), 3.561 (4.66), 7.090 (0.93), 7.255 (0.97), 7.278 (1.04), 7.328 (0.86), 7.347 (1.23), 7.366 (0.82), 9.538 (1.45).

LC-MS (method 2): $R_t$=0.48 min; MS (ESIpos): m/z=281 [M+H]$^+$

Intermediate 5-78

N-(2-bromo-3-chlorophenyl)-4-hydroxy-2-oxo-1,2,5,6-tetrahydropyridine-3-carbothioamide

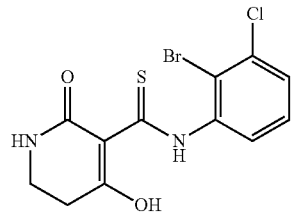 [SMILES: O=C1NCCC(O)=C1C(=S)Nc1cccc(Cl)c1Br]

Using an analogous method as described for intermediate 5-32 and using tert-butyl 5-[(2-bromo-3-chlorophenyl)carbamothioyl]-4-hydroxy-6-oxo-3,6-dihydropyridine-1(2H)-carboxylate (Intermediate 4-78, 4.04 g, 99% purity, 8.66 mmol) as the starting material, the title compound was prepared 3.27 g (97% purity, 99% yield).

$^1$H-NMR (400 MHz, DMSO-d6) δ [ppm]: 2.322 (1.82), 2.326 (2.41), 2.331 (1.77), 2.336 (0.86), 2.518 (10.50), 2.522 (6.41), 2.621 (4.09), 2.639 (7.77), 2.658 (4.82), 2.664 (2.59), 2.668 (2.73), 2.673 (1.95), 2.784 (3.50), 2.802 (7.36), 2.820 (3.91), 3.287 (2.95), 3.295 (3.36), 3.306 (6.00), 3.312 (6.95), 3.419 (2.73), 3.427 (3.05), 3.438 (4.86), 3.445 (4.73), 3.456 (2.73), 3.463 (2.36), 5.758 (1.45), 7.422 (2.00), 7.441 (5.86), 7.460 (7.45), 7.469 (15.68), 7.474 (7.59), 7.479 (8.23), 7.482 (8.86), 7.489 (2.82), 7.493 (1.73), 7.502 (0.77), 7.569 (4.23), 7.574 (3.95), 7.588 (3.27), 7.593 (3.23), 7.605 (3.55), 7.617 (3.59), 7.629 (2.45), 7.638 (0.41), 8.189 (2.82), 9.409 (2.73), 14.230 (6.18), 14.630 (5.05), 16.313 (16.00), 16.364 (11.64).

LC-MS (method 2): R, =0.51 min; MS (ESIneg): m/z=360 [M−H]$^-$

Syntheses of Intermediate 6 Compounds

Intermediate 6-1

4-({[3-(2-methoxyethoxy)pyridin-4-yl]methyl}amino)-2-oxo-N-phenyl-1,2,5,6-tetrahydropyridine-3-carbothioamide

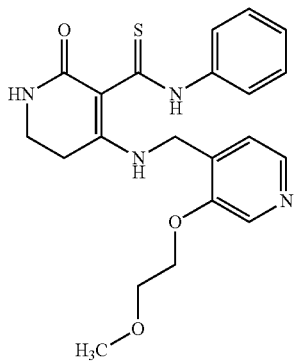 [SMILES: COCCOc1cnccc1CNC1=C(C(=S)Nc2ccccc2)C(=O)NCC1]

A mixture of 4-hydroxy-2-oxo-N-phenyl-1,2,5,6-tetrahydropyridine-3-carbothioamide (251 mg, 1.01 mmol—WO2016/120196) and 1-[3-(2-methoxyethoxy)pyridin-4-yl]methanamine (184 mg, 1.01 mmol) in DMA (2 ml) was heated in a sealed vial at 120° C. for 90 mins using a microwave. The reaction mixture was allowed to cool and purified by preparative HPLC (basic method) to give the titled compound (108 mg, 28% yield).

$^1$H-NMR (400 MHz, DMSO-d$_6$): δ [ppm]=14.76 (s, 1H), 13.63-13.72 (m, 1H), 8.39 (s, 1H), 8.24 (d, 1H), 7.68 (br s, 1H), 7.28-7.43 (m, 5H), 7.18 (t, 1H), 4.65 (d, 2H), 4.19-4.32 (m, 2H), 3.68-3.73 (m, 2H), 3.32 (s, 3H), 3.11-3.19 (m, 2H), 2.67-2.77 (m, 2H).

Intermediate 6-2

4-({[3-(3,3-dimethylbutoxy)pyridin-4-yl]methyl}amino)-N-(3-fluorophenyl)-2-oxo-1,2,5,6-tetrahydropyridine-3-carbothioamide

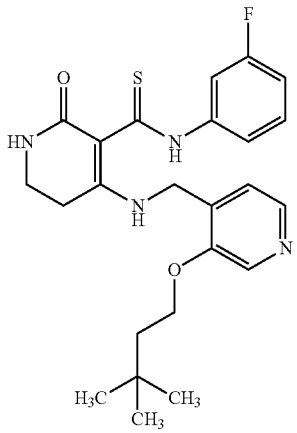 [SMILES: CC(C)(C)CCOc1cnccc1CNC1=C(C(=S)Nc2cccc(F)c2)C(=O)NCC1]

Using an analogous method as described for Intermediate 6-1,4-hydroxy-2-oxo-N-phenyl-1,2,5,6-tetrahydropyridine-3-carbothioamide (271 mg, 1.02 mmol—WO2016/120196) and 1-[3-(3,3-dimethylbutoxy)pyridin-4-yl]methanamine (293 mg, 1.41 mmol) as the starting materials, the title compound was prepared 88.0 mg (18% yield).

$^1$H-NMR (400 MHz, DMSO-d$_6$): δ [ppm]=14.97 (s, 1H), 13.61 (br s, 1H), 8.42 (s, 1H), 8.22 (d, 1H), 7.74 (br s, 1H), 7.55 (dt, 1H), 7.28-7.41 (m, 2H), 7.15 (m, 1H), 7.01 (t, 1H), 4.63 (d, 2H), 4.14-4.24 (m, 2H), 3.09-3.18 (m, 2H), 2.67-2.77 (m, 2H), 2.52-2.54 (m, 1H), 1.68-1.76 (m, 2H), 0.89-0.99 (m, 9H).

Intermediate 6-3

4-({[3-(benzyloxy)pyridin-4-yl]methyl}amino)-N-(3-fluorophenyl)-2-oxo-1,2,5,6-tetrahydropyridine-3-carbothioamide

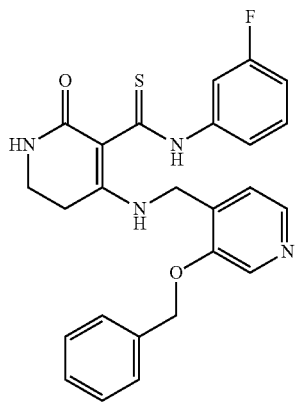 [SMILES: O=C1NCCC(NCc2ccncc2OCc2ccccc2)=C1C(=S)Nc1cccc(F)c1]

Using an analogous method as described for Intermediate 6-1, 4-hydroxy-2-oxo-N-phenyl-1,2,5,6-tetrahydropyridine-3-carbothioamide (250 mg, 939 μmol—WO2016/120196) and 1-[3-(benzyloxy)pyridin-4-yl]methanamine (302 mg, 1.41 mmol) as the starting materials, the title compound was prepared 86.0 mg (19% yield).

$^1$H-NMR (400 MHz, DMSO-d$_6$): δ [ppm]=14.98 (s, 1H), 13.65 (br s, 1H), 8.44 (s, 1H), 8.24 (d, 1H), 7.73 (br s, 1H), 7.48-7.56 (m, 3H), 7.30-7.43 (m, 5H), 7.16 (m, 1H), 7.01 (m, 1H), 5.32 (s, 2H), 4.72 (d, 2H), 3.09 (m, 2H), 2.67-2.74 (m, 2H).

Intermediate 6-4

N-(3-fluorophenyl)-4-({[3-(2-hydroxy-2-methylpropoxy)pyridin-4-yl]methyl}amino)-2-oxo-1,2,5,6-tetrahydropyridine-3-carbothioamide

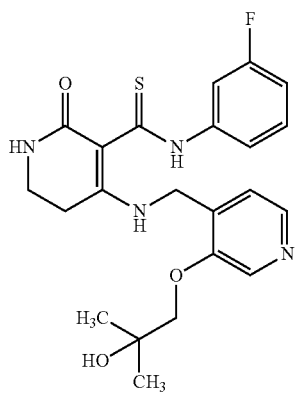 [SMILES: CC(C)(O)COc1cnccc1CNC1=C(C(=S)Nc2cccc(F)c2)C(=O)NCC1]

Using an analogous method as described for Intermediate 6-1, 4-hydroxy-2-oxo-N-phenyl-1,2,5,6-tetrahydropyridine-3-carbothioamide (250 mg, 939 μmol—WO2016/120196) and 1-{[4-(aminomethyl)pyridin-3-yl]oxy}-2-methylpropan-2-ol (276 mg, 1.41 mmol—WO2016/120196) as the starting materials, the title compound was prepared 158.0 mg (36% yield).

$^1$H-NMR (400 MHz, DMSO-d$_6$): δ [ppm]=14.97 (s, 1H), 13.64 (br s, 1H), 8.35 (s, 1H), 8.23 (d, 1H), 7.75 (br s, 1H), 7.54 (dt, 1H), 7.32-7.42 (m, 1H), 7.27 (d, 1H), 7.16 (d, 1H), 7.02 (m, 1H), 4.67-4.79 (m, 3H), 3.91 (s, 2H), 3.10-3.20 (m, 2H), 2.75 (t, 2H), 1.21-1.26 (m, 6H).

Intermediate 6-5

4-[({3-[2-(dimethylamino)ethoxy]pyridin-4-yl}methyl)amino]-N-(3-fluorophenyl)-2-oxo-1,2,5,6-tetrahydropyridine-3-carbothioamide

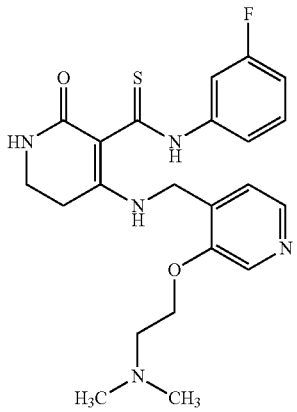 [SMILES: CN(C)CCOc1cnccc1CNC1=C(C(=S)Nc2cccc(F)c2)C(=O)NCC1]

Using an analogous method as described for Intermediate 6-1, -hydroxy-2-oxo-N-phenyl-1,2,5,6-tetrahydropyridine-3-carbothioamide (250 mg, 939 μmol—WO2016/120196) and 2-{[4-(aminomethyl)pyridin-3-yl]oxy}-N,N-dimethylethanamine (275 mg, 1.41 mmol—WO2016/120196) as the starting materials, the title compound was prepared 175.0 mg (41% yield).

$^1$H-NMR (400 MHz, DMSO-d$_6$): δ [ppm]=14.97 (s, 1H), 13.63 (br s, 1H), 8.41 (s, 1H), 8.23 (d, 1H), 7.74 (br s, 1H), 7.54 (dt, 1H), 7.29-7.41 (m, 2H), 7.16 (d, 1H), 7.02 (t, 1H), 4.65 (d, 2H), 4.17-4.26 (m, 2H), 3.11-3.18 (m, 2H), 2.76 (t, 2H), 2.65-2.72 (m, 2H), 2.17-2.24 (m, 6H).

Intermediate 6-6

N-(3-fluorophenyl)-4-({[3-(2-methoxy-2-methylpropoxy)pyridin-4-yl]methyl}amino)-2-oxo-1,2,5,6-tetrahydropyridine-3-carbothioamide

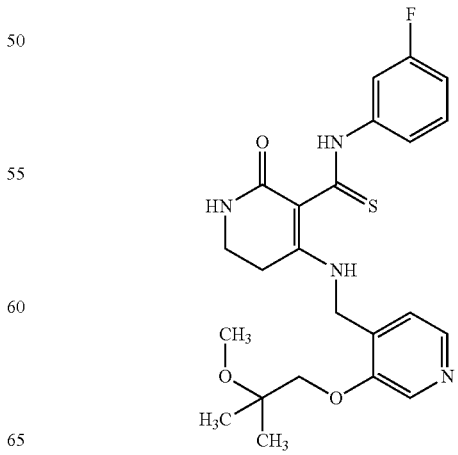

Using an analogous method as described for Intermediate 6-1, -hydroxy-2-oxo-N-phenyl-1,2,5,6-tetrahydropyridine-3-carbothioamide (250 mg, 939 μmol—WO2016/120196) and 1-[3-(2-methoxy-2-methylpropoxy)pyridin-4-yl]methanamine (395 mg, 1.88) as the starting materials, the title compound was prepared 220 mg (51% yield).

¹H-NMR (400 MHz, DMSO-$d_6$): δ [ppm]=14.96 (s, 1H), 13.62 (br s, 1H), 8.37-8.44 (m, 1H), 8.24 (d, 1H), 7.70-7.79 (m, 1H), 7.53 (dt, 1H), 7.39 (m, 1H), 7.28 (d, 1H), 7.10-7.19 (m, 1H), 7.01 (t, 1H), 4.70 (d, 2H), 4.00-4.06 (m, 2H), 3.11-3.21 (m, 5H), 2.74-2.78 (m, 2H), 1.24 (s, 6H).

Intermediate 6-7

N-(3-fluorophenyl)-4-[({3-[2-methyl-2-(morpholin-4-yl)propoxy]pyridin-4-yl}methyl)amino]-2-oxo-1,2,5,6-tetrahydropyridin-carbothioamide

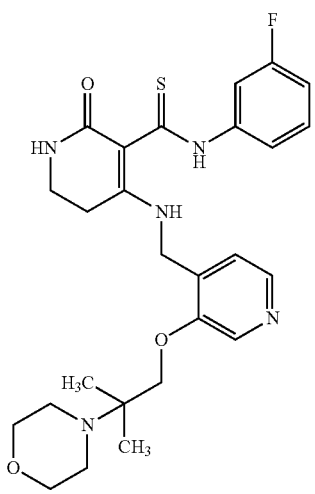 [SMILES: CC(C)(COc1cnccc1CNC1=C(C(=S)Nc2cccc(F)c2)C(=O)NCC1)N1CCOCC1]

Using an analogous method as described for Intermediate 6-1, -hydroxy-2-oxo-N-phenyl-1,2,5,6-tetrahydropyridine-3-carbothioamide (250 mg, 939 μmol—WO2016/120196) and 1-{3-[2-methyl-2-(morpholin-4-yl)propoxy]pyridin-4-yl}methanamine (498 mg, 1.88 mmol) as the starting materials, the title compound was prepared 220 mg (46% yield).

¹H-NMR (400 MHz, DMSO-$d_6$): δ [ppm]=14.96 (s, 1H), 13.60 (br s, 1H), 8.41 (s, 1H), 8.23 (d, 1H), 7.75 (br s, 1H), 7.53 (dt, 1H), 7.38 (m, 1H), 7.28 (d, 1H), 7.16 (m, 1H), 6.99-7.04 (m, 1H), 4.70 (d, 2H), 4.04 (s, 2H), 3.48-3.57 (m, 4H), 3.15 (m, 2H), 2.72-2.79 (m, 2H), 2.56-2.63 (m, 4H), 1.13 (s, 6H).

Intermediate 6-8

N-(3-fluorophenyl)-4-{[(3-{[(2S)-1-methylpyrrolidin-2-yl]methoxy}pyridin-4-yl)methyl]amino}-2-oxo-1,2,5,6-tetrahydropyridine-3-carbothioamide

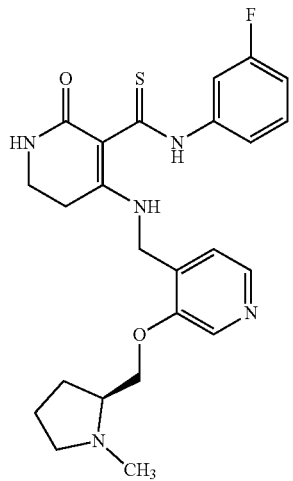 [SMILES: CN1CCC[C@H]1COc1cnccc1CNC1=C(C(=S)Nc2cccc(F)c2)C(=O)NCC1]

Using an analogous method as described for Intermediate 6-1, -hydroxy-2-oxo-N-phenyl-1,2,5,6-tetrahydropyridine-3-carbothioamide (250 mg, 939 μmol—WO2016/120196) and 1-(3-{[(2S)-1-methylpyrrolidin-2-yl]methoxy}pyridin-4-yl)methanamine (416 mg, 1.88 mmol) as the starting materials, the title compound was prepared 300 mg (58% yield).

¹H-NMR (500 MHz, DMSO-$d_6$): δ [ppm]=14.88-15.08 (m, 1H), 13.43-13.80 (m, 1H), 8.39 (s, 1H), 8.23 (d, 1H), 7.70-7.77 (m, 1H), 7.54 (br d, 1H), 7.35-7.41 (m, 1H), 7.29 (d, 1H), 7.16 (d, 1H), 7.02 (d, 1H), 4.35 (t, 1H), 4.17 (m, 1H), 3.97-4.03 (m, 1H), 3.11-3.17 (m, 2H), 2.89-3.00 (m, 2H), 2.74 (t, 2H), 2.36 (s, 3H), 2.11-2.32 (m, 1H), 1.93-2.01 (m, 1H), 1.59-1.74 (m, 4H).

Intermediate 6-9

N-(3,5-difluorophenyl)-4-({[3-(2-methoxyethoxy)pyridin-4-yl]methyl}amino)-2-oxo-1,2,5,6-tetrahydropyridine-3-carbothioamide

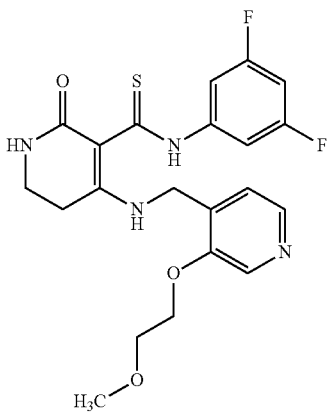 [SMILES: COCCOc1cnccc1CNC1=C(C(=S)Nc2cc(F)cc(F)c2)C(=O)NCC1]

Using an analogous method as described for Intermediate 6-1, intermediate 5-1 ((1 g, 3.52 mmol) and 1-[3-(2-methoxyethoxy)pyridin-4-yl]methanamine (961 mg, 5.28 mmol) as the starting materials, the title compound was prepared 860 mg (55% yield).

$^1$H-NMR (400 MHz, DMSO-d$_6$): δ [ppm]=15.11 (s, 1H), 13.62 (t, 1H), 8.40 (s, 1H), 8.24 (d, 1H), 7.80 (br s, 1H), 7.24-7.36 (m, 3H), 7.05 (tt, 1H), 4.67 (d, 2H), 4.30 (m, 2H), 3.68-3.74 (m, 2H), 3.32 (s, 3H), 3.15 (m, 2H), 2.74-2.81 (m, 2H).

Intermediate 6-10

N-(3,5-difluorophenyl)-4-({[3-(2-methoxy-2-methyl-propoxy)pyridin-4-yl]methyl}amino)-2-oxo-1,2,5,6-tetrahydropyridine-3-carbothioamide

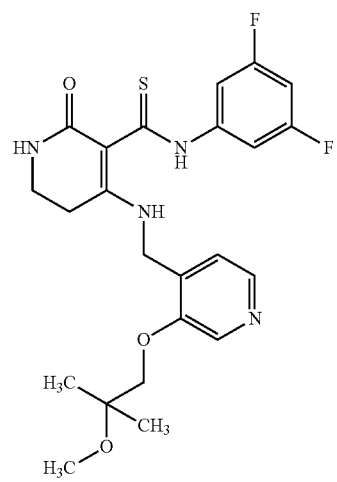 [SMILES: COC(C)(C)COc1cnccc1CNC1=C(C(=S)Nc2cc(F)cc(F)c2)C(=O)NCC1]

Using an analogous method as described for Intermediate 6-1, intermediate 5-1 ((250 mg, 879 μmol) and 1-[3-(2-methoxy-2-methylpropoxy)pyridin-4-yl]methanamine (370 mg, 1.76 mmol) as the starting materials, the title compound was prepared 210 mg (43% yield).

$^1$H-NMR (400 MHz, DMSO-d$_6$): δ [ppm]=15.11 (s, 1H), 13.60 (br s, 1H), 8.40 (s, 1H), 8.24 (d, 1H), 7.80 (br s, 1H), 7.26-7.33 (m, 3H), 7.05 (tt, 1H), 4.71 (d, 2H), 4.04 (s, 2H), 3.09-3.19 (m, 5H), 2.74-2.80 (m, 2H), 1.17-1.26 (m, 7H).

Intermediate 6-11

N-[2-(difluoromethoxy)phenyl]-4-({[3-(2-methoxy-ethoxy)pyridin-4-yl]methyl}amino)-2-oxo-1,2,5,6-tetrahydropyridine-3-carbothioamide

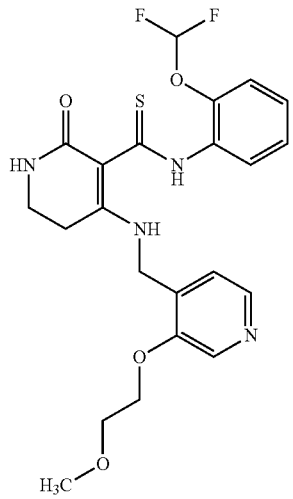 [SMILES: COCCOc1cnccc1CNC1=C(C(=S)Nc2ccccc2OC(F)F)C(=O)NCC1]

Using an analogous method as described for Intermediate 6-1, intermediate 5-2 ((950 mg, 3.02 mmol) and 1-[3-(2-methoxyethoxy)pyridin-4-yl]methanamine (826 mg, 4.53 mmol) as the starting materials, the title compound was prepared 890 mg (47% yield).

$^1$H-NMR (400 MHz, DMSO-d$_6$): δ [ppm]=14.68 (s, 1H), 13.69 (brt, 1H), 8.40 (s, 1H), 8.23 (d, 1H), 7.62-7.81 (m, 2H), 6.88-7.33 (m, 5H), 4.65 (d, 2H), 4.26-4.31 (m, 2H), 3.67-3.74 (m, 3H), 3.31 (s, 3H), 3.15 (m, 2H), 2.76 (t, 2H).

Intermediate 6-12

N-(2-bromo-3-fluorophenyl)-4-({[3-(2-methoxy-ethoxy)pyridin-4-yl]methyl}amino)-2-oxo-1,2,5,6-tetrahydropyridine-3-carbothioamide

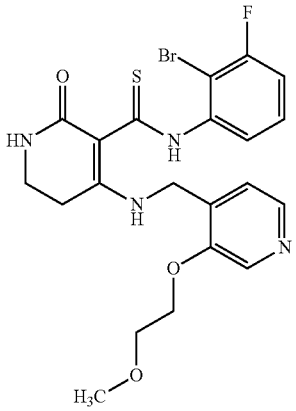 [SMILES: COCCOc1cnccc1CNC1=C(C(=S)Nc2cccc(F)c2Br)C(=O)NCC1]

Using an analogous method as described for Intermediate 6-1, intermediate 5-3 (250 mg, 724 μmol) and 1-[3-(2-methoxyethoxy)pyridin-4-yl]methanamine (264 mg, 1.45 mmol) as the starting materials, the title compound was prepared 58.8 mg (15% yield) after preparative HPLC purification (Instrument: Waters Autopurification system; Column: Waters XBridge C18 5μ 100×30 mm; Eluent A: Water+0.1 Vol-% Formic acid (99%), Eluent B: Acetonitrile; Gradient: 0.00-0.50 min 18% B (25 to 70 mL/min), 0.51-5.50 min 18-40% B (70 mL/min), DAD scan: 210-400 nm).

¹H-NMR (400 MHz, DMSO-d₆): δ [ppm]=14.82 (s, 1H), 13.70 (brt, 1H), 8.40 (s, 1H), 8.24 (d, 1H), 7.73 (br s, 1H), 7.21-7.43 (m, 4H), 4.66 (d, 2H), 4.25-4.32 (m, 2H), 3.67-3.73 (m, 2H), 3.30-3.32 (m, 3H), 3.17 (br d, 2H), 2.72-2.82 (m, 2H).

Intermediate 6-13

4-({[3-(2-methoxyethoxy)pyridin-4-yl]methyl}amino)-N-(2-methoxyphenyl)-2-oxo-1,2,5,6-tetrahydropyridine-3-carbothioamide

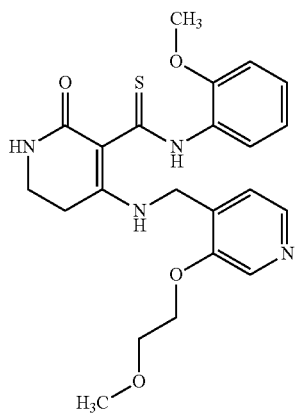 [SMILES: COCCOc1cnccc1CNC1=C(C(=S)Nc2ccccc2OC)C(=O)NCC1]

Using an analogous method as described for Intermediate 6-1, intermediate 5-4 (250 mg, 530 μmol) and 1-[3-(2-methoxyethoxy)pyridin-4-yl]methanamine (262 mg, 1.44 mmol) as the starting materials, the title compound was prepared 87 mg (26% yield).

¹H-NMR (400 MHz, DMSO-d₆): δ [ppm]=14.42 (s, 1H), 13.74 (brt, 1H), 8.39 (s, 1H), 8.23 (d, 1H), 7.72 (m, 1H), 7.58 (br s, 1H), 7.30 (d, 1H), 7.17 (t, 1H), 7.05 (m, 1H), 6.91 (m, 1H), 4.64 (d, 2H), 4.24-4.32 (m, 2H), 3.67-3.78 (m, 5H), 3.32 (s, 3H), 3.14 (m, 2H), 2.69-2.78 (m, 2H).

Intermediate 6-14

4-({[3-(2-methoxyethoxy)pyridin-4-yl]methyl}amino)-2-oxo-N-[2-(trifluoromethoxy)phenyl]-1,2,5,6-tetrahydropyridine-3-carbothioamide

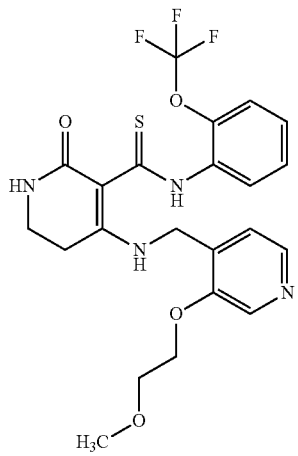 [SMILES: COCCOc1cnccc1CNC1=C(C(=S)Nc2ccccc2OC(F)(F)F)C(=O)NCC1]

Using an analogous method as described for Intermediate 6-1, intermediate 5-5 (250 mg, 752 μmol) and 1-[3-(2-methoxyethoxy)pyridin-4-yl]methanamine (274 mg, 1.50 mmol) as the starting materials, the title compound was prepared 155 mg (39% yield).

¹H-NMR (500 MHz, DMSO-d₆): δ [ppm]=14.94 (s, 1H), 13.70 (t, 1H), 8.40 (s, 1H), 8.24 (d, 1H), 7.88 (m, 1H), 7.75 (br s, 1H), 7.30-7.43 (m, 4H), 4.66 (d, 2H), 4.27-4.32 (m, 2H), 3.68-3.73 (m, 2H), 3.31 (s, 3H), 3.16 (m, 2H), 2.78 (t, 2H).

Intermediate 6-15

N-[2-(2,2-difluoroethyl)phenyl]-4-({[3-(2-methoxyethoxy)pyridin-4-yl]methyl}amino)-2-oxo-1,2,5,6-tetrahydropyridine-3-carbothioamide

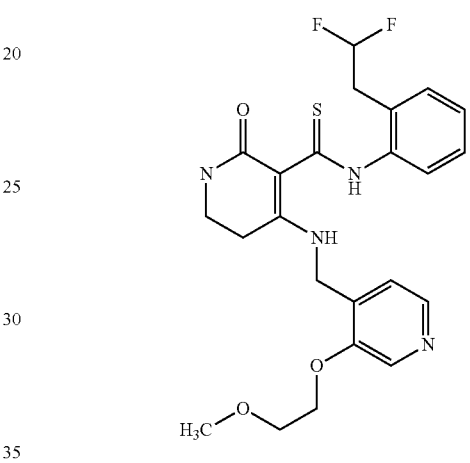

Using an analogous method as described for Intermediate 6-1, intermediate 5-6 (250 mg, 800 μmol) and 1-[3-(2-methoxyethoxy)pyridin-4-yl]methanamine (292 mg, 1.60 mmol) as the starting materials, the title compound was prepared 110 mg (27% yield).

¹H-NMR (400 MHz, DMSO-d₆): δ [ppm]=14.46 (s, 1H), 13.62 (brt, 1H), 8.39 (s, 1H), 8.36 (s, 1H), 8.28 (s, 1H), 8.23 (d, 1H), 7.67 (br s, 1H), 7.20-7.39 (m, 5H), 6.17 (br d, 1H), 6.17 (t, 1H), 4.64 (d, 2H), 4.26-4.31 (m, 2H), 3.67-3.73 (m, 2H), 3.31 (s, 2H), 3.17 (m, 2H), 3.01-3.13 (m, 2H), 2.77 (t, 2H).

Intermediate 6-16

N-(3-fluoro-2-methoxyphenyl)-4-({[3-(2-methoxyethoxy)pyridin-4-yl]methyl}amino)-2-oxo-1,2,5,6-tetrahydropyridine-3-carbothioamide

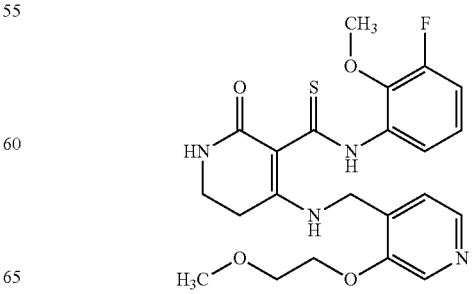

Using an analogous method as described for Intermediate 6-1, intermediate 5-7 (250 mg, 844 μmol) and 1-[3-(2-methoxyethoxy)pyridin-4-yl]methanamine (307 mg, 1.69 mmol) as the starting materials, the title compound was prepared 130 mg (32% yield).

$^1$H-NMR (400 MHz, DMSO-d$_6$): δ [ppm]=14.74 (s, 1H), 13.71 (brt, 1H), 8.36-8.44 (m, 1H), 8.24 (d, 1H), 7.64-7.74 (m, 2H), 7.31 (d, 1H), 7.01-7.15 (m, 2H), 4.66 (br d, 2H), 4.24-4.35 (m, 2H), 3.67-3.84 (m, 5H), 3.32 (s, 3H), 3.12-3.21 (m, 2H), 2.71-2.83 (m, 2H).

Intermediate 6-17

N-(3-fluoro-2-methoxyphenyl)-4-({[3-(2-methoxy-2-methylpropoxy)pyridin-4-yl]methyl}amino)-2-oxo-1,2,5,6-tetrahydropyridine-3-carbothioamide

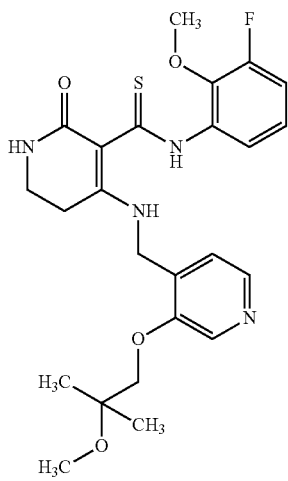 [SMILES: COc1c(F)cccc1NC(=S)C1=C(NCc2ccncc2OCC(C)(C)OC)CCNC1=O]

Using an analogous method as described for Intermediate 6-1, intermediate 5-7 (250 mg, 844 μmol) and 1-[3-(2-methoxy-2-methylpropoxy)pyridin-4-yl]methanamine (355 mg, 1.69 mmol) as the starting materials, the title compound was prepared 210 mg (51% yield).

$^1$H-NMR (400 MHz, DMSO-d$_6$): δ [ppm]=14.74 (s, 1H), 13.69 (br t, 1H), 8.34-8.41 (m, 1H), 8.24 (d, 1H), 7.64-7.73 (m, 2H), 7.29 (d, 1H), 7.03-7.17 (m, 2H), 4.69 (d, 2H), 4.00-4.06 (m, 2H), 3.78 (d, 3H), 3.33 (s, 4H), 3.12-3.21 (m, 5H), 2.73-2.78 (m, 2H), 2.52-2.53 (m, 1H), 1.23-1.26 (m, 6H).

Intermediate 6-18

N-[2-(difluoromethoxy)-3-fluorophenyl]-4-({[3-(2-methoxyethoxy)pyridin-4-yl]methyl}amino)-2-oxo-1,2,5,6-tetrahydropyridine-3-carbothioamide

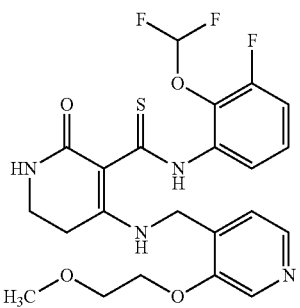 [SMILES: COCCOc1cnccc1CNC1=C(C(=S)Nc2cccc(F)c2OC(F)F)C(=O)NCC1]

Using an analogous method as described for Intermediate 6-1, intermediate 5-8 (250 mg, 752 μmol) and 1-[3-(2-methoxyethoxy)pyridin-4-yl]methanamine (274 mg, 1.50 mmol) as the starting materials, the title compound was prepared 99 mg (25% yield).

$^1$H-NMR (400 MHz, DMSO-d$_6$): δ [ppm]=14.82 (s, 1H), 13.67 (brt, 1H), 8.40 (s, 1H), 8.23 (d, 1H), 7.72 (br s, 1H), 7.56 (d, 1H), 7.22-7.34 (m, 3H), 7.20 (s, 1H), 4.66 (d, 2H), 4.25-4.34 (m, 2H), 3.67-3.74 (m, 2H), 3.31 (s, 3H), 3.15 (m, 2H), 2.78 (t, 2H).

Intermediate 6-19

N-[2-(difluoromethoxy)-3-fluorophenyl]-4-({[3-(2-methoxy-2-methylpropoxy)pyridin-4-yl]methyl}amino)-2-oxo-1,2,5,6-tetrahydropyridine-3-carbothioamide

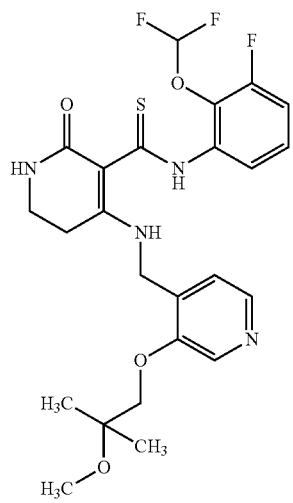 [SMILES: COC(C)(C)COc1cnccc1CNC1=C(C(=S)Nc2cccc(F)c2OC(F)F)C(=O)NCC1]

Using an analogous method as described for Intermediate 6-1, intermediate 5-8 (250 mg, 752 μmol) and 1-[3-(2-methoxy-2-methylpropoxy)pyridin-4-yl]methanamine (316 mg, 1.50 mmol) as the starting materials, the title compound was prepared 160 mg (41% yield).

$^1$H-NMR (400 MHz, DMSO-d$_6$): δ [ppm]=14.81 (s, 1H), 13.56-13.75 (m, 1H), 8.40 (s, 1H), 8.23 (d, 1H), 7.70-7.76

(m, 1H), 7.51-7.59 (m, 1H), 7.25-7.32 (m, 3H), 7.01 (m, 1H), 4.67-4.74 (m, 2H), 3.96-4.11 (m, 2H), 3.13-3.20 (m, 5H), 2.74-2.81 (m, 2H), 1.24 (s, 6H).

Intermediate 6-20

N-(3-fluoro-2-methylphenyl)-4-({[3-(2-methoxyethoxy)pyridin-4-yl]methyl}amino)-2-oxo-1,2,5,6-tetrahydropyridine-3-carbothioamide

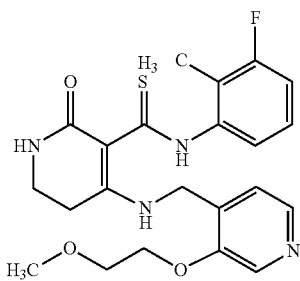

Using an analogous method as described for Intermediate 6-1, intermediate 5-9 (250 mg, 892 μmol) and 1-[3-(2-methoxyethoxy)pyridin-4-yl]methanamine (325 mg, 1.78 mmol) as the starting materials, the title compound was prepared 140 mg (34% yield).
$^1$H-NMR (400 MHz, DMSO-d$_6$): δ [ppm]=14.52 (s, 1H), 13.68 (brt, 1H), 8.39 (s, 1H), 8.23 (d, 1H), 7.68 (br s, 1H), 7.18-7.34 (m, 2H), 7.03-7.12 (m, 2H), 4.64 (d, 2H), 4.26-4.32 (m, 2H), 3.68-3.74 (m, 2H), 3.31 (s, 3H), 3.16 (m, 2H), 2.76 (t, 2H), 2.04 (d, 3H).

Intermediate 6-21

N-(3-fluoro-2-methylphenyl)-4-({[3-(2-methoxy-2-methylpropoxy)pyridin-4-yl]methyl}amino)-2-oxo-1,2,5,6-tetrahydropyridine-3-carbothioamide

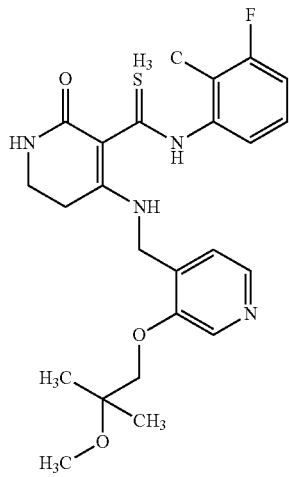

Using an analogous method as described for Intermediate 6-1, intermediate 5-9 (250 mg, 892 μmol) and 1-[3-(2-methoxy-2-methylpropoxy)pyridin-4-yl]methanamine (375 mg, 1.78 mmol) as the starting materials, the title compound was prepared 220 mg (52% yield).

$^1$H-NMR (400 MHz, DMSO-d$_6$): δ [ppm]=14.51 (s, 1H), 13.65 (t, 1H), 8.39 (s, 1H), 8.23 (d, 1H), 7.69 (br s, 1H), 7.28 (d, 1H), 7.18-7.26 (m, 1H), 7.03-7.10 (m, 2H), 4.68 (d, 2H), 4.03 (s, 2H), 3.14-3.20 (m, 5H), 2.76 (t, 2H), 2.04 (d, 3H), 1.22-1.26 (m, 6H).

Intermediate 6-22

N-[2-(2,2-difluoroethyl)-3-fluorophenyl]-4-({[3-(2-methoxyethoxy)pyridin-4-yl]methyl}amino)-2-oxo-1,2,5,6-tetrahydropyridine-3-carbothioamide

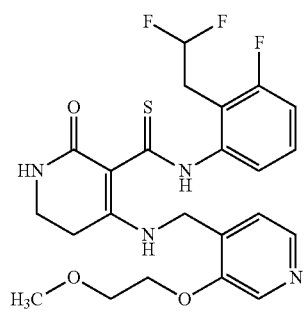 [SMILES: COCCOc1cnccc1CNC1=C(C(=S)Nc2cccc(F)c2CC(F)F)C(=O)NCC1]

Using an analogous method as described for Intermediate 6-1, intermediate 5-10 (250 mg, 757 μmol) and 1-[3-(2-methoxyethoxy)pyridin-4-yl]methanamine (276 mg, 1.51 mmol) as the starting materials, the title compound was prepared 140 mg (36% yield).
$^1$H-NMR (400 MHz, DMSO-d$_6$): δ [ppm]=14.57 (s, 1H), 13.60 (brt, 1H), 8.39 (s, 1H), 8.23 (d, 1H), 7.71 (brs, 1H), 7.29-7.40 (m, 2H), 7.10-7.19 (m, 2H), 5.97-6.32 (m, 1H), 4.65 (d, 2H), 4.29 (m, 2H), 3.67-3.72 (m, 2H), 3.31 (s, 3H), 3.04-3.20 (m, 4H), 2.74-2.81 (m, 2H).

Intermediate 6-23

N-[2-(2,2-difluoroethyl)-3-fluorophenyl]-4-({[3-(2-methoxy-2-methylpropoxy)pyridin-4-yl]methyl}amino)-2-oxo-1,2,5,6-tetrahydropyridine-3-carbothioamide

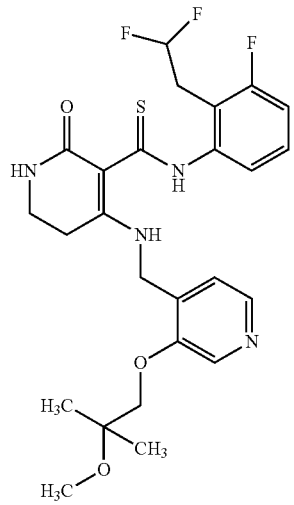 [SMILES: COC(C)(C)COc1cnccc1CNC1=C(C(=S)Nc2cccc(F)c2CC(F)F)C(=O)NCC1]

Using an analogous method as described for Intermediate 6-1, intermediate 5-10 (250 mg, 757 µmol) and 1-[3-(2-methoxy-2-methylpropoxy)pyridin-4-yl]methanamine (207 mg, 984 µmol) as the starting materials, the title compound was prepared 190 mg (48% yield).

$^1$H-NMR (400 MHz, DMSO-d$_6$): δ [ppm]=14.57 (s, 1H), 13.57 (br s, 1H), 8.40 (s, 1H), 8.23 (d, 1H), 7.72 (br s, 1H), 7.32-7.43 (m, 1H), 7.28 (d, 1H), 7.09-7.23 (m, 2H), 6.16 (br d, 1H), 5.98-6.32 (m, 1H), 4.64-4.74 (m, 2H), 3.99-4.06 (m, 2H), 3.03-3.20 (m, 7H), 2.72-2.82 (m, 2H), 1.21-1.26 (m, 6H).

Intermediate 6-24

N-[3-fluoro-2-(prop-2-en-1-yloxy)phenyl]-4-({[3-(2-methoxy-2-methylpropoxy)pyridin-4-yl]methyl}amino)-2-oxo-1,2,5,6-tetrahydropyridine-3-carbothioamide

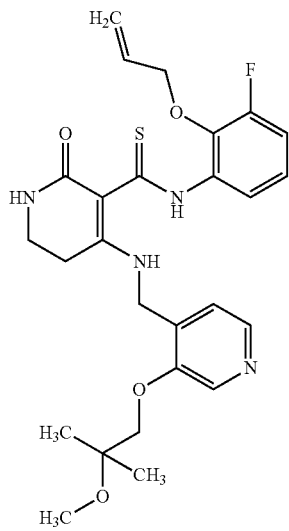 [SMILES: C=CCOc1c(F)cccc1NC(=S)C1=C(NCc2ccncc2OCC(C)(C)OC)CCNC1=O]

Using an analogous method as described for Intermediate 6-1, intermediate 5-11 (250 mg, 776 µmol) and 1-[3-(2-methoxy-2-methylpropoxy)pyridin-4-yl]methanamine (212 mg, 1.01 mmol) as the starting materials, the title compound was prepared 190 mg (48% yield).

$^1$H-NMR (400 MHz, DMSO-d$_6$): δ [ppm]=14.70 (s, 1H), 13.69 (brt, 1H), 8.40 (s, 1H), 8.24 (d, 1H), 7.73 (br s, 1H), 7.61 (m, 1H), 7.29 (d, 1H), 7.02-7.12 (m, 2H), 5.97-6.07 (m, 1H), 5.30 (dq, 1H), 5.15-5.20 (m, 1H), 4.69 (d, 2H), 4.48 (d, 2H), 3.99-4.05 (m, 2H), 3.12-3.21 (m, 5H), 2.76 (t, 2H), 1.24 (s, 6H).

Intermediate 6-25

N-(2-ethoxy-3-fluorophenyl)-4-({[3-(2-methoxyethoxy)pyridin-4-yl]methyl}amino)-2-oxo-1,2,5,6-tetrahydropyridine-3-carbothioamide

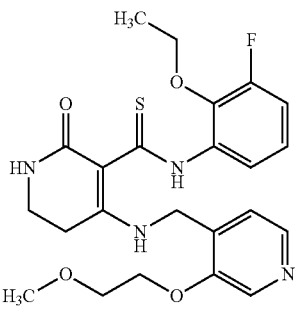 [SMILES: CCOc1c(F)cccc1NC(=S)C1=C(NCc2ccncc2OCCOC)CCNC1=O]

Using an analogous method as described for Intermediate 6-1, intermediate 5-12 (250 mg, 806 µmol) and 1-[3-(2-methoxyethoxy)pyridin-4-yl]methanamine (294 mg, 1.61 mmol) as the starting materials, the title compound was prepared 134 mg (33% yield).

$^1$H-NMR (400 MHz, DMSO-d$_6$): δ [ppm]=14.73 (s, 1H), 13.72 (brt, 1H), 8.40 (s, 1H), 8.24 (d, 1H), 7.68-7.75 (m, 2H), 7.31 (d, 1H), 7.01-7.11 (m, 2H), 4.66 (d, 2H), 4.26-4.33 (m, 2H), 4.00 (q, 2H), 3.66-3.76 (m, 2H), 3.32 (s, 3H), 3.09-3.21 (m, 2H), 2.72-2.81 (m, 2H), 1.26 (t, 3H).

Intermediate 6-26

N-(2-ethoxy-3-fluorophenyl)-4-({[3-(2-methoxy-2-methylpropoxy)pyridin-4-yl]methyl}amino)-2-oxo-1,2,5,6-tetrahydropyridine-3-carbothioamide

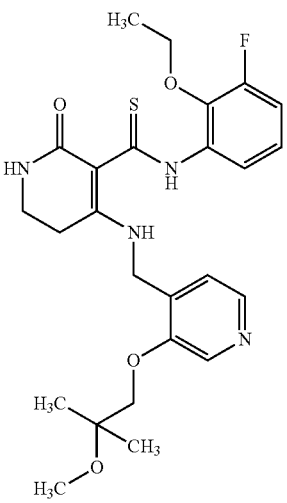 [SMILES: CCOc1c(F)cccc1NC(=S)C1=C(NCc2ccncc2OCC(C)(C)OC)CCNC1=O]

Using an analogous method as described for Intermediate 6-1, intermediate 5-12 (250 mg, 806 µmol) and 1-[3-(2-methoxy-2-methylpropoxy)pyridin-4-yl]methanamine (220 mg, 1.05 mmol) as the starting materials, the title compound was prepared 200 mg (49% yield).

$^1$H-NMR (400 MHz, DMSO-d$_6$): δ [ppm]=14.73 (s, 1H), 13.70 (br t, 1H), 8.34-8.42 (m, 1H), 8.24 (d, 1H), 7.68-7.75

(m, 2H), 7.29 (d, 1H), 7.01-7.11 (m, 2H), 4.69 (d, 2H), 3.92-4.08 (m, 4H), 3.04-3.19 (m, 5H), 2.76 (t, 2H), 1.21-1.31 (m, 9H).

Intermediate 6-27

N-[2-(2,2-difluoroethoxy)-3-fluorophenyl]-4-({[3-(2-methoxy-2-methylpropoxy)pyridin-4-yl]methyl}amino)-2-oxo-1,2,5,6-tetrahydropyridine-3-carbothioamide

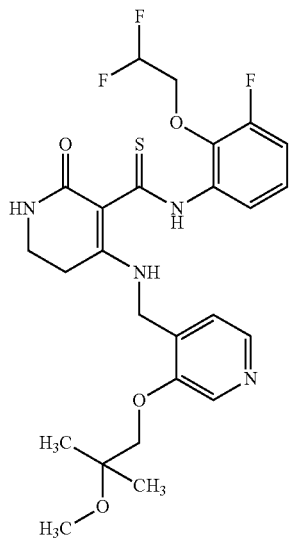 [SMILES: COC(C)(C)COc1cnccc1CNC1=C(C(=S)Nc2cccc(F)c2OCC(F)F)C(=O)NCC1]

Using an analogous method as described for Intermediate 6-1, intermediate 5-13 (250 mg, 722 μmol) and 1-[3-(2-methoxy-2-methylpropoxy)pyridin-4-yl]methanamine (197 mg, 938 μmol) as the starting materials, the title compound was prepared 220 mg (57% yield).

$^1$H-NMR (400 MHz, DMSO-d$_6$): δ [ppm]=14.72 (s, 1H), 13.65 (br t, 1H), 8.15-8.41 (m, 3H), 7.77 (br s, 1H), 7.58-7.65 (m, 1H), 7.28 (d, 1H), 7.08-7.17 (m, 2H), 6.30 (tt, 1H), 4.70 (d, 2H), 4.17-4.29 (m, 2H), 4.04 (s, 2H), 3.13-3.20 (m, 5H), 2.73-2.80 (m, 2H), 1.20-1.27 (m, 6H).

Intermediate 6-28

N-(3,4-difluoro-2-methoxyphenyl)-4-({[3-(2-methoxyethoxy)pyridin-4-yl]methyl}amino)-2-oxo-1,2,5,6-tetrahydropyridine-3-carbothioamide

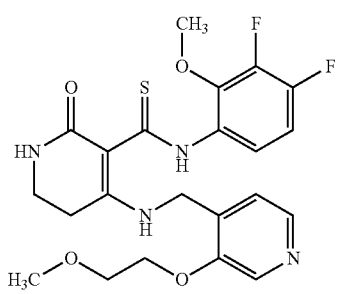 [SMILES: COCCOc1cnccc1CNC1=C(C(=S)Nc2ccc(F)c(F)c2OC)C(=O)NCC1]

Using an analogous method as described for Intermediate 6-1, intermediate 5-14 (250 mg, 795 μmol) and 1-[3-(2-methoxyethoxy)pyridin-4-yl]methanamine (290 mg, 1.59 mmol) as the starting materials, the title compound was prepared 115 mg (29% yield).

$^1$H-NMR (400 MHz, DMSO-d$_6$): δ [ppm]=14.64 (s, 1H), 13.67 (brt, 1H), 8.40 (s, 1H), 8.23 (d, 1H), 7.71 (brs, 1H), 7.48-7.54 (m, 1H), 7.31 (d, 1H), 7.10-7.19 (m, 1H), 4.65 (d, 2H), 4.25-4.33 (m, 2H), 3.84 (d, 3H), 3.68-3.73 (m, 2H), 3.31 (s, 3H), 3.12-3.19 (m, 2H), 2.71-2.80 (m, 2H).

Intermediate 6-29

N-(3,4-difluoro-2-methoxyphenyl)-4-({[3-(2-methoxy-2-methylpropoxy)pyridin-4-yl]methyl}amino)-2-oxo-1,2,5,6-tetrahydropyridine-3-carbothioamide

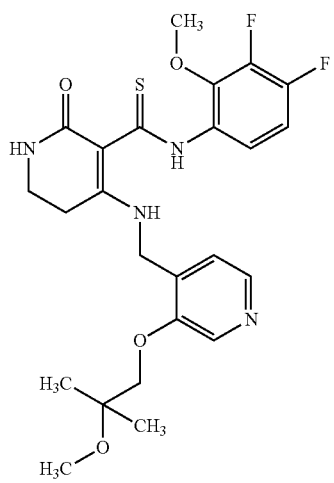 [SMILES: COc1c(NC(=S)C2=C(NCc3ccncc3OCC(C)(C)OC)CCNC2=O)ccc(F)c1F]

Using an analogous method as described for Intermediate 6-1, intermediate 5-14 (250 mg, 795 μmol) and 1-[3-(2-methoxy-2-methylpropoxy)pyridin-4-yl]methanamine (335 mg, 1.59 mmol) as the starting materials, the title compound was prepared 240 mg (60% yield).

$^1$H-NMR (400 MHz, DMSO-d$_6$): δ [ppm]=14.64 (s, 1H), 13.65 (brt, 1H), 8.40 (s, 1H), 8.24 (d, 1H), 7.72 (brs, 1H), 7.48-7.59 (m, 1H), 7.28 (d, 1H), 7.10-7.19 (m, 1H), 4.69 (d, 2H), 4.03 (s, 2H), 3.84 (d, 3H), 3.09-3.20 (m, 6H), 2.74-2.78 (m, 2H), 1.23-1.25 (m, 6H).

Intermediate 6-30

N-(3,5-difluoro-2-methoxyphenyl)-4-({[3-(2-methoxyethoxy)pyridin-4-yl]methyl}amino)-2-oxo-1,2,5,6-tetrahydropyridine-3-carbothioamide

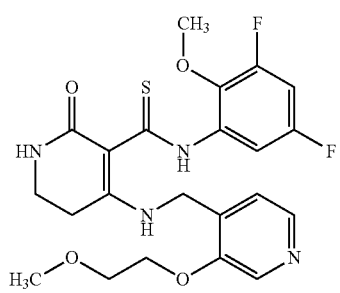 [SMILES: COCCOc1cnccc1CNC1=C(C(=S)Nc2cc(F)cc(F)c2OC)C(=O)NCC1]

Using an analogous method as described for Intermediate 6-1, intermediate 5-15 (250 mg, 795 µmol) and 1-[3-(2-methoxyethoxy)pyridin-4-yl]methanamine (290 mg, 1.59 mmol) as the starting materials, the title compound was prepared 160 mg (40% yield).

$^1$H-NMR (400 MHz, DMSO-d$_6$): δ [ppm]=15.06 (s, 1H), 13.67 (brt, 1H), 8.41 (s, 1H), 8.24 (d, 1H), 7.91-7.97 (m, 1H), 7.78 (brs, 1H), 7.32 (d, 1H), 7.14 (m, 1H), 4.67 (d, 2H), 4.27-4.33 (m, 2H), 3.70-3.77 (m, 5H), 3.32 (s, 3H), 3.15 (m, 2H), 2.78 (t, 2H).

Intermediate 6-31

N-(3,5-difluoro-2-methoxyphenyl)-4-({[3-(2-methoxy-2-methylpropoxy)pyridin-4-yl]methyl}amino)-2-oxo-1,2,5,6-tetrahydropyridine-3-carbothioamide

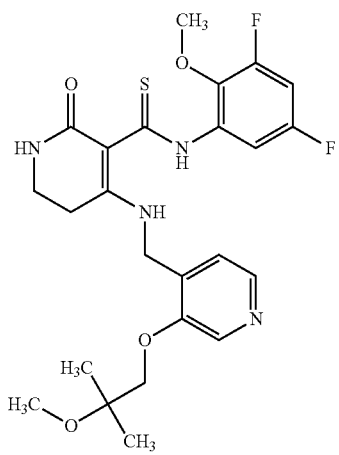 [SMILES: COc1c(F)cc(F)cc1NC(=S)C1=C(NCc2ccncc2OCC(C)(C)OC)CCNC1=O]

Using an analogous method as described for Intermediate 6-1, intermediate 5-15 (250 mg, 795 µmol) and 1-[3-(2-methoxy-2-methylpropoxy)pyridin-4-yl]methanamine (335 mg, 1.59 mmol) as the starting materials, the title compound was prepared 250 mg (62% yield).

$^1$H-NMR (400 MHz, DMSO-d$_6$): δ [ppm]=15.06 (s, 1H), 13.65 (t, 1H), 8.41 (s, 1H), 8.24 (d, 1H), 7.93 (dt, 1H), 7.78 (br s, 1H), 7.29 (d, 1H), 7.14 (m, 1H), 4.71 (d, 2H), 3.99-4.06 (m, 2H), 3.76 (d, 3H), 3.14-3.19 (m, 5H), 2.78 (t, 2H), 1.24 (s, 6H).

Intermediate 6-32

N-(3-chloro-2-methoxyphenyl)-4-({[3-(2-methoxyethoxy)pyridine-4-yl]methyl}amino)-2-oxo-1,2,5,6-tetrahydropyridine-3-carbothioamide

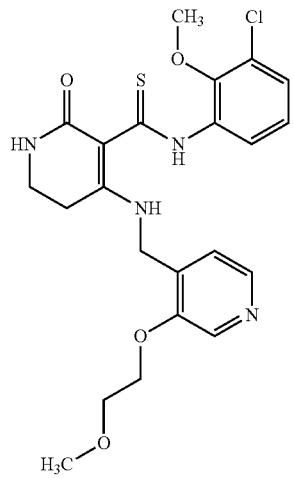 [SMILES: COCCOc1cnccc1CNC1=C(C(=S)Nc2cccc(Cl)c2OC)C(=O)NCC1]

In a microwave tube N-(3-chloro-2-methoxyphenyl)-4-hydroxy-2-oxo-1,2,5,6-tetrahydropyridine-3-carbothioamide (intermediate 5-32, 200 mg, 96% purity, 614 µmol) and 1-[3-(2-methoxyethoxy)pyridine-4-yl]methanamine (CAS: 1539076-88-4, 168 mg, 921 µmol) were heated by microwave irradiation for 2 h at 120° C. The reaction mixture was diluted with 2 mL dimethyl sulfoxide, filtered and purified by preparative HPLC to give 119 mg of the title compound (99% purity, 40% yield).

$^1$H-NMR (400 MHz, DMSO-d6) δ [ppm]: 2.518 (0.67), 2.522 (0.42), 2.774 (0.40), 3.315 (4.60), 3.331 (16.00), 3.695 (0.42), 3.718 (0.53), 4.285 (0.42), 4.297 (0.44), 4.652 (0.47), 4.667 (0.46), 7.111 (0.56), 7.306 (0.42), 7.310 (0.65), 8.233 (0.55), 8.244 (0.51), 8.400 (0.86), 14.789 (0.48).

LC-MS (method 2): R$_t$=1.09 min; MS (ESIpos): m/z=477 [M+H]$^+$

The examples in Table 2 were prepared analogous to the preparation of intermediate 6-32.

TABLE 2

| Intermediate | Structure Name | Analytical Data | Starting materials |
|---|---|---|---|
| 6-33 | ![structure] | $^1$H-NMR (400 MHz, DMSO-d6) δ (ppm): 1.154 (0.97), 1.172 (2.04), 1.190 (1 04), 1.225 (2.64), 1.239 (16.00), 1.987 (3.28), 2.518 (1.65), 2.523 (1.03), 2.756 (0.56), 2.774 (1.12), 2.790 (0.64), 3.141 (0.45), 3.149 (0.54), 3.159 (0.92), 3.166 (3.09), 3.169 (13.83), 3.174 (1.38), 3.180 (0.66), 3.188 (0.47), 3.711 (12.11), 3.965 (0.58), 4.017 (0.85), 4.035 (4.63), 4.688 (1.29), 4.703 (1.29), 7.087 (0.77), 7.108 | N-(3-chloro-2-methoxyphenyl)-4-hydroxy-2-oxo-1,2,5,6-tetrahydropyridine-3 carbothioamide (Intermediate 5-32, 306 mg, 978 µmol) 1-[3-(2-methoxy-2-methylpropoxy)pyridin-4-yl]methanamine (intermediate 2-2, 329 mg, 1.57 mmol) |

TABLE 2-continued

| Inter-mediate | Structure Name | Analytical Data | Starting materials |
|---|---|---|---|
| | N-(3-chloro-2-methoxyphenyl)-4-({[3-(2-methoxy-2-methylpropoxy)pyridin-4-yl]methyl}amino)-2-oxo-1,2,5,6-tetrahydropyridine-3-carbothioamide | (1.68), 7.128 (0.97), 7.284 (1.19), 7.288 (2.04), 7.301 (1.21), 7.304 (1.25), 7.308 (0.93), 7.733 (0.75), 7.789 (0.84), 7.793 (0.84), 7.809 (0.80), 7.813 (0.75), 8.234 (1.86), 8.246 (1.58), 8.401 (2.57), 13.681 (0.52), 14.787 (1.29). LC-MS (method 1): R$_t$ = 1.09 min; MS (ESIpos): m/z = 505 [M + H]$^+$ | |
| 6-34 | N-(2,3-dichlorophenyl)-4-({[3-(2-methoxy-2-methylpropoxy)pyridin-4-yl]methyl}amino)-2-oxo-1,2,5,6-tetrahydropyridine-3-carbothioamide | $^1$H-NMR (400 MHz, DMSO-d6) δ [ppm]: 1.154 (1.45), 1.172 (2.92), 1.190 (1.40), 1.238 (16.00), 1.988 (5.19), 2.518 (0.95), 2.523 (0.62), 2.767 (0.53), 2.784 (1.10), 2.801 (0.63), 3.150 (0.43), 3.167 (13.31), 4.017 (1.22), 4.033 (4.42), 4.053 (0.41), 4.692 (1.27), 4.707 (1.26), 7.278 (1.07), 7.290 (1.10), 7.330 (0.77), 7.350 (1.71), 7.370 (1.10), 7.497 (0.86), 7.500 (1.19), 7.517 (0.80), 7.521 (0.89), 7.525 (1.00), 7.528 (0.78), 7.546 (0.79), 7.549 (0.63), 7.749 (0.74), 8.229 (1.72), 8.241 (1.70), 8.398 (2.60), 13.655 (0.55), 14.890 (1.51). LC-MS (method 2): R$_t$ = 1.23 min; MS (ESIpos): m/z = 510 [M + H]$^+$ | N-(2,3-dichlorophenyl)-4-hydroxy-2-oxo-1,2,5,6-tetrahydropyridine-3-carbothioamide (intermediate 5-34, 200 mg, 631 μmol) 1-[3-(2-methoxy-2-methylpropoxy)pyridin-4-yl]methanamine (intermediate 2-2, 146 mg, 694 μmol) |
| 6-35 | N-(2-ethyl-3-fluorophenyl)-4-({[3-(2-methoxy-2-methylpropoxy)pyridin-4-yl]methyl}amino)-2-oxo-1,2,5,6-tetrahydropyridine-3-carbothioamide | LC-MS (method 2): R$_t$ = 1.19 min; MS (ESIpos): m/z = 487 [M + H]$^+$ | N-(2-ethyl-3-fluorophenyl)-4-hydroxy-2-oxo-1,2,5,6-tetrahydropyridine-3-carbothioamide (intermediate 5-35, 200 mg, 679 μmol) 1-[3-(2-methoxy-2-methylpropoxy)pyridin-4-yl]methanamine (intermediate 2-2, 143 mg, 679 μmol) |

TABLE 2-continued

| Intermediate | Structure Name | Analytical Data | Starting materials |
|---|---|---|---|
| 6-36 | 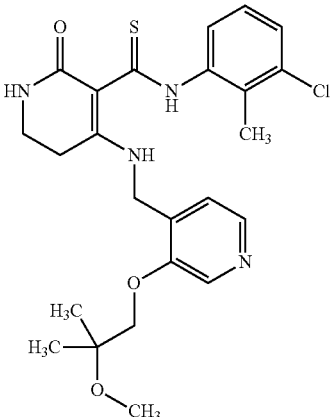<br>N-(3-chloro-2-methylphenyl)-4-({[3-(2-methoxy-2-methylpropoxy)pyridin-4-yl]methyl}amino)-2-oxo-1,2,5,6-tetrahydropyridine-3-carbothioamide | LC-MS (method 2): R$_t$ = 1.22 min; MS (ESIpos): m/z = 490 [M + H]$^+$ | N-(3-chloro-2-methylphenyl)-4-hydroxy-2-oxo-1,2,5,6-tetrahydropyridine-3-carbothioamide (intermediate 5-36, 389 mg, 1.31 mmol) 1-[3-(2-methoxy-2-methylpropoxy)pyridin-4-yl]methanamine (intermediate 2-2, 358 mg, 1.70 mmol) |
| 6-37 | 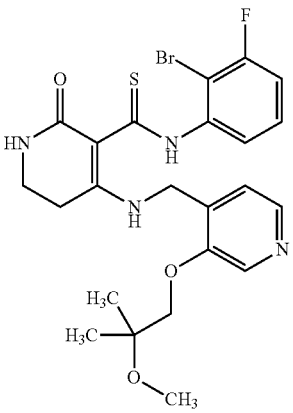 [SMILES: COC(C)(C)COc1cnccc1CNC1=C(C(=S)Nc2cccc(F)c2Br)C(=O)NCC1]<br>N-(2-bromo-3-fluorophenyl)-4-({[3-(2-methoxy-2-methylpropoxy)pyridin-4-yl]methyl}amino)-2-oxo-1,2,5,6-tetrahydropyridine-3-carbothioamide | $^1$H-NMR (400 MHz, DMSO-d6) δ [ppm]: 1.227 (0.72), 1.239 (16.00), 2.518 (1.63), 2.523 (1.06), 2.768 (0.58), 2.784 (1.19), 2.801 (0.69), 3.168 (13.69), 3.183 (0.50), 4.034 (4.29), 4.690 (1.37), 4.705 (1.37), 7.234 (0.60), 7.238 (0.73), 7.255 (0.45), 7.259 (0.46), 7.278 (1.10), 7.290 (1.13), 7.344 (0.41), 7.360 (1.13), 7.374 (0.69), 7.389 (0.63), 7.394 (0.70), 7.409 (0.72), 7.739 (0.79), 8.230 (1.63), 8.242 (1.58), 8.398 (2.58), 13.679 (0.60), 14.822 (1.55).<br>LC-MS (method 2): R$_t$ = 0.98 min; MS (ESIpos): m/z = 538 [M + H]$^+$ | N-(2-bromo-3-fluorophenyl)-4-hydroxy-2-oxo-1,2,5,6-tetrahydropyridine-3-carbothioamide (intermediate 5-37, 217 mg, 96% purity, 603 μmol) 1-[3-(2-methoxy-2-methylpropoxy)pyridin-4-yl]methanamine (intermediate 2-2, 140 mg, 664 μmol) |
| 6-38 | 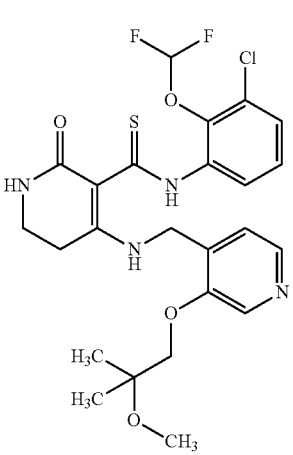 [SMILES: COC(C)(C)COc1cnccc1CNC1=C(C(=S)Nc2cccc(Cl)c2OC(F)F)C(=O)NCC1] | $^1$H-NMR (400 MHz, DMSO-d6) δ [ppm]: 1.236 (16.00), 2.765 (0.55), 2.781 (1.13), 2.798 (0.65), 3.141 (0.45), 3.151 (0.72), 3.166 (13.66), 4.033 (4.35), 4.689 (1.31), 4.704 (1.30), 5.757 (0.89), 6.720 (0.71), 6.903 (1.51), 7.085 (0.66), 7.276 (1.12), 7.289 (1.16), 7.294 (0.89), 7.314 (1.77), 7.334 (1.09), 7.449 (0.94), 7.452 (1.05), 7.469 (0.77), 7.473 (0.76), 7.581 (0.82), 7.585 (0.84), 7.601 | N-[3-chloro-2-(difluoromethoxy)phenyl]-4-hydroxy-2-oxo-1,2,5,6-tetrahydropyridine-3-carbothioamide (intermediate 5-38, 400 mg, 91% purity, 1.04 mmol) 1-[3-(2-methoxy-2-methylpropoxy)pyridin-4-yl]methanamine (intermediate 2-2, 395 mg, 1.88 mmol) |

TABLE 2-continued

| Intermediate | Structure Name | Analytical Data | Starting materials |
|---|---|---|---|
| | N-[3-chloro-2-(difluoromethoxy)phenyl]-4-({[3-(2-methoxy-2-methylpropoxy)pyridin-4-yl]methyl}amino)-2-oxo-1,2,5,6-tetrahydropyridine-3-carbothioamide | (0.74), 7.605 (0.69), 7.729 (0.75), 8.229 (1.76), 8.240 (1.74), 8.399 (2.69), 13.614 (0.44), 14.784 (1.03). LC-MS (method 2): R$_t$ = 1.20 min; MS (ESIpos): m/z = 542 [M + H]$^+$ | |
| 6-39 | N-(2-chlorophenyl)-4-({[3-(2-methoxy-2-methylpropoxy)pyridin-4-yl]methyl}amino)-2-oxo-1,2,5,6-tetrahydropyridine-3-carbothioamide | $^1$H-NMR (400 MHz, DMSO-d6) δ (ppm): 1.036 (0.90), 1.053 (2.03), 1.071 (1.03), 1.240 (16.00), 2.518 (0.53), 2.755 (0.52), 2.772 (1.05), 2.788 (0.60), 3.152 (0.45), 3.169 (13.97), 3.423 (0.46), 3.436 (0.48), 3.440 (0.45), 3.452 (0.45), 4.034 (4.08), 4.356 (0.61), 4.685 (1.23), 4.700 (1.22), 7.239 (0.68), 7.243 (0.68), 7.258 (0.59), 7.263 (0.58), 7.282 (1.03), 7.294 (1.07), 7.304 (0.52), 7.308 (0.56), 7.323 (0.70), 7.327 (0.76), 7.342 (0.41), 7.499 (0.96), 7.502 (1.01), 7.519 (0.87), 7.523 (0.83), 7.567 (0.77), 7.572 (0.78), 7.587 (0.68), 7.591 (0.65), 7.703 (0.70), 8.230 (1.77), 8.242 (1.66), 8.397 (2.53), 13.694 (0.51), 14.747 (1.35). LC-MS (method 1): R$_t$ = 1.02 min; MS (ESIpos): m/z = 475 [M + H]$^+$ | N-(2-chlorophenyl)-4-hydroxy-2-oxo-1,2,5,6-tetrahydropyridine-3-carbothioamide (intermediate 5-39, 600 mg, 2.12 mmol) 1-[3-(2-methoxy-2-methylpropoxy)pyridin-4-yl]methanamine (intermediate 2-2, 535 mg, 2.55 mmol) |
| 6-40 | | $^1$H-NMR (400 MHz, DMSO-d6) δ [ppm]: 1.237 (16.00), 2.011 (3.18), 2.518 (0.50), 2.756 (0.59), 2.774 (1.20), 2.790 (0.68), 3.145 (0.48), 3.153 (0.59), 3.167 (13.73), 3.178 (0.63), 3.183 (0.50), 4.034 (4.29), 4.684 (1.36), 4.698 (1.35), 7.095 (0.40), 7.102 (0.68), 7.113 (0.57), 7.125 (0.50), 7.138 (0.52), 7.277 (1.10), 7.289 (1.12), 7.745 (0.79), 8.230 (1.64), 8.242 (1.56), 8.398 (2.59), 13.626 (0.49), 14.680 (1.24). | N-(3,5-difluoro-2-methylphenyl)-4-hydroxy-2-oxo-1,2,5,6-tetrahydropyridine-3-carbothioamide (intermediate 5-40, 243 mg, 814 μmol) 1-[3-(2-methoxy-2-methylpropoxy)pyridin-4-yl]methanamine (intermediate 2-2, 222 mg, 1.06 mmol) |

TABLE 2-continued

| Intermediate | Structure Name | Analytical Data | Starting materials |
|---|---|---|---|
| | N-(3,5-difluoro-2-methylphenyl)-4-({[3-(2-methoxy-2-methylpropoxy)pyridin-4-yl]methyl}amino)-2-oxo-1,2,5,6-tetrahydropyridine-3-carbothioamide | LC-MS (method 2): R$_t$ = 1.05 min; MS (ESIpos): m/z = 491 [M + H]$^+$ | |
| 6-41 | 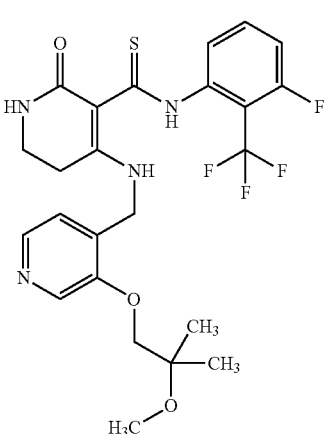 [SMILES: COC(C)(C)COc1cnccc1CNC1=C(C(=S)Nc2cccc(F)c2C(F)(F)F)C(=O)NCC1]<br>N-[3-fluoro-2-(trifluoromethyl)phenyl]-4-({[3-(2-methoxy-2-methylpropoxy)pyridin-4-yl]methyl}amino)-2-oxo-1,2,5,6-tetrahydropyridine-3-carbothioamide | $^1$H-NMR (400 MHz, DMSO-d6) δ [ppm]: 1.232 (16.00), 2.518 (0.78), 2.523 (0.56), 2.773 (0.54), 2.790 (1.12), 2.807 (0.64), 3.151 (0.45), 3.163 (15.20), 3.174 (0.81), 3.183 (0.44), 4.028 (4.27), 4.682 (1.26), 4 696 (1.25), 7.257 (0.66), 7.275 (1.58), 7.287 (1.07), 7.357 (0.41), 7.677 (0.47), 7.692 (0.47), 7.739 (0.74), 8.228 (1.38), 8.240 (1.34), 8.397 (2.17), 13.611 (0.56), 14.915 (1.21).<br>LC-MS (method 2): R$_t$ = 1.17 min; MS (ESIpos): m/z = 527 [M + H]$^+$ | N-[3-fluoro-2-(trifluoromethyl)phenyl]-4-hydroxy-2-oxo-1,2,5,6-tetrahydropyridine-3-carbothioamide (intermediate 5-41, 200 mg, 598 µmol) 1-[3-(2-methoxy-2-methylpropoxy)pyridin-4-yl]methanamine (intermediate 2-2, 126 mg, 598 µmol) |
| 6-42 | 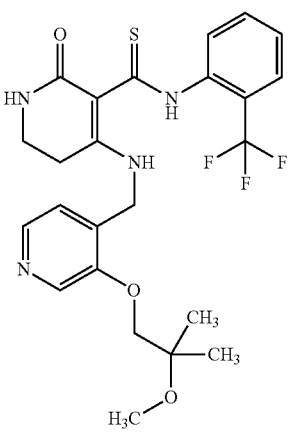 [SMILES: COC(C)(C)COc1cnccc1CNC1=C(C(=S)Nc2ccccc2C(F)(F)F)C(=O)NCC1]<br>4-({[3-(2-methoxy-2-methylpropoxy)pyridin-4-yl]methyl}amino)-2-oxo-N-[2-(trifluoromethyl)phenyl]-1,2,5,6-tetrahydropyridine-3-carbothioamide | $^1$H-NMR (400 MHz, DMSO-d6) δ (ppm): 1.234 (16.00), 2.618 (1.32), 2.523 (0.85), 2.768 (0.56), 2.784 (1.14), 2.801 (0.64), 3.165 (14.78), 3.183 (0.45), 3.190 (0.44). 4.030 (4.19), 4.681 (1.30), 4.695 (1.28), 7.282 (1.07), 7.294 (1.09), 7.426 (0.67), 7.445 (0.41), 7.540 (0.59), 7.560 (0.87), 7.628 (0.47), 7.646 (0.64), 7.704 (0.77), 7.721 (0.79), 7.740 (0.66), 8.230 (1.70), 8.242 (1.59), 8.397 (2.51), 13.693 (0.58), 14.908 (1.34).<br>LC-MS (method 2): R$_t$ = 1.16 min; MS (ESIpos): m/z = 509 [M + H]$^+$ | 4-hydroxy-2-oxo-N-[2-(trifluoromethyl)phenyl]-1,2,5,6-tetrahydropyridine-3-carbothioamide (intermediate 5-42, 200 mg, 71% purity, 449 µmol) 1-[3-(2-methoxy-2-methylpropoxy)pyridin-4-yl]methanamine (intermediate 2-2, 104 mg, 494 µmol) |

TABLE 2-continued

| Intermediate | Structure Name | Analytical Data | Starting materials |
|---|---|---|---|
| 6-43 | 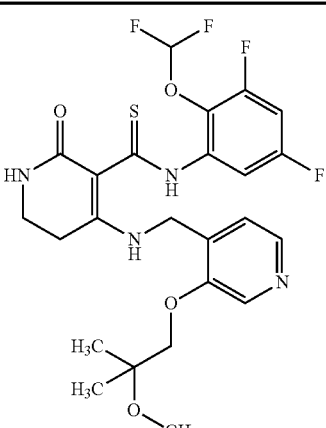<br>N-[2-(difluoromethoxy)-3,5-difluorophenyl]-4-({[3-(2-methoxy-2-methylpropoxy)pyridin-4-yl]methyl}amino)-2-oxo-1,2,5,6-tetrahydropyridine-3-carbothioamide | $^1$H-NMR (400 MHz, DMSO-d6) δ (ppm): 1.238 (16.00), 2.518 (0.86), 2.523 (0.55), 2.774 (0.47), 2.791 (0.97), 2.807 (0.57), 3.144 (0.44), 3.154 (0.74), 3.166 (14.85), 3.178 (0.45), 4.038 (4.00), 4.706 (1.14), 4.720 (1.14), 6.838 (0.47), 7.019 (0.92), 7.201 (0.43), 7.280 (0.97), 7.292 (1.00), 7.329 (0.41), 7.799 (0.65), 8.233 (1.54), 8.245 (1.53), 8.406 (2.34), 13.627 (0.47), 15.118 (1.13).<br>LC-MS (method 2): $R_t$ = 1.21 min; MS (ESIpos): m/z = 543 [M + H]$^+$ | N-[2-(difluoromethoxy)-3,5-difluorophenyl]-4-hydroxy-2-oxo-1,2,5,6-tetrahydropyridine-3-carbothioamide (intermediate 5-43, 200 mg, 571 μmol) 1-[3-(2-methoxy-2-methylpropoxy)pyridin-4-yl]methanamine (intermediate 2-2, 216 mg, 1.03 mmol) |
| 6-44 | 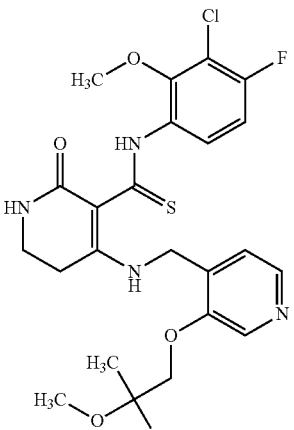<br>N-(3-chloro-4-fluoro-2-(intermediate 2-2, methoxyphenyl)-4-({[3-(2-methoxy-2-methylpropoxy)pyridin-4-yl]methyl}amino)-2-oxo-1,2,5,6-tetrahydropyridine-3-carbothioamide | $^1$H-NMR (400 MHz, DMSO-d6) δ (ppm): 1.165 (1.13), 1.206 (0.57), 1.225 (5.98), 1.236 (16.00), 2.518 (1.43), 2.523 (0.90), 2.759 (0.56), 2.776 (1.12), 2.793 (0.63), 3.104 (0.44), 3.136 (0.75), 3.144 (0.55), 3.150 (0.99), 3.167 (15.10), 3.176 (1.31), 3.183 (0.65), 3.722 (0.93), 3.749 (11.02), 3.967 (1.29), 4.034 (4.12), 4.687 (1.26), 4.702 (1.25), 5.758 (0.51), 7.174 (0.85), 7.196 (1.48), 7.219 (0.91), 7.282 (1.05), 7.294 (1.07), 7.672 (0.73), 7.688 (0.77), 7.695 (0.74), 7.710 (0.70), 7.739 (0.75), 8.162 (0.44), 8.174 (0.40), 8.231 (1.70), 8.243 (2.00), 8.399 (2.49), 13.640 (0.49), 14.707 (1.05).<br>LC-MS (method 2): $R_t$ = 1.12 min; MS (ESIneg): m/z = 521 [M-H]- | N-(3-chloro-4-fluoro-2-methoxyphenyl)-4-hydroxy-2-oxo-1,2,5,6-tetrahydropyridine-3-carbothioamide (intermediate 5-44, 150 mg, 453 μmol) 1-[3-(2-methoxy-2-methylpropoxy)pyridin-4-yl]methanamine (intermediate 2-2, 153 mg, 726 μmol) |

TABLE 2-continued

| Inter-mediate | Structure Name | Analytical Data | Starting materials |
|---|---|---|---|
| 6-45 | 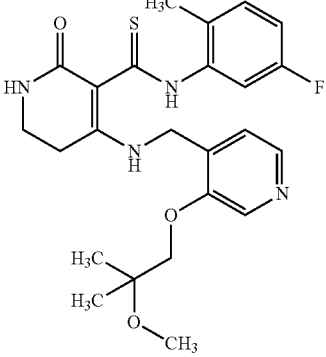<br>N-(5-fluoro-2-methylphenyl)-4-({[3-(2-methoxy-2-methylpropoxy)pyridin-4-yl]methyl}amino)-2-oxo-1,2,5,6-tetrahydropyridine-3-carbothioamide | $^1$H-NMR (400 MHz, DMSO-d6) δ [ppm]: 1.198 (0.64), 1.215 (0.73), 1.239 (16.00), 2.118 (4.83), 2.518 (2.13), 2.522 (1.28), 2.744 (0.55), 2.761 (1.11), 2.777 (0.64), 3.139 (0.44), 3.146 (0.53), 3.156 (0.86), 3.169 (12.65), 3.178 (0.62), 3.504 (0.44), 4.034 (4.10), 4.676 (1.26), 4.690 (1.25), 6.979 (0.60), 6.985 (0.66), 7.236 (0.59), 7.242 (0.60), 7.255 (0.55), 7.262 (0.67), 7.269 (0.91), 7.282 (1.00), 7.294 (1.23), 7.495 (0.50), 7.697 (0.72), 7.934 (0.44), 8.232 (1.16), 8.244 (1.11), 8.398 (1.87), 13.655 (0.43), 14.595 (1.05), LC-MS (method 2): R$_t$ = 1.16 min; MS (ESIpos): m/z = 473 [M + H]$^+$ | N-(5-fluoro-2-methylphenyl)-4-hydroxy-2-oxo-1,2,5,6-tetrahydropyridine-3-carbothioamide (intermediate 5-45, 200 mg, 91% purity, 649 μmol) 1-[3-(2-methoxy-2-methylpropoxy)pyridin-4-yl]methanamine (intermediate 2-2, 246 mg, 1.17 mmol) |
| 6-46 | 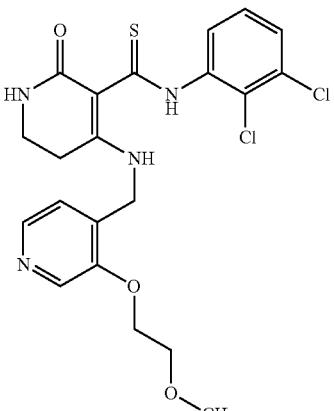<br>N-(2,3-dichlorophenyl)-4-({[3-(2-methoxyethoxy)pyridin-4-yl]methyl}amino)-2-oxo-1,2,5,6-tetrahydropyridine-3-carbothioamide | $^1$H-NMR (400 MHz, DMSO-d6) δ [ppm]: 2.518 (0.45). 2.786 (0.74), 2.803 (0.43), 3.164 (0.50), 3.171 (0.47), 3.312 (9.65), 3.330 (16.00), 3.690 (0.77). 3.698 (0.65), 3.701 (0.84), 3.705 (0.65), 3.713 (0.84), 4.281 (0.80), 4.289 (0.61), 4.292 (0.84), 4.296 (0.63), 4.304 (0.75), 4.654 (0.85), 4.669 (0.86), 7.302 (0.69), 7.314 (0.70), 7.331 (0.52), 7.352 (1.17), 7.372 (0.74), 7.497 (0.58), 7.501 (0.79), 7.518 (0.53), 7.521 (0.57), 7.530 (0.64), 7.533 (0.52), 7.549 (0.51), 7.553 (0.42), 7.743 (0.48), 8.228 (1.03), 8.240 (0.96), 8.397 (1.58), 14.892 (0.96). LC-MS (method 2): R$_t$ = 1.13 min; MS (ESIpos): m/z = 482 [M + H]$^+$ | N-(2,3-dichlorophenyl)-4-hydroxy-2-oxo-1,2,5,6-tetrahydropyridine-3-carbothioamide (intermediate 5-34, 200 mg, 631 μmol) 1-[3-(2-methoxyethoxy)pyridine-4-yl]methanamine (CAS:1539076-88-4, 126 mg, 694 μmol) |

TABLE 2-continued

| Intermediate | Structure Name | Analytical Data | Starting materials |
|---|---|---|---|
| 6-47 | 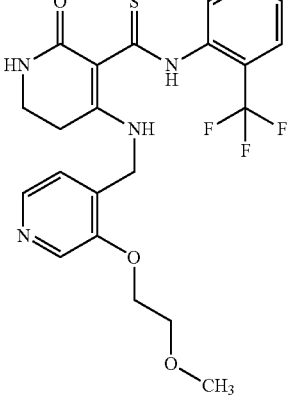<br>4-({[3-(2-methoxyethoxy)pyridin-4-yl]methyl}amino)-2-oxo-N-[2-(trifluoromethyl)phenyl]-1,2,5,6-tetrahydropyridine-3-carbothioamide | $^1$H-NMR (400 MHz, $^1$H-NMR (400 MHz, DMSO-d6) δ (ppm): 2.518 (1.57), 2.523 (1.01), 2.768 (0.60), 2.785 (1.19), 2.801 (0.69), 3.145 (0.45), 3.153 (0.51), 3.162 (0.81), 3.169 (0.77), 3.179 (0.44), 3.308 (16.00), 3.685 (1.24), 3.693 (1.06), 3.697 (1.38), 3.700 (1.06), 3.708 (1.34), 4.277 (1.31), 4.285 (1.01), 4.289 (1.37), 4.293 (1.02), 4.300 (1.21), 4.645 (1.41), 4.659 (1.41), 7.303 (1.14), 7.315 (1.16), 7.427 (0.70), 7.447 (0.43), 7.549 (0.60), 7.568 (0.91), 7.630 (0.49), 7.649 (0.66), 7.699 (0.78), 7.722 (0.78), 7.742 (0.69), 8.229 (1.85), 8.241 (1.78), 8.396 (2.79), 13.712 (0.59), 14.911 (1.39). LC-MS (method 2): $R_t$ = 1.07 min; MS (ESIpos): m/z = 481 [M + H]$^+$ | 4-hydroxy-2-oxo-N-[2-(trifluoromethyl)phenyl]-1,2,5,6-tetrahydropyridine-3-carbothioamide (intermediate 5-42, 200 mg, 71% purity, 449 μmol) methoxyethoxy)pyridine-4-yl]methanamine (CAS:1539076-88-4, 90.0 mg, 494 μmol) |
| 6-48 | 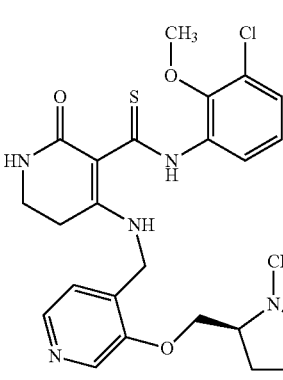<br>N-(3-chloro-2-methoxyphenyl)-4-{[(3-{[(2S)-1-methylpyrrolidin-2-yl]methoxy}pyridin-4-yl)methyl]amino}-2-oxo-1,2,5,6-tetrahydropyridine-3-carbothioamide | $^1$H-NMR (400 MHz, DMSO-d6) δ [ppm]: 1.657 (1.46), 1.667 (1.66), 1.678 (1.69), 1.688 (1.46), 1.701 (0.93), 1.708 (0.74), 1.965 (0.64), 2.181 (1.06), 2.190 (0.72), 2.202 (0.94), 2.276 (1.15), 2.326 (0.67), 2.357 (12.78), 2.362 (6.68), 2.369 (3.35), 2.375 (0.68), 2.518 (2.02), 2.522 (1.40), 2.746 (0.67), 2.762 (1.33), 2.779 (0.84), 2.946 (0.74), 2.951 (0.84), 2.960 (0.74), 3.050 (0.80), 3.144 (0.65), 3.153 (1.06), 3.160 (1.03), 3.423 (1.86), 3.711 (16.00), 3.974 (1.12), 3.989 (0.94), 3.998 (1.15), 4.012 (0.88), 4.146 (0.90), 4.159 (0.93), 4.170 (0.71), 4.183 (0.68), 4.646 (1.69), 4.661 (1.70), 7.088 (1.29), 7.109 (2.50), 7.129 (1.44), 7.284 (1.58), 7.288 (1.66), 7.295 (1.59), 7.304 (1.87), 7.308 (2.56), 7.725 (1.02), 7.794 (1.18), 7.797 (1.20), 7.814 (1.13), 7.818 (1.06), 8.172 (0.68), 8.224 (2.43), 8.236 (2.27), 8.240 (0.84), 8.266 (0.85), 8.286 (0.88), | N-(3-chloro-2-methoxyphenyl)-4-hydroxy-2-oxo-1,2,5,6-tetrahydropyridine-3-carbothioamide (intermediate 5-32, 200 mg, 639 μmol) 1-(3-{[(2S)-1-methylpyrrolidin-2-yl]methoxy}pyridin-4-yl)methanamine (intermediate 2-4, 226 mg, 1.02 mmol) |

TABLE 2-continued

| Inter-mediate | Structure Name | Analytical Data | Starting materials |
|---|---|---|---|
| | | 8.393 (3.52), 13.672 (0.70), 14.785 (1.64). LC-MS (method 1): R$_t$ = 0.82 min; MS (ESIneg): m/z = 514 [M − H]$^-$ | |
| 6-49 | 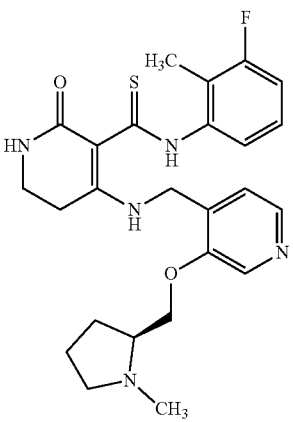 [SMILES: Cc1c(F)cccc1NC(=S)C1=C(NCc2ccncc2OC[C@@H]2CCCN2C)CCNC1=O] N-(3-fluoro-2-methylphenyl)-4-{[(3-{[(2S)-1-methylpyrrolidin-2-yl]methoxy}pyridin-4-yl)methyl]amino}-2-oxo-1,2,5,6-tetrahydropyridine-3-carbothioamide | LC-MS (method 2): R$_t$ = 1.13 min; MS (ESIpos): m/z = 484 [M + H]$^+$ | N-(3-fluoro-2-methylphenyl)-4-hydroxy-2-oxo-1,2,5,6-tetrahydropyridine-3-carbothioamide (intermediate 5-9, 250 mg, 892 μmol) yl]methoxy}pyridin-4-yl)methanamine (intermediate 2-4, 197 mg, 892 μmol) |
| 6-50 | 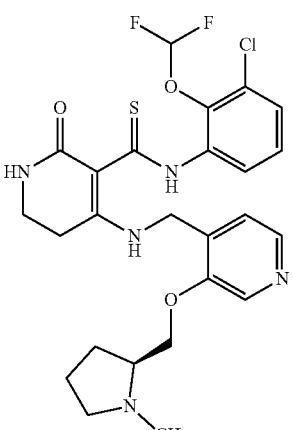 N-[3-chloro-2-(difluoromethoxy)phenyl]-4-{[(3-{[(2S)-1-methylpyrrolidin-2-yl]methoxy}pyridin-4-yl)methyl]amino}-2-oxo-1,2,5,6-tetrahydropyridine-3-carbothioamide | $^1$H-NMR (400 MHz, $^1$H-NMR (400 MHz, DMSO-d6) δ [ppm]: 1.636 (0.49), 1.654 (1.34), 1.670 (1.64), 1.679 (1.46), 1.688 (1.08), 1.701 (0.83), 1.709 (0.53), 1.952 (0.50), 1.961 (0.52), 1.973 (0.62), 1.984 (0.42), 1.992 (0.41), 2.160 (0.48), 2.182 (1.23), 2.203 (1.04), 2.355 (16.00), 2.518 (2.48), 2.522 (1.55), 2.605 (0.55), 2.619 (0.61), 2.625 (0.74), 2.639 (0.62), 2.751 (0.97), 2.768 (1.95), 2.785 (1.18), 2.929 (0.47), 2.936 (0.48), 2.945 (0.60), 2.951 (0.79), 2.960 (0.55), 2.967 (0.56), 3.142 (0.94), 3.151 (1.51), 3.158 (1.47), 3.971 (0.93), 3.985 (0.95), 3.994 (1.18), 4.009 (1.10), 4.141 (1.17), 4.154 (1.21), 4.165 (0.97), 4.178 (0.91), 4.646 (2.35), 4.660 (2.34), 6.721 (1.40), 6.903 (3.00), 7.086 (1.33), 7.282 (2.03), 7.294 (3.12), 7.315 (3.04), 7.336 (1.88), 7.451 (1.80), 7.455 (1.97), 7.471 (1.45), 7.475 (1.40), 7.583 (1.58), 7.587 (1.54), 7.603 (1.39), | N-[3-chloro-2-(difluoromethoxy)phenyl]-4-hydroxy-2-oxo-1,2,5,6-tetrahydropyridine-3-carbothioamide (intermediate 5-38, 150 mg, 430 μmol) 1-(3-{[(2S)-1-methylpyrrolidin-2-yl]methoxy}pyridin-4-yl)methanamine (intermediate 2-4, 95.2 mg, 430 μmol) |

TABLE 2-continued

| Intermediate | Structure Name | Analytical Data | Starting materials |
|---|---|---|---|
| | | 7.607 (1.26), 7.721 (1.44), 8.219 (3.12), 8.230 (2.82), 8.391 (4.66), 13.605 (0.88), 14.779 (2.00). LC-MS (method 2): $R_t$ = 1.18 min; MS (ESIpos): m/z = 553 [M + H]⁺ | |
| 6-51 | 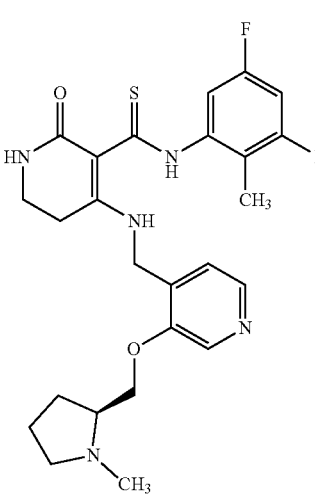 N-(3,5-difluoro-2-methylphenyl)-4-{[(3-{[(2S)-1-methylpyrrolidin-2-yl]methoxy}pyridin-4-yl)methyl]amino}-2-oxo-1,2,5,6-tetrahydropyridine-3-carbothioamide | ¹H-NMR (400 MHz, DMSO-d6) δ (ppm): 1.639 (0.46), 1.655 (1.32), 1.669 (1.53), 1.673 (1.53), 1.679 (1.43), 1.689 (1.12), 1.702 (0.80), 1.710 (0.52), 1.954 (0.51), 1.963 (0.51), 1.974 (0.62), 1.986 (0.47), 1.995 (0.52), 2.010 (5.78), 2.013 (5.80), 2.160 (0.47), 2.183 (1.13), 2.203 (1.00), 2.356 (16.00), 2.518 (1.01), 2.523 (0.66), 2.608 (0.49), 2.615 (0.48), 2.622 (0.56), 2.629 (0.70), 2.644 (0.58), 2.746 (0.89), 2.762 (1.78), 2.779 (1.13), 2.931 (0.44), 2.938 (0.47), 2.947 (0.59), 2.953 (0.76), 2.964 (0.52), 2.969 (0.53), 3.141 (0.80), 3.148 (0.91), 3.157 (1.49), 3.164 (1.46), 3.174 (0.80), 3.181 (0.68), 3.969 (0.91), 3.983 (0.95), 3.993 (1.16), 4.008 (1.11), 4.144 (1.18), 4.156 (1.20), 4.167 (0.97), 4.181 (0.93), 4.641 (2.34), 4.656 (2.36), 7.072 (0.46), 7.079 (0.64), 7.096 (0.75), 7.103 (1.16), 7.119 (1.23), 7.126 (1.28), 7.142 (0.89), 7.286 (2.03), 7.298 (2.05), 7.738 (1.42), 8.221 (3.12), 8.232 (2.86), 8.390 (4.67), 13.604 (0.48), 13.618 (0.89), 13.631 (0.45), 14.679 (2.23). LC-MS (method 1): $R_t$ = 0.72 min; MS (ESIpos): m/z = 502 [M + H]⁺ | N-(3,5-difluoro-2-methylphenyl)-4-hydroxy-2-oxo-1,2,5,6-tetrahydropyridine-3-carbothioamide (intermediate 5-40, 235 mg, 787 µmol) 1-(3-{[(2S)-1-methylpyrrolidin-2-yl]methoxy}pyridin-4-yl)methanamine (intermediate 2-4, 226 mg, 1.02 mmol) |

TABLE 2-continued

| Intermediate | Structure Name | Analytical Data | Starting materials |
|---|---|---|---|
| 6-52 | 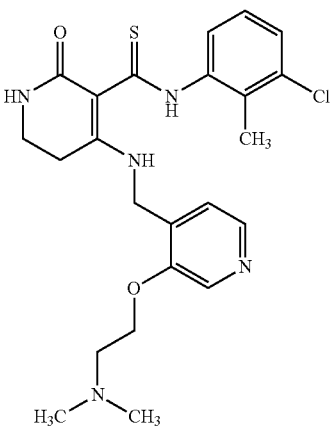 [SMILES: Cc1c(Cl)cccc1NC(=S)C1=C(NCc2ccncc2OCCN(C)C)CCNC1=O]<br>N-(3-chloro-2-methylphenyl)-4-[({3-[2-(dimethylamino)ethoxy]pyridin-4-yl}methyhamino]-2-oxo-1,2,5,6-tetrahydropyridine-3-carbothioamide | LC-MS (method 2): $R_t$ = 1.13 min; MS (ESIpos): m/z = 475 $[M + H]^+$ | N-(3-chloro-2-methylphenyl)-4-hydroxy-2-oxo-1,2,5,6-tetrahydropyridine-3-carbothioamide (intermediate 5-36, 379 mg, 1.28 mmol) 2-{(4-(aminomethyl)pyridin-3-yl]oxy}-N,N-dimethylethan-1-amine (CAS 1513085-25-0), 324 mg, 1.66 mmol) |
| 6-53 | 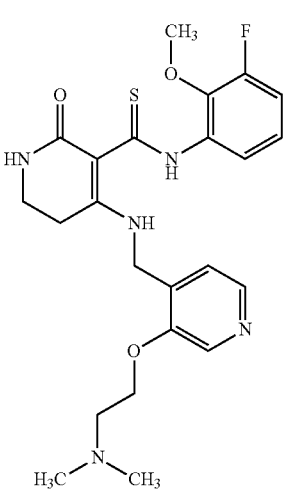 [SMILES: COc1c(F)cccc1NC(=S)C1=C(NCc2ccncc2OCCN(C)C)CCNC1=O]<br>4-[({3-[2-(dimethylamino)ethoxy]pyridin-4-yl}methyl)amino]-N-(3-fluoro-2-methoxyphenyl)-2-oxo-1,2,5,6-tetrahydropyridine-3-carbothioamide | LC-MS (method 2): $R_t$ = 1.03 min; MS (ESIpos): m/z = 474 $[M + H]^+$ | N-(3-fluoro-2-methoxyphenyl)-4-hydroxy-2-oxo-1,2,5,6-tetrahydropyridine-3-carbothioamide (intermediate 5-7, 200 mg, 675 µmol) 2-{[4-(aminomethyl)pyridin-3-yl]oxy}-N,N-dimethylethan-1-amine (CAS 1513085-25-0), 198 mg, 1.01 mmol) |

TABLE 2-continued

| Intermediate | Structure Name | Analytical Data | Starting materials |
|---|---|---|---|
| 6-54 | N-(3-chloro-2-methoxyphenyl)-4-[({3-[2-(dimethylamino)ethoxy]pyridin-4-yl}methyhamino]-2-oxo-1,2,5,6-tetrahydropyridine-3-carbothioamide | $^1$H-NMR (400 MHz, DMSO-d6) δ (ppm): 2.215 (16.00), 2.518 (1.03), 2.523 (0.67), 2.659 (0.92), 2.674 (1.98), 2.689 (0.86), 2.758 (0.46), 2.774 (0.92), 2.791 (0.53), 3.143 (0.40), 3.153 (0.63), 3.159 (0.60), 3.710 (9.07), 4.222 (0.86), 4.237 (1.76), 4.251 (0.81), 4.643 (1.07), 4.658 (1.05), 7.089 (0.60), 7.109 (1.28), 7.129 (0.74), 7.284 (0.86), 7.288 (0.90), 7.304 (1.44), 7.308 (0.82), 7.315 (0.91), 7.725 (0.61), 7.795 (0.66), 7.798 (0.67), 7.815 (0.64), 7.818 (0.60), 8.224 (1.32), 8.236 (1.27), 8.405 (2.03), 13.687 (0.43), 14.787 (1.12), LC-MS (method 2): $R_t$ = 1.09 min; MS (ESIpos): m/z = 491 [M + H]$^+$ | N-(3-chloro-2-methoxyphenyl)-4-hydroxy-2-oxo-1,2,5,6-tetrahydropyridine-3-carbothioamide (intermediate 5-32. 200 mg. 96% purity. 614 μmol)2-{[4-(aminomethyl)pyridin-3-yl]oxy}-N,N-dimethylethan-1-amine (CAS 1513085-25-0), 180 mg, 921 μmol) |
| 6-55 | N-(3,5-difluoro-2-methylphenyl)-4-[({3-[2-(dimethylamino)ethoxy]pyridin-4-yl}methyhamino]-2-oxo-1,2,5,6-tetrahydropyridine-3-carbothioamide | $^1$H-NMR (400 MHz, DMSO-d6) δ [ppm]: 2.012 (2.58), 2.214 (16.00), 2.518 (0.38), 2.523 (0.24), 2.658 (0.85), 2.672 (1.89), 2.687 (0.86), 2.758 (0.47), 2.775 (0.96), 2.791 (0.55), 3.140 (0.36), 3.148 (0.41), 3.157 (0.65), 3.164 (0.63), 3.174 (0.36), 3.181 (0.31), 4.219 (0.88), 4.234 (1.80), 4.248 (0.85), 4.638 (1.11), 4.653 (1.10), 7.071 (0.20), 7.077 (0.28), 7.094 (0.34), 7.101 (0.50), 7.120 (0.54), 7.125 (0.64), 7.145 (0.38), 7.294 (0.88), 7.306 (0.90), 7.736 (0.63), 8.221 (1.25), 8.232 (1.16), 8.403 (1.96), 13.619 (0.21), 13.634 (0.39), 13.648 (0.20), 14.683 (1.00). LC-MS (method 1): $R_t$ = 0.68 min; MS (ESIpos): m/z = 476 [M + H]$^+$ | N-(3,5-difluoro-2-methylphenyl)-4-hydroxy-2-oxo-1,2,5,6-tetrahydropyridine-3-carbothioamide (intermediate 5-40. 219 mg, 733 μmol) 2-{(4-(aminomethyl)pyridin-3-yl]oxy}-N,N-dimethylethan-1-amine (CAS 1513085-25-0), 186 mg, 953 μmol) |

TABLE 2-continued

| Intermediate | Structure Name | | Analytical Data | Starting materials |
|---|---|---|---|---|
| 6-56 | 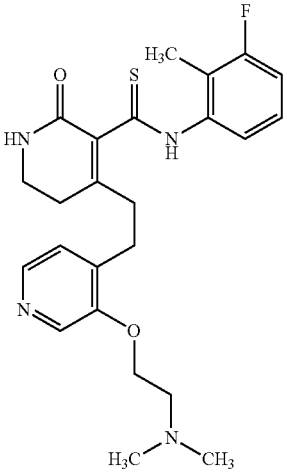 [SMILES: Cc1c(F)cccc1NC(=S)C1=C(CCc2ccncc2OCCN(C)C)CCNC1=O]<br>4-[({3-[2-(dimethylamino)ethoxy]pyridin-4-yl}methyl)amino]-N-(3-fluoro-2-methylphenyl)-2-oxo-1,2,5,6-tetrahydropyridine-3-carbothioamide | | LC-MS (method 2): R$_t$ = 1.05 min; MS (ESIpos): m/z = 458 [M + H]$^+$ | N-(3-fluoro-2-methylphenyl)-4-hydroxy-2-oxo-1,2,5,6-tetrahydropyridine-3-carbothioamide (intermediate 5-9, 200 mg, 713 µmol) 2-{[4-(aminomethyl)pyridin-3-yl]oxy}-N,N-dimethylethan-1-amine (CAS 1513085-25-0), 139 mg, 713 µmol) |
| 6-57 | 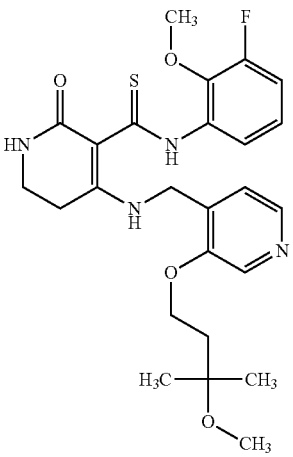 [SMILES: COc1c(F)cccc1NC(=S)C1=C(NCc2ccncc2OCCC(C)(C)OC)CCNC1=O]<br>N-(3-fluoro-2-methoxyphenyl)-4-({[3-(3-methoxy-3-methylbutoxy)pyridin-4-yl]methyl}amino)-2-oxo-1,2,5,6-tetrahydropyridine-3-carbothioamide | | $^1$H-NMR (400 MHz, DMSO-d6) δ [ppm]: 1.035 (8.82), 1.053 (16.00), 1.070 (9.01), 1.073 (2.17), 1.100 (0.68), 1.170 (15.23), 1.178 (5.66), 1.189 (0.55), 1.952 (0.63), 1.969 (1.09), 1.987 (1.91), 2.005 (0.84), 2.427 (0.49), 2.518 (0.83), 2.522 (0.54), 2.735 (0.53), 2.751 (1.07), 2.768 (0.72), 3.055 (1.11), 3.083 (0.55), 3.107 (12.25), 3.116 (4.09), 3.131 (0.43), 3.138 (0.47), 3.147 (0.71), 3.154 (0.67), 3.405 (1.40), 3.418 (1.58), 3.422 (4.15), 3.435 (4.25), 3.440 (4.04), 3.452 (4.12), 3.457 (1.28), 3.469 (1.19), 3.713 (1.75), 3.715 (1.84), 3.780 (5.82), 3.783 (5.94), 3.799 (1.04), 3.829 (3.65), 3.833 (3.58), 3.858 (1.75), 3.860 (1.69), 4.168 (0.63), 4.188 (0.97), 4.206 (1.70), 4.224 (1.08), 4.241 (0.41), 4.343 (2.69), 4.355 (5.17), 4.368 (2.46), 4.629 (1.18), 4.643 (1.16), 7.047 (0.57), 7.062 (0.69), 7.066 (0.88), 7.073 (0.74), 7.082 (0.63), 7.095 (0.67), 7.100 (0.75), 7.116 (0.51), 7.120 (0.74), 7.134 (0.50), 7.302 (0.99), 7.314 (0.99), 7.658 (0.87), | N-(3-fluoro-2-methoxyphenyl)-4-hydroxy-2-oxo-1,2,5,6-tetrahydropyridine-3-carbothioamide (intermediate 5-7, 200 mg, 675 µmol) 1-[3-(3-methoxy-3-methylbutoxy)pyridin-4-yl]methanamine (intermediate 2-57, 151 mg, 675 µmol) |

TABLE 2-continued

| Inter-mediate | Structure Name | Analytical Data | Starting materials |
|---|---|---|---|
| | | 7.662 (0.55), 7.677 (0.68), 7.699 (0.70), 8.138 (0.47), 8.150 (0.52), 8.217 (1.47), 8.229 (1.40), 8.287 (0.68), 8.394 (2.17), 13.689 (0.48), 14.737 (1.26). LC-MS (method 2): $R_t$ = 1.18 min; MS (ESIpos): m/z = 503 [M + H]$^+$ | |
| 6-58 | 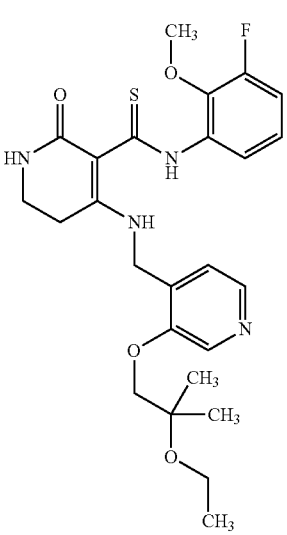 [SMILES: CCOC(C)(C)COc1cnccc1CNC1=C(C(=S)Nc2cccc(F)c2OC)C(=O)NCC1] 4-({[3-(2-ethoxy-2-methylpropoxy)pyridin-4-yl]methyl}amino)-N-(3-fluoro-2-methoxyphenyl)-2-oxo-1,2,5,6-tetrahydropyridine-3-carbothioamide | $^1$H-NMR (400 MHz, DMSO-d6) δ [ppm]: 1.024 (2.52), 1.042 (5.39), 1.059 (2.57), 1.251 (16.00), 2.518 (1.53), 2.522 (1.04), 2.745 (0.64), 2.762 (1.26), 2.779 (0.75), 3.137 (0.46), 3.144 (0.54), 3.154 (0.84), 3.160 (0.79), 3.411 (0.80), 3.428 (2.66), 3.445 (2.49), 3.463 (0.75), 3.780 (6.63), 3.782 (6.81), 3.826 (1.18), 4.034 (4.32), 4.685 (1.42), 4.699 (1.40), 7.049 (0.68), 7.065 (0.82), 7.068 (1.40), 7.074 (0.88), 7.084 (0.73), 7.096 (0.77), 7.101 (0.75), 7.285 (1.19), 7.297 (1.19), 7.651 (0.79), 7.656 (0.51), 7.668 (0.64), 7.710 (0.84), 8.231 (1.80), 8.243 (1.76), 8.400 (2.81), 13.692 (0.57), 14.737 (1.49). LC-MS (method 2): $R_t$ = 1.21 min; MS (ESIpos): m/z = 503 [M + H]$^+$ | N-(3-fluoro-2-methoxyphenyl)-4-hydroxy-2-oxo-1,2,5,6-tetrahydropyridine-3-carbothioamide (intermediate 5-7, 200 mg, 675 µmol) 1-[3-(2-ethoxy-2-methylpropoxy)pyridin-4-yl]methanamine (intermediate 2-58, 151 mg, 675 µmol) |
| 6-59 | 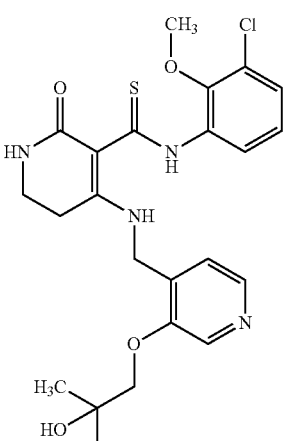 N-(3-chloro-2-methoxyphenyl)-4-({[3-(2-hydroxy-2-methylpropoxy)pyridin-4-yl]methyl}amino)-2-oxo-1,2,5,6- | $^1$H-NMR (400 MHz, DMSO-d6) δ [ppm]: 1.216 (0.53), 1.231 (16.00), 2.075 (0.89), 2.518 (1.91), 2.523 (1.39), 2.752 (0.58), 2.769 (1.18), 2.785 (0.67), 3.141 (0.45), 3.149 (0.50), 3.159 (0.81), 3.165 (0.75), 3.174 (0.44), 3.715 (12.53), 3.902 (4.27), 4.690 (3.06), 4.739 (1.36), 4.754 (1.34), 7.091 (0.90), 7.112 (1.90), 7.132 (1.10), 7.276 (1.13), 7.287 (2.37), 7.291 (1.55), 7.308 (1.02), 7.311 (0.96), 7.737 (0.81), 7.796 (0.91), 7.799 (0.91), 7.816 (0.88), 7.820 (0.81), 8.224 (1.82), 8.236 (1.64), 8.353 | N-(3-chloro-2-methoxyphenyl)-4-hydroxy-2-oxo-1,2,5,6-tetrahydropyridine-3-carbothioamide (intermediate 5-32, 166 mg, 96% purity, 510 µmol) 1-{[4-(aminomethyl)pyridin-3-yl]oxy}-2-methylpropan-2-ol (intermediate 2-1), 91.0 mg, 464 µmol) |

TABLE 2-continued

| Inter-mediate | Structure Name | Analytical Data | Starting materials |
|---|---|---|---|
| | tetrahydropyridine-3-carbothioamide | (2.67), 13.701 (0.57), 14.793 (1.50). LC-MS (method 2): $R_t$ = 1.07 min; MS (ESIpos): m/z = 492 [M + H]$^+$ | |
| 6-60 | N-(3-chloro-2-methylphenyl)-4-[({3-[2-(dimethylamino)-2-methylpropoxy]pyridin-4-yl}methyhamino]-2-oxo-1,2,5,6-tetrahydropyridine-3-carbothioamide | LC-MS (method 2): $R_t$ = 1.21 min; MS (ESIpos): m/z = 503 [M + H]$^+$ | N-(3-chloro-2-methylphenyl)-4-hydroxy-2-oxo-1,2,5,6-tetrahydropyridine-3-carbothioamide (intermediate 5-36, 408 mg, 1.37 mmol) 1-{[4-(aminomethyl)pyridin-3-yl]oxy}-N,N,2-trimethylpropan-2-amine (intermediate 2-60), 399 mg, 1.79 mmol) |
| 6-61 | 4-[({3-[2-(dimethylamino)-2-methylpropoxy]pyridin-4-yl}methyhamino]-N-(3-fluoro-2-methylphenyl)-2-oxo-1,2,5,6-tetrahydropyridine-3-carbothioamide | LC-MS (method 2): $R_t$ = 1.13 min; MS (ESIpos): m/z = 486 [M + H]$^+$ | N-(3-fluoro-2-methylphenyl)-4-hydroxy-2-oxo-1,2,5,6-tetrahydropyridine-3-carbothioamide (intermediate 5-9), 250 mg, 892 µmol) 1-{[(4-(aminomethyl)pyridin-3-yl]oxy}-N,N,2-trimethylpropan-2-amine (intermediate 2-60), 199 mg, 892 µmol) |

TABLE 2-continued

| Intermediate | Structure Name | | Analytical Data | Starting materials |
|---|---|---|---|---|
| 6-62 | 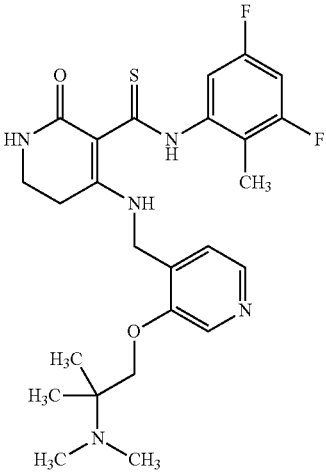 [SMILES: Cc1c(F)cc(F)cc1NC(=S)C1=C(NCc2ccncc2OCC(C)(C)N(C)C)CCNC1=O]<br>N-(3,5-difluoro-2-trimethylpropan-2-methylphenyl)-4-[({3-[2-(dimethylamino)-2-methylpropoxy]pyridin-4-yl}methypamino]-2-oxo-1,2,5,6-tetrahydropyridine-3-carbothioamide | | $^1$H-NMR (400 MHz, DMSO-d6) δ [ppm]: 1.107 (13.91), 2.010 (3.00), 2.222 (16.00), 2.518 (0.45), 2.772 (0.54), 2.789 (1.10), 2.806 (0.63), 3.146 (0.42), 3.153 (0.49), 3.163 (0.77), 3.170 (0.74), 3.179 (0.42), 4.006 (3.59), 4.680 (1.25), 4.695 (1.24), 7.100 (0.69), 7.108 (0.57), 7.117 (0.49), 7.124 (0.44), 7.133 (0.52), 7.274 (1.02), 7.286 (1.03), 7.747 (0.74), 8.224 (1.48), 8.235 (1.43), 8.404 (2.33), 13.607 (0.47), 14.679 (0.93).<br>LC-MS (method 1): $R_t$ = 0.73 min; MS (ESIpos): m/z = 504 [M + H]$^+$ | N-(3,5-difluoro-2-methylphenyl)-4-hydroxy-2-oxo-1,2,5,6-tetrahydropyridine-3-carbothioamide (intermediate 5-40, 260 mg, 871 µmol) 1-{[4-(aminomethyl)pyridin-3-yl]oxy}-N,N,2-trimethylpropan-2-amine (intermediate 2-60), 253 mg, 1.13 mmol) |
| 6-63 | 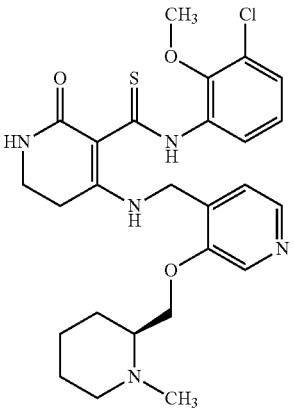 [SMILES: COc1c(Cl)cccc1NC(=S)C1=C(NCc2ccncc2OC[C@@H]2CCCCN2C)CCNC1=O]<br>N-(3-chloro-2-methoxyphenyl)-yl]methoxy}pyridin-4-4-{[(3-{[(2S)-1-methylpiperidin-yl)methanamine 2-yl]methoxy}pyridin-4-yl)methyl]amino}-2-oxo-1,2,5,6-tetrahydropyridine-3-carbothioamide | | $^1$H-NMR (400 MHz, DMSO-d6) δ [ppm]: 1.035 (1.32), 1.053 (2.16), 1.070 (1.37), 1.390 (0.65), 1.465 (0.72), 1.523 (0.78), 2.023 (0.80), 2.030 (1.08), 2.036 (0.66), 2.228 (6.95), 2.232 (11.51), 2.238 (2.91), 2.252 (0.76), 2.518 (1.34), 2.522 (0.87), 2.743 (0.72), 2.773 (1.13), 2.791 (1.19), 2.808 (0.74), 3.156 (1.00), 3.163 (0.98), 3.423 (1.51), 3.710 (16.00), 4.033 (0.71), 4.045 (0.66), 4.057 (0.77), 4.070 (0.76), 4.235 (0.90), 4.246 (0.91), 4.650 (0.88), 4.658 (0.96), 4.664 (0.97), 4.672 (0.87), 7.084 (1.21), 7.105 (2.65), 7.125 (1.49), 7.280 (1.51), 7.284 (1.55), 7.301 (2.72), 7.304 (1.65), 7.312 (1.48), 7.723 (0.96), 7.799 (1.25), 7.803 (1.29), 7.820 (1.21), 7.823 (1.10), 8.154 (0.99), 8.165 (0.99), 8.224 (2.25), 8.236 (2.28), 8.244 (1.43), 8.276 (0.87), 8.293 (0.69), 8.397 (3.30), 13.658 (0.66), 14.790 (1.18).<br>LC-MS (method 1): $R_t$ = 0.85 min; MS (ESIpos): m/z = 530 [M + H]$^+$ | N-(3-chloro-2-methoxyphenyl)-4-hydroxy-2-oxo-1,2,5,6-tetrahydropyridine-3-carbothioamide (intermediate 5-32, 200 mg, 639 µmol) 1-(3-{[(2S)-1-methylpiperidin-2-yl]methoxy}pyridin-4-yl)methanamine (intermediate 2-63, 241 mg, 1.02 mmol) |

TABLE 2-continued

| Intermediate | Structure Name | Analytical Data | Starting materials |
|---|---|---|---|
| 6-64 | 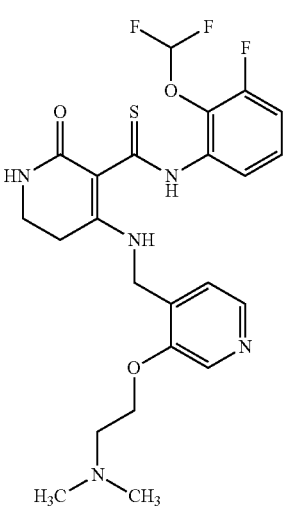 [SMILES: CN(C)CCOc1cnccc1CNC1=C(C(=S)Nc2cccc(F)c2OC(F)F)C(=O)NCC1]<br>N-[2-(difluoromethoxy)-3-fluorophenyl]-4-[({3-[2-(dimethylamino)ethoxy]pyridin-4-yl}methyhamino]-2-oxo-1,2,5,6-tetrahydropyridine-3-carbothioamide | LC-MS (method 2): R$_t$ = 1.06 min; MS (ESIpos): m/z = 510 [M + H]$^+$ | N-[2-(difluoromethoxy)-3-fluorophenyl]-4-hydroxy-2-oxo-1,2,5,6-tetrahydropyridine-3-carbothioamide (intermediate 5-8, 200 mg, 602 μmol) 2-{(4-(aminomethyl)pyridin-3-yl]oxy}-N,N-dimethylethan-1-amine (CAS 1513085-25-0), 176 mg, 903 μmol) |
| 6-65 | 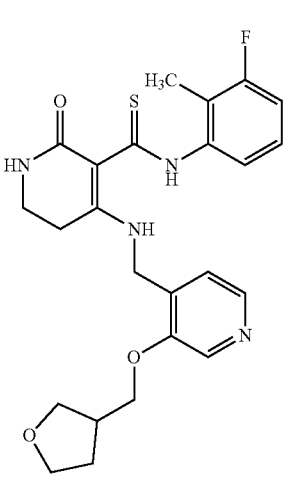 [SMILES: Cc1c(F)cccc1NC(=S)C1=C(NCc2ccncc2OCC2CCOC2)CCNC1=O]<br>N-(3-fluoro-2-methylphenyl)-2-oxo-4-({[3-(tetrahydrofuran-3-ylmethoxy)pyridin-4-yl]methyl}amino)-1,2,5,6-tetrahydropyridine-3-carbothioamide | LC-MS (method 2): R$_t$ = 1.08 min; MS (ESIpos): m/z = 471 [M + H]$^+$ | N-(3-fluoro-2-methylphenyl)-4-hydroxy-2-oxo-1,2,5,6-tetrahydropyridine-3-carbothioamide (intermediate 5-9), 250 mg, 892 μmol) 1-{3-[(oxolan-3-yl)methoxy]pyridin-4-yl}methanamine (intermediate 2-65), 186 mg, 892 μmol) |
| 6-66 | 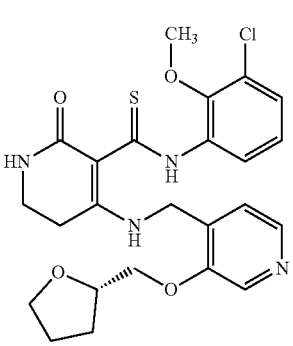 [SMILES: COc1c(Cl)cccc1NC(=S)C1=C(NCc2ccncc2OC[C@@H]2CCCO2)CCNC1=O]<br>N-(3-chloro-2-methoxyphenyl)-2-oxo-4-{[(3-{[(2S)-oxolan-2- | $^1$H-NMR (400 MHz, $^1$H-NMR (400 MHz, DMSO-d6) δ [ppm]: 1.736 (0.50), 1.743 (0.44), 1.764 (0.50), 1.817 (0.44), 1.836 (0.57), 1.855 (0.69), 1.872 (0.62), 1.888 (0.40), 1.980 (0.41), 2.518 (1.27), 2.523 (0.79), 2.755 (0.78), 2.771 (1.58), 2.788 (0.91), 3.138 (0.60), 3.145 (0.69), 3.155 (1.09), 3.161 (1.03), 3.171 (0.59), 3.179 (0.49), 3.654 (0.44), | N-(3-chloro-2-methoxyphenyl)-4-hydroxy-2-oxo-1,2,5,6-tetrahydropyridine-3-carbothioamide (intermediate 5-32, 250 mg, 90% purity, 719 μmol) 1-(3-{[(2S)-oxolan-2-yl]methoxy}pyridin-4-yl)methanamine (intermediate 2-66), 209 mg, 93% purity, 935 μmol) |

| Intermediate | Structure Name | Analytical Data | Starting materials |
|---|---|---|---|
| | yl]methoxy}pyridin-4-yl)methyl]amino}-1,2,5,6-tetrahydropyridine-3-carbothioamide | 3.670 (0.66), 3.674 (0.81), 3.690 (0.94), 3.692 (0.88), 3.712 (16.00), 3.761 (0.60), 3.778 (1.05), 3.794 (0.71), 3.797 (0.72), 4.111 (0.50), 4.122 (1.09), 4.137 (1.63), 4.143 (1.26), 4.153 (1.59), 4.179 (0.75), 4.196 (0.63), 4.206 (0.53), 4.212 (0.51), 4.655 (1.83), 4.670 (1.82), 7.090 (1.14), 7.110 (2.44), 7.131 (1.40), 7.286 (1.61), 7.289 (1.73), 7.296 (1.58), 7.306 (2.00), 7.309 (2.51), 7.729 (1.07), 7.790 (1.17), 7.794 (1.18), 7.811 (1.12), 7.814 (1.06), 8.230 (2.33), 8.241 (2.19), 8.394 (3.51), 13.686 (0.74), 14.789 (1.96). LC-MS (method 2): $R_t$ = 1.14 min; MS (ESIpos): m/z = 504 [M + H]$^+$ | |
| 6-67 | 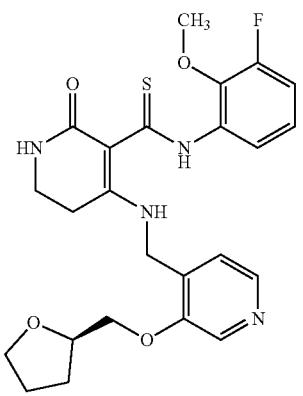 [SMILES: COc1c(F)cccc1NC(=S)C1=C(NCc2ccncc2OC[C@H]2CCCO2)CCNC1=O]<br>N-(3-chloro-2-methoxyphenyl)-2-oxo-4-{[(3-{[(2R)-oxolan-2-yl]methoxy}pyridin-4-yl)methyl]amino}-1,2,5,6-tetrahydropyridine-3-carbothioamide | $^1$H-NMR (400 MHz, DMSO-d6) δ [ppm]: 1.735 (0.48), 1.742 (0.43), 1.763 (0.49), 1.816 (0.42), 1.836 (0.56), 1.854 (0.68), 1.871 (0.60), 1.979 (0.40), 2.518 (0.94), 2.522 (0.62), 2.755 (0.76), 2.771 (1.55), 2.788 (0.90), 3.138 (1.00), 3.155 (1.05), 3.161 (1.00), 3.171 (0.57), 3.178 (0.48), 3.654 (0.43), 3.669 (0.62), 3.674 (0.80), 3.690 (0.90), 3.692 (0.86), 3.712 (16.00), 3.760 (0.59), 3.777 (1.05), 3.793 (0.70), 3.797 (0.71), 4.111 (0.49), 4.121 (1.07), 4.136 (1.59), 4.142 (1.21), 4.152 (1.57), 4.178 (0.74), 4.195 (0.62), 4.206 (0.51), 4.212 (0.51), 4.655 (1.80), 4.670 (1.80), 7.090 (1.11), 7.110 (2.38), 7.130 (1.37), 7.285 (1.45), 7.289 (1.56), 7.297 (1.55), 7.306 (1.71), 7.309 (2.72), 7.727 (1.05), 7.789 (1.15), 7.793 (1.18), 7.810 (1.11), 7.813 (1.06), 8.229 (2.33), 8.241 (2.18), 8.393 (3.52), 13.686 (0.72), 14.787 (1.92). LC-MS (method 2): $R_t$ = 1.14 min; MS (ESIpos): m/z = 504 [M + H]$^+$ | N-(3-chloro-2-methoxyphenyl)-4-hydroxy-2-oxo-1,2,5,6-tetrahydropyridine-3-carbothioamide (intermediate 5-32, 250 mg, 90% purity, 719 µmol) 1-(3-{[(2R)-oxolan-2-yl]methoxy}pyridin-4-yl)methanamine (intermediate 2-67, 195 mg, 935 µmol) |

TABLE 2-continued

| Intermediate | Structure Name | Analytical Data | Starting materials |
|---|---|---|---|
| 6-68 | 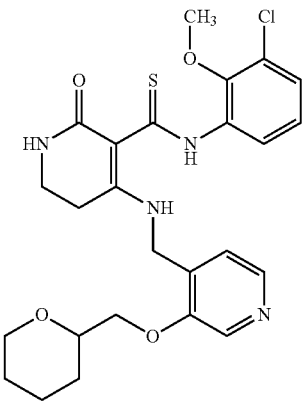 [SMILES: COc1c(Cl)cccc1NC(=S)C1=C(NCc2ccncc2OCC2CCCCO2)CCNC1=O]<br>N-(3-chloro-2-methoxyphenyl)-2-oxo-4-({[3-(tetrahydro-2H-pyran-2-ylmethoxy)pyridin-4-yl]methyl}amino)-1,2,5,6-tetrahydropyridine-3-carbothioamide | $^1$H-NMR (400 MHz, DMSO-d6) δ [ppm]: 1.467 (1.00), 1.476 (1.30), 1.482 (1.39), 1.663 (0.46), 1.799 (0.44), 2.518 (1.07), 2.522 (0.72), 2.757 (0.68), 2.774 (1.38), 2.791 (0.82), 3.139 (0.53), 3.147 (0.60), 3.156 (0.98), 3.163 (0.95), 3.172 (0.53), 3.180 (0.45), 3.385 (0.44), 3.658 (0.42), 3.713 (16.00), 3.875 (0.49), 3.879 (0.50), 3.906 (0.49), 4.098 (1.36), 4.108 (2.26), 4.123 (1.20), 4.656 (1.53), 4.670 (1.58), 7.088 (1.09), 7.109 (2.32), 7.129 (1.35), 7.284 (1.53), 7.288 (1.66), 7.297 (1.46), 7.304 (1.49), 7.308 (2.57), 7.726 (0.99), 7.801 (1.14), 7.804 (1.15), 7.821 (1.11), 7.825 (1.04), 8.224 (2.15), 8.235 (2.03), 8.385 (3.26), 13.680 (0.67), 14.791 (1.67). LC-MS (method 2): R$_t$ = 1.22 min; MS (ESIpos): m/z = 517 [M + H]$^+$ | N-(3-chloro-2-methoxyphenyl)-4-hydroxy-2-oxo-1,2,5,6-tetrahydropyridine-3-carbothioamide (intermediate 5-32, 250 mg. 90% purity, 719 μmol) 1-(3-{[(2S)-oxan-2-yl]methoxy}pyridin-4-yl)methanamine (intermediate 2-68, 335 mg, 62% purity, 935 μmol) |
| 6-69 | 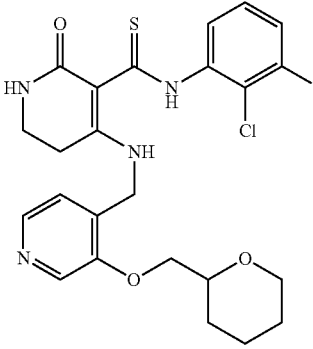<br>N-(2,3-dichlorophenyl)-2-oxo-4-({[3-(tetrahydro-2H-pyran-2-ylmethoxy)pyridin-4-yl]methyl}amino)-1,2,5,6-tetrahydropyridine-3-carbothioamide | $^1$H-NMR (400 MHz, DMSO-d6) δ (ppm): 0.851 (0.43), 1.232 (1.49), 1.282 (0.86), 1.291 (0.82), 1.312 (2.31), 1.341 (2.79), 1.372 (1.78), 1.434 (1.25), 1.480 (9.75), 1.511 (1.73), 1.660 (3.27), 1.691 (2.74), 1.799 (3.08), 1.812 (2.26), 1.907 (1.59), 2.074 (6.92), 2.518 (12.20), 2.523 (7.83), 2.545 (0.43), 2.768 (4.76), 2.786 (9.51), 2.802 (5.91), 3.149 (3.75), 3.156 (4.32), 3.166 (7.02), 3.172 (6.73), 3.345 (2.64), 3.358 (2.11), 3.382 (3.27), 3.398 (1.83), 3.409 (2.16), 3.655 (2.98), 3.660 (2.31), 3.670 (2.45), 3.682 (2.69), 3.692 (1.63), 3.698 (1.39), 3.831 (1.11), 3.876 (3.46), 3.903 (3.41), 4.068 (1.87), 4.078 (2.40), 4.094 (8.79), 4.104 (16.00), 4.118 (7.98), 4.129 (2.02), 4.144 (2.11), 4.657 (10.23), 4.672 (10.57), 7.292 (5.43), 7.303 | N-(2,3-dichlorophenyl)-4-hydroxy-2-oxo-1,2,5,6-tetrahydropyridine-3-carbothioamide (intermediate 5-34. 200 mg, 631 μmol) 1-[3-(tetrahydro-2H-pyran-2-ylmethoxy)pyridin-4-yl]methanamine (intermediate 2-68, 154 mg, 694 μmol) |

TABLE 2-continued

| Intermediate | Structure Name | Analytical Data | Starting materials |
|---|---|---|---|
| | | (5.91), 7.330 (6.87), 7.350 (15.86), 7.370 (10.23), 7.497 (8.22), 7.500 (10.67), 7.517 (7.35), 7.521 (7.78), 7.531 (8.79), 7.534 (7.35), 7.551 (7.21), 7.554 (6.05), 7.742 (6.82), 8.222 (4.13), 8.234 (4.04), 8.385 (6.20), 13.641 (2.50), 13.656 (5.00), 13.670 (2.35), 14.893 (13.89). LC-MS (method 2): $R_t$ = 1.23 min; MS (ESIpos): m/z = 522 [M + H]$^+$ | |
| 6-70 | 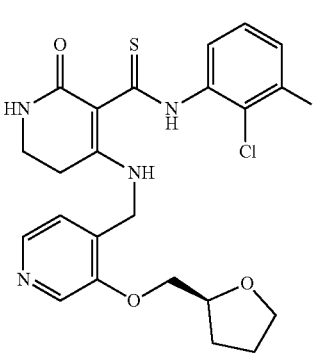<br><br>N-(2,3-dichlorophenyl)-2-oxo-4-{[(3-{[(2S)-oxolan-2-yl]methoxy}pyridin-4-yl)methyl]amino}-1,2,5,6-tetrahydropyridine-3-carbothioamide | $^1$H-NMR (400 MHz, DMSO-d6) δ [ppm]: 1.154 (0.70), 1.172 (1.12), 1.190 (0.56), 1.232 (0.64), 1.691 (0.80), 1.708 (1.95), 1.712 (1.36), 1.720 (1.26), 1.724 (1.47), 1.729 (2.60), 1.736 (2.41), 1.742 (1.63), 1.746 (1.82), 1.753 (1.69), 1.758 (2.73), 1.774 (2.43), 1.789 (0.99), 1.801 (1.31), 1.807 (1.26), 1.817 (2.25), 1.825 (1.47), 1.837 (3.02), 1.855 (4.17), 1.862 (1.10), 1.872 (3.34), 1.887 (2.03), 1.891 (1.79), 1.904 (1.71), 1.908 (1.55), 1.917 (0.62), 1.922 (0.70), 1.938 (0.45), 1.960 (1.71), 1.974 (1.44), 1.979 (2.22), 1.988 (2.54), 1.990 (2.19), 2.000 (1.77), 2.004 (1.74), 2.011 (1.95), 2.022 (1.55), 2.028 (1.23), 2.040 (0.72), 2.075 (1.31), 2.518 (5.99), 2.523 (4.25), 2.767 (4.07), 2.783 (8.35), 2.800 (4.82), 3.148 (3.05), 3.155 (3.51), 3.165 (5.67), 3.171 (5.35), 3.181 (3.05), 3.188 (2.57), 3.653 (2.35), 3.669 (3.18), 3.674 (4.33), 3.689 (5.11), 3.691 (4.23), 3.706 (2.92), 3.758 (3.29), 3.775 (5.75), 3.791 (3.80), 3.795 (3.88), 3.812 (2.06), 4.092 (1.90), 4.107 (2.65), 4.118 (5.81), 4.133 (9.12), 4.138 (6.98), 4.148 (8.78), 4.163 (1.58), 4.173 (3.88), 4.185 (1.34), 4.192 (3.37), 4.201 (2.81), 4.207 (2.76), 4.218 (2.17), 4.223 | N-(2,3-dichlorophenyl)-4-hydroxy-2-oxo-1,2,5,6-tetrahydropyridine-3-carbothioamide (intermediate 5-34, 200 mg, 631 μmol) 1-(3-{[(2S)-oxolan-2-yl]methoxy}pyridin-4-yl)methanamine (intermediate 2-66), 144 mg, 694 μmol) |

TABLE 2-continued

| Intermediate | Structure Name | Analytical Data | Starting materials |
|---|---|---|---|
| | | (1.15), 4.233 (0.86), 4.658 (9.58), 4.672 (9.53), 7.289 (7.44), 7.301 (7.65), 7.331 (5.91), 7.352 (13.73), 7.372 (8.86), 7.498 (6.66), 7.501 (9.39), 7.518 (6.21), 7.522 (6.98), 7.526 (7.71), 7.529 (5.99), 7.546 (5.99), 7.549 (4.90), 7.744 (5.59), 8.225 (10.17), 8.236 (9.63), 8.392 (16.00), 13.645 (2.09), 13.659 (4.12), 13.675 (1.90), 14.892 (11.45). LC-MS (method 2): $R_t$ = 1.15 min; MS (ESIpos): m/z = 508 [M + H]$^+$ | |
| 6-71 | 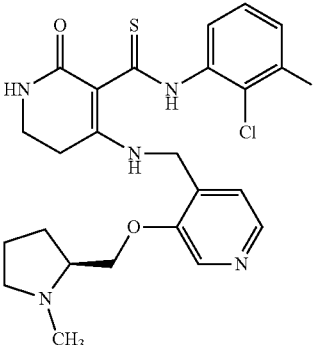<br>N-(2,3-dichlorophenyl)-4-{[(3-{[(2S)-1-methylpyrrolidin-2-yl]methoxy}pyridin-4-yl)methyl]amino}-2-oxo-1,2,5,6-tetrahydropyridine-3-carbothioamide | $^1$H-NMR (400 MHz, DMSO-d6) δ [ppm]: 1.638 (0.44), 1.654 (1.19), 1.670 (1.38), 1.679 (1.33), 1.689 (0.96), 1.702 (0.73), 1.709 (0.46), 1.952 (0.45), 1.961 (0.44), 1.972 (0.53), 1.987 (0.53), 2.159 (0.46), 2.181 (1.18), 2.202 (0.96), 2.355 (16.00), 2.518 (2.15), 2.523 (1.42), 2.604 (0.44), 2.610 (0.40), 2.618 (0.49), 2.625 (0.61), 2.639 (0.51), 2.756 (0.80), 2.774 (1.65), 2.790 (1.03), 2.936 (0.42), 2.945 (0.50), 2.950 (0.69), 2.961 (0.47), 2.967 (0.47), 3.146 (0.68), 3.154 (0.78), 3.163 (1.28), 3.169 (1.24), 3.969 (0.81), 3.983 (0.85), 3.993 (1.03), 4.007 (1.00), 4.142 (1.03), 4.155 (1.09), 4.166 (0.87), 4.179 (0.81), 4.648 (1.88), 4.663 (1.89), 7.287 (1.53), 7.299 (1.58), 7.330 (1.36), 7.350 (3.03), 7.371 (1.95), 7.496 (1.47), 7.500 (2.10), 7.516 (1.34), 7.520 (1.51), 7.526 (1.72), 7.530 (1.40), 7.546 (1.35), 7.549 (1.11), 7.741 (1.21), 8.220 (2.08), 8.231 (1.99), 8.390 (3.32), 13.632 (0.43), 13.646 (0.88), 13.661 (0.43), 14.887 (2.34). LC-MS (method 2): $R_t$ = 1.19 min; MS (ESIpos): m/z = 521 [M + H]$^+$ | N-(2,3-dichlorophenyl)-4-hydroxy-2-oxo-1,2,5,6-tetrahydropyridine-3-carbothioamide (intermediate 5-34, 200 mg, 631 µmol) 1-(3-{[(2S)-1-methylpyrrolidin-2-yl]methoxy}pyridin-4-yl)methanamine (intermediate 2-4, 153 mg, 694 µmol) |

TABLE 2-continued

| Intermediate | Structure Name | Analytical Data | Starting materials |
|---|---|---|---|
| 6-72 | 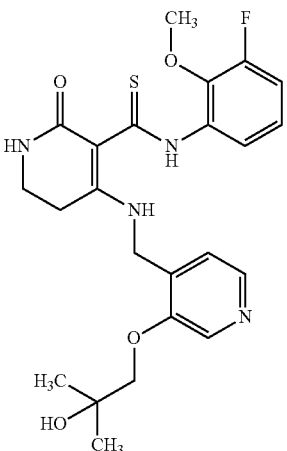 [SMILES: COc1c(F)cccc1NC(=S)C1=C(NCc2ccncc2OCC(C)(C)O)CCNC1=O]<br>N-(3-fluoro-2-methoxyphenyl)-4-({[3-(2-hydroxy-2-methylpropoxy)pyridin-4-yl]methyl}amino)-2-oxo-1,2,5,6-tetrahydropyridine-3-carbothioamide | LC-MS (method 2): $R_t$ = 1.02 min; MS (ESIpos): m/z = 475 [M + H]$^+$ | N-(3-fluoro-2-methoxyphenyl)-4-hydroxy-2-oxo-1,2,5,6-tetrahydropyridine-3-carbothioamide (intermediate 5-7). 200 mg, 675 µmol) 1-{[4-(aminomethyl)pyridin-3-yl]oxy}-2-methylpropan-2-ol (intermediate 2-1), 199 mg, 1.01 mmol) |
| 6-73 | 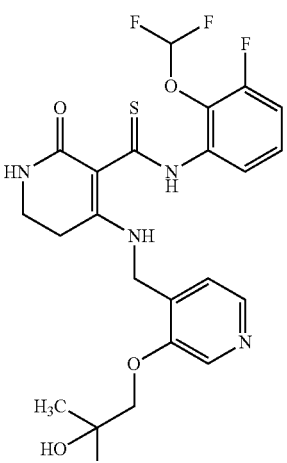<br>N-[2-(difluoromethoxy)-3-fluorophenyl]-4-({[3-(2-hydroxy-2-methylpropoxy)pyridin-4-yl]methyl}amino)-2-oxo-1,2,5,6-tetrahydropyridine-3-carbothioamide | LC-MS (method 2): $R_t$ = 1.04 min; MS (ESIpos): m/z = 510 [M + H]$^+$ | N-[2-(difluoromethoxy)-3-fluorophenyl]-4-hydroxy-2-oxo-1,2,5,6-tetrahydropyridine-3-carbothioamide (intermediate 5-8, 200 mg, 602 µmol) (aminomethyl)pyridin-3-yl]oxy}-2-methylpropan-2-ol (intermediate 2-1), 177 mg, 903 µmol) |

TABLE 2-continued

| Intermediate | Structure Name | Analytical Data | Starting materials |
|---|---|---|---|
| 6-74 | 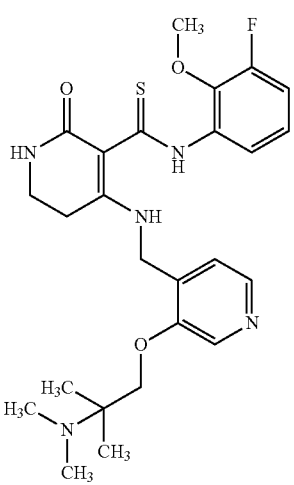 [SMILES: COc1c(F)cccc1NC(=S)C1=C(NCc2ccncc2OCC(C)(C)N(C)C)CCNC1=O]<br>4-[({3-[2-(dimethylamino)-2-methylpropoxy]pyridin-4-yl}methyhamino]-N-(3-fluoro-2-methoxyphenyl)-2-oxo-1,2,5,6-tetrahydropyridine-3-carbothioamide | LC-MS (method 2): $R_t$ = 1.04 min; MS (ESIpos): m/z = 502 [M + H]$^+$ | N-(3-fluoro-2-methoxyphenyl)-4-hydroxy-2-oxo-1.2,5,6-tetrahydropyridine-3-carbothioamide (intermdiate 5-7), 200 mg, 675 μmol) 1-{[4-(aminomethyl)pyridin-3-yl]oxy}-N,N,2-trimethylpropan-2-amine (intermediate 2-60), 226 mg, 1.01 mmol) |
| 6-75 | 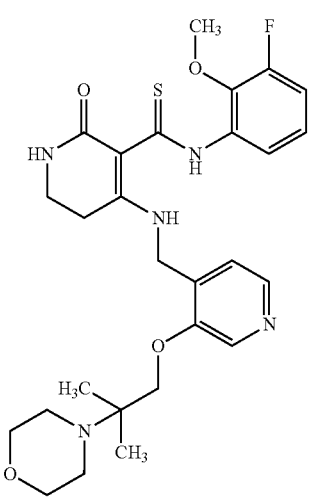 [SMILES: COc1c(F)cccc1NC(=S)C1=C(NCc2ccncc2OCC(C)(C)N2CCOCC2)CCNC1=O]<br>N-(3-fluoro-2-methoxyphenyl)-4-[({3-[2-methyl-2-(morpholin-4-yl)propoxy]pyridin-4-yl}methyhamino]-2-oxo-1,2,5,6-tetrahydropyridine-3-carbothioamide | LC-MS (method 2): $R_t$ = 1.10 min; MS (ESIpos): m/z = 544 [M + H]$^+$ | N-(3-fluoro-2-methoxyphenyl)-4-hydroxy-2-oxo-1.2,5,6-tetrahydropyridine-3-carbothioamide (intermediate 5-7), 200 mg, 675 μmol) 1-{3-[2-methyl-2-(morpholin-4-yl)propoxy]pyridin-4-yl}methanamine (intermediate 2-3), 269 mg, 1.01 mmol) |

TABLE 2-continued

| Inter-mediate | Structure Name | Analytical Data | Starting materials |
|---|---|---|---|
| 6-76 | 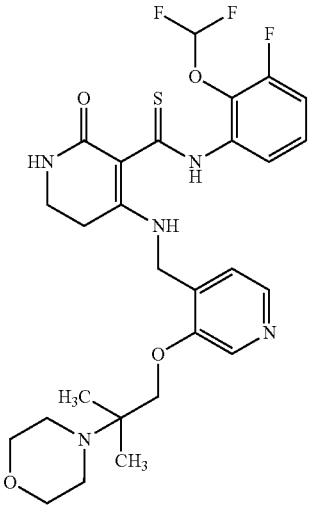 [SMILES: CC(C)(COc1cnccc1CNC1=C(C(=S)Nc2cccc(F)c2OC(F)F)C(=O)NCC1)N1CCOCC1]<br>N-[2-(difluoromethoxy)-3-fluorophenyl]-4-[({3-[2-methyl-2-(morpholin-4-yl)propoxy]pyridin-4-yl}methylamino]-2-oxo-1,2,5,6-tetrahydropyridine-3-carbothioamide | LC-MS (method 2): $R_t$ = 1.14 min; MS (ESIpos): m/z = 580 $[M + H]^+$ | N-[2-(difluoromethoxy)-3-fluorophenyl]-4-hydroxy-2-oxo-1,2,5,6-tetrahydropyridine-3-carbothioamide (intermediate 5-8, 200 mg, 602 μmol) 1-{3-[2-methyl-2-(morpholin-4-yl)propoxy]pyridin-4-yl}methanamine (intermediate 2-3) 269 mg, 1.01 mmol) |
| 6-77 | 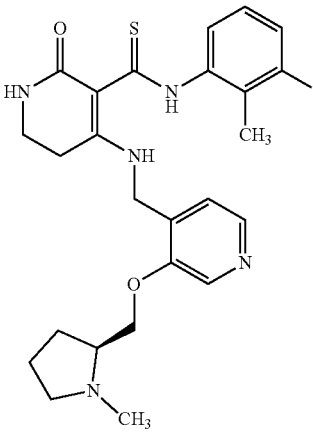<br>N-(3-chloro-2-methylphenyl)-4-{[(3-{[(2S)-1-methylpyrrolidin-2-yl]methoxy}pyridin-4-yl)methyl]amino}-2-oxo-1,2,5,6-tetrahydropyridine-3-carbothioamide | $^1$H-NMR (400 MHz, DMSO-d6) delta [ppm]: 1.654 (1.52), 1.670 (1.83), 1.679 (1.64), 1.684 (1.08), 1.689 (1.27), 1.702 (0.92), 1.971 (0.70), 2.075 (0.98), 2.157 (14.18), 2.183 (1.09), 2.204 (0.96), 2.357 (16.00), 2.518 (1.07), 2.523 (0.70), 2.627 (0.69), 2.735 (1.06), 2.752 (2.13), 2.769 (1.34), 2.947 (0.64), 2.953 (0.85), 3.142 (0.92), 3.150 (1.06), 3.159 (1.73), 3.166 (1.68), 3.175 (0.93), 3.183 (0.79), 3.965 (0.96), 3.980 (1.02), 3.989 (1.24), 4.004 (1.17), 4.140 (1.38), 4.153 (1.42), 4.164 (1.12), 4.176 (1.06), 4.627 (2.69), 4.642 (2.71), 7.148 (1.18), 7.165 (2.18), 7.168 (2.08), 7.198 (1.52), 7.218 (2.45), 7.238 (1.10), 7.284 (2.28), 7.296 (2.33), 7.325 (1.96), 7.328 (1.99), 7.345 (1.50), 7.348 (1.40), 7.684 (1.59), 8.217 (3.30), 8.229 (3.13), 8.385 (5.13), 13.625 (0.98), 14.533 (2.35). | N-(3-chloro-2-methylphenyl)-4-hydroxy-2-oxo-1,2,5,6-tetrahydropyridine-3-carbothioamide (intermediate 5-36, 461 mg, 1.55 mmol) 1-(3-{[(2S)-1-methylpyrrolidin-2-yl]methoxy}pyridin-4-yl)methanamine (intermediate 2-4, 447 mg, 2.02 mmol) |

TABLE 2-continued

| Intermediate | Structure Name | Analytical Data | Starting materials |
|---|---|---|---|
| | | LC-MS (method 2): $R_t$ = 1.19 min; MS (ESIpos): m/z = 501 [M + H]$^+$ | |
| 6-78 | 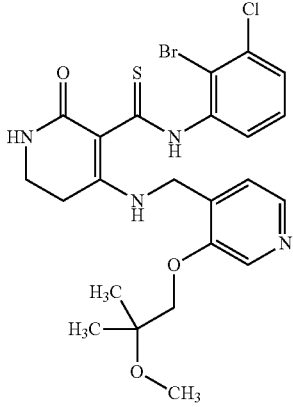 [SMILES: COC(C)(C)COc1cnccc1CNC1=C(C(=S)Nc2cccc(Cl)c2Br)C(=O)NCC1]<br>N-(2-bromo-3-chlorophenyl)-4-({[3-(2-methoxy-2-methylpropoxy)pyridin-4-yl]methyl}amino)-2-oxo-1,2,5,6-tetrahydropyridine-3-carbothioamide | $^1$H-NMR (400 MHz, DMSO-d6) δ [ppm]: 1.172 (0.49), 1.227 (3.01), 1.233 (4.64), 1.238 (16.00), 1.917 (1.09), 1.988 (0.67), 2.618 (2.76), 2.522 (1.75), 2.767 (0.47), 2.783 (0.97), 2.800 (0.59), 3.150 (0.78), 3.155 (1.53), 3.167 (13.22), 3.175 (1.72), 3.180 (2.87), 3.185 (1.48), 3.188 (1.47), 3.988 (0.94), 3.999 (0.63), 4.033 (3.79), 4.688 (1.15), 4.703 (1.15), 5.651 (0.41), 6.710 (0.47), 6.717 (0.47), 6.730 (0.58), 6.736 (0.56), 7.041 (0.62), 7.277 (0.97), 7.289 (1.08), 7.363 (0.49), 7.383 (1.31), 7.402 (1.32), 7.423 (0.84), 7.427 (1.17), 7.442 (0.57), 7.447 (0.41), 7.482 (1.04), 7.487 (0.91), 7.501 (0.73), 7.506 (0.63), 7.732 (0.67), 8.229 (1.59), 8.241 (1.44), 8.290 (0.42), 8.397 (2.35), 13.658 (0.50), 14.851 (1.29). LC-MS (method 2): $R_t$ = 1.20 min; MS (ESIpos): m/z = 554 [M + H]$^+$ | N-(2-bromo-3-chlorophenyl)-4-hydroxy-2-oxo-1,2,5,6-tetrahydropyridine-3-carbothioamide (intermediate 5-78), 350 mg. 968 μmol) 1-[3-(2-methoxy-2-methylpropoxy)pyridin-4-yl]methanamine (intermediate 2-2), 265 mg, 1.26 mmol) |
| 6-79 | 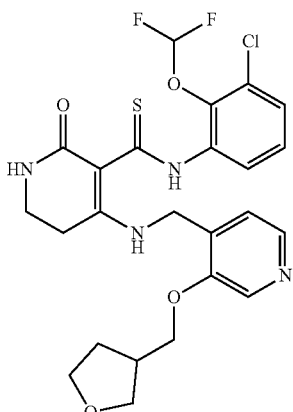<br>N-[3-chloro-2-(difluoromethoxy)phenyl]-2-oxo-4-({[3-(tetrahydrofuran-3-ylmethoxy)pyridin-4-yl]methyl}amino)-1,2,5,6-tetrahydropyridine-3-carbothioamide | $^1$H NMR (400 MHz, DMSO): d [ppm] = 1.64-1.76 (m, 1H), 1.96-2.09 (m, 1H), 2.65-2.84 (m, 3H), 3.11-3.22 (m, 2H), 3.55-3.70 (m. 2H), 3.72-3.85 (m, 2H), 4.02-4.20 (m, 2H), 4.66 (d, 2H), 6.91 (t, 1H), 7.27-7.37 (m, 2H), 7.46 (d, 1H), 7.60 (d, 1H), 7.72 (br s, 1H), 8.24 (d, 1H), 8.40 (s, 1H), 13.62 (br s, 1H), 14.79 (br s, 1H), 19F NMR (400 MHz, DMSO): d [ppm] = −80.12 (d), UPLC4-MS (Method 3): $R_t$ = 1.46 min, 95%., MS (ESIpos): m/z = (M + H)+ = 539 | N-[3-chloro-2-(difluoromethoxy)phenyl]-4-hydroxy-2-oxo-1.2,5,6-tetrahydropyridine-3-carbothioamide (intermediate 5-38), 402 mg, 1.15 mmol) 1-{3-[(oxolan-3-yl)methoxy]pyridin-4-yl}methanamine (intermediate 2-65), 480 mg, 2.30 mmol) |

TABLE 2-continued

| Intermediate | Structure Name | Analytical Data | Starting materials |
|---|---|---|---|
| 6-80 | (structure) | $^1$H-NMR (400 MHz, DMSO-d6) δ [ppm]: 1.154 (0.60), 1.172 (1.23), 1.190 (0.62), 1.232 (0.48), 1.379 (7.74), 1.393 (9.81), 1.417 (1.01), 1.789 (0.58), 1.798 (0.60), 1.807 (0.60), 1.815 (0.52), 1.820 (0.40), 1.907 (0.56), 1.917 (0.68), 1.921 (0.78), 1.927 (0.94), 1.936 (0.88), 1.941 (1.17), 1.948 (1.17), 1.955 (1.21), 1.987 (2.69), 2.336 (0.44), 2.518 (5.63), 2.522 (3.62), 2.678 (0.42), 2.752 (0.70), 2.768 (0.86), 3.053 (0.52), 3.141 (0.54), 3.148 (0.64), 3.157 (1.05), 3.164 (1.05), 3.181 (0.52), 3.280 (1.51), 3.294 (1.17), 3.425 (0.78), 3.669 (16.00), 3.710 (10.87), 3.806 (0.40), 3.813 (0.46), 4.017 (0.56), 4.035 (0.82), 4.053 (0.84), 4.071 (1.01), 4.135 (0.58), 4.143 (0.54), 4.157 (0.66), 4.166 (0.64), 4.225 (0.54), 4.420 (0.66), 4.440 (0.74), 4.442 (0.72), 4.462 (0.54), 4.654 (1.19), 4.669 (1.23), 5.232 (1.45), 6.526 (1.19), 6.530 (1.33), 6.546 (1.43), 6.550 (1.53), 6.608 (1.19), 6.612 (1.17), 6.628 (1.61), 6.632 (1.39), 6.768 (1.41), 6.788 (2.29), 6.808 (0.96), 7.084 (1.01), 7.105 (2.29), 7.125 (1.27), 7.284 (1.47), 7.288 (1.69), 7.304 (1.83), 7.308 (1.75), 7.733 (0.96), 7.794 (1.05), 7.797 (1.09), 7.814 (1.01), 7.817 (0.98), 8.234 (0.94), 8.246 (0.96), 8.426 (2.65), 13.691 (0.50), 14.787 (1.81). LC-MS (method 1): R$_t$ = 1.29 min; MS (ESIpos): m/z = 603 [M + H]$^+$ | N-(3-chloro-2-methoxyphenyl)-4-hydroxy-2-oxo-1,2,5,6-tetrahydropyridine-3-carbothioamide (intermediate 5-32), 400 mg, 90% purity, 1.15 mmol) tert-butyl (2S)-2-({(4-(aminomethyl)pyridin-3-yl]oxy}methyl)pyrrolidine-1-carboxylate (intermediate 2-80), 460 mg, 1.50 mmol) |

TABLE 2-continued

| Intermediate | Structure Name | Analytical Data | Starting materials |
|---|---|---|---|
| 6-81 | 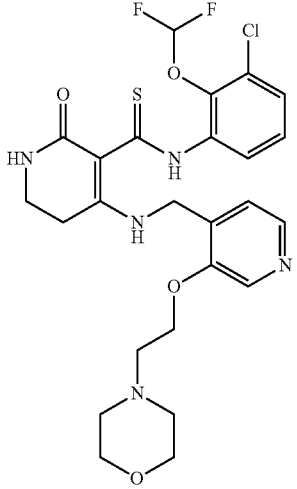 [SMILES: O=C1NCCC(NCc2ccncc2OCCN2CCOCC2)=C1C(=S)Nc1cccc(Cl)c1OC(F)F]<br>N-[3-chloro-2-(difluoromethoxy)phenyl]-4-[({3-[2-(morpholin-4-yl)ethoxy]pyridin-4-yl}methylamino]-2-oxo-1,2,5,6-tetrahydropyridine-3-carbothioamide | $^1$H NMR (400 MHz, CDCl3): d [ppm] = 2.54-2.65 (m, 4H), 2.70-2.76 (m, 2H), 2.80-2.90 (m, 4H), 3.32-3.39 (m, 2H), 3.68-3.80 (m, 4H), 4.20-4.35 (m, 2H), 5.92-5.99 (m, 1H), 6.30-6.75 (m, 1H), 7.20-7.26 (m, 2H), 7.35 (d, 1H), 7.65 (d, 1H), 8.20-8.34 (m, 2H), 14.4 (br s, 1H), 14.30 (br s, 1H) 19F NMR (400 MHz, CDCl$_3$): d [ppm] = 80.4 (d), UPLC-MS (Method 3): R$_t$ = 1.25 min, 69%., MS (ESIpos): m/z = (M + H)+ = 568 | N-[3-chloro-2-(difluoromethoxy)phenyl]-4-hydroxy-2-oxo-1,2,5,6-tetrahydropyridine-3-carbothioamide (intermediate 5-38), 525 mg, 1.50 mmol) 1-{3-[2-(morpholin-4-yl)ethoxy]pyridin-4-yl}methanamine (intermediate 2-81), 714 mg, 3.01 mmol) |
| 6-96 | 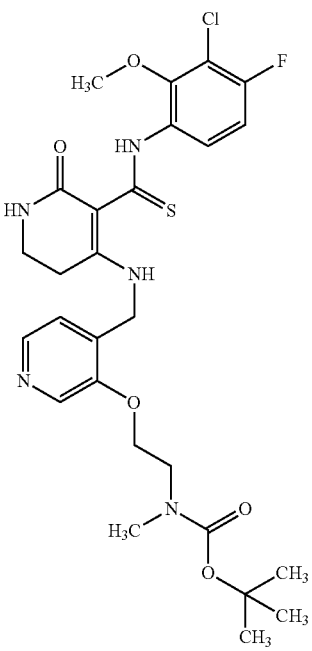 [SMILES: COc1c(NC(=S)C2=C(NCc3ccncc3OCCN(C)C(=O)OC(C)(C)C)CCNC2=O)ccc(F)c1Cl]<br>tert-butyl [2-({4-[({5-[(3-chloro-4-fluoro-2-methoxyphenyl)carbamothioyl]-6-oxo-1,2,3,6-tetrahydropyridin-4-yl}amino)methyl]pyridin-3-yl}oxy)ethyl]methylcarbamate | $^1$H-NMR (400 MHz, DMSO-d6) δ [ppm]: 1.035 (0.45), 1.052 (0.99), 1.070 (0.46), 1.335 (4.63), 1.363 (2.71), 1.381 (5.04), 1.417 (3.82), 2.518 (1.40), 2.522 (0.88), 2.734 (0.88), 2.751 (1.72), 2.767 (0.98), 2.875 (2.11), 2.891 (2.00), 3.144 (0.78), 3.154 (1.23), 3.160 (1.19), 3.575 (1.08), 3.588 (2.03), 3.601 (1.06), 3.750 (16.00), 3.763 (0.51), 4.268 (0.95), 4.636 (1.76), 4.651 (1.78), 7.173 (1.20), 7.195 (2.21), 7.218 (1.23), 7.298 (0.63), 7.681 (0.71), 7.696 (0.78), 7.704 (0.74), 7.719 (0.70), 7.743 (1.17), 8.234 (1.29), 8.245 (1.26), 8.396 (0.55), 8.419 (0.83), 13.677 (0.46), 14.707 (1.63),<br><br>LC-MS (method 1): R$_t$ = 1.24 min; MS (ESIneg): m/z = 592 [M − H]$^−$ | N-(3-chloro-4-fluoro-2-methoxyphenyl)-4-hydroxy-2-oxo-1,2,5,6-tetrahydropyridine-3-carbothioamide (intermediate 5-44, 150 mg, 453 µmol) tert-butyl (2-{[4-(aminomethyl)pyridin-3-yl]oxy}ethyl)methylcarbamate (intermediate 2-96), 204 mg, 726 µmol) |

Intermediate 6-82

N-[3-chloro-2-(difluoromethoxy)phenyl]-2-oxo-4-({[3-(tetrahydro-2H-pyran-4-ylmethoxy)pyridin-4-yl]methyl}amino)-1,2,5,6-tetrahydropyridine-3-carbothioamide

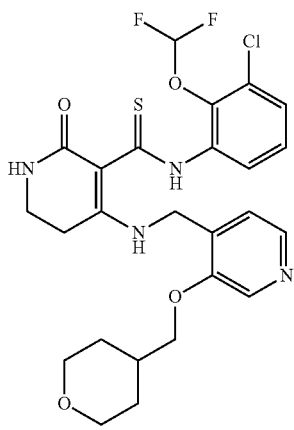 [SMILES: O=C1NCCC(NCc2ccncc2OCC2CCOCC2)=C1C(=S)Nc1cccc(Cl)c1OC(F)F]

A mixture of N-[3-chloro-2-(difluoromethoxy)phenyl]-4-hydroxy-2-oxo-1,2,5,6-tetrahydropyridine-3-carbothioamide, 384 mg (1.10 mmol, intermediate 5-38), and 1-[3-(tetrahydro-2H-pyran-4-ylmethoxy)pyridin-4-yl]methanamine, 490 mg (2.20 mmol, intermediate 2-82), mixed in dichloromethane and was heated at 120° C. in a pre-heated bath for 90 minutes. Cooled to room temperature then sonicated in methanol for 45 minutes gave the product, 259 mg (43%).

$^1$H NMR (400 MHz, DMSO-d6): δ [ppm]=1.29-1.45 (m, 2H), 1.65-1.79 (m, 2H), 2.44-2.63 (m, 2H), 2.71-2.83 (, 2H), 3.11-3.22 (m, 2H), 3.3-3.39 (m, 2H), 3.83-3.93 (m, 2H), 4.03 (d, 2H), 4.67 (d, 2H), 6.92 (t, 1H), 7.27-7.37 (m, 2H), 7.46 (d, 1H), 7.60 (d, 1H), 7.12 (br s, 1H), 8.22 (d, 1H), 8.37 (s, 1H);

UPLC4-MS (Method 3): $R_t$=1.48 min, 69%., MS (ESI-pos): m/z=(M+H)$^+$=553.

Intermediate 6-84

N-(3-fluoro-2-methoxyphenyl)-4-(((3-hydroxypyridin-4-yl)methyl)amino)-2-oxo-1,2,5,6-tetrahydropyridine-3-carbothioamide

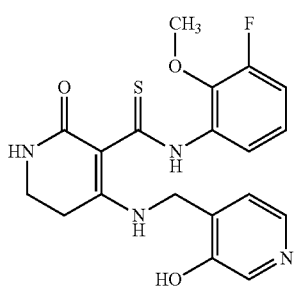 [SMILES: COc1c(F)cccc1NC(=S)C1=C(NCc2ccncc2O)CCNC1=O]

A mixture of 4-(aminomethyl)pyridin-3-ol (CAS: 20485-35-2, 75 g, 0.604 mol) and N-(3-fluoro-2-methoxy-phenyl)-4-hydroxy-6-oxo-2,3-dihydro-1H-pyridine-5-carbothioamide (intermediate 5-7, 150 g, 0.506 mol) in DMA (1.2 L) was stirred at 120° C. for 2.5 h under nitrogen. The mixture was concentrated in vacuum to remove most of solvent. The dark brown solution was slowly added to EtOAc (8 L) with stirring. The resulting mixture was washed with water (2.5 L) and brine (2.5 L×2). The organic phase was dried over Na$_2$SO$_4$, filtered and concentrated in vacuum. The residue was slurried with EtOAc (300 ml.) and filtered. The cake was dried in vacuum to afford the title compound (87 g, 47% yield) as a yellow solid.

$^1$H NMR (400 MHz, DMSO-d$_6$): δ=14.73 (s, 1H), 13.69 (t, 1H), 10.28 (s, 1H), 8.21-8.13 (m, 2H), 7.67-7.66 (m, 2H), 7.10 (br.s, 1H), 7.09-7.04 (m, 2H), 4.61 (d, 2H), 3.79 (s, 3H), 3.16 (t, 2H), 2.77 (t, 2H).

Intermediate 6-87

N-(3-chloro-2-methoxyphenyl)-4-{[(3-hydroxypyridin-4-yl)methyl]amino}-2-oxo-1,2,5,6-tetrahydropyridine-3-carbothioamide

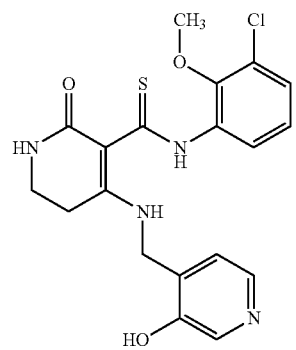 [SMILES: COc1c(Cl)cccc1NC(=S)C1=C(NCc2ccncc2O)CCNC1=O]

N-(3-chloro-2-methoxyphenyl)-4-hydroxy-2-oxo-1,2,5,6-tetrahydropyridine-3-carbothioamide (intermediate 5-32, 1.14 g, 3.64 mmol) and 4-(aminomethyl)pyridin-3-ol (CAS: 20485-35-2, 587 mg, 4.73 mmol) were given together, mixed well and than heated up to 120° C. for 1 h. Substrates did not melt. DMSO (4.0 ml) was added and the mixture stirred at 100° C. for 1 h. The product was concentrated and used in the next step without any further purification.

Intermediate 7-24

3-{[3-fluoro-2-(prop-2-en-1-yloxy)phenyl]amino}-2-[3-(2-methoxy-2-methylpropoxy)pyridin-4-yl]-1,5,6,7-tetrahydro-4H-pyrrolo[3,2-c]pyridin-4-one

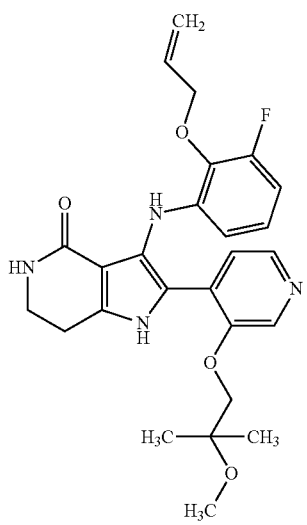 [SMILES: C=CCOc1c(F)cccc1Nc1c(-c2ccncc2OCC(C)(C)OC)[nH]c2c1C(=O)NCC2]

Using an analogous method as described for Example 6; Intermediate 6-24 (190 mg, 369 µmol) as the starting material, the title compound was prepared (77 mg, 41% yield) after concentration of the reaction mixture and crystallization of the residue.

$^1$H-NMR (400 MHz, DMSO-d$_6$): δ [ppm]=11.15 (s, 1H), 8.41 (s, 1H), 7.98 (d, 1H), 7.55 (s, 1H), 7.23 (d, 1H), 7.19-7.22 (m, 1H), 6.66 (m, 1H), 6.51 (m, 1H), 6.16-6.26 (m, 1H), 6.03 (d, 1H), 5.44 (dq, 1H), 5.24-5.28 (m, 1H), 4.64 (d, 2H), 4.19 (s, 2H), 3.43 (m, 2H), 3.25 (s, 3H), 2.84 (t, 2H), 1.28 (s, 6H).

Intermediate 84-1

3-((3-fluoro-2-methoxyphenyl)amino)-2-(3-hydroxypyridin-4-yl)-6,7-dihydro-1H-pyrrolo[3,2-c]pyridin-4(5H)-one

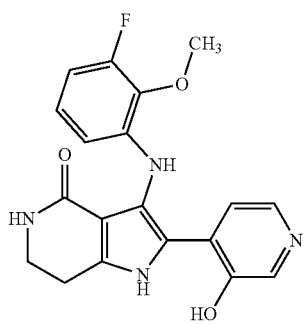 [SMILES: COc1c(F)cccc1Nc1c(-c2ccncc2O)[nH]c2c1C(=O)NCC2]

To a suspension of N-(3-fluoro-2-methoxy-phenyl)-4-[(3-hydroxy-4-pyridyl)methylamino]-6-oxo-2,3-dihydro-1H-pyridine-5-carbothioamide (intermediate 6-84, 41 g, 101.88 mmol) in MeOH (410 mL) was added TFA (0.75 mL, 10.13 mmol), followed by hydrogen peroxide (18 mL, 30% in water). The mixture was heated to 60° C. and stirred for 16 h. Additional TFA (6.8 mL, 91.84 mmol) and hydrogen peroxide (1.5 mL, 30% in water) were added. The suspension was stirred at 60° C. for further 3 h. The mixture was cooled to room temperature and stand overnight. The suspension was combined with a second batch that was generated identically. The combined suspension was filtered and the cake was washed with water (250 mL) and MeOH (150 mL), and then slurried in MeOH (150 mL). The suspension was filtered. The cake was washed with MeOH (75 mL) and dried in vacuum to afford the title compound (25.4 g, 33.8%) as a yellow solid.

$^1$H NMR (400 MHz, DMSO-d$_6$): δ=11.45 (s, 1H), 8.18 (s, 1H), 7.98 (d, 1H), 7.39 (d, 1H), 7.18 (s, 1H), 6.67 (t, 1H), 6.54 (t, 1H), 6.04 (d, 1H), 3.92 (s, 3H), 3.40 (t, 2H), 2.90 (t, 2H).

LC-MS (method 5): R$_t$=1.851 min; m/z=369.0 (M+H)$^+$.

Intermediate 87-1

3-(3-chloro-2-methoxyanilino)-2-(3-hydroxypyridin-4-yl)-1,5,6,7-tetrahydro-4H-pyrrolo[3,2-c]pyridin-4-one

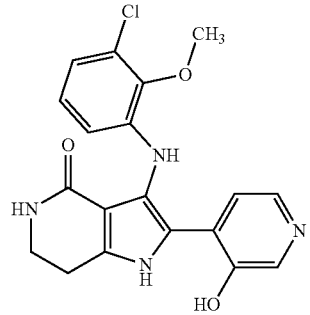 [SMILES: COc1c(Cl)cccc1Nc1c(-c2ccncc2O)[nH]c2c1C(=O)NCC2]

N-(3-chloro-2-methoxyphenyl)-4-{[(3-hydroxypyridin-4-yl)methyl]amino}-2-oxo-1,2,5,6-tetrahydropyridine-3-carbothioamide (intermediate 6-87, 1.50 g, 3.58 mmol) was solved in methanol and treated with TFA (280 µl, 3.6 mmol). After addition of hydrogen peroxide (220 µl, 7.2 mmol) the reaction mixture was heated to 50° C. and stirred overnight. The reaction mixture was quenched with saturated sodium thiosulfate solution and stirred for 2 h. TEA (1.0 ml, 7.5 mmol) was added and the mixture was diluted with water and extracted with DCM. The combined organic layers were dried by hydrophobic filter paper and concentrated under reduced pressure. The mixture was purified by prep. HPLC (basic) to give the title compound (95.7 mg, 90% purity, 6% yield) brown solid.

$^1$H-NMR (400 MHz, DMSO-d6) δ [ppm]: 2.518 (5.69), 2.523 (3.86), 2.843 (1.31), 2.859 (2.82), 2.876 (1.49), 3.370 (1.01), 3.376 (1.08), 3.387 (1.97), 3.393 (1.91), 3.404 (0.96), 3.410 (0.86), 3.700 (1.23), 3.757 (0.91), 3.865 (16.00), 3.882 (0.55), 6.174 (1.79), 6.179 (1.74), 6.192 (1.86), 6.198 (1.79), 6.653 (0.78), 6.667 (2.75), 6.673 (4.08), 6.691 (1.71), 6.711 (0.53), 7.072 (1.71), 7.241 (1.54), 7.254 (1.54), 7.430 (2.32), 7.864 (0.91), 7.877 (0.86), 8.192 (1.39), 10.461 (1.16), 11.279 (1.08).

LC-MS (method 2): R$_t$=0.59 min; MS (ESIpos): m/z=385 [M+H]$^+$

Intermediate 95-1 tert-butyl (2S)-2-[({4-[3-(3-chloro-2-methoxyanilino)-4-oxo-4,5,6,7-tetrahydro-1H-pyrrolo[3,2-c]pyridin-2-yl]pyridin-3-yl}oxy)methyl]pyrrolidine-1-carboxylate

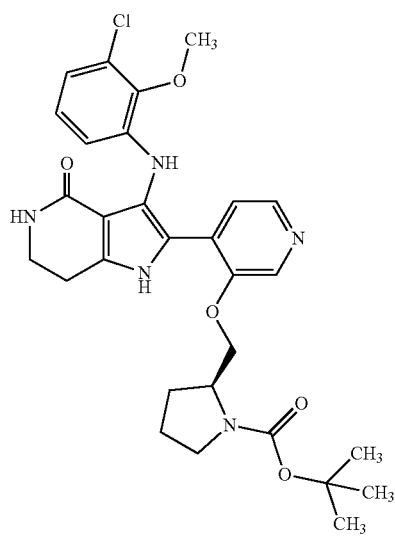 [SMILES: COc1c(Cl)cccc1Nc1c(-c2ccncc2OC[C@@H]2CCCN2C(=O)OC(C)(C)C)[nH]c2c1C(=O)NCC2]

To a solution of tert-butyl (2S)-2-[({4-[({5-[(3-chloro-2-methoxyphenyl)carbamothioyl]-6-oxo-1,2,3,6-tetrahydropyridin-4-yl}amino)methyl]pyridin-3-yl}oxy)methyl]pyrrolidine-1-carboxylate (intermediate 6-80, 507 mg, 76% purity, 640 µmol) in 6.0 mL methanol was added TFA (99 µl, 1.3 mmol) and stirred for 5 min at rt. Then meta-chloroperoxybenzoic acid (221 mg, 1.28 mmol) was added and the mixture was heated 1 h at 50° C. The reaction mixture was cooled down to rt and quenched with an aqueous saturated sodium thiosulfate solution and stirred for 30 min at rt. Triethylamine (190 µl, 1.3 mmol) and water was added and the mixture was extracted with dichloromethane two times. The combined organic layers were filtered through a hydrophobic filter paper and the filtrate was concentrated under reduced pressure. The residue was purified by flash chromatography and then by preparative HPLC to give 9 mg of the title compound (90% purity, 2% yield).

¹H-NMR (400 MHz, DMSO-d6) δ [ppm]: 1.154 (4.77), 1.172 (9.54), 1.190 (4.64), 1.232 (1.54), 1.406 (14.27), 1.824 (1.22), 1.988 (16.00), 2.332 (1.34), 2.336 (0.61), 2.518 (8.22), 2.523 (5.18), 2.673 (1.41), 2.678 (0.64), 2.841 (0.42), 2.932 (1.41), 3.413 (2.46), 3.762 (0.61), 3.883 (4.86), 4.000 (1.31), 4.017 (3.81), 4.035 (4.06), 4.053 (2.34), 4.068 (1.95), 4.086 (0.64), 4.331 (1.41), 6.107 (1.28), 6.119 (2.11), 6.131 (1.38), 6.673 (2.05), 7.151 (1.06), 7.349 (1.31), 7.486 (1.31), 7.998 (0.99), 8.417 (2.18), 11.433 (0.90).

LC-MS (method 2): $R_t$=1.29 min; MS (ESIpos): m/z=569 [M+H]⁺

Intermediate 96-1 tert-butyl [2-({4-[3-(3-chloro-4-fluoro-2-methoxyanilino)-4-oxo-4,5,6,7-tetrahydro-1H-pyrrolo[3,2-c]pyridin-2-yl]pyridin-3-yl}oxy)ethyl]methylcarbamate

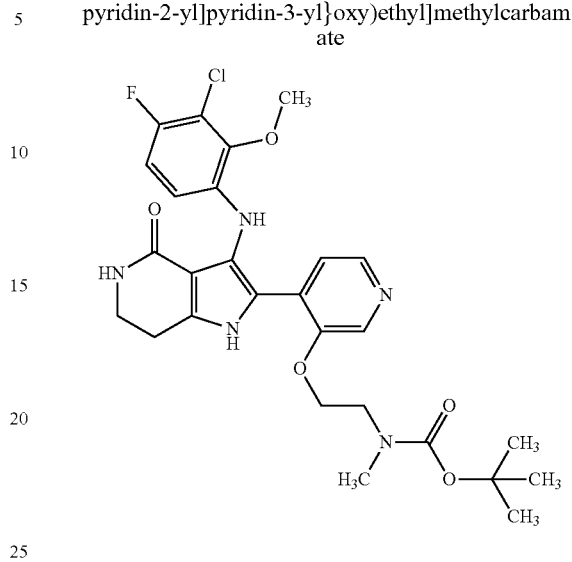

To a solution of tert-butyl [2-({4-[({5-[(3-chloro-4-fluoro-2-methoxyphenyl)carbamothioyl]-6-oxo-1,2,3,6-tetrahydropyridin-4-yl}amino)methyl]pyridin-3-yl}oxy)ethyl]methylcarbamate (intermediate 6-96), 129 mg, 217 µmol) in 2.2 mL methanol were added TFA (17 µl, 220 µmol) and hydrogen peroxide (38 µl, 35% purity, 430 µmol) and the mixture was heated 20 h at 50° C. The reaction mixture was concentrated under reduced pressure and the residue was purified by preparative HPLC to give 67 mg of the title compound (90% purity, 50% yield).

LC-MS (method 2): $R_t$=1.22 min; MS (ESIneg): m/z=558 [M−H]⁻

¹H-NMR (400 MHz, DMSO-d6) δ [ppm]: 1.232 (0.51), 1.287 (1.02), 1.369 (16.00), 2.075 (1.77), 2.518 (4.72), 2.523 (3.27), 2.540 (9.93), 2.674 (0.97), 2.776 (0.55), 2.895 (2.87), 2.952 (1.19), 3.392 (1.63), 3.404 (2.65), 3.420 (1.43), 3.719 (1.21), 3.803 (0.42), 3.922 (4.66), 4.316 (1.57), 6.065 (0.86), 6.078 (1.04), 6.086 (1.10), 6.100 (0.93), 6.779 (0.77), 7.167 (0.82), 7.355 (0.99), 7.411 (0.90), 8.013 (0.97), 8.395 (5.58), 11.175 (3.38).

Intermediate 96-2

3-(3-chloro-4-fluoro-2-methoxyanilino)-2-{3-[2-(methylamino)ethoxy]pyridin-4-yl}-1,5,6,7-tetrahydro-4H-pyrrolo[3,2-c]pyridin-4-one

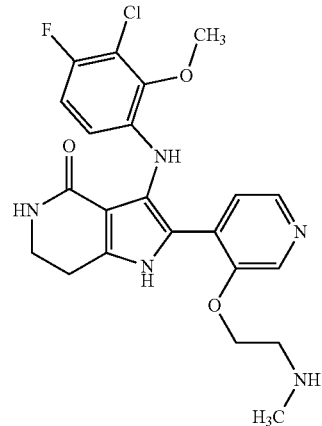 [SMILES: CNCCOc1cnccc1-c1[nH]c2c(c1Nc1ccc(F)c(Cl)c1OC)C(=O)NCC2]

Using an analogous method as described for Intermediate 5-32, tert-butyl [2-({4-[3-(3-chloro-4-fluoro-2-methoxyanilino)-4-oxo-4,5,6,7-tetrahydro-1H-pyrrolo[3,2-c]pyridin-2-yl]pyridin-3-yl}oxy)ethyl]methylcarbamate (intermediate 96-1, 67.0 mg, 120 µmol) as the starting material, the title compound was prepared 14 mg (90% purity, 19% yield).

¹H-NMR (400 MHz, DMSO-d6) δ [ppm]: 0.850 (0.47), 1.154 (0.67), 1.172 (1.23), 1.190 (0.78), 1.230 (1.93), 1.262 (0.65), 1.369 (16.00), 1.751 (1.19), 2.074 (4.82), 2.326 (0.69), 2.442 (0.52), 2.539 (4.65), 2.669 (0.75), 2.894 (3.01), 2.952 (1.53), 3.082 (0.51), 3.100 (0.48), 3.404 (2.97), 3.719 (1.66), 3.922 (4.70), 4.314 (1.63), 6.066 (0.81), 6.087 (1.13), 6.101 (0.94), 6.779 (0.81), 7.042 (0.48), 7.063 (0.71), 7.091 (0.41), 7.164 (1.21), 7.214 (0.50), 7.236 (0.85), 7.258 (0.66), 7.291 (0.50), 7.355 (0.98), 7.416 (0.88), 7.796 (0.52), 8.014 (0.84), 8.133 (5.43), 8.396 (2.02), 8.478 (0.47), 8.537 (0.67), 11.176 (2.95).

LC-MS (method 1): $R_t$=0.70 min; MS (ESIpos): m/z=460 $[M+H]^+$

SYNTHESES OF EXAMPLES

Example 1

2-[3-(2-methoxyethoxy)pyridin-4-yl]-3-(phenylamino)-1,5,6,7-tetrahydro-4H-pyrrolo[3,2-c]pyridin-4-one

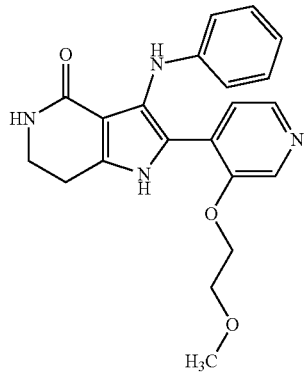 [SMILES: COCCOc1cnccc1-c1[nH]c2c(c1Nc1ccccc1)C(=O)NCC2]

To a solution of 4-({[3-(2-methoxyethoxy)pyridin-4-yl]methyl}amino)-2-oxo-N-phenyl-1,2,5,6-tetrahydropyridine-3-carbothioamide (Intermediate 6-1; 95.1 mg, 231 µmol) in MeOH (4 ml) was added aqueous hydrogen peroxide (42 µl, 34% purity, 460 µmol) and heated at 90° C. for 16 h. The reaction mixture was concentrated and was purified by preparative HPLC (basic method) to give the title compound 33.0 mg (34% yield).

¹H-NMR (400 MHz, DMSO-d₆): δ [ppm]=10.97 (s, 1H), 8.37 (s, 1H), 7.97 (d, 1H), 7.39-7.46 (m, 1H), 7.32 (d, 1H), 7.11 (s, 1H), 7.00 (t, 2H), 6.54-6.62 (m, 3H), 4.25-4.35 (m, 2H), 3.76-3.81 (m, 2H), 3.37-3.45 (m, 5H), 2.85 (t, 2H).

Example 2

2-[3-(3,3-dimethylbutoxy)pyridin-4-yl]-3-[(3-fluorophenyl)amino]-1,5,6,7-tetrahydro-4H-pyrrolo[3,2-c]pyridin-4-one

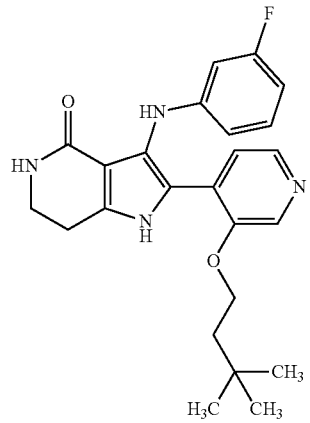 [SMILES: CC(C)(C)CCOc1cnccc1-c1[nH]c2c(c1Nc1cccc(F)c1)C(=O)NCC2]

Using an analogous method as described for Example 1; Intermediate 6-2 (173 mg, 379 µmol) as the starting material and heated for 2 h, the title compound was prepared 38.0 mg (21% yield).

¹H-NMR (400 MHz, DMSO-d₆): δ [ppm]=11.15 (s, 1H), 8.36 (s, 1H), 8.04 (d, 1H), 7.56 (s, 1H), 7.29 (d, 1H), 7.03 (s, 1H), 6.95 (m, 1H), 6.38 (d, 1H), 6.29 (t, 1H), 6.18 (dt, 1H), 4.10 (t, 2H), 3.34-3.41 (m, 2H), 2.82 (t, 2H), 2.52-2.54 (m, 1H), 1.65-1.73 (m, 2H), 0.92 (s, 9H).

Example 3

2-[3-(benzyloxy)pyridin-4-yl]-3-[(3-fluorophenyl)amino]-1,5,6,7-tetrahydro-4H-pyrrolo[3,2-c]pyridin-4-one

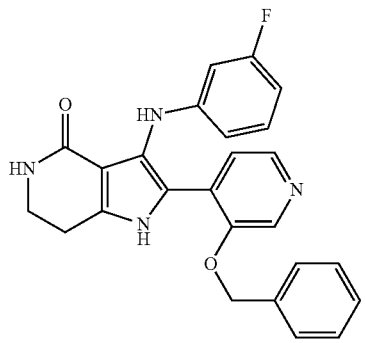 [SMILES: O=C1NCCc2[nH]c(-c3ccncc3OCc3ccccc3)c(Nc3cccc(F)c3)c21]

Using an analogous method as described for Example 1; Intermediate 6-3 (188 mg, 406 µmol) as the starting material and heated for 2 h, the title compound was prepared 48.0 mg (26% yield).

¹H-NMR (400 MHz, DMSO-d₆): δ [ppm]=11.27 (s, 1H), 8.38-8.43 (m, 1H), 8.33 (s, 1H), 8.01 (d, 1H), 7.51-7.59 (m, 1H), 7.28-7.49 (m, 7H), 7.05 (s, 1H), 6.93-7.02 (m, 1H), 6.35 (d, 1H), 6.31 (t, 1H), 6.21 (dt, 1H), 5.33 (s, 2H), 3.35-3.43 (m, 2H), 2.84 (t, 2H).

Example 4

3-[(3-fluorophenyl)amino]-2-[3-(2-hydroxy-2-methylpropoxy)pyridin-4-yl]-1,5,6,7-tetrahydro-4H-pyrrolo[3,2-c]pyridin-4-one

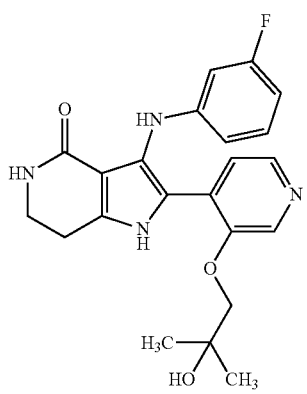 [SMILES: CC(C)(O)COc1cnccc1-c1[nH]c2c(c1Nc1cccc(F)c1)C(=O)NCC2]

Using an analogous method as described for Example 1; Intermediate 6-4 (156 mg, 351 µmol) as the starting material and heated for 2 h, the title compound was prepared 46.0 mg (30% yield).

$^1$H-NMR (400 MHz, DMSO-d$_6$): δ [ppm]=11.70 (s, 1H), 8.39 (s, 1H), 8.02 (d, 1H), 7.58-7.69 (m, 1H), 7.36 (d, 1H), 6.95-7.11 (m, 2H), 6.24-6.44 (m, 3H), 5.49 (s, 1H), 4.06 (s, 2H), 3.35-3.44 (m, 2H), 2.81 (t, 2H), 1.27 (s, 6H).

Example 5

2-{3-[2-(dimethylamino)ethoxy]pyridin-4-yl}-3-[(3-fluorophenyl)amino]-1,5,6,7-tetrahydro-4H-pyrrolo[3,2-c]pyridin-4-one

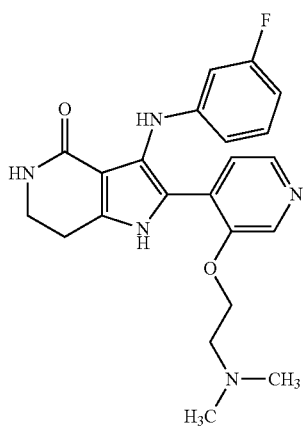 [SMILES: CN(C)CCOc1cnccc1-c1[nH]c2c(c1Nc1cccc(F)c1)C(=O)NCC2]

Using an analogous method as described for Example 1; Intermediate 6-5 (181 mg, 408 µmol) as the starting material, the title compound was prepared 5.0 mg (3% yield).

1H-NMR (400 MHz, DMSO-d6): Shift [ppm]=11.82 (s, 1H), 10.91 (br s, 1H), 8.56 (s, 1H), 8.32 (d, 1H), 8.11 (br s, 1H), 7.70 (d, 1H), 7.31 (br s, 1H), 7.01-7.09 (m, 1H), 6.34-6.47 (m, 3H), 4.55-4.63 (m, 2H), 3.43 (brt, 3H), 2.98 (t, 2H), 2.78-2.89 (m, 6H).

Example 6

3-[(3-fluorophenyl)amino]-2-[3-(2-methoxy-2-methylpropoxy)pyridin-4-yl]-1,5,6,7-tetrahydro-4H-pyrrolo[3,2-c]pyridin-4-one

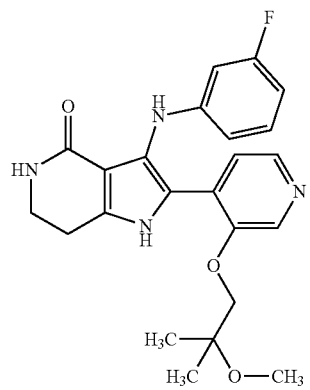 [SMILES: COC(C)(C)COc1cnccc1-c1[nH]c2c(c1Nc1cccc(F)c1)C(=O)NCC2]

N-(3-fluorophenyl)-4-({[3-(2-methoxy-2-methylpropoxy)pyridin-4-yl]methyl}amino)-2-oxo-1,2,5,6-tetrahydropyridine-3-carbothioamide (Intermediate 6-6; 217 mg, 90% purity, 426 µmol) in MeOH (8 ml) was added TFA (33 µl, 430 µmol) followed by aqueous hydrogen peroxide (87 µl, 30% purity, 850 µmol) and heated at 50° C. for 16 h. The reaction mixture was allowed to ccol sat. sodium thiosulfate solution and TEA (0.5 ml) were added and the reaction mixture was extracted with DCM, the organics were dried with Na2SO4, filtered and concentrated in vacuo. The residue was purified twice by preparative TLC (DCM:EtOH) to give the titled compound 31.7 mg (17% yield).

$^1$H-NMR (400 MHz, DMSO-d$_6$): δ [ppm]=11.19 (s, 1H), 8.41 (s, 1H), 8.03 (d, 1H), 7.62 (s, 1H), 7.38 (d, 1H), 6.99-7.10 (m, 2H), 6.42 (d, 1H), 6.35 (t, 1H), 6.26 (dt, 1H), 4.17 (s, 2H), 3.38-3.44 (m, 2H), 3.25 (s, 3H), 2.83 (t, 2H), 1.27 (s, 6H).

Example 7

3-[(3-fluorophenyl)amino]-2-{3-[2-methyl-2-(morpholin-4-yl)propoxy]pyridin-4-yl}-1,5,6,7-tetrahydro-4H-pyrrolo[3,2-c]pyridin-4-one

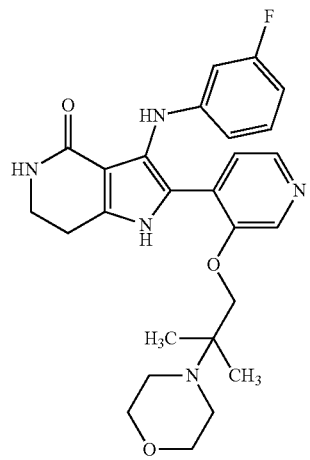 [SMILES: CC(C)(COc1cnccc1-c1[nH]c2c(c1Nc1cccc(F)c1)C(=O)NCC2)N1CCOCC1]

Using an analogous method as described for Example 6; Intermediate 6-7 (220 mg, 428 µmol) as the starting material, the title compound was prepared 44.0 mg (19% yield).

$^1$H-NMR (400 MHz, DMSO-d$_6$): δ [ppm]=11.16 (s, 1H), 8.41 (s, 1H), 8.00 (d, 1H), 7.41 (s, 1H), 7.29 (d, 1H), 7.15 (s, 1H), 6.67 (m, 1H), 6.51 (m, 1H), 6.03 (d, 1H), 4.16-4.23 (m, 4H), 3.73 (m, 2H), 3.38-3.49 (m, 2H), 3.32 (s, 3H), 3.25 (s, 3H), 2.83 (t, 2H), 1.28 (s, 6H).

Example 8

3-[(3-fluorophenyl)amino]-2-(3-{[(2S)-1-methylpyrrolidin-2-yl]methoxy}pyridin-4-yl)-1,5,6,7-tetrahydro-4H-pyrrolo[3,2-c]pyridin-4-one

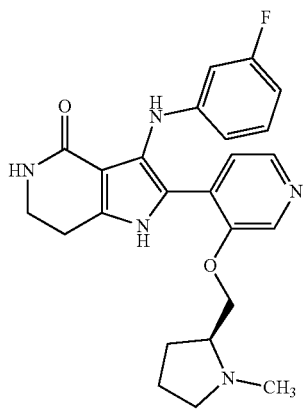 [SMILES: CN1CCC[C@H]1COc1cnccc1-c1[nH]c2c(c1Nc1cccc(F)c1)C(=O)NCC2]

Using an analogous method as described for Example 6; Intermediate 6-8 (300 mg, 543 µmol) as the starting material, the title compound was prepared 8.0 mg (3% yield) after preparative HPLC (acidic method).

$^1$H-NMR (400 MHz, DMSO-d$_6$): δ [ppm]=12.06 (s, 1H), 8.43 (s, 1H), 7.99 (d, 1H), 7.70 (s, 1H), 7.41 (d, 1H), 7.09 (s, 1H), 7.00-7.07 (m, 1H), 6.42 (m, 1H), 6.36 (m, 1H), 6.28 (dt, 1H), 4.49 (m, 1H), 4.19 (m, 1H), 3.36-3.45 (m, 2H), 3.15-3.22 (m, 1H), 2.75-2.89 (m, 2H), 2.30-2.33 (m, 3H), 1.69-2.01 (m, 4H).

Example 9

3-[(3,5-difluorophenyl)amino]-2-[3-(2-methoxyethoxy)pyridin-4-yl]-1,5,6,7-tetrahydro-4H-pyrrolo[3,2-c]pyridin-4-one

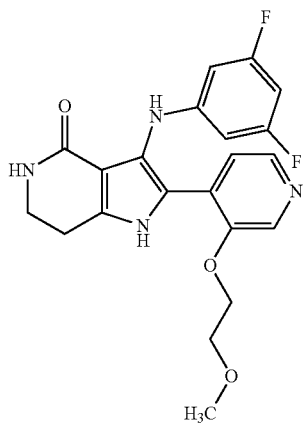 [SMILES: COCCOc1cnccc1-c1[nH]c2c(c1Nc1cc(F)cc(F)c1)C(=O)NCC2]

Using an analogous method as described for Example 1; Intermediate 6-9 (124 mg, 276 µmol) as the starting material, the title compound was prepared 32 mg (27% yield).

$^1$H-NMR (500 MHz, DMSO-d$_6$): δ [ppm]=11.18 (s, 1H), 8.42 (s, 1H), 8.10 (d, 1H), 7.82 (s, 1H), 7.36 (d, 1H), 7.05 (s, 1H), 6.25 (tt, 1H), 6.14 (brd, 1H), 6.10-6.13 (m, 1H), 4.31 (m, 2H), 3.71-3.76 (m, 2H), 3.41 (m, 2H), 3.37 (s, 3H), 2.84 (t, 2H).

Example 10

3-[(3,5-difluorophenyl)amino]-2-[3-(2-methoxy-2-methylpropoxy)pyridin-4-yl]-1,5,6,7-tetrahydro-4H-pyrrolo[3,2-c]pyridin-4-one

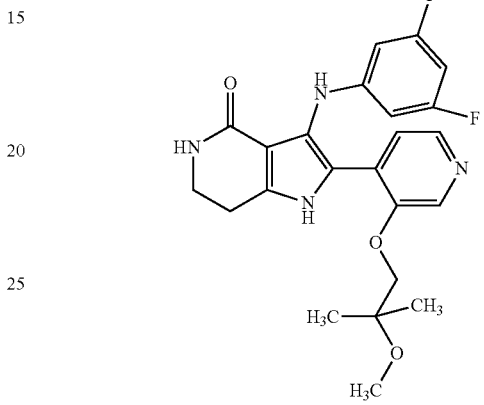

Using an analogous method as described for Example 6; Intermediate 6-10 (210 mg, 375 µmol) as the starting material, the title compound was prepared 69 mg (40% yield).

$^1$H-NMR (400 MHz, DMSO-d$_6$): δ [ppm]=11.25 (s, 1H), 8.43 (s, 1H), 8.09 (d, 1H), 7.88 (s, 1H), 7.38 (d, 1H), 7.07 (s, 1H), 6.26 (tt, 1H), 6.15 (br d, 1H), 6.10-6.13 (m, 1H), 4.15 (s, 2H), 3.36-3.44 (m, 2H), 3.24 (s, 3H), 2.83 (t, 2H), 1.25 (s, 6H).

Example 11

3-{[2-(difluoromethoxy)phenyl]amino}-2-[3-(2-methoxyethoxy)pyridin-4-yl]-1,5,6,7-tetrahydro-4H-pyrrolo[3,2-c]pyridin-4-one

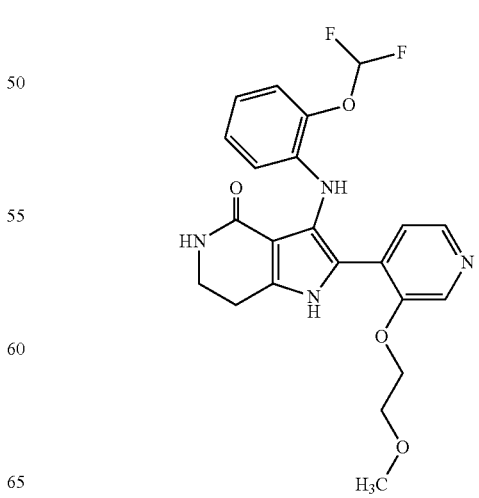

Using an analogous method as described for Example 1; Intermediate 6-11 ((1.03 g, 2.15 mmol) as the starting material, the title compound was prepared 562 mg (59% yield) after silica chromatography (DCM:MeOH) and further purification of impure fraction by preparative HPLC (acidic method).

$^1$H-NMR (400 MHz, DMSO-d$_6$): δ [ppm]=11.06 (s, 1H), 8.40 (s, 1H), 8.00 (d, 1H), 7.01-7.42 (m, 5H), 6.79 (t, 1H), 6.66 (m, 1H), 6.31 (m, 1H), 4.31 (m, 2H), 3.74-3.80 (m, 2H), 3.35-3.44 (m, 5H), 2.85 (t, 2H).

Example 12

3-[(2-bromo-3-fluorophenyl)amino]-2-[3-(2-methoxyethoxy)pyridin-4-yl]-1,5,6,7-tetrahydro-4H-pyrrolo[3,2-c]pyridin-4-one

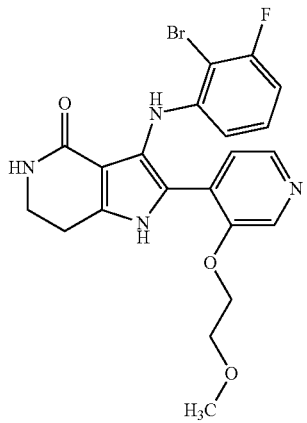 [SMILES: COCCOc1cnccc1-c1[nH]c2c(c1Nc1cccc(F)c1Br)C(=O)NCC2]

Using an analogous method as described for Example 1; Intermediate 6-12 (28.0 mg, 55.0 μmol) as the starting material and heated for 5 h, the title compound was prepared 3.0 mg (10% yield).

$^1$H-NMR (400 MHz, DMSO-d$_6$): δ [ppm]=11.19 (s, 1H), 8.39 (s, 1H), 8.02-8.09 (m, 1H), 7.58 (s, 1H), 7.22 (d, 1H), 7.17 (s, 1H), 6.91 (m, 1H), 6.60 (m, 1H), 6.13 (d, 1H), 4.23-4.30 (m, 2H), 3.71-3.77 (m, 2H), 3.40-3.47 (m, 2H), 3.35 (s, 3H), 2.86 (t, 2H).

Example 13

2-[3-(2-methoxyethoxy)pyridin-4-yl]-3-[(2-methoxyphenyl)amino]-1,5,6,7-tetrahydro-4H-pyrrolo[3,2-c]pyridin-4-one

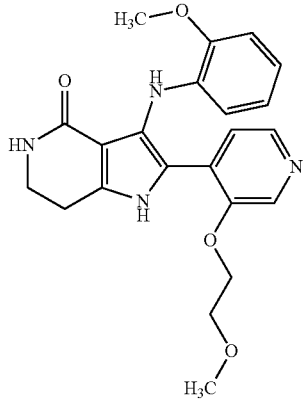 [SMILES: COCCOc1cnccc1-c1[nH]c2c(c1Nc1ccccc1OC)C(=O)NCC2]

Using an analogous method as described for Example 1; Intermediate 6-13 (85.0 mg, 192 μmol) as the starting material and heated for 2 h, the title compound was prepared 15.0 mg (17% yield).

$^1$H-NMR (400 MHz, DMSO-d$_6$): δ [ppm]=10.96 (s, 1H), 8.33-8.41 (m, 1H), 7.96 (d, 1H), 7.52 (s, 1H), 7.10-7.18 (m, 2H), 6.90 (m, 1H), 6.62 (m, 1H), 6.48 (m, 1H), 6.15 (m, 1H), 4.25-4.31 (m, 2H), 3.87 (s, 3H), 3.75-3.82 (m, 2H), 3.36-3.46 (m, 5H), 2.84 (t, 2H).

Example 14

2-[3-(2-methoxyethoxy)pyridin-4-yl]-3-{[2-(trifluoromethoxy)phenyl]amino}-1,5,6,7-tetrahydro-4H-pyrrolo[3,2-c]pyridin-4-one

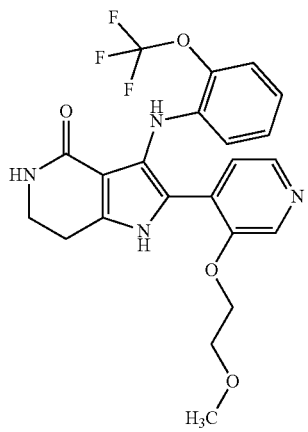 [SMILES: COCCOc1cnccc1-c1[nH]c2c(c1Nc1ccccc1OC(F)(F)F)C(=O)NCC2]

Using an analogous method as described for Example 1; Intermediate 6-14 (152.0 mg, 306 μmol) as the starting material and heated for 2 h, the title compound was prepared 52.0 mg (35% yield).

$^1$H-NMR (400 MHz, DMSO-d$_6$): δ [ppm]=11.08 (s, 1H), 8.40 (s, 1H), 7.99 (d, 1H), 7.56 (s, 1H), 7.24 (s, 1H), 7.21-7.24 (m, 1H), 7.14 (s, 1H), 6.91 (t, 1H), 6.69 (m, 1H), 6.37 (m, 1H), 4.31 (m, 2H), 3.76 (m, 2H), 3.43 (m, 2H), 3.38 (s, 3H), 2.86 (t, 2H).

Example 15

3-{[2-(2,2-difluoroethyl)phenyl]amino}-2-[3-(2-methoxyethoxy)pyridin-4-yl]-1,5,6,7-tetrahydro-4H-pyrrolo[3,2-c]pyridin-4-one

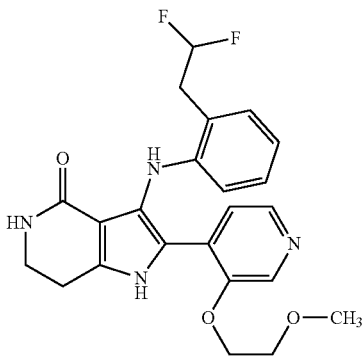 [SMILES: COCCOc1cnccc1-c1[nH]c2c(c1Nc1ccccc1CC(F)F)C(=O)NCC2]

Using an analogous method as described for Example 1; Intermediate 6-15 (126 mg, 264 μmol) as the starting material and heated for 2 h, the title compound was prepared 20.0 mg (16% yield).

¹H-NMR (400 MHz, DMSO-d₆): δ [ppm]=10.99 (s, 1H), 8.40 (s, 1H), 7.96 (d, 1H), 7.31 (d, 2H), 7.07-7.23 (m, 2H), 6.86 (t, 1H), 6.66 (m, 1H), 6.30-6.63 (m, 2H), 4.36 (m, 2H), 3.79 (m, 2H), 3.41 (s, 3H) 3.21-3.46 (m, 4H), 2.87 (t, 2H).

Example 16

3-[(3-fluoro-2-methoxyphenyl)amino]-2-[3-(2-methoxyethoxy)pyridin-4-yl]-1,5,6,7-tetrahydro-4H-pyrrolo[3,2-c]pyridin-4-one

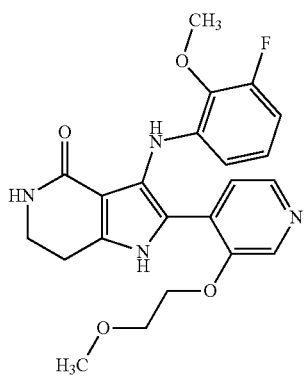 [SMILES: COCCOc1cnccc1-c1[nH]c2c(c1Nc1cccc(F)c1OC)C(=O)NCC2]

Using an analogous method as described for Example 1; Intermediate 6-16 (115 mg, 250 μmol) as the starting material and heated for 2 h, the title compound was prepared 46.0 mg (41% yield).

¹H-NMR (400 MHz, DMSO-d₆): δ [ppm]=11.03 (s, 1H), 8.41 (s, 1H), 8.03 (d, 1H), 7.52 (s, 1H), 7.29 (d, 1H), 7.15 (s, 1H), 6.64 (m, 1H), 6.49 (m, 1H), 6.01 (d, 1H), 4.34 (m, 2H), 3.89-3.93 (m, 3H), 3.78 (m, 2H), 3.39 (s, 4H), 2.85 (t, 2H).

Example 17

3-[(3-fluoro-2-methoxyphenyl)amino]-2-[3-(2-methoxy-2-methylpropoxy)pyridin-4-yl]-1,5,6,7-tetrahydro-4H-pyrrolo[3,2-c]pyridin-4-one

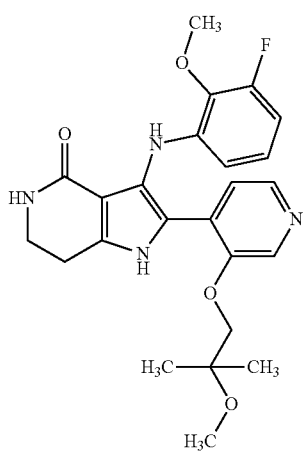 [SMILES: COc1c(F)cccc1Nc1c(-c2ccncc2OCC(C)(C)OC)[nH]c2c1C(=O)NCC2]

Using an analogous method as described for Example 6; Intermediate 6-17 (3.50 g, 7.16 mmol) as the starting material, the title compound was prepared after crystallization from EtOH (1.24 g, 36% yield). Further crystallization of the mother liquor gave (300 mg, 9% yield).

¹H-NMR (400 MHz, DMSO-d₆): δ [ppm]=11.17 (s, 1H), 8.42 (s, 1H), 8.01 (d, 1H), 7.51 (s, 1H), 7.28 (d, 1H), 7.17 (s, 1H), 6.66 (m, 1H), 6.51 (m, 1H), 6.03 (d, 1H), 4.19 (s, 2H), 3.91 (s, 3H), 3.42 (m, 2H), 3.25 (s, 3H), 2.78-2.86 (m, 2H), 1.28 (s, 6H).

Example 18

3-{[2-(difluoromethoxy)-3-fluorophenyl]amino}-2-[3-(2-methoxyethoxy)pyridin-4-yl]-1,5,6,7-tetrahydro-4H-pyrrolo[3,2-c]pyridin-4-one

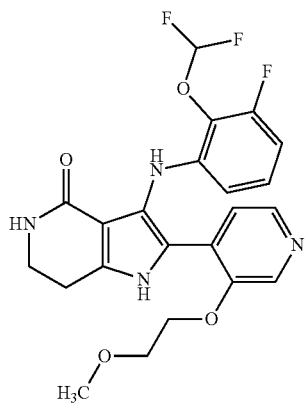 [SMILES: COCCOc1cnccc1-c1[nH]c2c(c1Nc1cccc(F)c1OC(F)F)C(=O)NCC2]

Using an analogous method as described for Example 1; Intermediate 6-18 (99.0 mg, 199 μmol) as the starting material and heated for 2 h, the title compound was prepared 20.0 mg (21% yield).

¹H-NMR (400 MHz, DMSO-d₆): δ [ppm]=11.11 (s, 1H), 8.42 (s, 1H), 8.04 (d, 1H), 7.42 (s, 1H), 7.33-7.37 (m, 1H), 7.09-7.15 (m, 1H), 6.98-7.38 (m, 1H), 6.84 (m, 1H), 6.57 (m, 1H), 6.13 (d, 1H), 4.26-4.39 (m, 2H), 3.74-3.80 (m, 2H), 3.41 (m, 2H), 3.37 (s, 3H), 2.85 (t, 2H).

Example 19

3-{[2-(difluoromethoxy)-3-fluorophenyl]amino}-2-[3-(2-methoxy-2-methylpropoxy)pyridin-4-yl]-1,5,6,7-tetrahydro-4H-pyrrolo[3,2-c]pyridin-4-one

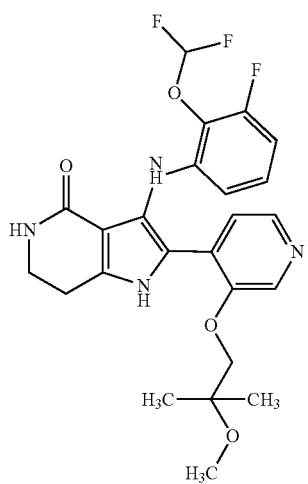 [SMILES: COC(C)(C)COc1cnccc1-c1[nH]c2c(c1Nc1cccc(F)c1OC(F)F)C(=O)NCC2]

Using an analogous method as described for Example 6; Intermediate 6-19 (160 mg, 305 µmol) as the starting material, the title compound was prepared (61 mg, 39% yield) after preparative TLC purification (DCM:MeOH).

$^1$H-NMR (400 MHz, DMSO-d$_6$): δ [ppm]=11.22 (s, 1H), 8.42 (s, 1H), 8.02 (d, 1H), 7.45 (s, 1H), 7.34-7.38 (m, 1H), 7.14 (m, 1H), 7.00-7.40 (m, 1H), 6.87 (m, 1H), 6.59 (m, 1H), 6.14 (d, 1H), 4.17 (s, 2H), 3.39-3.45 (m, 2H), 3.24 (s, 3H), 2.84 (t, 2H), 1.27 (s, 6H).

Example 20

3-[(3-fluoro-2-methylphenyl)amino]-2-[3-(2-methoxyethoxy)pyridin-4-yl]-1,5,6,7-tetrahydro-4H-pyrrolo[3,2-c]pyridin-4-one

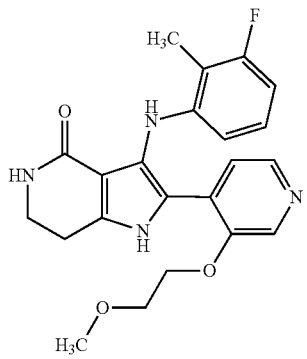 [SMILES: COCCOc1cnccc1-c1[nH]c2c(c1Nc1cccc(F)c1C)C(=O)NCC2]

Using an analogous method as described for Example 1; Intermediate 6-20 (140 mg, 315 µmol) as the starting material and heated for 2 h, the title compound was prepared 33.0 mg (23% yield).

$^1$H-NMR (400 MHz, DMSO-d$_6$): δ [ppm]=11.00 (s, 1H), 8.39 (s, 1H), 7.99 (d, 1H), 7.32 (s, 1H), 7.24 (d, 1H), 7.18 (s, 1H), 6.72-6.84 (m, 1H), 6.46 (t, 1H), 6.07 (d, 1H), 4.29-4.36 (m, 2H), 3.74-3.80 (m, 2H), 3.37-3.46 (m, 5H), 2.86 (t, 2H), 2.18 (d, 3H).

Example 21

3-[(3-fluoro-2-methylphenyl)amino]-2-[3-(2-methoxy-2-methylpropoxy)pyridin-4-yl]-1,5,6,7-tetrahydro-4H-pyrrolo[3,2-c]pyridin-4-one

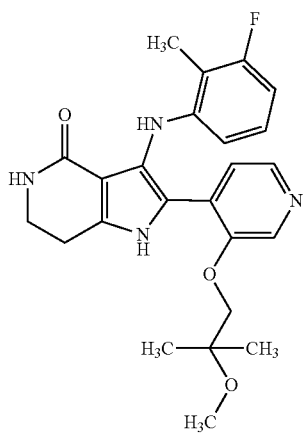 [SMILES: COC(C)(C)COc1cnccc1-c1[nH]c2c(c1Nc1cccc(F)c1C)C(=O)NCC2]

Using an analogous method as described for Example 6; Intermediate 6-21 (220 mg, 466 µmol) as the starting material, the title compound was prepared (5 mg, 2% yield) after preparative two separate TLC purifications (DCM:MeOH).

$^1$H-NMR (400 MHz, DMSO-d$_6$): δ [ppm]=11.15 (s, 1H), 8.39 (s, 1H), 7.97 (d, 1H), 7.31 (s, 1H), 7.23 (d, 1H), 7.19 (s, 1H), 6.76-6.82 (m, 1H), 6.48 (t, 1H), 6.09 (d, 1H), 4.18 (s, 2H), 3.39-3.46 (m, 2H), 3.26 (s, 3H), 2.84 (t, 2H), 2.18-2.21 (m, 3H), 1.28 (s, 6H).

Example 22

3-{[2-(2,2-difluoroethyl)-3-fluorophenyl]amino}-2-[3-(2-methoxyethoxy)pyridin-4-yl]-1,5,6,7-tetrahydro-4H-pyrrolo[3,2-c]pyridin-4-one

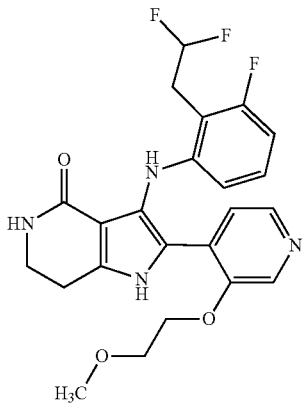 [SMILES: COCCOc1cnccc1-c1[nH]c2c(c1Nc1cccc(F)c1CC(F)F)C(=O)NCC2]

Using an analogous method as described for Example 1; Intermediate 6-22 (140 mg, 283 µmol) as the starting material and heated for 5 h. After 5 h another portion of aqueous hydrogen peroxide was added and heated at 90° C. for a further 2 h. The title compound was prepared 20.0 mg (15% yield) after preparative HPLC (basic method) and silica chromatography (DCM:MeOH).

$^1$H-NMR (400 MHz, DMSO-d$_6$): δ [ppm]=11.05 (s, 1H), 8.40 (br s, 1H), 8.00 (br s, 1H), 7.36-7.39 (m, 1H), 7.33 (s, 1H), 7.09 (s, 1H), 6.85-6.92 (m, 1H), 6.42-6.50 (m, 1H), 6.43 (br t, 1H), 6.13 (d, 1H), 4.34 (m, 2H), 3.77 (m, 2H), 3.23-3.45 (m, 7H), 2.82-2.94 (m, 2H).

Example 23

3-{[2-(2,2-difluoroethyl)-3-fluorophenyl]amino}-2-[3-(2-methoxy-2-methylpropoxy)pyridin-4-yl]-1,5,6,7-tetrahydro-4H-pyrrolo[3,2-c]pyridin-4-one

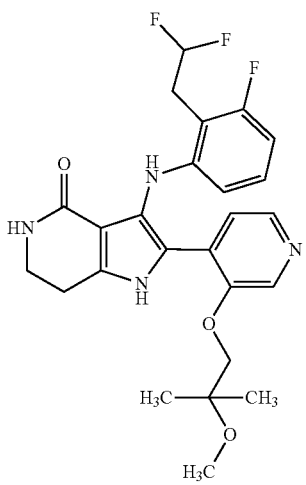

Using an analogous method as described for Example 6; Intermediate 6-23 (220 mg, 466 µmol) as the starting material, the title compound was prepared (31 mg, 17% yield) after preparative separate TLC purification (DCM:MeOH).

$^1$H-NMR (400 MHz, DMSO-d$_6$): δ [ppm]=11.18 (s, 1H), 8.40 (s, 1H), 7.98 (d, 1H), 7.35-7.40 (m, 2H), 7.11 (s, 1H), 6.87-6.93 (m, 1H), 6.29-6.65 (m, 2H), 6.13 (d, 1H), 4.17 (s, 2H), 3.23-3.44 (m, 7H), 2.84 (t, 2H), 1.27 (s, 6H).

Example 24

3-[(3-fluoro-2-hydroxyphenyl)amino]-2-[3-(2-methoxy-2-methylpropoxy)pyridin-4-yl]-1,5,6,7-tetrahydro-4H-pyrrolo[3,2-c]pyridin-4-one

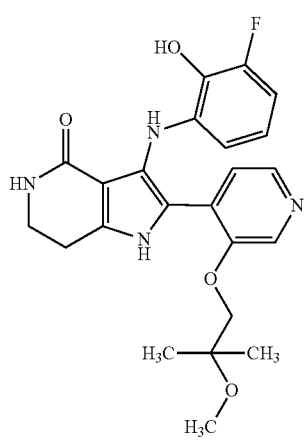 [SMILES: COC(C)(C)COc1cnccc1-c1[nH]c2c(c1Nc1cccc(F)c1O)C(=O)NCC2]

To a solution of Intermediate 7-24 (30.0 mg, 62.4 µmol) in MeOH (0.5 ml) under an argon atmosphere was added Pd/C 5% on activated charcoal (2 mg), followed by ammonium formate (23.6 mg, 375 µmol). The reaction was heated under reflux conditions for 16 h. Another portion of ammonium formate (23.6 mg, 375 µmol) was added and heated at reflux for 24 h. A further portion of ammonium formate (3 eq) was added and heated at reflux for 24 h. A further portion of ammonium formate (2 eq) was added and heated at reflux for 24 h. The reaction mixture was allowed to cool tor RT, filtered and the catalyst was washed with MeOH. The filtrate was concentrated and the residue purified by preparative TLC (DCM:MeOH) to give the title compound (2 mg, 7% yield).

$^1$H-NMR (400 MHz, DMSO-d$_6$): δ [ppm]=11.05-11.17 (m, 1H), 8.38 (s, 1H), 7.95 (d, 1H), 7.53 (s, 1H), 7.19 (brs, 1H), 7.15 (d, 1H), 6.42-6.50 (m, 1H), 6.28-6.40 (m, 1H), 5.96 (br d, 1H), 3.42 (m, 2H), 3.26 (s, 3H), 2.81-2.85 (m, 2H), 1.29 (s, 6H).

Example 25

3-[(2-ethoxy-3-fluorophenyl)amino]-2-[3-(2-methoxyethoxy)pyridin-4-yl]-1,5,6,7-tetrahydro-4H-pyrrolo[3,2-c]pyridin-4-one

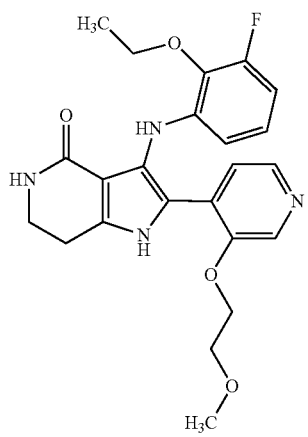 [SMILES: CCOc1c(F)cccc1Nc1c(-c2ccncc2OCCOC)[nH]c2c1C(=O)NCC2]

Using an analogous method as described for Example 1; Intermediate 6-25 (130 mg, 274 µmol) as the starting material and heated for 5 h, the title compound was prepared 31.0 mg (23% yield).

$^1$H-NMR (400 MHz, DMSO-d$_6$): δ [ppm]=11.00 (s, 1H), 8.40 (s, 1H), 8.01 (d, 1H), 7.56-7.63 (m, 1H), 7.23 (d, 1H), 7.17 (brs, 1H), 6.61 (m, 1H), 6.49 (m, 1H), 5.99 (d, 1H), 4.29-4.37 (m, 2H), 4.14 (q, 2H), 3.78 (m, 2H), 3.36-3.44 (m, 5H), 2.85 (t, 2H), 1.41 (t, 3H).

Example 26

3-[(2-ethoxy-3-fluorophenyl)amino]-2-[3-(2-methoxy-2-methylpropoxy)pyridin-4-yl]-1,5,6,7-tetrahydro-4H-pyrrolo[3,2-c]pyridin-4-one

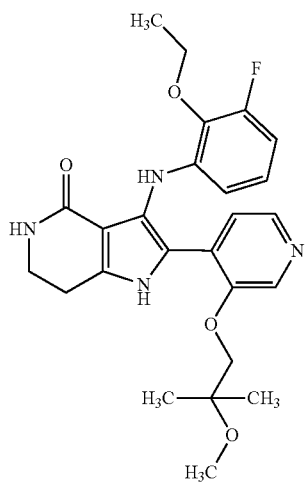 [SMILES: CCOc1c(F)cccc1Nc1c(-c2ccncc2OCC(C)(C)OC)[nH]c2c1C(=O)NCC2]

Using an analogous method as described for Example 6; Intermediate 6-26 (200 mg, 398 µmol) as the starting material, the title compound was prepared (43 mg, 22% yield) after two separate preparative TLC purifications (DCM: MeOH).

¹H-NMR (400 MHz, DMSO-d₆): δ [ppm]=11.15 (s, 1H), 8.41 (s, 1H), 7.99 (d, 1H), 7.58 (s, 1H), 7.22 (d, 1H), 7.18-7.20 (m, 1H), 6.65 (m, 1H), 6.51 (t, 1H), 6.02 (d, 1H), 4.08-4.22 (m, 4H), 3.43 (m, 2H), 3.25 (s, 3H), 2.83 (t, 2H), 1.41 (t, 3H).

Example 27

3-{[2-(2,2-difluoroethoxy)-3-fluorophenyl]amino}-2-[3-(2-methoxy-2-methylpropoxy)pyridin-4-yl]-1,5,6,7-tetrahydro-4H-pyrrolo[3,2-c]pyridin-4-one

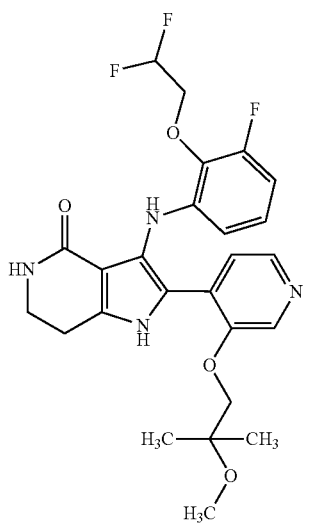 [SMILES: COC(C)(C)COc1cnccc1-c1[nH]c2c(c1Nc1cccc(F)c1OCC(F)F)C(=O)NCC2]

Using an analogous method as described for Example 6; Intermediate 6-27 (220 mg, 408 μmol) as the starting material, the title compound was prepared (80 mg, 37% yield) after preparative TLC purification (DCM:MeOH).

¹H-NMR (400 MHz, DMSO-d₆): δ [ppm]=11.19 (s, 1H), 8.42 (s, 1H), 8.02 (d, 1H), 7.38 (s, 1H), 7.36 (d, 1H), 7.15-7.21 (m, 1H), 6.73 (m, 1H), 6.49-6.57 (m, 1H), 6.50 (br t, 1H), 6.05 (d, 1H), 4.38 (m, 2H), 4.19 (s, 2H), 3.35-3.45 (m, 2H), 3.25 (s, 3H), 2.84 (t, 2H), 1.28 (s, 6H).

Example 28

3-[(3,4-difluoro-2-methoxyphenyl)amino]-2-[3-(2-methoxyethoxy)pyridin-4-yl]-1,5,6,7-tetrahydro-4H-pyrrolo[3,2-c]pyridin-4-one

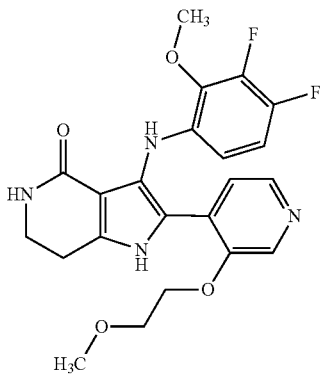 [SMILES: COCCOc1cnccc1-c1[nH]c2c(c1Nc1ccc(F)c(F)c1OC)C(=O)NCC2]

Using an analogous method as described for Example 1; Intermediate 6-28 (115 mg, 240 μmol) as the starting material and heated for 2 h, the title compound was prepared 51.0 mg (45% yield).

¹H-NMR (400 MHz, DMSO-d₆): δ [ppm]=11.04 (s, 1H), 8.42 (s, 1H), 8.04 (d, 1H), 7.39 (s, 1H), 7.28 (d, 1H), 7.15 (s, 1H), 6.69-6.78 (m, 1H), 5.94 (m, 1H), 4.34 (m, 2H), 3.97 (s, 3H), 3.78 (m, 2H), 3.38-3.45 (m, 5H), 2.85 (t, 2H).

Example 29

3-[(3,4-difluoro-2-methoxyphenyl)amino]-2-[3-(2-methoxy-2-methylpropoxy)pyridin-4-yl]-1,5,6,7-tetrahydro-4H-pyrrolo[3,2-c]pyridin-4-one

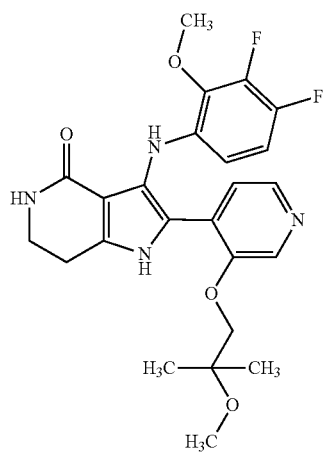 [SMILES: COc1c(Nc2c(-c3ccncc3OCC(C)(C)OC)[nH]c3c2C(=O)NCC3)ccc(F)c1F]

Using an analogous method as described for Example 8; Intermediate 6-29 (240 mg, 474 μmol) as the starting material, the title compound was prepared (80 mg, 34% yield) after preparative TLC purification (DCM:MeOH).

¹H-NMR (400 MHz, DMSO-d₆): δ [ppm]=11.17 (s, 1H), 8.42 (s, 1H), 8.03 (d, 1H), 7.39 (s, 1H), 7.27 (d, 1H), 7.17 (s, 1H), 6.72-6.80 (m, 1H), 5.95 (m, 1H), 4.19 (s, 2H), 3.96-4.01 (m, 3H), 3.42 (m, 2H), 3.25 (s, 3H), 2.83 (t, 2H), 1.28 (s, 6H).

Example 30

3-[(3,5-difluoro-2-methoxyphenyl)amino]-2-[3-(2-methoxyethoxy)pyridin-4-yl]-1,5,6,7-tetrahydro-4H-pyrrolo[3,2-c]pyridin-4-one

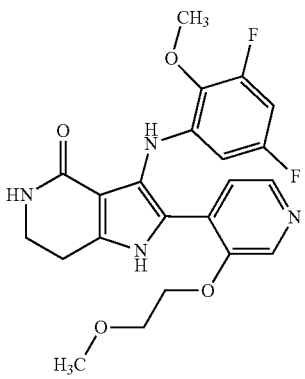 [SMILES: COCCOc1cnccc1-c1[nH]c2c(c1Nc1cc(F)cc(F)c1OC)C(=O)NCC2]

Using an analogous method as described for Example 1; Intermediate 6-30 (160 mg, 334 µmol) as the starting material and heated for 2 h, the title compound was prepared 57.0 mg (36% yield).

¹H-NMR (400 MHz, DMSO-d₆): δ [ppm]=11.17 (s, 1H), 8.44 (s, 1H), 8.10 (d, 1H), 7.62 (s, 1H), 7.32 (d, 1H), 7.12 (s, 1H), 6.43 (m, 1H), 5.73 (dt, 1H), 4.27-4.35 (m, 2H), 3.85 (s, 3H), 3.71-3.77 (m, 2H), 3.42 (m, 2H), 3.35 (s, 3H), 2.89-2.96 (m, 1H), 2.85 (t, 1H).

Example 31

3-[(3,5-difluoro-2-methoxyphenyl)amino]-2-[3-(2-methoxy-2-methylpropoxy)pyridin-4-yl]-1,5,6,7-tetrahydro-4H-pyrrolo[3,2-c]pyridin-4-one

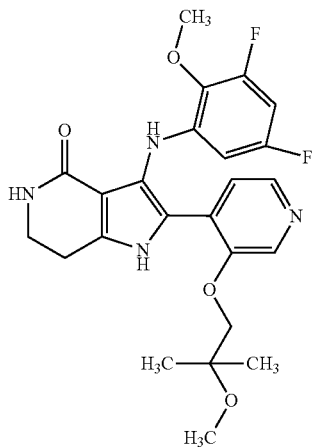 [SMILES: COc1c(F)cc(F)cc1Nc1c(-c2ccncc2OCC(C)(C)OC)[nH]c2c1C(=O)NCC2]

Using an analogous method as described for Example 6; Intermediate 6-31 (250 mg, 494 µmol) as the starting material, the title compound was prepared (103 mg, 42% yield) after concentration of the reaction mixture and crystallization from DMSO.

¹H-NMR (400 MHz, DMSO-d₆): δ [ppm]=11.25 (s, 1H), 8.45 (s, 1H), 8.08 (d, 1H), 7.60 (s, 1H), 7.33 (d, 1H), 7.13 (s, 1H), 6.44 (m, 1H), 5.71-5.76 (m, 1H), 4.15 (s, 2H), 3.85 (s, 3H), 3.38-3.46 (m, 2H), 3.22 (s, 3H), 2.84 (t, 2H), 1.25 (s, 6H).

Example 32

3-(3-chloro-2-methoxyanilino)-2-[3-(2-methoxyethoxy)pyridin-4-yl]-1,5,6,7-tetrahydro-4H-pyrrolo[3,2-c]pyridin-4-one N-(3-chloro-2-methoxyphenyl)-4-({[3-(2-methoxyethoxy)pyridin-4-yl]methyl}amino)-2-oxo-1,2,5,6-tetrahydropyridine-3-carbothioamide (intermediate 6-32, 119 mg, 249 µmol) was solubilised in 5.0 mL methanol, trifluoroacetic acid (19 µL, 250 µmol) and hydrogen peroxide (44 µL, 35% purity, 500 µmol) were added and the mixture was stirred over night at 50° C. The reaction mixture was quenched with a saturated aqueous sodium thiosulfate solution and stirred for 2 h. The mixture was diluted with triethylamine (72.9 µL, 726 µmol) and water and extracted with dichloromethane two times. The combined organic layers were filtered through a waterresistant filter, the filtrate was concentrated under reduced pressure and the residue was purified by preparative HPLC to give 30.7 mg of the title compound (99% purity, 28% yield).

¹H-NMR (400 MHz, DMSO-d6) δ [ppm]: 2.332 (0.65), 2.518 (3.28), 2.523 (2.30), 2.673 (0.65), 2.839 (0.86), 2.857 (1.88), 2.874 (0.96), 3.389 (16.00), 3.401 (0.76), 3.407 (0.74), 3.418 (1.26), 3.423 (1.23), 3.435 (0.62), 3.441 (0.57), 3.768 (1.23), 3.779 (1.50), 3.791 (1.34), 3.878 (11.67), 4.336 (1.28), 4.347 (1.48), 4.359 (1.20), 6.138 (1.05), 6.152 (1.17), 6.162 (1.09), 6.675 (4.15), 6.685 (2.40), 6.688 (2.22), 7.150 (1.14), 7.278 (1.91), 7.290 (1.93), 7.526 (2.37), 8.028 (2.56), 8.041 (2.36), 8.419 (3.42), 11.052 (1.20).

LC-MS (method 2): R, =1.00 min; MS (ESIpos): m/z=443 [M+H]⁺

The examples in Table 3 were prepared analogous to the preparation of example 32 starting from the corresponding intermediates 6-x.

TABLE 3

| Example | Structure Name | Analytical Data |
|---|---|---|
| 33 | 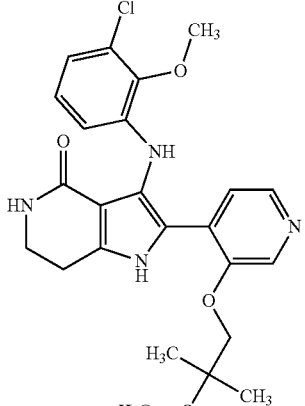<br>3-(3-chloro-2-methoxyanilino)-2-[3-(2-methoxy-2-methylpropoxy)pyridin-4-yl]-1,5,6,7-tetrahydro-4H-pyrrolo[3,2-c]pyridin-4-one | $^1$H-NMR (500 MHz, DMSO-d6) δ [ppm]: -0.006 (1.16), 0.007 (1.06), 1.283 (16.00), 2.368 (0.57), 2.518 (2.55), 2.522 (2.45), 2.525 (2.02), 2.543 (0.67), 2.830 (0.73), 2.844 (1.59), 2.857 (0.82), 3.257 (12.80), 3.415 (0.50), 3.420 (0.53), 3.428 (1.02), 3.433 (0.97), 3.442 (0.49), 3.447 (0.44), 3.894 (10.71), 4.193 (4.06), 5.752 (2.91), 6.163 (0.90), 6.170 (0.73), 6.175 (0.90), 6.182 (0.92), 6.697 (3.93), 6.704 (1.79), 6.709 (1.62), 7.165 (0.89), 7.270 (1.56), 7.280 (1.56), 7.521 (2.05), 8.009 (1.89), 8.019 (1.73), 8.314 (0.97), 8.417 (2.58), 11.180 (0.95).<br>LC-MS (method 1): Rt = 0.89 min; m/z = 471 (M + H)+ |
| 34 | 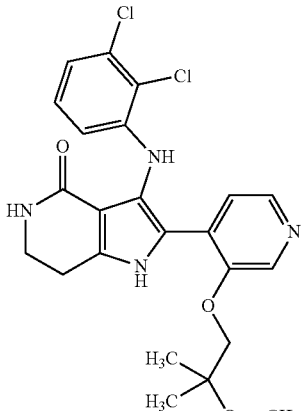<br>3-(2,3-dichloroanilino)-2-[3-(2-methoxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.052 (0.52), 1.221 (0.50), 1.258 (16.00), 2.518 (1.08), 2.522 (0.69), 2.829 (0.81), 2.846 (1.72), 2.863 (0.90), 3.230 (13.03), 3.408 (0.60), 3.414 (0.65), 3.425 (1.16), 3.431 (1.15), 3.442 (0.59), 3.448 (0.53), 4.158 (4.34), 6.289 (1.04), 6.293 (1.06), 6.309 (1.11), 6.313 (1.02), 6.861 (0.68), 6.866 (0.81), 6.881 (1.80), 6.886 (1.55), 6.903 (1.37), 6.922 (1.63), 6.942 (0.57), 7.174 (1.06), 7.235 (1.76), 7.248 (1.78), 7.619 (2.36), 8.030 (2.37), 8.043 (2.17), 8.424 (3.12), 11.266 (1.11).<br>LC-MS (method 2): Rt = 1.15 min; m/z = 475 (M + H)+ |
| 35 | 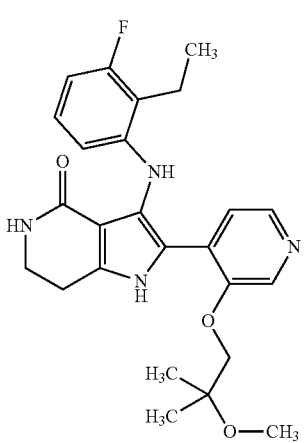 [SMILES: CCc1c(F)cccc1Nc1c(-c2ccncc2OCC(C)(C)OC)[nH]c2c1C(=O)NCC2]<br>3-(2-ethyl-3-fluoroanilino)-2-[3-(2-methoxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.172 (0.60), 1.214 (1.49), 1.233 (3.96), 1.252 (1.65), 1.282 (16.00), 1.987 (0.98), 2.518 (0.99), 2.522 (0.62), 2.539 (0.62), 2.703 (0.78), 2.720 (0.78), 2.829 (0.75), 2.846 (1.64), 2.864 (0.85), 3.250 (0.43), 3.259 (12.16), 3.417 (0.54), 3.423 (0.59), 3.434 (1.14), 3.440 (1.05), 3.451 (0.53), 3.457 (0.48), 4.186 (4.11), 6.110 (0.98), 6.131 (1.02), 6.449 (0.46), 6.471 (0.82), 6.492 (0.53), 6.768 (0.75), 6.785 (0.73), 7.183 (2.04), 7.195 (1.89), 7.396 (1.82), 7.936 (1.42), 7.949 (1.35), 8.388 (2.17), 11.142 (1.04).<br>LC-MS (method 2): Rt = 1.17 min; m/z = 453 (M + H)+ |

TABLE 3-continued

| Example | Structure Name | Analytical Data |
|---|---|---|
| 36 | 3-(3-chloro-2-methylanilino)-2-[3-(2-methoxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.171 (0.67), 1.232 (0.85), 1.241 (0.68), 1.278 (16.00), 2.361 (7.22), 2.518 (2.02), 2.522 (1.27), 2.669 (0.50), 2.829 (0.75), 2.846 (1.62), 2.863 (0.84), 3.173 (0.43), 3.178 (0.68), 3.255 (12.52), 3.410 (0.56), 3.416 (0.60), 3.428 (1.10), 3.433 (1.07), 3.444 (0.53), 3.450 (0.49), 4.184 (4.08), 6.215 (0.83), 6.218 (0.83), 6.235 (0.90), 6.238 (0.84), 6.735 (0.56), 6.738 (0.65), 6.754 (1.42), 6.758 (1.19), 6.778 (1.00), 6.797 (1.18), 6.818 (0.41), 7.193 (1.00), 7.221 (1.67), 7.233 (1.69), 7.331 (1.90), 7.972 (2.20), 7.985 (2.06), 8.399 (2.98), 11.163 (1.04). LC-MS (method 1): Rt = 0.93 min; m/z = 455 (M + H)+ |
| 37 | 3-(2-bromo-3-fluoroanilino)-2-[3-(2-methoxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.263 (16.00), 2.518 (2.79), 2.523 (1.84), 2.830 (0.79), 2.847 (1.73), 2.864 (0.89), 3.234 (12.43), 3.413 (0.58), 3.419 (0.62), 3.430 (1.12), 3.436 (1.11), 3.447 (0.55), 3.453 (0.51), 4.166 (4.32), 6.153 (0.99), 6.174 (1.02), 6.606 (0.50), 6.609 (0.51), 6.627 (0.97), 6.630 (0.95), 6.647 (0.57), 6.651 (0.53), 6.928 (0.43), 6.944 (0.51), 6.949 (0.81), 6.965 (0.80), 6.969 (0.45), 7.179 (1.66), 7.192 (2.58), 7.543 (2.29), 8.007 (1.42), 8.019 (1.34), 8.135 (0.67), 8.418 (2.24), 11.250 (1.11). LC-MS (method 1): Rt = 0.79 min; m/z = 503 (M + H)+ |
| 38 | 3-[3-chloro-2-(difluoromethoxy)anilino]-2-[3-(2-methoxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.154 (0.71), 1.173 (1.53), 1.190 (0.80), 1.230 (0.60), 1.235 (1.15), 1.267 (16.00), 1.988 (2.92), 2.518 (1.22), 2.523 (0.82), 2.820 (0.78), 2.838 (1.68), 2.855 (0.87), 3.218 (0.86), 3.239 (13.11), 3.400 (0.57), 3.406 (0.63), 3.416 (1.12), 3.423 (1.11), 3.434 (0.55), 3.440 (0.50), 4.017 (0.65), 4.035 (0.64), 4.178 (4.17), 6.275 (1.01), 6.278 (1.06), 6.295 (1.06), 6.299 (1.03), 6.785 (0.93), 6.789 (1.04), 6.805 (1.50), 6.809 (1.35), 6.865 (1.18), 6.886 (1.70), 6.906 (0.68), 7.027 (0.80), 7.155 (1.04), 7.212 (1.65), 7.333 (1.75), 7.345 (1.78), 7.398 (0.73), 7.434 (2.18), 8.012 (2.46), 8.025 (2.24), 8.425 (3.13), 11.226 (1.11). LC-MS (method 2): Rt = 1.14 min; m/z = 507 (M + H)+ |

TABLE 3-continued

| Example | Structure Name | Analytical Data |
|---|---|---|
| 39 | 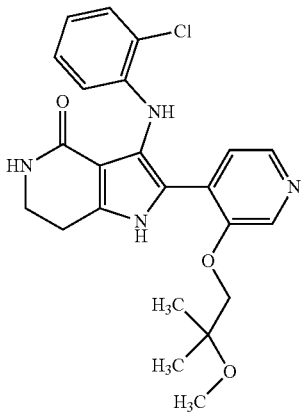 [SMILES: COC(C)(C)COc1cnccc1-c1[nH]c2c(c1Nc1ccccc1Cl)C(=O)NCC2]<br>3-(2-chloroanilino)-2-[3-(2-methoxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.273 (16.00), 1.988 (0.75), 2.518 (0.60), 2.523 (0.46), 2.831 (0.74), 2.848 (1.63), 2.865 (0.83), 3.330 (13.28), 3.416 (0.53), 3.422 (0.58), 3.433 (1.05), 3.439 (1.02), 3.450 (0.50), 3.456 (0.45), 4.174 (4.17), 6.345 (0.90), 6.348 (0.92), 6.365 (0.97), 6.369 (0.92), 6.656 (0.52), 6.660 (0.53), 6.675 (0.84), 6.679 (0.80), 6.694 (0.64), 6.698 (0.58), 6.880 (0.51), 6.884 (0.51), 6.901 (0.77), 7.157 (1.75), 7.169 (1.77), 7.203 (0.95), 7.334 (1.10), 7.338 (1.16), 7.354 (1.08), 7.357 (1.03), 7.553 (2.12), 7.976 (2.39), 7.988 (2.21), 8.409 (3.09), 11.208 (0.97).<br>LC-MS (method 1): Rt = 0.82 min; MS (ESIneg): m/z = 439 [M − H]$^−$ |
| 40 | 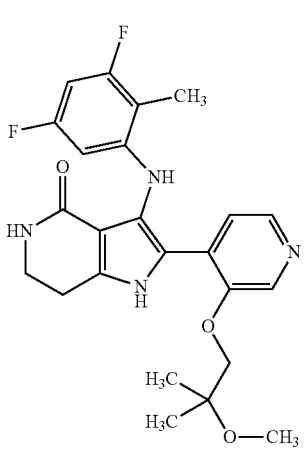 [SMILES: COC(C)(C)COc1cnccc1-c1[nH]c2c(c1Nc1cc(F)cc(F)c1C)C(=O)NCC2]<br>3-(3,5-difluoro-2-methylanilino)-2-[3-(2-methoxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.215 (0.56), 1.218 (0.73), 1.254 (16.00), 2.128 (3.69), 2.518 (1.88), 2.522 (1.18), 2.831 (0.72), 2.848 (1.59), 2.865 (0.82), 3.173 (0.58), 3.205 (0.42), 3.230 (12.58), 3.408 (0.59), 3.414 (0.61), 3.425 (1.08), 3.431 (1.06), 3.442 (0.53), 3.448 (0.48), 4.158 (4.03), 5.772 (0.51), 5.802 (0.49), 6.383 (0.51), 6.388 (0.53), 7.163 (0.91), 7.306 (1.23), 7.318 (1.26), 7.428 (1.23), 8.056 (1.02), 8.069 (0.96), 8.441 (1.61), 11.235 (0.96).<br>LC-MS (method 1): Rt = 0.93 min; m/z = 457 (M + H)+ |
| 41 | 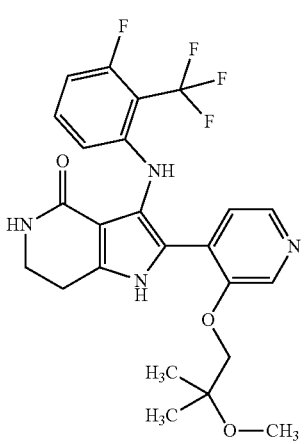 [SMILES: COC(C)(C)COc1cnccc1-c1[nH]c2c(c1Nc1cccc(F)c1C(F)(F)F)C(=O)NCC2]<br>3-[3-fluoro-2-(trifluoromethyl)anilino]-2-[3-(2-methoxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.251 (16.00), 2.518 (0.91), 2.523 (0.59), 2.826 (0.77), 2.843 (1.68), 2.860 (0.87), 3.224 (12.69), 3.415 (0.65), 3.420 (0.70), 3.432 (1.17), 3.437 (1.16), 3.449 (0.59), 3.454 (0.54), 4.151 (4.17), 6.354 (0.84), 6.375 (0.86), 6.599 (0.43), 6.620 (0.49), 6.629 (0.46), 6.649 (0.45), 7.159 (0.63), 7.174 (1.55), 7.220 (1.25), 7.233 (1.26), 7.718 (0.89), 7.723 (0.91), 8.006 (0.93), 8.019 (0.89), 8.416 (1.49), 11.257 (1.06). |

TABLE 3-continued

| Example | Structure Name | Analytical Data |
|---|---|---|
| 42 | 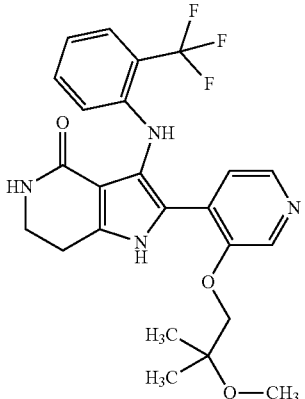<br>2-[3-(2-methoxy-2-methylpropoxy)pyridin-4-yl]-3-[2-(trifluoromethyl)anilino]-1,5,6,7-tetrahydro-4H-pyrrolo[3,2-c]pyridin-4-one | $^1$H-NMR (400 MHz, DMSO-d6) δ [ppm]: 1.273 (16.00), 2.518 (0.74), 2.522 (0.46), 2.836 (0.77), 2.853 (1.68), 2.870 (0.86), 3.247 (13.32), 3.431 (0.56), 3.437 (0.60), 3.448 (1.09), 3.454 (1.08), 3.465 (0.53), 3.471 (0.49), 4.179 (4.21), 6.582 (0.89), 6.602 (0.94), 6.808 (0.41), 6.827 (0.83), 6.845 (0.47), 7.108 (1.63), 7.121 (1.66), 7.162 (0.42), 7.181 (0.71), 7.201 (0.45), 7.219 (0.99), 7.533 (0.80), 7.551 (0.74), 7.678 (1.41), 7.898 (1.76), 7.911 (1.65), 8.397 (2.53), 11.191 (1.03).<br>LC-MS (method 2): Rt = 1.13 min; m/z = 475 (M + H)+ |
| 43 | 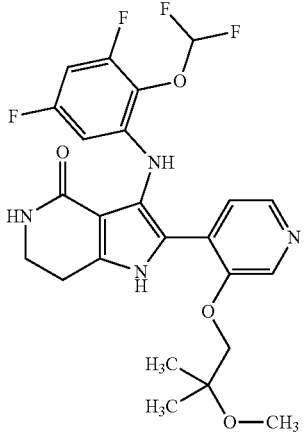 [SMILES: COC(C)(C)COc1cnccc1-c1[nH]c2c(c1Nc1cc(F)cc(F)c1OC(F)F)C(=O)NCC2]<br>3-[2-(difluoromethoxy)-3,5-difluoroanilino]-2-[3-(2-methoxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.172 (0.46), 1.239 (16.00), 2.084 (0.47), 2.518 (0.91), 2.523 (0.69), 2.820 (0.70), 2.837 (1.54), 2.854 (0.79), 3.212 (14.17), 3.397 (0.51), 3.403 (0.55), 3.414 (1.00), 3.420 (0.98), 3.430 (0.48), 3.437 (0.46), 4.140 (3.95), 5.758 (2.83), 5.814 (0.41), 5.817 (0.49), 5.822 (0.46), 5.843 (0.42), 5.845 (0.48), 5.850 (0.40), 6.542 (0.40), 6.547 (0.45), 6.550 (0.48), 6.554 (0.45), 6.962 (0.55), 7.113 (0.93), 7.147 (1.09), 7.332 (0.50), 7.405 (1.60), 7.418 (1.62), 7.670 (1.23), 7.674 (1.28), 8.079 (2.44), 8.091 (2.09), 8.448 (2.95), 11.299 (0.98).<br>LC-MS (method 2): Rt = 1.13 min; m/z = 509 (M + H)+ |
| 44 | 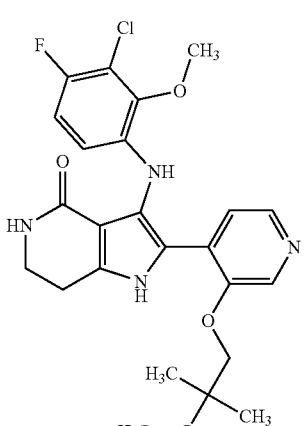<br>3-(3-chloro-4-fluoro-2-methoxyanilino)-2-[3-(2-methoxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.227 (0.63), 1.248 (0.52), 1.277 (16.00), 2.518 (1.85), 2.523 (1.24), 2.823 (0.76), 2.840 (1.67), 2.857 (0.87), 3.167 (0.42), 3.251 (12.86), 3.405 (0.55), 3.411 (0.60), 3.422 (1.11), 3.428 (1.11), 3.439 (0.53), 3.445 (0.51), 3.926 (10.48), 4.192 (4.19), 6.127 (0.81), 6.141 (0.85), 6.151 (0.94), 6.164 (0.89), 6.792 (0.88), 6.815 (1.66), 6.838 (0.81), 7.172 (1.05), 7.264 (1.71), 7.277 (1.74), 7.407 (2.29), 8.022 (2.12), 8.034 (1.99), 8.421 (2.99), 11.184 (1.10).<br>LC-MS (method 2): Rt = 1.14 min; MS (ESIpos): m/z = 489 [M + H]$^+$ |

TABLE 3-continued

| Example | Structure Name | Analytical Data |
|---|---|---|
| 45 | 3-(5-fluoro-2-methylanilino)-2-[3-(2-methoxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.218 (0.59), 1.233 (0.72), 1.270 (16.00), 2.250 (5.44), 2.327 (0.47), 2.522 (1.71), 2.539 (0.66), 2.669 (0.48), 2.831 (0.79), 2.849 (1.70), 2.866 (0.88), 3.245 (12.24), 3.422 (0.67), 3.433 (1.14), 3.439 (1.14), 3.450 (0.58), 3.456 (0.53), 4.177 (4.14), 5.759 (1.57), 5.903 (0.69), 5.909 (0.76), 5.933 (0.69), 5.939 (0.73), 6.351 (0.41), 6.364 (0.73), 6.371 (0.75), 6.392 (0.41), 7.048 (0.53), 7.067 (0.80), 7.085 (0.53), 7.203 (1.46), 7.216 (0.87), 7.334 (1.48), 7.996 (0.41), 8.426 (0.53), 11.179 (1.05). LC-MS (method 2): Rt = 1.08 min; m/z = 439 (M + H)+ |
| 46 | 3-(2,3-dichloroanilino)-2-[3-(2-methoxyethoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.035 (1.06), 1.052 (2.48), 1.070 (1.22), 2.518 (0.47), 2.843 (0.46), 2.860 (1.00), 2.877 (0.52), 3.332 (16.00), 3.354 (9.29), 3.405 (0.41), 3.422 (0.93), 3.429 (0.67), 3.434 (0.50), 3.439 (0.61), 3.720 (0.67), 3.729 (0.69), 3.732 (0.80), 3.735 (0.66), 3.743 (0.74), 4.259 (0.69), 4.267 (0.63), 4.271 (0.78), 4.282 (0.65), 6.268 (0.65), 6.272 (0.66), 6.287 (0.70), 6.292 (0.66), 6.841 (0.54), 6.856 (1.35), 6.860 (1.02), 6.869 (0.98), 6.888 (1.00), 7.157 (0.60), 7.250 (1.07), 7.263 (1.09), 7.634 (1.37), 8.065 (1.61), 8.078 (1.47), 8.399 (1.90), 11.203 (0.62). LC-MS (method 2): Rt = 1.05 min; m/z = 447 (M + H)+ |
| 47 | 2-[3-(2-methoxyethoxy)pyridin-4-yl]-3-[2-(trifluoromethyl)anilino]-1,5,6,7-tetrahydro-4H-pyrrolo[3,2-c]pyridin-4-one | $^1$H-NMR (400 MHz, DMSO-d6) δ [ppm]: 2.518 (1.07), 2.522 (0.67), 2.852 (0.77), 2.869 (1.71), 2.886 (0.88), 3.373 (16.00), 3.425 (0.69), 3.431 (0.71), 3.442 (1.19), 3.448 (1.16), 3.459 (0.60), 3.465 (0.56), 3.746 (1.10), 3.758 (1.30), 3.762 (1.14), 3.770 (1.23), 4.310 (1.14), 4.319 (1.07), 4.323 (1.29), 4.334 (1.06), 6.556 (0.90), 6.577 (0.95), 6.785 (0.41), 6.804 (0.84), 6.823 (0.49), 7.130 (0.42), 7.150 (2.27), 7.163 (1.78), 7.203 (1.11), 7.516 (0.80), 7.532 (0.75), 7.535 (0.74), 7.705 (1.36), 7.950 (1.73), 7.963 (1.60), 8.133 (1.08), 8.394 (2.61), 11.090 (1.02). LC-MS (method 1): Rt = 0.84 min; m/z = 446 (M + H)+ |

TABLE 3-continued

| Example | Structure Name | Analytical Data |
|---|---|---|
| 48 | 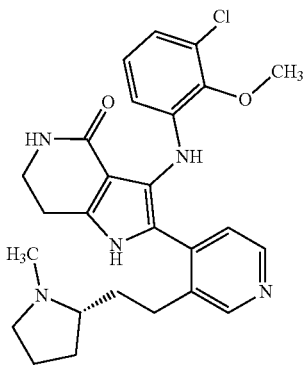 [SMILES: COc1c(Cl)cccc1Nc1c(-c2ccncc2CC[C@@H]2CCCN2C)[nH]c2c1C(=O)NCC2]<br>3-(3-chloro-2-methoxyanilino)-2-(3-{[(2S)-1-methylpyrrolidin-2-yl]methoxy}pyridin-4-yl)-1,5,6,7-tetrahydro-4H-pyrrolo[3,2-c]pyridin-4-one | $^1$H-NMR (400 MHz, DMSO-d6) δ [ppm]: 0.815 (0.40), 0.821 (0.40), 0.904 (0.44), 1.154 (4.31), 1.172 (8.82), 1.190 (4.36), 1.735 (0.53), 1.755 (0.53), 1.987 (16.00), 2.074 (4.29), 2.309 (1.34), 2.317 (6.58), 2.326 (0.75), 2.332 (0.73), 2.518 (1.79), 2.522 (1.16), 2.575 (0.45), 2.669 (0.41), 2.798 (0.56), 2.853 (0.47), 3.192 (0.41), 3.415 (0.47), 3.432 (0.84), 3.448 (0.41), 3.901 (8.47), 4.000 (1.20), 4.017 (3.60), 4.035 (3.61), 4.053 (1.21), 4.183 (0.43), 4.191 (0.45), 4.209 (0.52), 4.217 (0.49), 4.510 (0.56), 4.514 (0.61), 4.535 (0.50), 4.540 (0.47), 6.148 (0.75), 6.158 (0.68), 6.162 (0.76), 6.172 (0.75), 6.707 (3.18), 6.717 (1.60), 6.721 (1.46), 7.160 (0.87), 7.283 (1.46), 7.296 (1.44), 7.586 (1.84), 7.974 (1.84), 7.986 (1.71), 8.438 (2.59), 12.130 (0.84).<br>LC-MS (method 2): Rt = 1.13 min; MS (ESIpos): m/z = 482 [M + H]$^+$ |
| 49 | 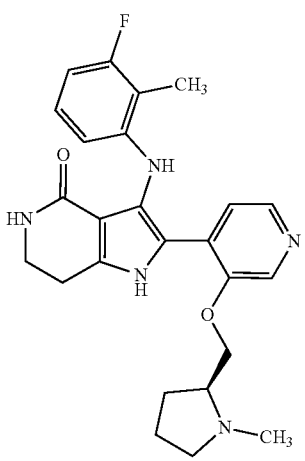 [SMILES: Cc1c(F)cccc1Nc1c(-c2ccncc2OC[C@@H]2CCCN2C)[nH]c2c1C(=O)NCC2]<br>3-(3-fluoro-2-methylanilino)-2-(3-{[(2S)-1-methylpyrrolidin-2-yl]methoxy}pyridin-4-yl)-1,5,6,7-tetrahydro-4H-pyrrolo[3,2-c]pyridin-4-one | $^1$H-NMR (400 MHz, DMSO-d6) δ [ppm]: 0.833 (0.52), 0.852 (0.92), 1.232 (4.76), 1.256 (0.85), 1.717 (0.57), 1.724 (0.65), 1.741 (1.20), 1.760 (1.28), 1.781 (0.59), 1.848 (0.54), 1.868 (0.60), 1.884 (0.49), 1.907 (0.77), 1.947 (0.81), 1.957 (0.42), 1.967 (0.83), 1.978 (0.55), 1.987 (0.45), 1.997 (0.43), 2.205 (8.12), 2.208 (8.14), 2.293 (0.57), 2.318 (16.00), 2.337 (1.46), 2.361 (0.55), 2.518 (2.55), 2.523 (1.71), 2.551 (0.51), 2.571 (0.94), 2.591 (0.45), 2.665 (0.43), 2.669 (0.58), 2.674 (0.42), 2.760 (0.62), 2.784 (0.65), 2.800 (1.33), 2.817 (0.63), 2.838 (0.57), 2.857 (1.06), 2.874 (0.74), 2.898 (0.48), 3.159 (2.70), 3.172 (3.02), 3.188 (0.62), 3.197 (0.93), 3.213 (0.51), 3.220 (0.45), 3.421 (1.07), 3.430 (1.46), 3.437 (1.91), 3.454 (0.96), 4.097 (0.53), 4.109 (0.52), 4.173 (0.99), 4.181 (1.08), 4.199 (1.20), 4.207 (1.12), 4.500 (1.27), 4.504 (1.36), 4.525 (1.15), 4.530 (1.14), 5.759 (4.64), 6.076 (1.95), 6.096 (2.03), 6.464 (0.89), 6.487 (1.66), 6.509 (1.03), 6.769 (0.61), 6.789 (1.30), 6.806 (1.25), 6.827 (0.54), 7.183 (1.99), 7.237 (3.26), 7.250 (3.32), 7.376 (3.86), 7.929 (3.65), 7.941 (3.32), 8.416 (5.15), 12.100 (1.91).<br>LC-MS (method 2): Rt = 1.12 min; m/z = 450 (M + H)+ |

TABLE 3-continued

| Example | Structure Name | Analytical Data |
|---|---|---|
| 50 | 3-[3-chloro-2-(difluoromethoxy)anilino]-2-(3-{[(2S)-1-methylpyrrolidin-2-yl]methoxy}pyridin-4-yl)-1,5,6,7-tetrahydro-4H-pyrrolo[3,2-c]pyridin-4-one | $^1$H-NMR (400 MHz, DMSO-d6) δ [ppm]: 1.726 (1.09), 1.750 (1.22), 1.768 (0.68), 1.826 (0.61), 1.847 (0.56), 1.861 (0.46), 1.905 (0.52), 1.941 (0.78), 1.961 (0.74), 1.973 (0.50), 1.988 (0.51), 2.284 (0.59), 2.314 (16.00), 2.327 (2.15), 2.351 (0.47), 2.518 (2.79), 2.523 (1.78), 2.556 (0.55), 2.576 (1.00), 2.597 (0.50), 2.665 (0.58), 2.669 (0.77), 2.673 (0.55), 2.728 (0.42), 2.764 (0.58), 2.787 (0.72), 2.805 (1.48), 2.822 (0.84), 2.846 (1.37), 2.863 (0.79), 2.888 (0.88), 3.167 (0.58), 3.183 (1.04), 3.200 (0.55), 3.410 (1.23), 3.426 (2.06), 3.440 (1.00), 3.667 (1.18), 4.181 (1.06), 4.189 (1.11), 4.206 (1.27), 4.215 (1.15), 4.498 (1.34), 4.503 (1.39), 4.524 (1.20), 4.529 (1.14), 6.271 (2.01), 6.274 (2.01), 6.291 (2.14), 6.295 (2.01), 6.799 (1.85), 6.803 (1.88), 6.819 (2.94), 6.823 (2.53), 6.879 (2.33), 6.900 (3.39), 6.920 (1.38), 7.039 (1.59), 7.150 (2.21), 7.224 (3.21), 7.351 (3.21), 7.363 (3.30), 7.408 (1.47), 7.502 (4.30), 7.975 (3.26), 7.988 (2.99), 8.444 (4.87), 12.155 (2.10). LC-MS (method 1): Rt = 0.58 min; m/z = 518 (M + H)+ |
| 51 | 3-(3,5-difluoro-2-methylanilino)-2-(3-{[(2S)-1-methylpyrrolidin-2-yl]methoxy}pyridin-4-yl)-1,5,6,7-tetrahydro-4H-pyrrolo[3,2-c]pyridin-4-one | $^1$H-NMR (400 MHz, DMSO-d6) δ [ppm]: 1.707 (0.61), 1.722 (1.21), 1.730 (0.98), 1.743 (1.26), 1.751 (0.91), 1.763 (0.67), 1.780 (0.41), 1.811 (0.57), 1.825 (0.51), 1.832 (0.54), 1.846 (0.43), 1.929 (0.79), 1.939 (0.41), 1.949 (0.81), 1.960 (0.51), 1.979 (0.43), 2.145 (7.85), 2.193 (0.49), 2.275 (0.53), 2.299 (1.71), 2.308 (16.00), 2.318 (1.75), 2.324 (1.69), 2.332 (0.55), 2.342 (0.48), 2.518 (1.62), 2.523 (1.03), 2.539 (0.91), 2.562 (0.93), 2.582 (0.44), 2.669 (0.43), 2.775 (0.54), 2.798 (0.68), 2.815 (1.45), 2.833 (0.90), 2.854 (1.34), 2.871 (0.75), 2.895 (0.51), 3.148 (0.51), 3.156 (0.57), 3.164 (0.67), 3.171 (1.01), 3.188 (0.59), 3.195 (0.58), 3.413 (1.42), 3.419 (1.49), 3.436 (2.17), 3.448 (1.11), 4.164 (1.01), 4.173 (1.08), 4.189 (1.23), 4.198 (1.14), 4.467 (1.24), 4.472 (1.33), 4.492 (1.09), 4.498 (1.07), 5.768 (1.11), 5.797 (1.06), 6.375 (0.67), 6.382 (0.73), 6.399 (1.09), 6.406 (1.14), 6.423 (0.67), 6.430 (0.67), 7.154 (1.98), 7.297 (3.41), 7.309 (3.43), 7.495 (2.87), 8.006 (4.18), 8.019 (3.76), 8.208 (0.81), 8.449 (5.62), 12.118 (1.72). LC-MS (method 2): Rt = 0.54 min; m/z = 469 (M + H)+ |

TABLE 3-continued

| Example | Structure Name | Analytical Data |
|---|---|---|
| 52 | 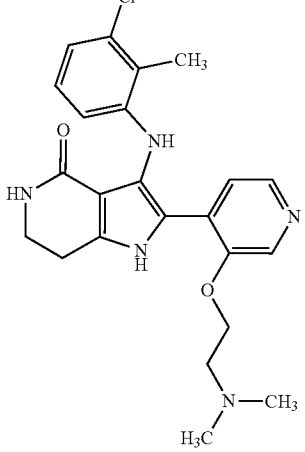<br>3-(3-chloro-2-methylanilino)-2-{3[2-(dimethylamino)ethoxy]pyridin-4-yl}-1,5,6,7-tetrahydro-4H-pyrrolo[3,2-c]pyridin-4-one | $^1$H-NMR (400 MHz, DMSO-d6) δ [ppm]: 2.164 (0.91), 2.203 (0.93), 2.312 (16.00), 2.322 (1.13), 2.327 (1.05), 2.332 (0.76), 2.362 (1.90), 2.369 (8.88), 2.389 (0.73), 2.518 (2.96), 2.523 (1.98), 2.540 (0.69), 2.665 (0.61), 2.669 (0.83), 2.673 (0.60), 2.708 (0.94), 2.721 (1.55), 2.734 (1.06), 2.840 (0.91), 2.857 (1.95), 2.874 (1.02), 3.413 (0.78), 3.420 (0.82), 3.430 (1.38), 3.436 (1.35), 3.447 (0.70), 3.453 (0.63), 4.383 (1.01), 4.397 (1.57), 4.409 (1.01), 6.212 (0.97), 6.215 (0.95), 6.231 (1.07), 6.235 (1.01), 6.732 (0.58), 6.736 (0.85), 6.752 (1.89), 6.756 (1.55), 6.767 (1.35), 6.787 (1.41), 6.807 (0.48), 7.178 (1.26), 7.228 (2.08), 7.240 (2.07), 7.379 (2.42), 7.934 (2.66), 7.948 (2.46), 8.164 (2.48), 8.423 (3.57), 12.260 (1.18).<br>LC-MS (method 1): Rt = 0.69 min; m/z = 440 (M + H)+ |
| 53 | 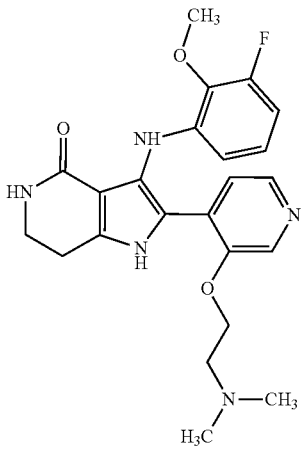 [SMILES: COc1c(F)cccc1Nc1c(-c2ccncc2OCCN(C)C)[nH]c2c1C(=O)NCC2]<br>2-{3-[2-(dimethylamino)ethoxy]pyridin-4-yl}-3-(3-fluoro-2-methoxyanilino)-1,5,6,7-tetrahydro-4H-pyrrolo[3,2-c]pyridin-4-one | $^1$H-NMR (400 MHz, DMSO-d6) δ [ppm]: 2.310 (16.00), 2.322 (0.79), 2.327 (0.72), 2.332 (0.49), 2.518 (1.72), 2.523 (1.26), 2.669 (0.54), 2.713 (0.88), 2.726 (1.44), 2.739 (0.92), 2.832 (0.92), 2.848 (2.01), 2.865 (1.04), 3.408 (0.71), 3.414 (0.75), 3.425 (1.36), 3.430 (1.33), 3.442 (0.66), 3.448 (0.60), 3.668 (0.53), 3.927 (9.60), 4.395 (1.03), 4.408 (1.62), 4.421 (1.02), 6.005 (1.11), 6.025 (1.15), 6.487 (0.53), 6.490 (0.55), 6.508 (0.74), 6.511 (0.75), 6.514 (0.63), 6.518 (0.57), 6.535 (0.71), 6.538 (0.67), 6.625 (0.56), 6.641 (0.61), 6.646 (0.95), 6.661 (0.95), 6.666 (0.47), 6.682 (0.42), 7.157 (1.25), 7.287 (2.16), 7.300 (2.17), 7.572 (2.81), 7.969 (2.68), 7.982 (2.50), 8.442 (3.56), 12.276 (1.10).<br>LC-MS (method 2): Rt = 1.02 min; m/z = 440 (M + H)+ |
| 54 | 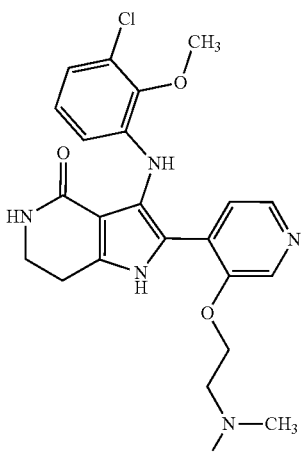 | $^1$H-NMR (400 MHz, DMSO-d6) δ [ppm]: 1.154 (3.77), 1.172 (7.37), 1.190 (3.66), 1.233 (0.81), 1.250 (0.66), 1.988 (14.22), 2.312 (15.54), 2.327 (1.17), 2.332 (0.84), 2.518 (2.73), 2.523 (1.80), 2.664 (0.55), 2.669 (0.77), 2.673 (0.57), 2.713 (0.99), 2.725 (1.57), 2.737 (1.00), 2.836 (1.17), 2.853 (2.46), 2.869 (1.26), 3.222 (0.47), 3.410 (0.85), 3.415 (0.91), 3.426 (1.65), 3.432 (1.64), 3.443 (0.81), 3.449 (0.74), 3.901 (16.00), 4.000 (1.08), 4.017 (3.26), 4.035 (3.21), 4.053 (1.04), 4.398 (1.28), 4.411 (1.99), 4.424 (1.24), 6.143 (1.41), 6.154 (1.54), 6.156 (1.35), 6.167 (1.42), 6.690 (3.05), 6.693 (3.52), 6.704 (5.36), 7.158 (1.60), 7.278 (2.59), 7.291 (2.63), 7.582 (3.49), 7.974 (3.17), 7.987 (2.90), 8.447 (4.52), 12.301 (1.12). |

TABLE 3-continued

| Example | Structure Name | Analytical Data |
|---|---|---|
| | 3-(3-chloro-2-methoxyanilino)-2-{3-[2-(dimethylamino)ethoxy]pyridin-4-yl}-1,5,6,7-tetrahydro-4H-pyrrolo[3,2-c]pyridin-4-one | LC-MS (method 1): Rt = 0.64 min; MS (ESIpos): m/z = 457 [M + H]$^+$ |
| 55 | 3-(3,5-difluoro-2-methylanilino)-2-{3-[2-(dimethylamino)ethoxy]pyridin-4-yl}-1,5,6,7-tetrahydro-4H-pyrrolo[3,2-c]pyridin-4-one | $^1$H-NMR (400 MHz, DMSO-d6) δ [ppm]: 1.232 (1.99), 2.145 (4.77), 2.199 (0.52), 2.222 (0.50), 2.227 (0.52), 2.235 (0.66), 2.242 (0.77), 2.303 (16.00), 2.323 (0.62), 2.327 (0.73), 2.331 (0.59), 2.344 (1.24), 2.518 (2.29), 2.523 (1.48), 2.665 (0.51), 2.669 (0.63), 2.673 (0.50), 2.696 (1.02), 2.708 (1.60), 2.721 (1.06), 2.844 (0.90), 2.862 (1.96), 2.879 (1.00), 3.413 (0.70), 3.419 (0.77), 3.430 (1.33), 3.436 (1.29), 3.447 (0.65), 3.453 (0.61), 4.390 (1.06), 4.403 (1.62), 4.416 (1.08), 5.769 (0.65), 5.798 (0.62), 6.370 (0.44), 6.376 (0.46), 6.394 (0.67), 6.400 (0.68), 7.154 (1.19), 7.282 (1.96), 7.296 (1.99), 7.493 (1.77), 8.001 (2.31), 8.014 (2.21), 8.463 (3.32), 12.343 (1.11). LC-MS (method 2): Rt = 0.67 min; MS (ESIpos): m/z = 442 [M + H]$^+$ |
| 56 | 2-{3-[2-(dimethylamino)ethoxy]pyridin-4-yl}-3-(3-fluoro-2-methylanilino)-1,5,6,7-tetrahydro-4H-pyrrolo[3,2-c]pyridin-4-one | $^1$H-NMR (400 MHz, DMSO-d6) δ [ppm]: 2.122 (0.58), 2.202 (6.28), 2.223 (1.15), 2.311 (16.00), 2.361 (1.79), 2.669 (1.15), 2.708 (1.72), 2.722 (2.39), 2.734 (1.70), 2.838 (1.39), 2.855 (2.48), 2.872 (1.39), 3.420 (1.25), 3.431 (1.86), 3.448 (1.01), 4 384 (1.37), 4.396 (2.03), 4.409 (1.23), 5.758 (4.75), 6.078 (1.41), 6.098 (1.38), 6.453 (0.74), 6.474 (1.20), 6.497 (0.71), 6.749 (0.50), 6.768 (0.99), 6.786 (0.90), 7.178 (1.48), 7.228 (1.92), 7.241 (1.88), 7.357 (2.51), 7.927 (2.07), 7.939 (1.86), 8.421 (3.30), 12.247 (1.38). LC-MS (method 2): Rt = 1.05 min; m/z = 424 (M + H)+ |

TABLE 3-continued

| Example | Structure Name | Analytical Data |
|---|---|---|
| 57 | 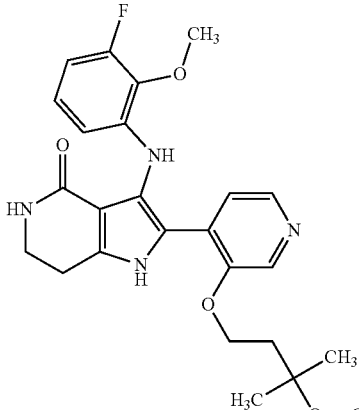<br>3-(3-fluoro-2-methoxyanilino)-2-[3-(3-methoxy-3-methylbutoxy)pyridin-4-yl]1,5,6,7-tetrahydro-4H-pyrrolo[3,2-c]pyridin-4-one | $^1$H-NMR (400 MHz, DMSO-d6) δ (ppm): 1.154 (1.07), 1.167 (16.00), 1.172 (3.58), 1.190 (0.79), 1.983 (0.91), 1.988 (2.73), 2.000 (1.80), 2.017 (0.87), 2.518 (1.31), 2.522 (0.79), 2.822 (0.75), 2.839 (1.62), 2.855 (0.86), 3.117 (12.28), 3.385 (0.56), 3.391 (0.61), 3.403 (1.09), 3.408 (1.07), 3.419 (0.55), 3.425 (0.50), 3.887 (7.39), 4.017 (0.56), 4.035 (0.55), 4.172 (0.86), 4.190 (1.80), 4.207 (0.85), 5.964 (0.90), 5.985 (0.94), 6.423 (0.42), 6.427 (0.45), 6.444 (0.59), 6.447 (0.63), 6.451 (0.53), 6.454 (0.48), 6.471 (0.58), 6.474 (0.55), 6.564 (0.42), 6.579 (0.48), 6.585 (0.76), 6.600 (0.74), 7.104 (1.05), 7.289 (1.72), 7.301 (1.73), 7.483 (2.28), 8.028 (2.23), 8.040 (2.08), 8.360 (2.79), 11.215 (1.05).<br>LC-MS (method 2): Rt = 1.07 min; m/z = 469 (M + H)+ |
| 58 | 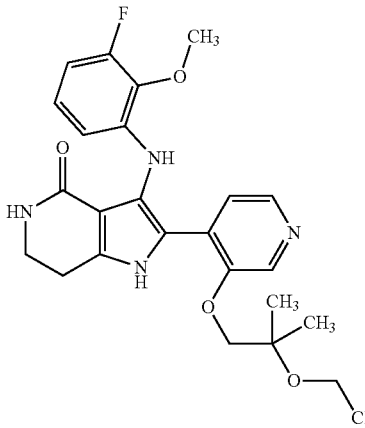<br>2-[3-(2-ethoxy-2-methylpropoxy)pyridin-4-yl]-3-(3-fluoro-2-methoxyanilino)-1,5,6,7-tetrahydro-4H-pyrrolo[3,2-c]pyridin-4-one | $^1$H-NMR (400 MHz, DMSO-d6) δ [ppm]: 1.038 (2.31), 1.055 (5.14), 1.073 (2.35), 1.284 (16.00), 2.522 (0.82), 2.798 (0.87), 2.815 (1.87), 2.833 (0.97), 3.403 (0.67), 3.409 (0.75), 3.420 (1.96), 3.425 (1.43), 3.437 (2.95), 3.455 (2.41), 3.472 (0.69), 3.909 (8.56), 4.176 (4.30), 6.003 (1.00), 6.024 (1.04), 6.473 (0.45), 6.476 (0.46), 6.494 (0.65), 6.497 (0.68), 6.504 (0.51), 6.521 (0.60), 6.525 (0.57), 6.619 (0.46), 6.634 (0.54), 6.640 (0.83), 6.655 (0.81), 6.660 (0.42), 7.169 (1.17), 7.283 (1.80), 7.295 (1.82), 7.480 (2.49), 8.010 (2.17), 8.022 (2.01), 8.398 (3.13), 11.048 (1.23).<br>LC-MS (method 2): Rt = 1.12 min; m/z = 469 (M + H)+ |
| 59 | 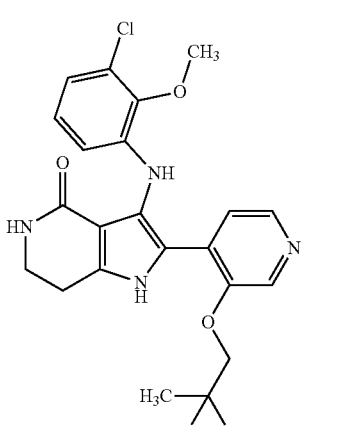<br>3-(3-chloro-2-methoxyanilino)-2-[3-(2-hydroxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.142 (0.87), 1.232 (1.27), 1.279 (16.00), 2.084 (0.49), 2.327 (0.66), 2.331 (0.49), 2.518 (3.05), 2.522 (1.84), 2.539 (0.59), 2.669 (0.67), 2.673 (0.49), 2.789 (0.86), 2.806 (1.83), 2.824 (0.96), 3.397 (0.65), 3.403 (0.71), 3.414 (1.24), 3.419 (1.22), 3.431 (0.62), 3.436 (0.55), 3.623 (0.64), 3.669 (0.81), 3.889 (11.40), 4.082 (4.35), 5.535 (3.06), 6.161 (0.99), 6.169 (0.92), 6.178 (0.99), 6.185 (1.00), 6.684 (0.48), 6.697 (3.97), 6.704 (1.95), 6.714 (1.55), 7.151 (1.21), 7.255 (1.77), 7.267 (1.80), 7.523 (2.51), 7.992 (2.08), 8.005 (1.92), 8.405 (3.07), 11.762 (1.21).<br>LC-MS (method 2): Rt = 1.00 min; m/z = 457 (M + H)+ |

TABLE 3-continued

| Example | Structure Name | Analytical Data |
|---|---|---|
| 60 | 3-(3-chloro-2-methylanilino)-2-{3-[2-(dimethylamino)-2-methylpropoxy]pyridin-4-yl}-1,5,6,7-tetrahydro-4H-pyrrolo[3,2-c]pyridin-4-one | ¹H-NMR (400 MHz, DMSO-d6) δ [ppm]: 1.132 (14.72), 1.232 (0.43), 2.074 (0.69), 2.243 (16.00), 2.310 (0.26), 2.336 (0.48), 2.377 (8.32), 2.518 (6.05), 2.522 (4.11), 2.673 (1.12), 2.678 (0.51), 2.846 (0.94), 2.863 (1.99), 2.880 (1.02), 3.422 (0.74), 3.427 (0.79), 3.438 (1.38), 3.444 (1.35), 3.455 (0.69), 4.222 (4.13), 6.211 (1.05), 6.228 (1.15), 6.748 (0.66), 6.751 (0.79), 6.769 (1.61), 6.771 (1.45), 6.793 (1.17), 6.812 (1.43), 6.832 (0.51), 7.188 (1.25), 7.214 (1.99), 7.227 (2.04), 7.416 (2.35), 7.911 (2.19), 7.924 (1.99), 8.350 (3.16), 12.549 (1.22). LC-MS (method 2): Rt = 1.12 min; m/z = 469 (M + H)+ |
| 61 | 2-{3-[2-(dimethylamino)-2-methylpropoxy]pyridin-4-yl}-3-(3-fluoro-2-methylanilino)-1,5,6,7-tetrahydro-4H-pyrrolo[3,2-c]pyridin-4-one | ¹H-NMR (400 MHz, DMSO-d6) δ [ppm]: 1.107 (0.61), 1.133 (14.44), 1.145 (1.59), 1.154 (1.71), 1.173 (2.83), 1.190 (1.42), 1.988 (5.29), 2.210 (4.86), 2.213 (4.85), 2.230 (1.49), 2.243 (16.00), 2.311 (1.09), 2.323 (0.49), 2.327 (0.66), 2.332 (0.45), 2.518 (2.73), 2.523 (1.82), 2.540 (5.80), 2.665 (0.47), 2.669 (0.63), 2.673 (0.47), 2.845 (0.85), 2.862 (1.84), 2.879 (0.94), 3.429 (0.74), 3.439 (1.24), 3.445 (1.23), 3.456 (0.63), 4.000 (0.44), 4.017 (1.19), 4.035 (1.18), 4.221 (3.95), 5.758 (0.90), 6.076 (1.11), 6.096 (1.16), 6.470 (0.57), 6.491 (0.97), 6.513 (0.57), 6.795 (0.74), 6.812 (0.75), 7.187 (1.19), 7.218 (1.96), 7.231 (2.02), 7.392 (2.22), 7.904 (2.56), 7.917 (2.44), 8.348 (3.36), 12.535 (1.06). LC-MS (method 2): Rt = 1.18 min; m/z = 452 (M + H)+ |
| 62 | 3-(3,5-difluoro-2-methylanilino)-2-{3-[2-(dimethylamino)-2-methylpropoxy]pyridin-4-yl}-1,5,6,7-tetrahydro-4H-pyrrolo[3,2-c]pyridin-4-one | ¹H-NMR (400 MHz, DMSO-d6) δ [ppm]: 1.132 (14.72), 1.232 (0.43), 2.074 (0.69), 2.243 (16.00), 2.310 (0.26), 2.336 (0.48), 2.377 (8.32), 2.518 (6.05), 2.522 (4.11), 2.673 (1.12), 2.678 (0.51), 2.846 (0.94), 2.863 (1.99), 2.880 (1.02), 3.422 (0.74), 3.427 (0.79), 3.438 (1.38), 3.444 (1.35), 3.455 (0.69), 4.222 (4.13), 6.211 (1.05), 6.228 (1.15), 6.748 (0.66), 6.751 (0.79), 6.769 (1.61), 6.771 (1.45), 6.793 (1.17), 6.812 (1.43), 6.832 (0.51), 7.188 (1.25), 7.214 (1.99), 7.227 (2.04), 7.416 (2.35), 7.911 (2.19), 7.924 (1.99), 8.350 (3.16), 12.549 (1.22). LC-MS (method 1): Rt = 0.70 min; m/z = 470 (M + H)+ |

TABLE 3-continued

| Example | Structure Name | Analytical Data |
|---|---|---|
| 63 | 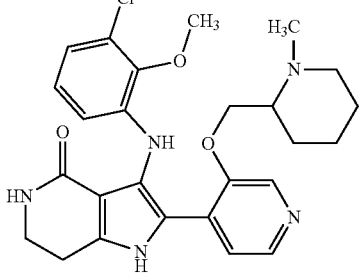<br>3-(3-chloro-2-methoxyanilino)-2-(3-{[1-methylpiperidin-2-yl]methoxy}pyridin-4-yl)-1,5,6,7-tetrahydro-4H-pyrrolo[3,2-c]pyridin-4-one | $^1$H-NMR (400 MHz, DMSO-d6) δ [ppm]: 1.035 (0.89), 1.052 (1.76), 1.070 (0.94), 1.526 (0.44), 1.558 (0.46), 1.651 (1.18), 1.677 (1.60), 1.750 (0.52), 1.782 (0.46), 2.180 (0.55), 2.230 (9.58), 2.261 (0.84), 2.286 (0.84), 2.318 (0.48), 2.322 (0.55), 2.326 (0.61), 2.332 (0.45), 2.518 (2.59), 2.522 (1.77), 2.669 (0.54), 2.673 (0.41), 2.813 (0.59), 2.831 (1.59), 2.848 (1.48), 2.865 (0.63), 3.031 (0.61), 3.061 (0.57), 3.285 (0.41), 3.422 (0.92), 3.427 (0.82), 3.435 (1.56), 3.440 (1.38), 3.452 (1.47), 3.457 (0.76), 3.915 (16.00), 4.356 (0.82), 4.387 (1.74), 4.400 (1.34), 6.156 (1.37), 6.168 (2.35), 6.180 (1.43), 6.721 (4.61), 6.733 (3.82), 7.182 (1.65), 7.294 (2.71), 7.307 (2.71), 7.635 (3.42), 7.957 (3.49), 7.970 (3.11), 8.379 (4.78), 12.282 (1.61).<br>LC-MS (method 2): Rt = 1.21 min; m/z = 496 (M + H)+ |
| 64 | 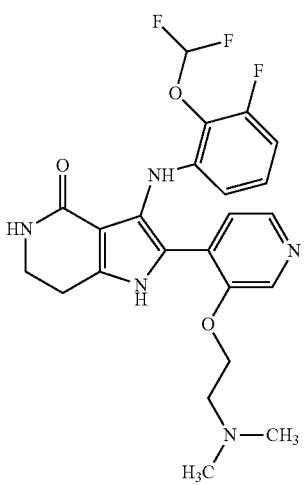 [SMILES: CN(C)CCOc1cnccc1-c1[nH]c2c(c1Nc1cccc(F)c1OC(F)F)C(=O)NCC2]<br>3-[2-(difluoromethoxy)-3-fluoroanilino]-2-{3-[2-(dimethylamino)ethoxy]pyridin-4-yl}-1,5,6,7-tetrahydro-4H-pyrrolo[3,2-c]pyridin-4-one | $^1$H-NMR (400 MHz, DMSO-d6) δ (ppm): 2.307 (16.00), 2.322 (0.41), 2.327 (0.42), 2.518 (091), 2.523 (0.67), 2.705 (0.88), 2.718 (1.44), 2.731 (0.90), 2.835 (0.87), 2.852 (1.89), 2.869 (0.98), 3.404 (0.64), 3.411 (0.67), 3.422 (1 25), 3.427 (1.23), 3.438 (0-61), 3.444 (0.55), 3.672 (0.57), 4.395 (0.98), 4.408 (1.53), 4.421 (0.96), 6.114 (1.08), 6.135 (1.10), 6.569 (0.53), 6.572 (0.53), 6.590 (0.68), 6.594 (0.96), 6.597 (0.58), 6.615 (0.62), 6.618 (0.58), 6.833 (0.46), 6.848 (0.52), 6.853 (0.90), 6.869 (0.87), 6.874 (0.44), 7.032 (0.73), 7.141 (1.20), 7.218 (1.46), 7.364 (2.07), 7.376 (2.12), 7.402 (0.67), 7.521 (2.63), 7.972 (3.10), 7.984 (2.73), 8.452 (3.70), 12.341 (1.17).<br>LC-MS (method 2): Rt = 1.05 min; m/z = 476 (M + H)+ |
| 65 | 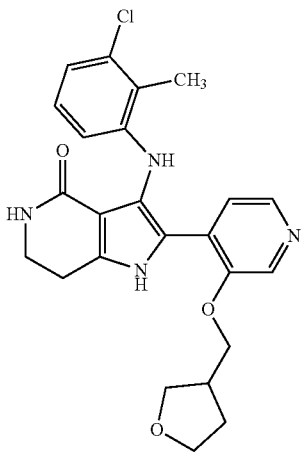 [SMILES: Cc1c(Cl)cccc1Nc1c(-c2ccncc2OCC2CCOC2)[nH]c2c1C(=O)NCC2] | $^1$H-NMR (400 MHz, DMSO-d6) δ [ppm]: 1.154 (2.91), 1.172 (5.85), 1.190 (3.05), 1.686 (0.58), 1.699 (0.72), 1.705(1.17), 1.717 (1.57), 1.724 (0.92), 1.730 (0.99), 1.737 (1.66), 1.749 (1.28), 1.769 (0.67), 1.987 (11.68), 2.023 (0.74), 2.035 (0.81), 2.043 (1.08), 2.054 (1.48), 2.066 (1.50), 2.074 (2.71), 2.088 (0.90), 2.096 (0.69), 2.108 (0.63), 2.145 (0.49), 2.168 (16.00), 2.171 (15.82), 2.518 (5.02), 2.522 (3.16), 2.704 (0.63), 2.718 (1.12), 2.732 (1.32), 2.740 (1.28), 2.755 (1.08), 2.768 (0.54), 2.831 (3.00), 2.848 (6.41), 2.865 (3.45), 3.390 (2.31), 3.396 (2.46), 3.407 (4.46), 3.412 (4.30), 3.424 (2.13), 3.430 (1.95), 3.592 (1.37), 3.611 (3.43), 3.632 (3.63), 3.651 (1.61), 3.692 (1.12), 3.714 (5.80), 3.719 (5.22), |

TABLE 3-continued

| Example | Structure Name | Analytical Data |
|---|---|---|
| | 3-(3-fluoro-2-methylanilino)-2-(3-{[oxolan-3-yl]methoxy}pyridin-4-yl)-1,5,6,7-tetrahydro-4H-pyrrolo[3,2-c]pyridin-4-one | 3.730 (8.02), 3.741 (1.05), 3.754 (0.52), 3.837 (2.73), 3.848 (1.64), 3.857 (2.67), 3.869 (2.67), 3.878 (1.30), 3.890 (1.17), 3.999 (0.94), 4.017 (2.71), 4.035 (2.69), 4.053 (0.96), 4.083 (1.41), 4.098 (1.59), 4.106 (3.29), 4.122 (3.32), 4.130 (3.38), 4.144 (3.34), 4.154 (1.46), 4.167 (1.30), 5.759 (2.73), 6.027 (3.92), 6.047 (3.99), 6.418 (1.97), 6.440 (3.25), 6.462 (2.02), 6.717 (1.25), 6.737 (2.60), 6.755 (2.51), 6.775 (1.05), 7.143 (3.90), 7.267 (7.19), 7.280 (7.75), 7.288 (8.13), 7.983 (9.57), 7.996 (8.83), 8.351 (11.65), 11.108 (3.05). LC-MS (method 2): Rt = 0.99 min; m/z = 437 (M + H)+ |
| 66 | 3-(3-chloro-2-methoxyanilino)-2-(3-{[(2S)-oxolan-2-yl]methoxy}pyridin-4-yl)-1,5,6,7-tetrahydro-4H-pyrrolo[3,2-c]pyridin-4-one | $^1$H-NMR (400 MHz, DMSO-d6) δ [ppm]: 1.667 (0.48), 1.676 (0.52), 1.681 (0.43), 1.698 (0.60), 1.869 (0.83), 1.884 (1.47), 1.902 (1.17), 1.998 (0.45), 2.011 (0.57), 2.025 (0.43), 2.030 (0.52), 2.044 (0.41), 2.518 (2.49), 2.523 (1.71), 2.820 (0.81), 2.837 (1.69), 2.841 (1.61), 2.857 (0.90), 3.398 (0.86), 3.404 (0.91), 3.415 (1.67), 3.421 (1.67), 3.432 (0.76), 3.438 (0.72), 3.746 (0.47), 3.763 (0.90), 3.766 (0.93), 3.783 (1.35), 3.800 (0.69), 3.831 (0.78), 3.847 (1.55), 3.871 (16.00), 3.884 (0.62), 4.012 (0.79), 4.031 (1.07), 4.036 (1.05), 4.055 (0.95), 4.308 (0.60), 4.316 (0.81), 4.326 (0.54), 4.334 (0.83), 4.352 (1.62), 4.360 (0.69), 4.376 (1.05), 4.385 (0.81), 6.151 (1.40), 6.160 (1.24), 6.166 (1.48), 6.176 (1.45), 6.660 (0.60), 6.670 (6.25), 6.680 (2.93), 6.686 (2.57), 7.138 (1.55), 7.268 (2.12), 7.280 (2.16), 7.487 (3.42), 8.025 (1.83), 8.038 (1.73), 8.425 (2.88), 11.255 (1.62). LC-MS (method 1): Rt = 0.97 min; m/z = 469 (M + H)+ |
| 67 | 3-(3-chloro-2-methoxyanilino)-2-(3-{[(2R)-oxolan-2-yl]methoxy}pyridin-4-1)-1,5,6,7-tetrahydro-4H-pyrrolo[3,2-c]pyridin-4-one | $^1$H-NMR (400 MHz, DMSO-d6) δ [ppm]: 1.668 (0.49), 1.677 (0.53), 1.681 (0.42), 1.698 (0.61), 1.869 (0.80), 1.885 (1.45), 1.902 (1.15), 1.998 (0.42), 2.011 (0.55), 2.030 (0.51), 2.044 (0.42), 2.518 (3.33), 2.523 (2.33), 2.823 (0.80), 2.837 (1.69), 2.841 (1.61), 2.857 (0.91), 3.397 (0.81), 3.404 (0.85), 3.415 (1.65), 3.421 (1.66), 3.432 (0.74), 3.438 (0.72), 3.746 (0.45), 3.763 (0.87), 3.766 (0.91), 3.783 (1.34), 3.800 (0.66), 3.831 (0.70), 3.848 (1.53), 3.871 (16.00), 3.884 (0.58), 4.012 (0.79), 4.030 (1.07), 4.036 (1.03), 4.055 (0.95), 4.308 (0.60), 4.316 (0.81), 4.326 (0.51), 4.334 (0.81), 4.351 (1.64), 4.359 (0.69), 4.376 (1.04), 4.384 (0.83), 6.152 (1.42), 6.160 (1.25), 6.167 (1.45), 6.176 (1.49), 6.659 (0.61), 6.670 (6.46), 6.679 (2.96), 6.686 (2.56), 7.138 (1.54), 7.266 (2.56), 7.278 (2.59), 7.484 (3.40), 8.024 (3.29), 8.037 (3.01), 8.425 (4.52), 11.252 (1.62). |

TABLE 3-continued

| Example | Structure Name | Analytical Data |
|---|---|---|
| | | LC-MS (method 2): Rt = 1.07 min; m/z = 469 (M + H)+ |
| 68 | 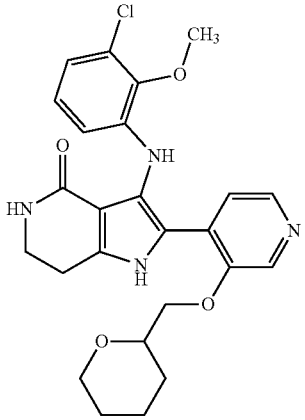 [SMILES: COc1c(Cl)cccc1Nc1c(-c2ccncc2OCC2CCCCO2)[nH]c2c1C(=O)NCC2]<br>3-(3-chloro-2-methoxyanilino)-2-{3-[(oxan-2-yhmethoxy]pyridin-4-yl}-1,5,6,7-tetrahydro-4H-pyrrolo[3,2-c]pyridin-4-one | ¹H-NMR (400 MHz, DMSO-d6) δ [ppm]: 1.345 (0.39), 1.374 (0.52), 1.524 (0.63), 1.550 (1.81), 1.629 (0.63), 1.660 (0.52), 1.837 (0.58), 2.327 (0.73), 2.331 (0.55), 2.518 (3.33), 2.522 (2.04), 2.539 (0.76), 2.669 (0.76), 2.673 (0.55), 2.843 (1.10), 2.860 (2.23), 2.877 (1.23), 3.405 (0.89), 3.412 (0.94), 3.423 (1.73), 3.429 (1.70), 3.440 (0.81), 3.445 (0.73), 3.528 (0.42), 3.555 (0.71), 3.674 (0.45), 3.818 (0.55), 3.840 (0.42), 3.891 (16.00), 4.058 (1.47), 4.077 (1.41), 4.083 (1.60), 4.102 (0.92), 4.330 (1.00), 4.337 (1.02), 4.356 (0.89), 4.363 (0.79), 6.141 (1.44), 6.153 (2.41), 6.165 (1.44), 6.690 (3.74), 6.703 (4.27), 7.174 (1.60), 7.274 (2.72), 7.286 (2.72), 7.562 (3.54), 8.005 (3.51), 8.018 (3.17), 8.408 (4.79), 11.076 (1.75).<br>LC-MS (method 2): Rt = 1.15 min; m/z = 483 (M + H)+ |
| 69 | 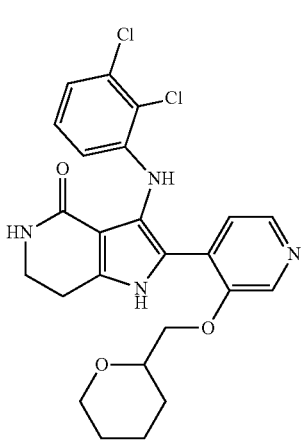 [SMILES: O=C1NCCc2[nH]c(-c3ccncc3OCC3CCCCO3)c(Nc3cccc(Cl)c3Cl)c21]<br>3-(2,3-dichloroanilino)-2-{3-[(oxan-2-yl)methoxy]pyridin-4-yl}-1,5,6,7-tetrahydro-4H-pyrrolo[3,2-c]pyridin-4-one | ¹H-NMR (400 MHz, DMSO-d6) δ [ppm]: 0.929 (0.40), 0.946 (0.68), 1.053 (0.40), 1.173 (0.90), 1.232 (1.02), 1.305 (1.24), 1.334 (1.53), 1.504 (1.98), 1.529 (5.26), 1.558 (1.87), 1.585 (2.26), 1.618 (1.64), 1.821 (1.70), 1.906 (2.49), 1.988 (0.90), 2.075 (0.40), 2.454 (0.73), 2.518 (16.00), 2.523 (9.95), 2.539 (2.88), 2.848 (3.34), 2.865 (7.18), 2.883 (3.90), 3.416 (2.83), 3.428 (4.98), 3.434 (5.03), 3.445 (2.54), 3.480 (1.36), 3.507 (2.37), 3.535 (1.07), 3.753 (1.58), 3.776 (1.13), 4.009 (2.04), 4.026 (3.05), 4.044 (3.34), 4.052 (3.45), 4.070 (2.83), 4.175 (3.00), 4.182 (3.11), 4.200 (2.32), 4.208 (2.09), 6.264 (4.35), 6.269 (4.35), 6.283 (4.52), 6.288 (4.47), 6.857 (1.53), 6.862 (3.11), 6.876 (9.10), 6.882 (9.50), 6.903 (6.61), 6.922 (2.09), 7.184 (4.81), 7.246 (4.75), 7.259 (4.86), 7.705 (10.63), 8.043 (3.17), 8.056 (3.05), 8.391 (5.09), 11.200 (5.03).<br>LC-MS (method 2): Rt = 1.17 min; m/z = 487 (M + H)+ |

TABLE 3-continued

| Example | Structure Name | Analytical Data |
|---|---|---|
| 70 | 3-(2,3-dichloroanilino)-2-(3-{[(2S)-oxolan-2-yl]methoxy}pyridin-4-yl)-1,5,6,7-tetrahydro-4H-pyrrolo[3,2-c]pyridin-4-one | $^1$H-NMR (400 MHz, DMSO-d6) δ [ppm]: 1.602 (0.60), 1.620 (1.37), 1.639 (1.76), 1.648 (1.55), 1.670 (1.78), 1.687 (0.92), 1.824 (1.01), 1.829 (1.18), 1.844 (3.16), 1.860 (5.69), 1.877 (4.27), 1.898 (1.44), 1.907 (1.07), 1.953 (1.10), 1.971 (1.55), 1.984 (1.76), 2.002 (1.65), 2.017 (1.31), 2.035 (0.49), 2.518 (6.64), 2.523 (4.42), 2.827 (3.39), 2.845 (7.04), 2.862 (4.06), 3.169 (0.92), 3.403 (2.88), 3.409 (3.07), 3.420 (5.73), 3.426 (5.67), 3.437 (2.71), 3.443 (2.51), 3.716 (1.55), 3.732 (3.01), 3.736 (3.16), 3.753 (4.60), 3.769 (2.32), 3.792 (2.62), 3.808 (5.50), 3.826 (3.03), 3.829 (3.50), 3.846 (1.50), 3.991 (1.80), 4.010 (3.63), 4.016 (3.65), 4.034 (2.38), 4.225 (3.14), 4.233 (4.98), 4.243 (1.63), 4.256 (8.03), 4.273 (2.86), 4.280 (1.93), 4.290 (0.92), 4.298 (0.69), 6.276 (5.48), 6.280 (5.58), 6.295 (5.88), 6.300 (5.63), 6.831 (3.01), 6.836 (4.19), 6.852 (9.99), 6.856 (8.59), 6.867 (7.75), 6.887 (8.42), 6.906 (2.86), 7.149 (5.30), 7.240 (9.08), 7.253 (9.28), 7.602 (11.94), 8.059 (12.76), 8.072 (11.79), 8.406 (16.00), 11.362 (5.56). LC-MS (method 2): Rt = 1.09 min; m/z = 473 (M + H)+ |
| 71 | 3-(2,3-dichloroanilino)-2-(3-{[(2S)-1-methylpyrrolidin-2-yl]methoxy}pyridin-4-yl)-1,5,6,7-tetrahydro-4H-pyrrolo[3,2-c]pyridin-4-one | $^1$H-NMR (400 MHz, DMSO-d6) δ [ppm]: 1.723 (1.04), 1.745 (1.14), 1.764 (0.70), 1.906 (0.73), 1.933 (0.74), 1.953 (0.71), 1.987 (0.65), 2.074 (2.50), 2.142 (0.92), 2.306 (16.00), 2.319 (1.54), 2.322 (1.55), 2.326 (1.07), 2.331 (0.67), 2.518 (2.85), 2.522 (1.79), 2.565 (0.89), 2.669 (0.68), 2.810 (1.36), 2.827 (0.66), 2.859 (1.20), 2.876 (0.76), 3.170 (0.94), 3.382 (1.15), 3.398 (0.82), 3.419 (1.09), 3.435 (1.95), 3.451 (0.95), 3.673 (0.65), 4.144 (0.99), 4.153 (1.10), 4.170 (1.21), 4.179 (1.12), 4.453 (1.22), 4.458 (1.31), 4.479 (1.09), 4 484 (1.06), 6.280 (2.02), 6.284 (2.14), 6.300 (2.22), 6.305 (2.10), 6.878 (1.34), 6.882 (1.83), 6.898 (3.78), 6.903 (3.22), 6.915 (2.95), 6.934 (3.24), 6.954 (1.09), 7.174 (2.00), 7.244 (3.51), 7.257 (3.62), 7.710 (4.46), 7.995 (5.33), 8.007 (4.65), 8.435 (6.18), 12.152 (1.83). LC-MS (method 2): Rt = 1.18 min; m/z = 486(M + H)+ |

Example 72

3-(3-fluoro-2-methoxyanilino)-2-[3-(2-hydroxy-2-methylpropoxy)pyridin-4-yl]-1,5,6,7-tetrahydro-4H-pyrrolo[3,2-c]pyridin-4-one

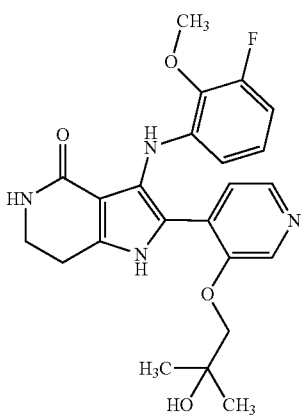 [SMILES: COc1c(F)cccc1Nc1c(-c2ccncc2OCC(C)(C)O)[nH]c2c1C(=O)NCC2]

N-(3-fluoro-2-methoxyphenyl)-4-({[3-(2-hydroxy-2-methylpropoxy)pyridin-4-yl]methyl}amino)-2-oxo-1,2,5,6-tetrahydropyridine-3-carbothioamide (88.0 mg, 185 μmol, intermediate 6-72) was solubilised in 1.8 mL methanol, hydrogen peroxide (32 μl, 36% purity, 370 μmol) was added and the mixture was stirred 2 h at 90° C. The reaction mixture was concentrated under reduced pressure, the residue was purified by preparative HPLC to give 13 mg of the title compound (90% purity, 14% yield).

$^1$H-NMR (400 MHz, DMSO-d6) δ [ppm]: 1.146 (0.88), 1.231 (0.56), 1.249 (0.79), 1.279 (16.00), 2.331 (0.45), 2.518 (2.35), 2.523 (1.54), 2.539 (0.56), 2.673 (0.51), 2.786 (0.83), 2.803 (1.77), 2.819 (0.90), 3.396 (0.64), 3.402 (0.68), 3.412 (1.18), 3.418 (1.15), 3.429 (0.58), 3.436 (0.55), 3.693 (0.47), 3.712 (0.41), 3.916 (8.50), 3.925 (0.73), 4.080 (4.47), 5.534 (2.61), 6.023 (0.98), 6.043 (1.00), 6.485 (0.49), 6.489 (0.51), 6.506 (0.64), 6.509 (0.70), 6.512 (0.60), 6.516 (0.51), 6.533 (0.58), 6.537 (0.55), 6.639 (0.47), 6.654 (0.55), 6.659 (0.81), 6.675 (0.79), 6.680 (0.41), 7.152 (1.15), 7.262 (1.88), 7.275 (1.86), 7.516 (2.44), 7.988 (2.37), 8.000 (2.20), 8.401 (3.31), 11.747 (1.13).

LC-MS (method 1): Rt=0.76 min; m/z=441 (M+H)+

The examples in Table 4 were prepared analogous to the preparation of example 72 starting from the corresponding intermediates by reacting with the corresponding aldehydes.

TABLE 4

| Example | Structure | Name | Analytical Data |
|---|---|---|---|
| 73 | | 3-[2-(difluoromethoxy)-3-fluoroanilino]-2-[3-(2-hydroxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.271 (16.00), 2.518 (0.96), 2.523 (0.68), 2.790 (0.80), 2.807 (1.73), 2.824 (0.89), 3.392 (0.59), 3.398 (0.64), 3.409 (1.15), 3.415 (1.11), 3.426 (0.56), 3.432 (0.51), 4.072 (4.19), 5.508 (3.71), 6.132 (0.97), 6.153 (1.00), 6.564 (0.51), 6.567 (0.51), 6.585 (0.65), 6.589 (0.88), 6.592 (0.54), 6.610 (0.55), 6.613 (0.52), 6.844 (0.42), 6.859 (0.48), 6.865 (0.78), 6.880 (0.77), 6.885 (0.41), 7.020 (0.65), 7.133 (1.10), 7.206 (1.29), 7.342 (1.56), 7.355 (1.57), 7.391 (0.61), 7.467 (2.43), 7.992 (1.47), 8.005 (1.35), 8.408 (2.27), 11.774 (1.14). LC-MS (method 2): Rt = 0.98 min; m/z = 477 (M + H)+ |

TABLE 4-continued

| Example | Structure Name | Analytical Data |
|---|---|---|
| 74 | 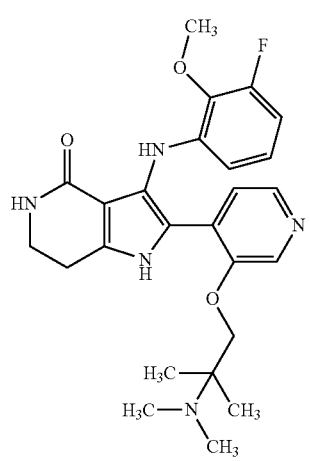 [SMILES: COc1c(F)cccc1Nc1c(-c2ccncc2OCC(C)(C)N(C)C)[nH]c2c1C(=O)NCC2]<br>2-{3-[2-(dimethylamino)-2-methylpropoxy]pyridin-4-yl}-3-(3-fluoro-2-methoxyanilino)-1,5,6,7-tetrahydro-4H-pyrrolo[3,2-c]pyridin-4-one | $^1$H-NMR (400 MHz, DMSO-d6) δ [ppm]: 1.133 (14.39), 2.242 (16.00), 2.518 (1.56), 2.523 (1.15), 2.539 (1.63), 2.838 (0.85), 2.855 (1.82), 2.872 (0.95), 3.417 (0.65), 3.423 (0.70), 3.434 (1.25), 3.439 (1.24), 3.450 (0.63), 3.936 (8.83), 4.229 (3.98), 6.004 (1.00), 6.024 (1.05), 6.504 (0.44), 6.507 (0.47), 6.525 (0.65), 6.528 (0.68), 6.535 (0.52), 6.552 (0.61), 6.556 (0.59), 6.651 (0.47), 6.666 (0.54), 6.672 (0.83), 6.687 (0.83), 6.692 (0.43), 7.167 (1.20), 7.283 (1.76), 7.297 (1.81), 7.609 (2.51), 7.947 (1.80), 7.960 (1.72), 8.368 (2.76), 12.556 (1.14).<br>LC-MS (method 2): Rt = 1.15 min; m/z = 468 (M + H)+ |
| 75 | 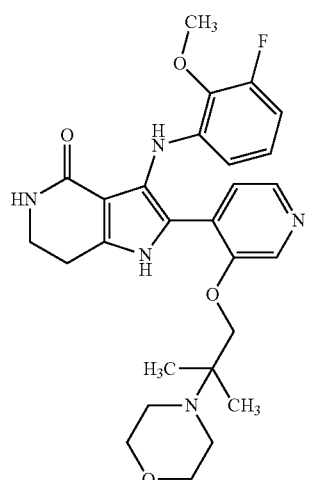<br>3-(3-fluoro-2-methoxyanilino)-2-{3-[2-methyl-2-(morpholin-4-yl)propoxy]pyridin-4-yl}-1,5,6,7-tetrahydro-4H-pyrrolo[3,2-c]pyridin-4-one | $^1$H-NMR (400 MHz, DMSO-d6) δ [ppm]: 0.795 (0.94), 1.143 (0.73), 1.159 (16.00), 2.518 (2.68), 2.523 (3.10), 2.534 (2.34), 2.539 (2.39), 2.544 (1.78), 2.874 (0.86), 2.891 (1.84), 2.908 (0.95), 3.335 (2.93), 3.357 (1.14), 3.359 (1.04), 3.415 (0.71), 3.421 (0.76), 3.432 (1.31), 3.437 (1.26), 3.448 (0.72), 3.454 (0.61), 3.530 (1.92), 3.541 (2.44), 3.551 (1.83), 3.668 (2.11), 3.806 (1.25), 3.809 (1.12), 3.913 (9.47), 3.915 (9.66), 3.936 (0.44), 3.939 (0.46), 4.179 (3.96), 5.967 (1.10), 5.988 (1.15), 6.472 (0.53), 6.475 (0.53), 6.493 (0.74), 6.496 (0.75), 6.499 (0.65), 6.502 (0.57), 6.520 (0.70), 6.523 (0.66), 6.616 (0.52), 6.631 (0.59), 6.637 (0.94), 6.652 (0.93), 6.658 (0.46), 7.194 (1.26), 7.307 (2.24), 7.319 (2.28), 7.471 (2.87), 7.989 (2.88), 8.002 (2.59), 8.378 (3.48), 11.327 (1.31).<br>LC-MS (method 2): Rt = 1.03 min; m/z = 510 M + H)+ |

TABLE 4-continued

| Example | Structure Name | Analytical Data |
|---|---|---|
| 76 | 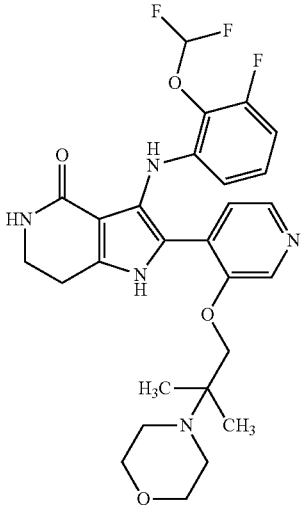

3-[2-(difluoromethoxy)-3-fluoroanilino]-2-{3-[2-methyl-2-(morpholin-4-yl)propoxy]pyridin-4-yl}-1,5,6,7-tetrahydro-4H-pyrrolo[3,2-c]pyridin-4-one | $^1$H-NMR (400 MHz, DMSO-d6) δ [ppm]: 1.153 (16.00), 2.073 (2.25), 2.331 (0.44), 2.518 (4.10), 2.523 (3.49), 2.539 (4.26), 2.673 (0.44), 2.865 (0.86), 2.883 (1.83), 2.900 (0.96), 3.407 (0.93), 3.412 (0.96), 3.423 (1.44), 3.429 (1.40), 3.440 (0.78), 3.446 (0.70), 3.520 (1.90), 3.532 (2.45), 3.541 (1.91), 4.170 (3.80), 6.084 (1.11), 6.105 (1.14), 6.548 (0.51), 6.552 (0.56), 6.569 (0.69), 6.573 (0.97), 6.577 (0.62), 6.594 (0.63), 6.598 (0.59), 6.820 (0.46), 6.835 (0.52), 6.841 (0.89), 6.856 (0.88), 6.861 (0.47), 6.877 (0.41), 7.017 (0.74), 7.169 (1.27), 7.202 (1.51), 7.383 (1.63), 7.396 (1.62), 7.424 (2.84), 7.995 (0.94), 8.008 (0.92), 8.386 (1.46), 11.417 (1.35).<br>LC-MS (method 2): Rt = 1.07 min; m/z = 546 (M + H)+ |

Example 77

3-(3-chloro-2-methylanilino)-2-(3-{[(2S)-1-methylpyrrolidin-2-yl]methoxy}pyridin-4-yl)-1,5,6,7-tetrahydro-4H-pyrrolo[3,2-c]pyridin-4-one

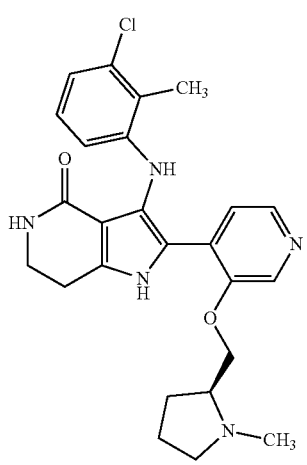 [SMILES: Cc1c(Cl)cccc1Nc1c(-c2ccncc2OC[C@@H]2CCCN2C)[nH]c2c1C(=O)NCC2]

To a solution of N-(3-chloro-2-methylphenyl)-4-{[(3-{[(2S)-1-methylpyrrolidin-2-yl]methoxy}pyridin-4-yl)methyl]amino}-2-oxo-1,2,5,6-tetrahydropyridine-3-carbothioamide (244 mg, 488 μmol) in 5.0 mL methanol was added trifluoroacetic acid (75 μl, 980 μmol) and stirred for 5 min at rt. Then meta-chloroperoxybenzoic acid (168 mg, 976 μmol) was added and the mixture was stirred for 6 h at 50° C. The reaction mixture was diluted with water and adjusted to pH 8 with sodium hydroxide (1M in water). The aqueous layer was extracted with ethyl acetate. The organic layer was filtered through a waterresistant filter, the filtrate was concentrated under reduced pressure and the residue was purified by preparative HPLC. The product fractions were combined and lyophilised to give 27.8 mg of the title compound (93% purity, 11% yield).

$^1$H-NMR (400 MHz, DMSO-d6) δ [ppm]: 1.232 (0.56), 1.722 (0.44), 1.739 (0.82), 1.758 (0.85), 1.779 (0.41), 1.946 (0.53), 1.966 (0.56), 2.317 (11.38), 2.327 (1.84), 2.332 (1.50), 2.335 (1.26), 2.345 (1.02), 2.371 (9.96), 2.387 (0.82), 2.518 (5.58), 2.523 (3.75), 2.539 (16.00), 2.567 (0.63), 2.660 (0.46), 2.664 (1.02), 2.669 (1.45), 2.673 (1.04), 2.678 (0.46), 2.786 (0.41), 2.803 (0.89), 2.819 (0.44), 2.857 (0.75), 2.874 (0.48), 3.195 (0.60), 3.419 (0.70), 3.430 (0.97), 3.436 (1.28), 3.452 (0.63), 4.171 (0.68), 4.180 (0.75), 4.197 (0.85), 4.206 (0.77), 4.497 (0.87), 4.501 (0.92), 4.523 (0.77), 4.527 (0.75), 6.207 (1.16), 6.210 (1.16), 6.226 (1.28), 6.230 (1.18), 6.743 (0.85), 6.747 (0.92), 6.763 (2.01), 6.767 (1.72), 6.786 (1.43), 6.805 (1.64), 6.826 (0.58), 7.181 (1.35), 7.235 (2.42), 7.247 (2.42), 7.397 (2.61), 7.936 (3.58), 7.949 (3.19), 8.418 (4.28), 12.111 (1.35).

LC-MS (method 2): Rt=1.18 min; m/z=466 (M+H)+

The examples in Table 5 were prepared analogous to the preparation of example 77 starting from the corresponding intermediates by reacting with the corresponding aldehydes.

TABLE 5

| Example | Structure Name | Analytical Data |
|---|---|---|
| 78 | 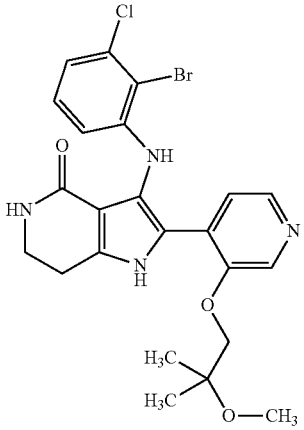 [SMILES: COC(C)(C)COc1cnccc1-c1[nH]c2c(c1Nc1cccc(Cl)c1Br)C(=O)NCC2]<br>3-(2-bromo-3-chloroanilino)-2-[3-(2-methoxy-2-methylpropoxy)pyridin-4-yl]-1,5,6,7-tetrahydro-4H-pyrrolo[3,2-c]pyridin-4-one | $^1$H-NMR (400 MHz, DMSO-d6) δ [ppm]: 1.263 (16.00), 2.518 (2.26), 2.523 (1.55), 2.539 (0.92), 2.831 (0.74). 2.848 (1.61), 2.865 (0.83), 3.234 (13.85), 3.413 (0.53), 3.418 (0.58). 3.429 (1.05), 3.436 (1.03), 3.446 (0.52), 3.452 (0.47), 4.170 (4.06), 6.271 (1.02), 6.275 (1.07), 6.291 (1.06), 6.295 (1.02), 6.881 (0.78), 6.884 (0.94), 6.900 (1.64), 6.904 (1.46), 6.936 (1.21), 6.956 (1.64), 6.976 (0.62), 7.181 (1.81), 7.194 (2.70), 7.573 (2.10), 8.016 (2.35), 8.029 (2.17), 8.423 (3.07), 11.262 (1.04).<br>LC-MS (method 1): Rt = 0.93 min; m/z = 519 (M + H)+ |
| 79 | 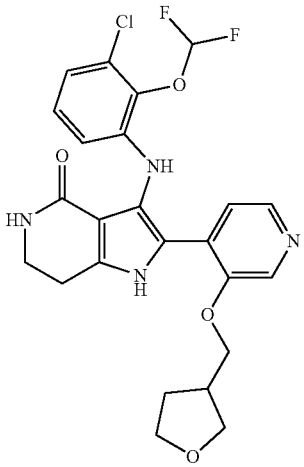 [SMILES: O=C1NCCc2[nH]c(-c3ccncc3OCC3CCOC3)c(Nc3cccc(Cl)c3OC(F)F)c21]<br>3-[3-chloro-2-(difluoromethoxy)anilino]-2-{3-[(oxolan-3-yl)methoxy]pyridin-4-yl}-1,5,6,7-tetrahydro-4H-pyrrolo[3,2-c]pyridin-4-one | $^1$H NMR (400 MHz, CDCl$_3$): □ [ppm] = 2.01-2.17 (m, 1H), 2.31-2.44 (m, 1H), 2.83-3.10 (m, 3H), 3.54-3.66 (m, 2H), 3.68-3.91 (m 2H), 4.17-4.30 (m, 2H), 4.33 (s, 2H), 5.17 (br s, 1H), 6.32-6.42 (m, 1H), 6.60-7.02 (m, 3H), 7.18 (s, 1H), 7.57 (d, 1H), 8.05 (d, 1H), 8.28 (s, 1H), 11.00 (br s, 1H).<br>UPLC4-MS (Method 11): R$_t$ = 3.28 min., 100%. MS (ESIpos): m/z = (M + H)$^+$ 505 |
| 80 | 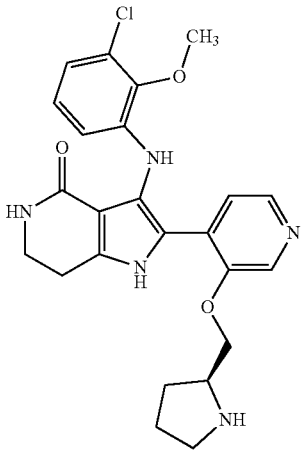 [SMILES: COc1c(Cl)cccc1Nc1c(-c2ccncc2OC[C@@H]2CCCN2)[nH]c2c1C(=O)NCC2]<br>3-(3-chloro-2-methoxyanilino)-2-(3-{[(2S)-pyrrolidin-2-yl]methoxy}pyridin-4-yl)-1,5,6,7-tetrahydro-4H-pyrrolo[3,2-c]pyridin-4-one | $^1$H-NMR (400 MHz, DMSO-d6) δ [ppm]: 1.683 (0.43), 1.768 (0.41), 1.780 (0.41), 1.853 (0.40), 1.904 (0.43), 2.518 (3.67), 2.523 (2.51), 2.792 (0.48), 2.801 (0.86), 2.820 (0.92), 2.842 (1.10), 2.860 (0.51), 2.881 (0.46), 2.896 (1.10), 2.912 (0.56), 2.936 (0.73), 2.952 (0.65), 2.964 (0.44), 3.397 (0.84), 3.403 (0.87), 3.418 (1.46), 3.431 (0.76), 3.437 (0.70), 3.604 (0.41), 3.655 (0.60), 3.871 (0.51), 3.898 (16.00), 3.913 (0.52), 4.353 (0.83), 4.362 (0.87), 4.377 (0.83), 4.387 (0.73), 6.164 (1.37), 6.174 (1.21), 6.178 (1.38), 6.188 (1.38), 6.683 (0.49), 6.693 (5.70), 6.703 (2.84), 6.707 (2.59), 7.140 (1.54), 7.270 (2.56), 7.283 (2.61), 7.577 (3.37), 7.970 (3.18), 7.983 (2.81), 8.442 (4.73).<br>LC-MS (method 1): Rt = 0.64 min; m/z = 468 (M + H)+ |

| Example | Structure Name | Analytical Data |
|---|---|---|
| 81 | 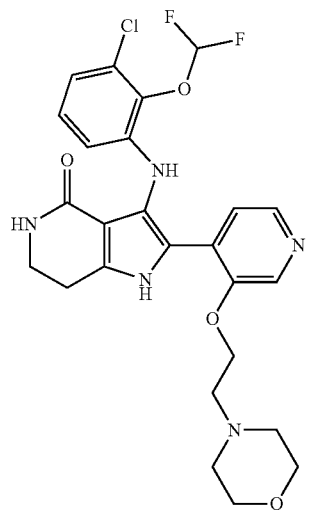 [SMILES: O=C1NCCc2[nH]c(-c3ccncc3OCCN3CCOCC3)c(Nc3cccc(Cl)c3OC(F)F)c21]<br>3-[3-chloro-2-(difluoromethoxy)anilino]-2-{3-[2-(morpholin-4-yl)ethoxy]pyridin-4-yl}-1,5,6,7-tetrahydro-4H-pyrrolo[3,2-c]pyridin-4-one | $^1$H NMR (400 MHz, CDCl$_3$): □ [ppm] = 2.54 (t, 4H), 2.86 (t, 2H), 2.92 (t, 2H), 3.53-3.60 (m, 2H), 3.71 (t, 4H), 4.32 (t, 2H), 5.22 (br s, 1H), 6.23-6.28 (m, 1H), 6.47-6.89 (m, 3H), 7.17 (s, 1H), 7.36 (d, 1H), 7.96 (d, 1H), 8.22 (s, 1H), 10.80 (s, 1H).<br>UPLC4-MS (Method 11): R$_t$ = 1.88 min., 100%. MS (ESIpos): m/z = (M + H)$^+$ 534 |
| 82 | 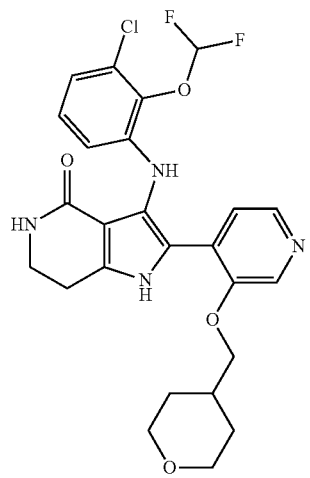 [SMILES: O=C1NCCc2[nH]c(-c3ccncc3OCC3CCOCC3)c(Nc3cccc(Cl)c3OC(F)F)c21]<br>3-[3-chloro-2-(difluoromethoxy)anilino]-2-{3-[(oxan-4-yl)-methoxy]pyridin-4-yl}-1,5,6,7-tetrahydro-4H-pyrrolo[3,2-c]pyridin-4-one | $^1$H NMR (400 MHz, CDCl$_3$): □ [ppm] = 1.60-1.68 (m, 2H), 1.75-1.86 (m, 2H), 2.19-2.38 (m, 1H), 2.92-3.00 (m, 2H), 3.45-3.57 (t, 2H), 3.62-3.70 (m, 2H), 4.07-4.16 (m, 2H), 4.19 (d, 2H), 5.32 (br s, 1H), 6.32-6.40 (m, 1H), 6.57-6.99 (m, 3H), 7.22 (s, 1H), 7.43 (d, 1H), 8.08 (br s, 1H), 8.36 (br s, 1H), 9.85 (br s, 1H).<br>UPLC4-MS (Method 11): R$_t$ = 3.29 min., 100%. MS (ESIpos): m/z = (M + H)$^+$ 519 |

Example 83

3-[2-(difluoromethoxy)-3-fluoroanilino]-2-[3-(2-methoxy-2-methylpropoxy)pyridin-4-yl]-1,5,6,7-tetrahydro-4H-pyrrolo[3,2-c]pyridin-4-one-hydrogen chloride (1/1) Salt

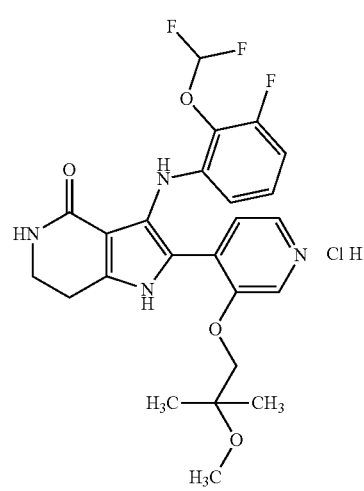

The hydrogen chloride salt of example 27 was prepared by treatment of the free base (example 27) with aqueous hydrogen chloride followed by lyophilization of the frozen mixture.

$^{1}$H-NMR (500 MHz, DMSO-d6) δ [ppm]: 0.000 (3.64), 1.294 (16.00), 2.518 (1.39), 2.522 (1.31), 2.525 (0.99), 2.911 (0.82), 2.924 (1.75), 2.938 (0.90), 3.448 (0.66), 3.461 (1.21), 3.475 (0.58), 4.334 (4.09), 6.195 (0.92), 6.213 (0.94), 6.710 (0.42), 6.712 (0.43), 6.726 (0.56), 6.729 (0.82), 6.746 (0.50), 6.749 (0.47), 6.925 (0.43), 6.930 (0.74), 6.942 (0.73), 7.086 (0.63), 7.233 (1.25), 7.381 (0.59), 7.418 (0.63), 7.664 (1.69), 7.676 (1.73), 7.981 (1.70), 8.268 (1.33), 8.281 (1.27), 8.660 (2.37), 11.410 (1.22).

Example 84

3-(3-fluoro-2-methoxyanilino)-2-{3-[2-(morpholin-4-yl)ethoxy]pyridin-4-yl}-1,5,6,7-tetrahydro-4H-pyrrolo[3,2-c]pyridin-4-one

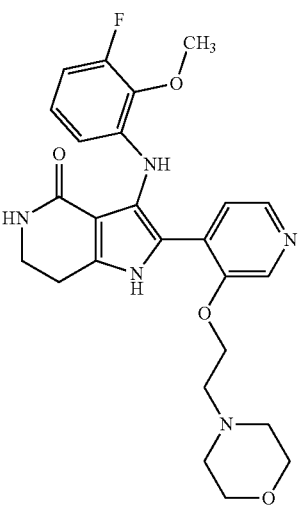 [SMILES: COc1c(F)cccc1Nc1c(-c2ccncc2OCCN2CCOCC2)[nH]c2c1C(=O)NCC2]

A solution of 3-(3-fluoro-2-methoxyanilino)-2-(3-hydroxypyridin-4-yl)-1,5,6,7-tetrahydro-4H-pyrrolo[3,2-c]pyridin-4-one (intermediate 84-1, 150 mg, 407 μmol) in 2 mL dimethyl formamide was treated with 4-(2-bromoethyl)morpholine (238 mg, 1.22 mmol) and potassium carbonate (169 mg, 1.22 mmol) and the mixture was heated overnight at 100° C. The reaction mixture was filtered and the filtrate purified by preparative HPLC to give 22.5 mg of the title compound (99% purity, 11% yield).

$^{1}$H-NMR (400 MHz, DMSO-d6) δ [ppm]: 2.085 (0.62), 2.331 (1.10), 2.337 (0.57), 2.518 (13.66), 2.523 (11.14), 2.674 (1.14), 2.678 (0.60), 2.791 (1.36), 2.869 (1.57), 2.886 (3.34), 2.903 (1.86), 3.402 (1.45), 3.409 (1.53), 3.419 (2.46), 3.425 (2.43), 3.436 (1.38), 3.442 (1.26), 3.587 (4.01), 3.907 (16.00), 4.325 (1.43), 4.339 (2.74), 4.353 (1.55), 5.963 (1.86), 5.966 (1.31), 5.984 (2.00), 6.456 (0.88), 6.460 (0.93), 6.477 (1.26), 6.481 (1.29), 6.483 (1.17), 6.487 (1.07), 6.504 (1.24), 6.508 (1.19), 6.590 (0.88), 6.605 (1.03), 6.611 (1.62), 6.626 (1.62), 6.631 (0.88), 6.647 (0.74), 7.165 (2.17), 7.301 (3.48), 7.314 (3.60), 7.524 (4.79), 8.009 (2.62), 8.021 (2.58), 8.400 (5.37), 11.142 (2.27).

LC-MS (method 2): Rt=0.94 min; m/z=482 (M+H)+

The examples in Table 6 were prepared analogous to the preparation of example 84 starting from the corresponding intermediates by reacting with the corresponding aldehydes.

TABLE 6
| Example | Structure Name | Analytical Data |
|---|---|---|
| 85 | 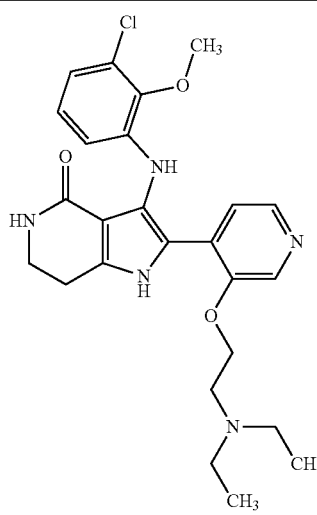<br>2-{3-[2-(diethylamino)ethoxy]pyridin-4-yl}-3-(3-fluoro-2-methoxyanilino)-1,5,6,7-tetrahydro-4H-pyrrolo[3,2-c]pyridin-4-one | $^1$H-NMR (400 MHz, DMSO-d6) δ [ppm]: 0.780 (0.42), 0.788 (0.62), 0.806 (0.85), 0.824 (0.71), 0.833 (0.57), 0.844 (0.71), 0.851 (0.59), 0.856 (0.59), 0.861 (0.54), 0.889 (0.42), 0.909 (0.62), 0.917 (0.57), 0.928 (1.02), 0.935 (1.50), 0.946 (3.59), 0.964 (11.11), 0.982 (16.00), 1.000 (6.19), 1.186 (0.62), 1.231 (0.54), 2.084 (4.01), 2.194 (0.45), 2.318 (0.65), 2.322 (1.33), 2.326 (1.75), 2.331 (1.30), 2.336 (0.68), 2.403 (0.51), 2.414 (0.54), 2.430 (0.68), 2.445 (0.88), 2.518 (7.94), 2.523 (5.43), 2.616 (1.70), 2.634 (5.31), 2.652 (5.29), 2.665 (2.09), 2.669 (3.39), 2.673 (2.12), 2.747 (1.07), 2.813 (1.64), 2.830 (4.01), 2.834 (3.56), 2.848 (2.94), 3.088 (1.95), 3.391 (1.41), 3.402 (1.84), 3.407 (1.84), 3.419 (2.26), 3.424 (2.15), 3.435 (1.13), 3.442 (1.02), 3.920 (13.94), 3.941 (1.16), 3.951 (0.42), 4.349 (1.44), 4.362 (2.66), 4.375 (1.47), 5.996 (1.67), 6.017 (1.72), 6.482 (0.79), 6.485 (0.82), 6.502 (1.10), 6.506 (1.13), 6.509 (0.96), 6.513 (0.85), 6.530 (1.02), 6.533 (0.96), 6.618 (0.82), 6.633 (0.93), 6.638 (1.41), 6.654 (1.39), 6.659 (0.73), 6.675 (0.62), 7.181 (1.81), 7.293 (3.00), 7.306 (3.05), 7.588 (4.07), 7.975 (3.79), 7.988 (3.56), 8.425 (5.00), 8.550 (1.41), 11.757 (1.58).<br>LC-MS (method 2): Rt = 0.99 min; m/z = 468 (M + H)+ |
| 86 | 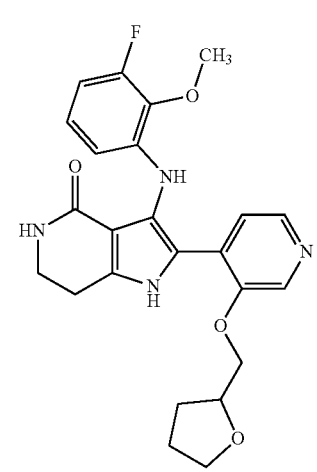 [SMILES: COc1c(F)cccc1Nc1c(-c2ccncc2OCC2CCCO2)[nH]c2c1C(=O)NCC2]<br>3-(3-fluoro-2-methoxyanilino)-2-{3-[(oxolan-2-yl)methoxy]pyridin-4-yl}-1,5,6,7-tetrahydro-4H-pyrrolo[3,2-c]pyridin-4-one | $^1$H-NMR (400 MHz, DMSO-d6) δ [ppm]: 1.232 (0.77), 1.649 (0.50), 1.661 (0.46), 1.669 (0.64), 1.678 (0.72), 1.682 (0.60), 1.700 (0.83), 1.717 (0.43), 1.849 (0.43), 1.856 (0.48), 1.873 (1.08), 1.886 (1.80), 1.904 (1.47), 1.909 (0.91), 1.921 (0.50), 1.925 (0.46), 1.982 (0.44), 1.988 (0.52), 2.000 (0.58), 2.012 (0.75), 2.031 (0.68), 2.045 (0.54), 2.331 (0.83), 2.518 (4.57), 2.523 (2.90), 2.673 (0.87), 2.816 (1.06), 2.820 (1.04), 2.832 (2.24), 2.838 (2.11), 2.850 (1.14), 2.854 (1.12), 3.396 (1.12), 3.402 (1.20), 3.413 (2.26), 3.419 (2.24), 3.430 (1.03), 3.436 (0.95), 3.747 (0.58), 3.764 (1.16), 3.767 (1.20), 3.783 (1.72), 3.801 (0.89), 3.833 (0.93), 3.849 (1.99), 3.866 (1.18), 3.870 (1.33), 3.886 (0.75), 3.900 (16.00), 4.004 (0.93), 4.022 (1.47), 4.028 (1.39), 4.047 (1.16), 4.303 (0.44), 4.313 (0.83), 4.321 (1.16), 4.330 (0.70), 4.339 (1.18), 4.353 (2.21), 4.360 (0.87), 4.377 (1.45), 4.385 (1.10), 6.011 (1.88), 6.031 (1.92), 6.458 (0.93), 6.462 (0.91), 6.479 (1.26), 6.483 (1.26), 6.485 (1.10), 6.489 (0.95), 6.506 (1.16), 6.510 (1.04), 6.608 (0.87), 6.623 (1.01), 6.628 (1.57), 6.644 (1.55), 6.649 (0.75), 6.664 (0.68), 7.138 (2.07), 7.269 (3.48), 7.282 (3.52), 7.481 (4.59), 8.019 (4.86), 8.032 (4.47), 8.419 (6.31), 11.236 (2.13).<br>LC-MS (method 2): Rt = 1.02 min; m/z = 453 (M + H)+ |

TABLE 6-continued

| Example | Structure Name | Analytical Data |
|---|---|---|
| 87 | 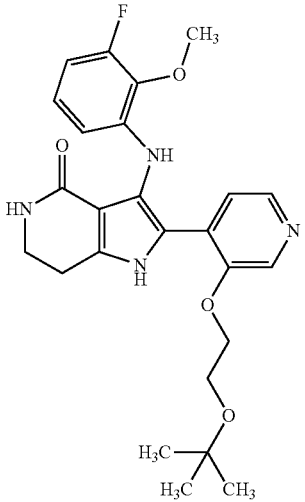<br>2-[3-(2-tert-butoxyethoxy)pyridin-4-yl]-3-(3-chloro-2-methoxyanilino)-1,5,6,7-tetrahydro-4H-pyrrolo[3,2-c]pyridin-4-one | $^1$H-NMR (400 MHz, DMSO-d6) δ [ppm]: 0.983 (0.44), 1.030 (0.40), 1.047 (0.44), 1.054 (0.44), 1.094 (1.13), 1.112 (12.89), 1.146 (16.00), 1.162 (0.93), 2.447 (0.42), 2.518 (1.11), 2.523 (0.73), 2.83 (0.78), 2.855 (0.45), 3.387 (0.51), 3.403 (0.65), 3.409 (0.62), 3.510 (0.45), 3.672 (2.93), 3.711 (0.56), 3.720 (0.69), 3.735 (0.53), 3.853 (0.60), 3.862 (5.49), 3.866 (2.20), 4.245 (0.49), 4.258 (0.71), 4.268 (0.56), 6.126 (0.47), 6.137 (0.71), 6.150 (0.53), 6.642 (1.22), 6.645 (1.33), 6.656 (1.65), 7.063 (0.65), 7.082 (0.44), 7.116 (0.60), 7.122 (0.58), 7.278 (0.98), 7.291 (0.78), 7.467 (1.09), 8.018 (0.85), 8.030 (0.82), 8.157 (0.42), 8.244 (0.64), 8.389 (1.15).<br>LC-MS (method 2): Rt = 1.03 min; m/z = 485 (M + H)+ |

Example 88

3-(3-fluoro-2-methoxyanilino)-2-{3-[(oxolan-2-yl)methoxy]pyridin-4-yl}-1,5,6,7-tetrahydro-4H-pyrrolo[3,2-c]pyridin-4-one (enantiomer 1)

37 mg of the racemic title compound (example 86) was separated into enantiomers by preparative chiral HPLC (method 8) to give enantiomer 1 (16.0 mg, example 88) and its enantiomer 2 (16.0 mg, example 89).

Analytical chiral HPLC (method 9): $R_t$=2.03 min

LC.MS (method 10): R, =0.74 min; MS (ESIpos): m/z=453 [M+H]$^+$ optical rotation: $[\alpha]_D^{20}$=0.7°+/−2.06° (c=1.00; methanol)

$^1$H-NMR (400 MHz, DMSO-d6) δ [ppm]: 1.232 (1.61), 1.649 (0.49), 1.662 (0.45), 1.669 (0.64), 1.678 (0.73), 1.683 (0.60), 1.695 (0.49), 1.700 (0.84), 1.717 (0.47), 1.857 (0.45), 1.866 (0.99), 1.872 (1.07), 1.887 (1.80), 1.903 (1.50), 1.908 (0.92), 1.921 (0.54), 1.925 (0.52), 1.983 (0.45), 2.000 (0.60), 2.012 (0.75), 2.027 (0.58), 2.031 (0.69), 2.045 (0.56), 2.336 (0.41), 2.518 (4.81), 2.523 (3.37), 2.816 (1.03), 2.820 (1.03), 2.833 (2.26), 2.838 (2.13), 2.850 (1.14), 2.854 (1.14), 3.396 (1.12), 3.403 (1.20), 3.413 (2.30), 3.420 (2.28), 3.430 (1.03), 3.437 (0.97), 3.747 (0.60), 3.764 (1.16), 3.767 (1.22), 3.784 (1.76), 3.802 (0.90), 3.833 (0.97), 3.850 (2.08), 3.866 (1.46), 3.870 (1.40), 3.886 (0.75), 3.900 (16.00), 4.004 (0.97), 4.022 (1.48), 4.028 (1.44), 4.047 (1.16), 4.303 (0.41), 4.313 (0.82), 4.321 (1.12), 4.331 (0.67), 4.339 (1.18), 4.354 (2.23), 4.361 (0.86), 4.377 (1.48), 4.385 (1.12), 6.011 (1.89), 6.032 (1.93), 6.458 (0.90), 6.462 (0.94), 6.479 (1.27), 6.483 (1.29), 6.485 (1.07), 6.489 (0.99), 6.506 (1.20), 6.510 (1.12), 6.608 (0.90), 6.623 (1.01), 6.628 (1.63), 6.644 (1.59), 6.649 (0.79), 6.665 (0.71), 7.138 (2.08), 7.270 (2.21), 7.282 (2.26), 7.481 (4.75), 8.020 (1.35), 8.033 (1.31), 8.420 (2.15), 11.235 (2.15).

Example 89

3-(3-fluoro-2-methoxyanilino)-2-{3-[(oxolan-2-yl)methoxy]pyridin-4-yl}-1,5,6,7-tetrahydro-4H-pyrrolo[3,2-c]pyridin-4-one (enantiomer 2)

Analytical chiral HPLC (Method 9): $R_t$=4.04 min.

LC.MS (method 10): R, =0.74 min; MS (ESIpos): m/z=453 [M+H]$^+$ optical rotation: $[\alpha]_D^{20}$=−1.1°+/−2.17° (c=1.00; methanol)

$^1$H-NMR (400 MHz, DMSO-d6) δ [ppm]: 1.155 (0.64), 1.232 (1.55), 1.650 (0.51), 1.661 (0.49), 1.669 (0.66), 1.678 (0.75), 1.682 (0.62), 1.695 (0.53), 1.700 (0.84), 1.717 (0.44), 1.849 (0.46), 1.857 (0.49), 1.873 (1.11), 1.886 (1.84), 1.904 (1.50), 1.921 (0.53), 1.925 (0.49), 1.982 (0.46), 2.000 (0.62), 2.012 (0.77), 2.031 (0.71), 2.045 (0.58), 2.331 (0.97), 2.336 (0.44), 2.518 (5.58), 2.523 (3.43), 2.673 (1.00), 2.678 (0.44), 2.816 (1.06), 2.820 (1.06), 2.832 (2.24), 2.838 (2.10), 2.850 (1.17), 2.854 (1.13), 3.396 (1.15), 3.402 (1.24), 3.413 (2.30), 3.419 (2.28), 3.430 (1.06), 3.436 (1.00), 3.747 (0.60), 3.764 (1.17), 3.767 (1.22), 3.783 (1.70), 3.801 (0.89), 3.833 (0.95), 3.849 (2.01), 3.866 (1.24), 3.870 (1.35), 3.886 (0.75), 3.900 (16.00), 4.004 (0.93), 4.022 (1.44), 4.028 (1.37), 4.047 (1.15), 4.303 (0.44), 4.313 (0.84), 4.321 (1.17), 4.330 (0.71), 4.339 (1.20), 4.353 (2.21), 4.360 (0.86), 4.377 (1.42), 4.385 (1.08), 6.011 (1.86), 6.031 (1.95), 6.458 (0.91), 6.462 (0.93), 6.479 (1.24), 6.483 (1.28), 6.485 (1.11), 6.489 (0.97), 6.506 (1.15), 6.510 (1.06), 6.608 (0.86), 6.623 (1.02), 6.628 (1.55), 6.644 (1.55), 6.649 (0.77), 6.664 (0.66), 7.138 (2.06), 7.269 (2.17), 7.282 (2.21), 7.481 (4.54), 8.019 (1.35), 8.032 (1.31), 8.420 (2.15), 11.236 (2.12).

Example 90

3-(3-fluoro-2-methoxyanilino)-2-(3-{[1-methylpiperidin-2-yl]methoxy}pyridin-4-yl)-1,5,6,7-tetrahydro-4H-pyrrolo[3,2-c]pyridin-4-one

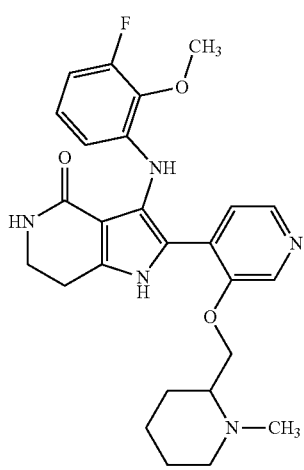 [SMILES: COc1c(F)cccc1Nc1c(-c2ccncc2OCC2CCCCN2C)[nH]c2c1C(=O)NCC2]

To a solution of 3-(3-fluoro-2-methoxyanilino)-2-(3-hydroxypyridin-4-yl)-1,5,6,7-tetrahydro-4H-pyrrolo[3,2-c]pyridin-4-one (intermediate 84-1, 163 mg, 441 µmol) in 1 ml. DMF, 2-(bromomethyl)-1-methylpiperidine-hydrogen bromide (1/1) (181 mg, 662 µmol) and potassium carbonate (183 mg, 1.323 mmol) were added and heated for 2.5 h at 60° C. The solvent was evaporated and the residue was purified by preparative HPLC to give 6.2 mg of the title compound (90% purity, 3% yield).

LC-MS (method 2): R, =0.97 min; MS (ESIpos): m/z=480 [M+H]$^+$ $^1$H-NMR (500 MHz, DMSO-d6) δ [ppm]: –0.007 (1.96), 0.006 (1.81), 1.361 (0.76), 1.538 (0.80), 1.564 (0.76), 1.674 (1.81), 1.756 (0.87), 1.786 (0.73), 2.127 (0.94), 2.164 (0.87), 2.235 (12.41), 2.261 (1.05), 2.274 (0.73), 2.287 (1.23), 2.307 (0.83), 2.323 (1.67), 2.361 (1.89), 2.365 (2.39), 2.368 (1.89), 2.372 (1.27), 2.518 (6.86), 2.522 (6.24), 2.525 (4.90), 2.543 (0.69), 2.631 (0.83), 2.635 (1.71), 2.638 (2.25), 2.642 (1.67), 2.645 (0.80), 2.811 (0.80), 2.825 (1.41), 2.837 (1.16), 2.851 (1.20), 2.863 (0.83), 3.036 (0.91), 3.060 (0.73), 3.246 (0.80), 3.425 (0.80), 3.439 (1.52), 3.444 (1.27), 3.452 (1.41), 3.946 (16.00), 4.384 (1.89), 4.395 (1.52), 4.402 (1.52), 6.024 (1.71), 6.041 (1.74), 6.517 (0.76), 6.519 (0.87), 6.533 (1.05), 6.536 (1.12), 6.541 (0.91), 6.555 (0.98), 6.558 (0.94), 6.661 (0.80), 6.673 (0.87), 6.677 (1.38), 6.689 (1.34), 6.694 (0.69), 7.177 (2.14), 7.308 (3.27), 7.319 (3.27), 7.621 (3.99), 7.951 (4.17), 7.962 (4.03), 8.313 (3.30), 8.373 (5.66), 8.566 (1.31), 12.255 (1.85).

Example 91

2-[3-(2-tert-butoxyethoxy)pyridin-4-yl]-3-(3-fluoro-2-methoxyanilino)-1,5,6,7-tetrahydro-4H-pyrrolo[3,2-c]pyridin-4-one

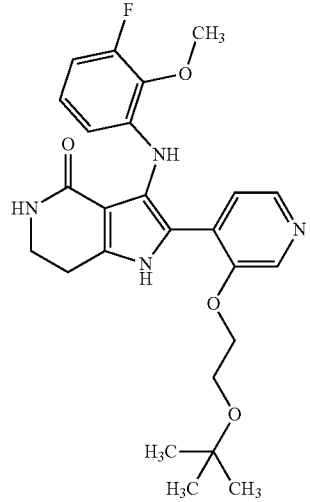 [SMILES: COc1c(F)cccc1Nc1c(-c2ccncc2OCCOC(C)(C)C)[nH]c2c1C(=O)NCC2]

3-(3-fluoro-2-methoxyanilino)-2-(3-hydroxypyridin-4-yl)-1,5,6,7-tetrahydro-4H-pyrrolo[3,2-c]pyridin-4-one (Intermediate 84-1, 88.2 mg, 239 µmol) and 2-tributylphosphoranylidene)acetonitrile (82 µl, 310 µmol) were solved in 4.0 ml. toluene, 2-tert-butoxyethan-1-ol (38 µl, 290 µmol) was added and the mixture was stirred 2.5 h at 120° C. The reaction mixture was cooled down to rt and concentrated under reduced pressure. The residue was purified by preparative HPLC to give 38.8 mg of the yellow title compound (purity, yield).

$^1$H-NMR (400 MHz, DMSO-d6) δ [ppm]: 0.861 (0.75), 0.879 (1.91), 0.896 (1.01), 1.149 (16.00), 1.359 (0.46), 1.374 (0.45), 2.819 (0.46), 2.836 (0.99), 2.853 (0.52), 3.403 (0.66), 3.408 (0.67), 3.718 (0.56), 3.729 (0.85), 3.742 (0.64), 3.894 (4.70), 4.238 (0.60), 4.251 (0.84), 4.262 (0.58), 5.982 (0.52), 6.003 (0.55), 6.596 (0.42), 6.611 (0.40), 7.125 (0.63), 7.283 (0.89), 7.295 (0.90), 7.473 (1.30), 8.017 (0.92), 8.029 (0.89), 8.384 (1.51), 10.945 (0.69).

LC-MS (method 2): R, =1.10 min; MS (ESIpos): m/z=469 [M+H]$^+$

Example 92

3-(3-fluoro-2-methoxyanilino)-2-{3-[(2R)-2-methoxypropoxy]pyridin-4-yl}-1,5,6,7-tetrahydro-4H-pyrrolo[3,2-c]pyridin-4-one

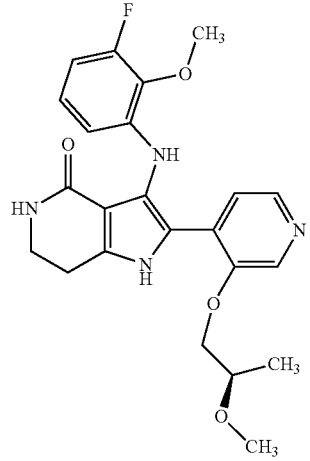 [SMILES: COc1c(F)cccc1Nc1c(-c2ccncc2OC[C@@H](C)OC)[nH]c2c1C(=O)NCC2]

3-(3-fluoro-2-methoxyanilino)-2-(3-hydroxypyridin-4-yl)-1,5,6,7-tetrahydro-4H-pyrrolo[3,2-c]pyridin-4-one (Intermediate 84-1, 155 mg, 421 µmol) and (tributyl-lambda⁵-phosphanylidene)acetonitrile (200 µl, 760 µmol) were solved in 5.0 ml. 1,4-dioxane, (2R)-2-methoxypropan-1-ol [CAS 6131-59-5] (56.9 mg, 631 µmol) was added and the mixture was stirred for 1 h at 150° C. in the microwave. The reaction mixture was cooled down to rt and concentrated under reduced pressure. The residue was purified by preparative HPLC to give 34.0 mg of the title compound (95% purity, 17% yield).

¹H-NMR (400 MHz, DMSO-d6) δ [ppm]: 1.194 (9.65), 1.209 (9.72), 2.518 (3.12), 2.522 (2.02), 2.539 (0.66), 2.830 (0.99), 2.834 (1.00), 2.846 (2.23), 2.852 (2.20), 2.864 (1.17), 2.869 (1.17), 3.330 (4.42), 3.353 (1.93), 3.397 (1.31), 3.404 (1.34), 3.415 (2.46), 3.421 (2.40), 3.432 (1.14), 3.438 (1.06), 3.820 (0.68), 3.829 (0.80), 3.836 (1.09), 3.845 (1.17), 3.852 (0.77), 3.861 (0.77), 3.905 (16.00), 4.091 (1.30), 4.107 (1.23), 4.117 (1.70), 4.133 (1.53), 4.240 (1.58), 4.249 (1.62), 4.266 (1.21), 4.275 (1.13), 5.997 (1.90), 6.017 (1.95), 6.464 (0.92), 6.468 (0.93), 6.485 (1.27), 6.488 (1.27), 6.492 (1.07), 6.495 (0.98), 6.513 (1.21), 6.516 (1.12), 6.610 (0.92), 6.625 (1.02), 6.630 (1.66), 6.646 (1.63), 6.651 (0.80), 6.666 (0.71), 7.146 (2.09), 7.281 (3.24), 7.294 (3.26), 7.513 (4.80), 8.020 (2.37), 8.033 (2.22), 8.161 (1.55), 8.407 (3.61), 11.074 (2.12).

LC-MS (method 1): $R_t$=0.78 min; MS (ESIpos): m/z=441 [M+H]⁺

Example 93

3-(3-fluoro-2-methoxyanilino)-2-{3-[(1-phenylpropan-2-yl)oxy]pyridin-4-yl}-1,5,6,7-tetrahydro-4H-pyrrolo[3,2-c]pyridin-4-one

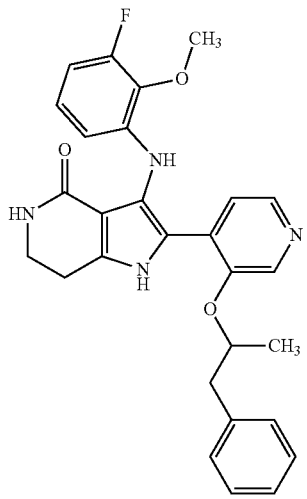 [SMILES: COc1c(F)cccc1Nc1c(-c2ccncc2OC(C)Cc2ccccc2)[nH]c2c1C(=O)NCC2]

3-(3-fluoro-2-methoxyanilino)-2-(3-hydroxypyridin-4-yl)-1,5,6,7-tetrahydro-4H-pyrrolo[3,2-c]pyridin-4-one (intermediate 84-1, 157 mg, 425 µmol) and 2-(tributylphosphoranylidene) acetonitrile (330 µl, 1.3 mmol) were solved in 4.0 ml. 1,4-dioxane under argon atmosphere. 1-phenylpropan-2-ol (116 mg, 851 µmol) were added and stirred overnight at 80° C. The reaction mixture was cooled down to rt and concentrated under reduced pressure. The residue was purified by preparative HPLC to give 16.5 mg of the title compound (95% purity, 8% yield).

¹H-NMR (400 MHz, DMSO-d6) δ [ppm]: 1.008 (0.74), 1.023 (0.69), 1.232 (0.61), 1.259 (8.00), 1.273 (7.82), 1.654 (0.61), 2.332 (1.12), 2.337 (0.48), 2.518 (5.92), 2.523 (3.96), 2.674 (1.12), 2.679 (0.56), 2.823 (0.97), 2.838 (1.09), 2.858 (1.85), 2.861 (1.80), 2.873 (2.01), 2.878 (3.10), 2.896 (1.75), 2.910 (0.56), 2.921 (0.51), 3.069 (1.14), 3.086 (1.19), 3.103 (0.99), 3.120 (0.97), 3.415 (1.12), 3.422 (1.22), 3.432 (2.18), 3.439 (2.23), 3.450 (1.02), 3.456 (0.91), 3.870 (16.00), 4.756 (0.58), 4.772 (1.22), 4.787 (1.22), 4.802 (0.58), 5.878 (1.80), 5.899 (1.88), 6.389 (0.76), 6.392 (0.86), 6.409 (1.37), 6.413 (1.35), 6.420 (0.89), 6.437 (1.32), 6.441 (1.22), 6.473 (1.02), 6.488 (1.12), 6.494 (1.60), 6.509 (1.55), 6.514 (0.79), 6.530 (0.61), 7.101 (2.16), 7.135 (0.69), 7.143 (0.63), 7.150 (1.19), 7.155 (0.99), 7.159 (0.81), 7.166 (1.27), 7.171 (1.40), 7.185 (1.65), 7.189 (1.19), 7.199 (15.29), 7.206 (4.11), 7.212 (2.97), 7.214 (3.05), 7.232 (0.61), 7.235 (0.43), 7.277 (3.63), 7.289 (3.63), 7.399 (4.88), 7.998 (4.22), 8.010 (3.73), 8.153 (1.19), 8.325 (5.13), 10.977 (2.36).

LC-MS (method 2): $R_t$=1.17 min; MS (ESIpos): m/z=487 [M+H]⁺

Example 94

2-fluoro-6-({2-[3-(2-methoxy-2-methylpropoxy)pyridin-4-yl]-4-oxo-4,5,6,7-tetrahydro-1H-pyrrolo[3,2-c]pyridin-3-yl}amino)benzonitrile

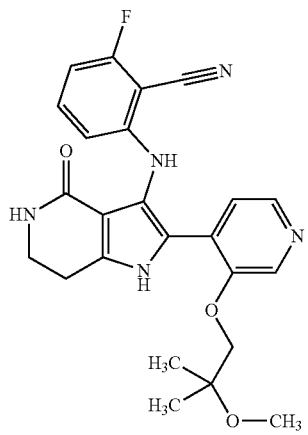 [SMILES: COC(C)(C)COc1cnccc1-c1[nH]c2c(c1Nc1cccc(F)c1C#N)C(=O)NCC2]

3-(2-bromo-3-fluoroanilino)-2-[3-(2-methoxy-2-methylpropoxy)pyridin-4-yl]-1,5,6,7-tetrahydro-4H-pyrrolo[3,2-c]pyridin-4-one (example 37, 87.0 mg, 173 µmol), palladium (pi-cinnamyl) chloride dimer (4.48 mg, 8.64 µmol) and Xphos (20.6 mg, 43.2 µmol) were solubilised in 1.6 ml. isopropanol, N,N-diisopropylethylamine (60 µl, 350 µmol) was added and the mixture was degassed with argon and heated up to 80° C. Then a solution of 2-hydroxy-2-methylpropanenitrile (70 µl, 760 µmol) in 990 µL iso-propanol was added carefully under argon and the mixture was stirred 2.5 h at 80° C. The reaction mixture was quenched with a saturated aqueous solution sodium bicarbonate and stirred for several minutes. The aqueous phase was extracted with dichloromethane three times. The combined organic layers were filtered using a waterresistant filter and the filtrate was concentrated under reduced pressure. The residue was purified by preparative HPLC to give 3.4 mg of the title compound (95% purity, 4% yield).

¹H-NMR (400 MHz, DMSO-d6) δ [ppm]: 1.107 (10.64), 1.263 (16.00), 2.326 (0.47), 2.522 (1.58), 2.669 (0.47), 2.829 (0.84), 2.846 (1.79), 2.863 (0.93), 3.233 (11.99), 3.413 (0.68), 3.419 (0.74), 3.429 (1.24), 3.435 (1.21), 3.447 (0.63), 3.452 (0.56), 4.165 (4.38), 4.194 (0.98), 6.152 (1.02), 6.173 (1.05), 6.605 (0.51), 6.608 (0.51), 6.626 (1.00), 6.629 (0.98), 6.647 (0.56), 6.650 (0.54), 6.927 (0.42), 6.944 (0.54), 6.948 (0.82), 6.965 (0.81), 6.968 (0.49), 7.179 (1.82), 7.191 (2.75), 7.542 (2.30), 8.006 (1.73), 8.018 (1.63), 8.417 (2.66), 11.251 (1.17).

LC-MS (method 1): $R_t$=0.93 min; MS (ESIpos): m/z=450 [M+H]$^+$

Example 95

3-(3-chloro-2-methoxyanilino)-2-(3-{[(2S)-1-(2,2,2-trifluoroethyl)pyrrolidin-2-yl]methoxy}pyridin-4-yl)-1,5,6,7-tetrahydro-4H-pyrrolo[3,2-c]pyridin-4-one

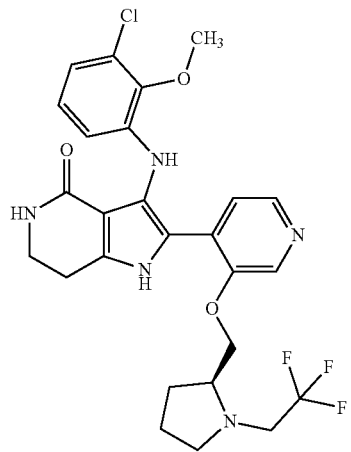 [SMILES: COc1c(Cl)cccc1Nc1c(-c2ccncc2OC[C@@H]2CCCN2CC(F)(F)F)[nH]c2c1C(=O)NCC2]

A solution of 3-(3-chloro-2-methoxyanilino)-2-(3-{[(2S)-pyrrolidin-2-yl]methoxy}pyridin-4-yl)-1,5,6,7-tetrahydro-4H-pyrrolo[3,2-c]pyridin-4-one (example 80, 36.0 mg, 76.9 µmol) in 2 mL anhydrous DMF was treated with triethylamine (64.3 µl, 0.462 mmol) followed by 2,2,2-trifluoroethyl trifluoromethanesulfonate (49.9 µl, 0.346 mmol) and the mixture was stirred at rt overnight. The reaction mixture was filtrated and the filtrate was purified by preparative. HPLC The product rich fractions pooled and acetonitrile was evaporated off. The water phase was extracted with ethyl acetate two times. The combined organic phases were washed with brine, dried, using a waterresistant filter and the filtrate was concentrated under reduced pressure to give 7.9 mg of the title compound (95% purity, 18% yield).

$^1$H-NMR (400 MHz, DMSO-d6) δ [ppm]: 1.154 (5.15), 1.172 (9.05), 1.189 (4.35), 1.231 (0.97), 1.759 (0.66), 1.771 (0.81), 1.781 (0.69), 1.790 (0.78), 1.814 (0.41), 1.824 (0.42), 1.975 (0.45), 1.987 (16.00), 2.518 (0.95), 2.522 (0.58), 2.588 (0.45), 2.606 (0.50), 2.766 (0.83), 2.783 (1.61), 2.800 (0.92), 3.151 (0.71), 3.164 (0.49), 3.174 (0.48), 3.188 (0.44), 3.274 (0.45), 3.399 (0.65), 3.407 (0.87), 3.413 (1.04), 3.429 (0.54), 3.661 (0.54), 3.879 (11.65), 3.999 (1.17), 4.017 (3.53), 4.035 (3.50), 4.053 (1.18), 4.186 (0.43), 4.201 (0.74), 4.212 (0.67), 4.249 (0.72), 4.258 (0.76), 4.274 (0.43), 6.116 (1.03), 6.123 (0.98), 6.132 (0.96), 6.140 (1.04), 6.655 (1.79), 6.664 (2.22), 6.671 (4.25), 6.683 (0.45), 7.146 (1.20), 7.281 (1.84), 7.294 (1.86), 7.529 (2.57), 8.007 (2.18), 8.020 (2.02), 8.372 (2.89), 11.149 (1.28).

LC-MS (method 2): $R_t$=1.20 min; MS (ESIpos): m/z=550 [M+H]$^+$

Example 96

3-(3-chloro-4-fluoro-2-methoxyanilino)-2-(3-{2-[methyl(2,2,2-trifluoroethyl)amino]ethoxy}pyridin-4-yl)-1,5,6,7-tetrahydro-4H-pyrrolo[3,2-c]pyridin-4-one

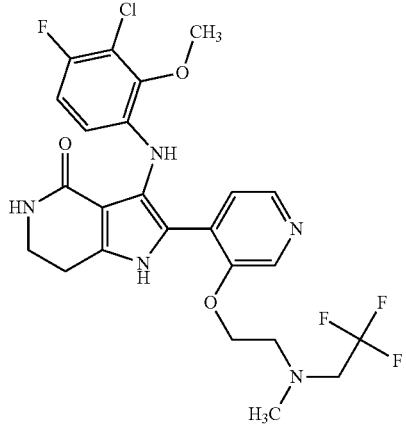 [SMILES: COc1c(Nc2c(-c3ccncc3OCCN(C)CC(F)(F)F)[nH]c3c2C(=O)NCC3)ccc(F)c1Cl]

Using an analogous method as described for Example 95 formic acid-3-(3-chloro-4-fluoro-2-methoxyanilino)-2-{3-[2-(methylamino)ethoxy]pyridin-4-yl}-1,5,6,7-tetrahydro-4H-pyrrolo[3,2-c]pyridin-4-one (1/1) (intermediate 96-2, 27.0 mg, 53.4 µmol) as the starting material, the title compound was prepared 3 mg (85% purity, 9% yield).

LC-MS (method 2): $R_t$=1.17 min; MS (ESIpos): m/z=542 [M+H]$^+$ $^1$H-NMR (400 MHz, DMSO-d6) δ [ppm]: 0.849 (1.48), 0.866 (3.59), 0.885 (3.18), 0.904 (5.77), 0.923 (2.62), 1.231 (2.57), 1.279 (1.43), 1.288 (1.65), 1.299 (1.82), 1.315 (1.47), 1.337 (1.00), 1.353 (1.10), 1.373 (0.99), 1.391 (1.18), 1.411 (2.91), 1.426 (0.83), 1.430 (0.87), 1.683 (0.51), 1.698 (0.61), 1.713 (0.44), 2.331 (0.42), 2.518 (2.65), 2.523 (2.60), 2.529 (8.46), 2.673 (0.43), 2.808 (1.15), 2.825 (2.44), 2.843 (1.28), 3.018 (1.14), 3.031 (2.14), 3.044 (1.16), 3.307 (0.82), 3.358 (1.88), 3.384 (0.76), 3.390 (0.97), 3.396 (0.98), 3.407 (1.70), 3.413 (1.66), 3.424 (0.85), 3.430 (0.76), 3.918 (16.00), 4.227 (1.48), 4.233 (1.61), 4.241 (1.59), 4.247 (1.48), 4.309 (1.26), 4.322 (2.33), 4.335 (1.20), 6.091 (1.21), 6.105 (1.27), 6.114 (1.36), 6.128 (1.32), 6.756 (1.29), 6.778 (2.41), 6.801 (1.20), 7.155 (1.61), 7.281 (0.89), 7.293 (0.91), 7.421 (3.43), 8.025 (0.51), 8.087 (10.06), 8.398 (0.59), 11.154 (1.72).

Experimental Section—Biological Assays

The pharmacological activity of the compounds according to the invention can be assessed using in vitro- and/or in vivo-assays, as known to the person skilled in the art. The following examples describe the biological activity of the compounds according to the invention, without the invention being limited to said examples.

Example compounds according to the invention were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

Expression and Purification of the EGFR Proteins Used in the Biochemical Kinase Assays The different EGFR proteins used in the biochemical kinase activity inhibition assays were generated inhouse by expression in insect cells using Baculo Virus system and subsequent purification as described in the following paragraphs.

Expression Constructs:

The cDNAs encoding the various protein sequences from human EGFR (UniProt Accession No. P00533) were optimized for expression in eukaryotic cells and synthesized by the GeneArt Technology at Life Technologies. These DNA sequences encoded the following sequence:

Construct EGFR #1 amino acid R669 to A1210

Construct EGFR #2 amino acid R669 to A1210 and the insertion of the amino acids sequence ASV between V769 and D770

Construct EGFR #3 amino acid R669 to A1210 and the insertion of the amino acids sequence SVD between D770 and N771

Additionally all constructs EGFR #1 to #3 encoded: at the N-terminus a TEV (Tobacco etch virus) protease cleavage site (DYDIPTTENLYFQG (SEQ ID NO: 8)), at the C-terminus two stop codons and additionally 5' and 3' att-DNA sequences for Gateway Cloning.

Each of the four EFGR constructs was subcloned using the Gateway Technology into the Destination vector pD-Ins1. The vector pD-Ins1 is a Baculovirus transfer vector (based on vector pVL1393, Pharmingen) which provides a N-terminal fusion of a GST-tag to the integrated gene construct. The respective transfer vectors were termed pD-Ins1_EGFR #1, pD-Ins1_EGFR #2, pD-Ins1_EGFR #3.

EGFR amino acid sequences:

GST-EGFR #1 (Wild Type) - SEQ ID NO: 1
MSPILGYWKIKGLVQPTRLLLEYLEEKYEEHLYERDEGDKWRNKKFELGLEFPNLPYYID
GDVKLTQSMAIIRYIADKHNMLGGCPKERAEISMLEGAVLDIRYGVSRIAYSKDFETLKVD
FLSKLPEMLKMFEDRLCHKTYLNGDHVTHPDFMLYDEDRLLYMDPMCLDAFPKLVCFK
KRIEAIPQIDKYLKSSKYIAWPLQGWQATFGGGDHPPKSDPITSLYKKAGSDYDIPTTTEN
LYFQGRRRHIVRKRTLRRLLQERELVEPLTPSGEAPNQALLRILKETEFKKIKVLGSGAFG
TVYKGLWIPEGEKVKIPVAIKELREATSPKANKEILDEAYVMASVDNPHVCRLLGICLT-
STV
QLITQLMPFGCLLDYVREHKDNIGSQYLLNWCVQIAKGMNYLEDRRLVHRDLAARNVLV
KTPQHVKITDFGLAKLLGAEEKEYHAEGGKVPIKWMALESILHRIYTHQSDVWSYGVTVW
ELMTFGSKPYDGIPASEISSILEKGERLPQPPICTIDVYMIMVKCWMIDADSRPKFRE-
LIIEF
SKMARDPQRYLVIQGDERMHLPSPTDSNFYRALMDEEDMDDVVDADEYLIPQQGFFSS
PSTSRTPLLSSLSATSNNSTVACIDRNGLQSCPIKEDSFLQRYSSDPTGALTEDSIDDTFL
PVPEYINQSVPKRPAGSVQNPVYHNQPLNPAPSRDPHYQDPHSTAVGNPEYLNTVQPT
CVNSTFDSPAHWAQKGSHQISLDNPDYQQDFFPKEAKPNGIFKGSTAENAEYLRVAPQS
SEFIGA GST-EGFR #2 (ASV between V769 and D770) SEQ ID NO: 2
MSPILGYWKIKGLVQPTRLLLEYLEEKYEEHLYERDEGDKWRNKKFELGLEFPNLPYYID
GDVKLTQSMAIIRYIADKHNMLGGCPKERAEISMLEGAVLDIRYGVSRIAYSKDFETLKVD
FLSKLPEMLKMFEDRLCHKTYLNGDHVTHPDFMLYDALDVVLYMDPMCLDAFPKLVCFK
KRIEAIPQIDKYLKSSKYIAWPLQGWQATFGGGDHPPKSDPITSLYKKAGSDYDIPTTTEN
LYFQGRRRHIVRKRTLRRLLQERELVEPLTPSGEAPNQALLRILKETEFKKIKVLGSGAFG
TVYKGLWIPEGEKVKIPVAIKELREATSPKANKEILDEAYVMASVDASVNPHVCRLLGI-
CLT
STVQLITQLMPFGCLLDYVREHKDNIGSQYLLNWCVQIAKGMNYLEDRRLVHRDLAARN
VLVKTPQHVKITDFGLAKLLGAEEKEYHAEGGKVPIKWMALESILHRIYTHQSDVWSYGV
TVWELMTFGSKPYDGIPASEISSILEKGERLPQPPICTIDVYMIMVKCWMIDADSRPKFRE
LIIEFSKMARDPQRYLVIQGDERMHLPSPTDSNFYRALMDEEDMDDVVDADEYLIPQQGF
FSSPSTSRTPLLSSLSATSNNSTVACIDRNGLQSCPIKEDSFLQRYSSDPTGALTEDSIDD
TFLPVPEYINQSVPKRPAGSVQNPVYHNQPLNPAPSRDPHYQDPHSTAVGNPEYLNTVQ
PTCVNSTFDSPAHWAQKGSHQISLDNPDYQQDFFPKEAKPNGIFKGSTAENAEYLRVAP
QSSEFIGA GST-EGFR #3 (SVD between D770 and N771) - SEQ ID NO: 3
MSPILGYWKIKGLVQPTRLLLEYLEEKYEEHLYERDEGDKWRNKKFELGLEFPNLPYYID
GDVKLTQSMAIIRYIADKHNMLGGCPKERAEISMLEGAVLDIRYGVSRIAYSKDFETLKVD
FLSKLPEMLKMFEDRLCHKTYLNGDHVTHPDFMLYDALDVVLYMDPMCLDAFPKLVCFK
KRIEAIPQIDKYLKSSKYIAWPLQGWQATFGGGDHPPKSDPITSLYKKAGSDYDIPTTTEN
LYFQGRRRHIVRKRTLRRLLQERELVEPLTPSGEAPNQALLRILKETEFKKIKVLGSGAFG
TVYKGLWIPEGEKVKIPVAIKELREATSPKANKEILDEAYVMASVDSVDNPHVCRLLGI-
CLT
STVQLITQLMPFGCLLDYVREHKDNIGSQYLLNWCVQIAKGMNYLEDRRLVHRDLAARN
VLVKTPQHVKITDFGLAKLLGAEEKEYHAEGGKVPIKWMALESILHRIYTHQSDVWSYGV
TVWELMTFGSKPYDGIPASEISSILEKGERLPQPPICTIDVYMIMVKCWMIDADSRPKFRE
LIIEFSKMARDPQRYLVIQGDERMHLPSPTDSNFYRALMDEEDMDDVVDADEYLIPQQGF
FSSPSTSRTPLLSSLSATSNNSTVACIDRNGLQSCPIKEDSFLQRYSSDPTGALTEDSIDD EGFR amino acid sequences:

TFLPVPEYINQSVPKRPAGSVQNPVYHNQPLNPAPSRDPHYQDPHSTAVGNPEYLNTVQ
PTCVNSTFDSPAHWAQKGSHQISLDNPDYQQDFFPKEAKPNGIFKGSTAENAEYLRVAP
QSSEFIGA

Generation of Recombinant Baculovirus:

In separate approaches each of the three transfer vectors was co-transfected in Sf9 cells with Baculovirus DNA (Flashbac Gold DNA, Oxford Expression Technologies) using Fugene HD (Roche). After 5 days the supernatant of the transfected cells containing the recombinant Baculovirus encoding the various EGFR proteins was used for further infection of Sf9 cells for virus amplification whereby the virus titer was monitored using qPCR.

EGFR Expression in Sf9 Cells Using Bioreactor:

Sf9 cells cultured (Insect-xpress medium, Lonza, 27° C.) in a Wave-bioreactor with a disposable culture bag were infected at a cell density of 106 cells/ml with one of the recombinant baculovirus stocks at a multiplicity of infection of 1 and incubated for 48 h. Subsequently the cells were harvested by centrifugation and the cell pellet frozen at −80° C.

Purification of the GST-EGFR Fusion Proteins:

Purification of the GST-EGFR fusion proteins was achieved by affinity chromatography using Glutathion Sepharose 4B matrix (GE Healthcare Life Sciences).

The pelleted cells (from 4 l cell culture) were resuspended in Lysis-Buffer (50 mM HEPES pH 7.4, 150 mM NaCl, 5% Glycerol, 1 mM MgCl2, 1 mM MnCl2, 0.5 mM Na3VO4) and lysed by a freeze-thaw cycle followed by an incubation on ice for 60 min. The supernatant was centrifuged at 4000×g for 30 min. at 4° C. The supernatant was than incubated with Glutathion Sepharose 4B matrix (in a glass bottle rotating for 16 h, at 4° C.) for binding of the GST EGFR fusion protein, rinsed with Wash-Buffer and finally the bound protein was eluted using Elusion-Buffer (Lysis Buffer plus 25 mM Glutathione) and shock frozen with liquid nitrogen.

WT-EGFR Kinase Assay

Inhibitory activity of compounds of the present invention against wild-type Epidermal Growth Factor Receptor (EGFR) was quantified employing the TR-FRET based EGFR assay as described in the following paragraphs.

Recombinant fusion protein of N-terminal Glutathion-S-Transferase (GST) and a fragment of human EGFR (amino acids R669 to A1210), expressed in Sf9 insect cells and purified via affinity chromatography using Glutathion Sepharose as described above, was used as a kinase. As substrate for the kinase reaction the biotinylated peptide biotin-Ahx-AEEEEYFELVAKKK—SEQ ID NO: 4 (C-terminus in amide form) was used, which can be purchased e.g. from the company Biosynthan GmbH (Berlin-Buch, Germany).

For the assay 50 nl of a 100 fold concentrated solution of the test compound in DMSO was pipetted into either a black low volume 384 well microtiter plate or a black 1536 well microtiter plate (both Greiner Bio-One, Frickenhausen, Germany), 2 µl of a solution of EGFR in aqueous assay buffer [50 mM Hepes pH 7.0, 10 mM MgCl2, 1 mM dithiothreitol, 0.5 mM EGTA, 0.3 mM activated sodium ortho-vanadate, 0.005% (w/v) bovine serum albumin, 0.005% (v/v) Tween-20] were added and the mixture was incubated for 15 min at 22° C. to allow pre binding of the test compounds to the enzyme before the start of the kinase reaction. Then the kinase reaction was started by the addition of 3 µL of a solution of adenosine tri phosphate (ATP, 3.33 mM=>final conc. in the 5 µL assay volume is 2 mM) and substrate (1.67 µM=>final conc. in the 5 µL assay volume is 1 µM) in assay buffer and the resulting mixture was incubated for a reaction time of 30 min at 22° C. The concentration of EGFR was adjusted depending of the activity of the enzyme lot and was chosen appropriate to have the assay in the linear range, typical concentration was 7.6 pg/µl. The reaction was stopped by the addition of 3 µl of a solution of HTRF detection reagents (83.3 nM streptavidine-XL665 [Cisbio Bioassays, Codolet, France] and 1.67 nM PT66-Tb-Cryptate, an terbium-cryptate labelled anti-phospho-tyrosine antibody from Cisbio Bioassays [instead of the PT66 Tb cryptate PT66 Eu Chelate from Perkin Elmer can also be used]) in an aqueous EDTA-solution (133.3 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Tb-Cryptate. Subsequently the amount of phosphorylated substrate was evaluated by measurement of the resonance energy transfer from the PT66-Tb-Cryptate to the streptavidine-XL665. Therefore, the fluorescence emissions at 620 nm and 665 nm after excitation at 337 nm were measured in a HTRF reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100-fold concentrated solutions in DMSO by serial dilutions, exact concentrations may vary depending pipettors used) in duplicate values for each concentration and IC50 values were calculated using Genedata Screener™ software.

Exon 20-Mutant-EGFR(D770_N771insSVD) Kinase Assay

Inhibitory activity of compounds of the present invention against an Epidermal Growth Factor Receptor (EGFR) with an insertion of the amino acids sequence SVD between D770 and N771 was quantified employing the TR-FRET based kinase activity assay as described in the following paragraphs.

A recombinant fusion protein of N-terminal Glutathion-S-Transferase (GST) and a fragment of human EGFR variant (amino acids R669 to A1210 with insertion of the amino acids sequence SVD between D770 and N771 ("EGFR ins SVD"), expressed in Sf9 insect cells and purified via affinity chromatography using Glutathion Sepharose as described above, was used as a kinase. As substrate for the kinase reaction the biotinylated peptide biotin-Ahx-AEEEEYFELVAKKK—SEQ ID NO: 4 (C-terminus in amide form) was used which can be purchased e.g. form the company Biosynthan GmbH (Berlin-Buch, Germany).

For the assay 50 nl of a 100-fold concentrated solution of the test compound in DMSO was pipetted into either a black low volume 384 well microtiter plate or a black 1536 well microtiter plate (both Greiner Bio-One, Frickenhausen, Germany), 2 µl of a solution of EGFR in aqueous assay buffer [50 mM Hepes pH 7.0, 10 mM MgCl2, 1 mM dithiothreitol, 0.5 mM EGTA, 0.3 mM activated sodium ortho-vanadate, 0.005% (w/v) bovine serum albumin, 0.005% (v/v) Tween-20] were added and the mixture was incubated for 15 min at 22° C. to allow pre binding of the test compounds to the enzyme before the start of the kinase reaction. Then the kinase reaction was started by the addition of 3 µL of a solution of adenosine tri phosphate (ATP, 3.33 mM=>final conc, in the 5 µL assay volume is 2 mM) and substrate (1.67 µM=>final conc, in the 5 µL assay volume is 1 µM) in assay buffer and the resulting mixture was incubated for a reaction time of 30 min at 22° C. The concentration of EGFR was adjusted depending of the activity of the enzyme lot and was chosen appropriate to have the assay in the linear range, typical concentration was 15 pg/µl. The reaction was stopped by the addition of 3 µl of a solution of HTRF detection reagents (83.3 nM streptavidine-XL665 [Cisbio Bioassays, Codolet, France] and 1.67 nM PT66-Tb-Cryptate, a terbium-cryptate labelled anti-phospho-tyrosine antibody from Cisbio Bioassays [instead of the PT66 Tb cryptate PT66 Eu Chelate from Perkin Elmer can also be used]) in an aqueous EDTA-solution (133.3 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Tb-Cryptate. Subsequently the amount of phosphorylated substrate was evaluated by measurement of the resonance energy transfer from the PT66-Tb-Cryptate to the streptavidine-XL665. Therefore, the fluorescence emissions at 620 nm and 665 nm after excitation at 337 nm were measured in a HTRF reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and IC50 values were calculated using Genedata Screener™ software.

Exon 20-Mutant-EGFR(V769_D770insASV) Kinase Assay

Inhibitory activity of compounds of the present invention against an Epidermal Growth Factor Receptor (EGFR) with an insertion of the amino acids sequence ASV between V769 and D770 was quantified employing the TR-FRET based kinase activity assay as described in the following paragraphs.

A recombinant fusion protein of N-terminal Glutathion-S-Transferase (GST) and a fragment of human EGFR variant (amino acids R669 to A1210 with insertion of the amino acids sequence ASV between V769 and D770; ("EGFR ins ASV"), expressed in Sf9 insect cells and purified via affinity chromatography using Glutathion Sepharose as described above, was used as kinase. As substrate for the kinase reaction the biotinylated peptide biotin-Ahx-AEEEEYFEL-VAKKK—SEQ ID NO: 4 (C-terminus in amide form) was used which can be purchased e.g. form the company Biosynthan GmbH (Berlin-Buch, Germany).

For the assay 50 nl of a 100-fold concentrated solution of the test compound in DMSO was pipetted into either a black low volume 384well microtiter plate or a black 1536 well microtiter plate (both Greiner Bio-One, Frickenhausen, Germany), 2 µl of a solution of EGFR in aqueous assay buffer [50 mM Hepes pH 7.0, 10 mM MgCl2, 1 mM dithiothreitol, 0.5 mM EGTA, 0.3 mM activated sodium ortho-vanadate, 0.005% (w/v) bovine serum albumin, 0.005% (v/v) Tween-20] were added and the mixture was incubated for 15 min at 22° C. to allow pre binding of the test compounds to the enzyme before the start of the kinase reaction. Then the kinase reaction was started by the addition of 3 µL of a solution of adenosine tri phosphate (ATP, 3.33 mM=>final conc, in the 5 µL assay volume is 2 mM) and substrate (1.67 µM=>final conc, in the 5 µL assay volume is 1 µM) in assay buffer and the resulting mixture was incubated for a reaction time of 30 min at 22° C. The concentration of EGFR was adjusted depending of the activity of the enzyme lot and was chosen appropriate to have the assay in the linear range, typical concentration was 2.5 pg/µl. The reaction was stopped by the addition of 3 µl of a solution of HTRF detection reagents (83.3 nM streptavidine-XL665 [Cisbio Bioassays, Codolet, France] and 1.67 nM PT66-Tb-Cryptate, an terbium-cryptate labelled anti-phospho-tyrosine antibody from Cisbio Bioassays [instead of the PT66 Tb cryptate PT66 Eu Chelate from Perkin Elmer can also be used]) in an aqueous EDTA-solution (133.3 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Tb-Cryptate. Subsequently the amount of phosphorylated substrate was evaluated by measurement of the resonance energy transfer from the PT66-Tb-Cryptate to the streptavidine-XL665. Therefore, the fluorescence emissions at 620 nm and 665 nm after excitation at 337 nm were measured in a HTRF reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100-fold concentrated solutions in DMSO by serial dilutions, exact concentrations may vary depending pipettors used) in duplicate values for each concentration and $IC_{50}$ values were calculated using Genedata Screener™ software and the results for each EGFR assay are shown in Table 7.

TABLE 7

| Example No. | EGFR ins SVD $IC_{50}$ [mol/l] (mean) | EGFR ins ASV $IC_{50}$ [mol] (mean) |
|---|---|---|
| 1 | 7.79E−10 | 5.87E−9 |
| 2 | 3.99E−9 | 2.64E−8 |

TABLE 7-continued

| Example No. | EGFR ins SVD IC$_{50}$ [mol/l] (mean) | EGFR ins ASV IC$_{50}$ [mol] (mean) |
|---|---|---|
| 3 | 2.80E−10 | 6.85E−9 |
| 4 | <7.2E−11 | 1.31E−10 |
| 5 | 1.56E−9 | 4.31E−9 |
| 6 | <7.2E−11 | 2.12E−10 |
| 7 | 7.18E−10 | — |
| 8 | 3.10E−10 | — |
| 9 | <7.2E−11 | 6.15E−9 |
| 10 | <7.2E−11 | — |
| 11 | 2.20E−10 | 4.25E−9 |
| 12 | 8.57E−11 | 2.18E−10 |
| 13 | 4.41E−9 | 3.89E−8 |
| 14 | 2.66E−9 | 2.39E−8 |
| 15 | 4.89E−10 | 1.34E−9 |
| 16 | 1.38E−10 | 2.12E−10 |
| 17 | 1.13E−10 | 1.77E−10 |
| 18 | 1.20E−10 | 3.00E−10 |
| 19 | 1.55E−10 | 2.39E−10 |
| 20 | 1.49E−10 | 3.22E−10 |
| 21 | 1.38E−10 | 2.13E−10 |
| 22 | 1.76E−10 | 3.09E−10 |
| 23 | 2.59E−10 | 3.42E−10 |
| 24 | 5.41E−10 | 6.34E−10 |
| 25 | 1.09E−9 | 2.93E−8 |
| 26 | 2.68E−10 | 9.43E−10 |
| 27 | 2.14E−9 | 7.09E−9 |
| 28 | 7.38E−10 | 2.69E−8 |
| 29 | 2.46E−10 | 6.08E−9 |
| 30 | 9.69E−11 | 2.09E−10 |
| 31 | 9.88E−11 | 1.61E−10 |

Bub1 Kinase Assay

Bub1-inhibitory activities of compounds described in the present invention were quantified using a time-resolved fluorescence energy transfer (TR-FRET) kinase assay which measures phosphorylation of the synthetic peptide Biotin-Ahx-VLLPKKSFAEPG—SEQ ID NO: 5 (C-terminus in amide form), purchased from e.g. Biosyntan (Berlin, Germany) by the (recombinant) catalytic domain of human Bub1 (amino acids 704-1085), expressed in Hi5 insect cells with an N-terminal His6-tag (SEQ ID NO: 9) and purified by affinity-(Ni-NTA) and size exclusion chromatography.

In a typical assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were tested in duplicate within the same microtiter plate. To this end, 100-fold concentrated compound solutions (in DMSO) were previously prepared by serial dilution (1:3.4) of 2 mM stocks in a clear low volume 384-well source microtiter plate (Greiner Bio-One, Frickenhausen, Germany), from which 50 nl of compounds were transferred into a black low volume test microtiter plate from the same supplier. Subsequently, 2 µl of Bub1 (the final concentration of Bub1 was adjusted depending on the activity of the enzyme lot in order to be within the linear dynamic range of the assay: typically ~ 200 ng/ml were used) in aqueous assay buffer [50 mM Tris/HCl pH 7.5, 10 mM magnesium chloride (MgCl2), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Triton X-100 (Sigma), 1× Complete EDTA-free protease inhibitor mixture (Roche)] were added to the compounds in the test plate and the mixture was incubated for 15 min at 22° C. to allow pre-equilibration of the putative enzyme-inhibitor complexes before the start of the kinase reaction, which was initiated by the addition of 3 µl 1.67-fold concentrated solution (in assay buffer) of adenosine-tri-phosphate (ATP, 10 µM final concentration) and peptide substrate (1 µM final concentration). The resulting mixture (5 µl final volume) was incubated at 22° C. during 60 min., and the reaction was stopped by the addition of 5 µl of an aqueous EDTA-solution (50 mM EDTA, in 100 mM HEPES pH 7.5 and 0.2% (w/v) bovine serum albumin) which also contained the TR-FRET detection reagents (0.2 µM streptavidin-XL665 [Cisbio Bioassays, Codolet, France] and 1 nM anti-phosho-Serine antibody [Merck Millipore, cat. #35-002] and 0.4 nM LANCE EU-W1024 labeled anti-mouse IgG antibody [Perkin-Elmer, product no. AD0077, alternatively a Terbium-cryptate-labeled anti-mouse IgG antibody from Cisbio Bioassays can be used]). The stopped reaction mixture was further incubated 1 h at 22° C. in order to allow the formation of complexes between peptides and detection reagents. Subsequently, the amount of product was evaluated by measurement of the resonance energy transfer from the Eu-chelate-antibody complex recognizing the Phosphoserine residue to the streptavidin-XL665 bound to the biotin moiety of the peptide. To this end, the fluorescence emissions at 620 nm and 665 nm after excitation at 330-350 nm were measured in a TR-FRET plate reader, e.g. a Rubystar or Pherastar (both from BMG Labtechnologies, Offenburg, Germany) or a Viewlux (Perkin-Elmer) and the ratio of the emissions (665 nm/622 nm) was taken as indicator for the amount of phosphorylated substrate. The data were normalised using two sets of control wells for high-(=enzyme reaction without inhibitor=0%=Minimum inhibition) and low-(=all assay components without enzyme=100%=Maximum inhibition) Bub1 activity. IC$_{50}$ values were calculated by fitting the normalized inhibition data to a 4-parameter logistic equation (Minimum, Maximum, IC50, Hill; Y=Max+(Min−Max)/(1+(X/IC50)Hill)). The IC$_{50}$ values for the examples are shown in Table 8.

TABLE 8

| Example No. | Bub1 kinase assay IC$_{50}$ [mol/l] (mean) |
|---|---|
| 1 | 1.45E−8 |
| 2 | 4.41E−8 |
| 3 | 4.76E−8 |
| 4 | 1.25E−8 |
| 5 | 3.24E−8 |
| 6 | 2.69E−8 |
| 7 | 3.97E−7 |
| 8 | 6.58E−8 |
| 9 | 2.72E−8 |
| 10 | 1.24E−8 |
| 11 | 1.92E−7 |
| 12 | — |
| 13 | 3.50E−7 |
| 14 | 7.04E−7 |
| 15 | 1.87E−7 |
| 16 | 1.45E−7 |
| 17 | 5.51E−8 |
| 18 | 3.75E−7 |
| 19 | 1.49E−7 |
| 20 | 6.74E−8 |
| 21 | — |
| 22 | 1.11E−7 |
| 23 | 6.73E−8 |
| 24 | — |
| 25 | 2.28E−7 |
| 26 | 8.58E−8 |
| 27 | 7.01E−8 |
| 28 | 5.65E−7 |
| 29 | 2.01E−7 |
| 30 | 3.23E−7 |
| 31 | 2.65E−7 |

Bub1 High ATP Kinase Assay

Bub1-inhibitory activity of compounds of the present invention at a high ATP concentration was quantified employing the Bub1 TR-FRET high ATP kinase assay as described in the following paragraphs.

N-terminally $His_6$-tagged (SEQ ID NO: 9) recombinant catalytic domain of human Bub1 (amino acids 704-1085), expressed in insect cells (Hi5) and purified by Ni-NTA affinity chromatography and subsequent size exclusion chromatography, was used as enzyme. As substrate for the kinase reaction the biotinylated peptide biotin-Ahx-VLLPKKS-FAEPG—SEQ ID NO: 5 (C-terminus in amid form) was used which can be purchased e.g. form the company Biosyntan (Berlin, Germany).

For the assay 50 nl of a 100-fold concentrated solution of the test compound in DMSO was pipetted into either a black low volume 384well microtiter plate or a black 1536well microtiter plate (both Greiner Bio-One, Frickenhausen, Germany), 3 µl of a solution of adenosine-tri-phosphate (ATP, 3.33 mM=>final conc, in the 5 µl assay volume is 2 mM) and substrate (1.67 µM=>final conc, in the 5 µl assay volume is 1 µM) in aqueous assay buffer [50 mM Tris/HCl pH 7.5, 10 mM magnesium chloride ($MgCl_2$), 200 mM potassium chloride (KOl), 1.0 mM dithiothreitol (DTT), 0.1 mM sodium ortho-vanadate, 1% (v/v) glycerol, 0.01% (w/v) bovine serum albumine (BSA), 0.005% (v/v) Triton X-100 (Sigma), 1× Complete EDTA-free protease inhibitor mixture (Roche)] were added. Then the kinase reaction was started by the addition of 2 µl of a solution of Bub1 in assay buffer and the resulting mixture was incubated for a reaction time of 60 min at 22° C. The concentration of Bub1 was adjusted depending of the activity of the enzyme lot and was chosen appropriate to have the assay in the linear range, a typical concentration is about 200 ng/ml. The reaction was stopped by the addition of 3 µl of a solution of TR-FRET detection reagents (0.167 µM streptavidine-XL665 [Cisbio Bioassays, Codolet, France] and 1.67 nM anti-phosho-Serine antibody [Merck Millipore, cat. #35-002] and 0.67 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (83.3 mM EDTA, 0.2% (w/v) bovine serum albumin in 100 mM HEPES pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidin-XL. Therefore, the fluorescence emissions at 620 nm and 665 nm after excitation at 350 nm was measured in a TR-FRET reader, e.g. a Pherastar or Pherastar FS (both from BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.7 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated by a 4 parameter fit.

Table 9 shows the results of the inhibition in mutant EGFR biochemical assay.

TABLE 9

| Example No. | mutEGFR (D770_N771insSVD) kinase assay $IC_{50}$ [mol/l] |
|---|---|
| 1 | 7.79E−10 |
| 2 | 3.99E−9 |
| 3 | 2.80E−10 |
| 4 | <7.25E−11 |
| 5 | 1.56E−9 |
| 6 | <7.25E−11 |
|   | <7.25E−11 |
|   | 1.04E−10 |
|   | 9.49E−11 |
| 7 | 1.13E−9 |
| 8 | 3.24E−10 |
| 9 | 3.60E−10 |
|   | 3.88E−10 |
|   | 7.76E−11 |
|   | <7.25E−11 |
|   | 1.00E−10 |
|   | 9.62E−11 |
|   | 1.96E−10 |
|   | 2.06E−10 |
| 10 | <7.25E−11 |
|   | <7.25E−11 |
|   | 1.33E−10 |
|   | <7.25E−11 |
|   | <7.25E−11 |
| 11 | 2.92E−10 |
| 12 | 8.57E−11 |
| 13 | 4.41E−9 |
| 14 | 2.66E−9 |
| 15 | 4.89E−10 |
| 16 | 1.58E−10 |
| 17 | 1.13E−10 |
| 18 | 1.53E−10 |
| 19 | 1.48E−10 |
| 20 | 1.49E−10 |
| 21 | 1.47E−10 |
| 22 | 1.76E−10 |
| 23 | 1.91E−10 |
| 24 | 5.41E−10 |
| 25 | 1.26E−9 |
| 26 | 4.15E−10 |
| 27 | 2.14E−9 |
| 28 | 5.40E−10 |
| 29 | 2.45E−10 |
| 30 | 1.09E−10 |
| 31 | 1.93E−10 |
| 32 | 7.60E−11 |
|   | <7.25E−11 |
| 33 | 2.25E−10 |
|   | 3.34E−10 |
|   | 1.66E−10 |
|   | 1.61E−10 |
|   | 2.75E−10 |
|   | <7.25E−11 |
| 34 | 9.46E−11 |
| 35 | 1.85E−10 |
| 36 | 1.94E−10 |
| 37 | 1.20E−10 |
|   | 7.95E−11 |
|   | 1.07E−10 |
|   | 9.58E−11 |
|   | <7.25E−11 |
|   | <7.25E−11 |
| 38 | 1.30E−10 |
| 39 | 1.04E−10 |
| 40 | 9.94E−11 |
| 41 | 1.24E−10 |
| 42 | 1.90E−10 |
| 43 | 1.00E−10 |
| 44 | 9.22E−11 |
|   | <7.25E−11 |

TABLE 9-continued

| Example No. | mutEGFR (D770_N771insSVD) kinase assay IC$_{50}$ [mol/l] |
|---|---|
| 45 | 3.19E-10 |
| 46 | 9.12E-11 |
| 47 | 1.69E-10 |
| 48 | 3.58E-10 |
| 49 | 5.18E-10 |
| 50 | 1.26E-9 |
| 51 | 7.32E-10 |
| 52 | 5.50E-10 |
| 53 | 3.32E-10 |
| 54 | 9.12E-10 |
| 55 | 4.65E-10 |
| 56 | 5.62E-10 |
| 57 | 2.28E-10 |
| 58 | 1.13E-10 |
| 59 | <7.25E-11 |
| 60 | 6.95E-10 |
| 61 | 1.12E-9 |
| 62 | 6.63E-10 |
| 63 | 5.09E-10 |
| 64 | 4.43E-10 |
| 65 | 5.22E-10 |
| 66 | 9.32E-11 |
| 67 | 9.08E-11 |
| 68 | 1.15E-10 |
| 69 | 1.06E-10 |
| 70 | 9.18E-11 |
| 71 | 2.58E-10 |
| 72 | 1.44E-10 |
| 73 | 1.67E-10 |
| 74 | 8.65E-10 |
| 75 | 9.03E-10 |
| 76 | 8.45E-10 |
| 77 | 7.27E-10 |
| 78 | <7.25E-11 |
|  | 7.36E-11 |
| 79 | 2.42E-10 |
| 80 | 5.03E-10 |
| 81 | 4.41E-10 |
| 82 | 3.99E-10 |
| 83 | 1.67E-10 |
| 84 | 2.23E-10 |
| 85 | 2.00E-9 |
| 86 | 1.22E-10 |
| 87 | 2.04E-10 |
| 88 | 8.88E-11 |
| 89 | 1.08E-10 |
| 90 | 6.90E-10 |
| 91 | 1.35E-10 |
| 92 | 1.18E-10 |
| 93 | 2.77E-10 |
| 94 | 2.28E-10 |
| 95 | 1.87E-10 |
| 96 | 3.05E-10 |

Cellular Data Description (WT, insSVD, Ins ASV)

293T cells from ATCC were transfected with pBABEpuro expression constructs for WT EGFR or EGFR-insSVD and pCL-Eco packaging vector using Fugene-6 transfection reagent from Promega. Plates were incubated at 37° C. for 48 h. Retrovirus was harvested by filtering the media supernatant through a 0.45 µm filter.

Ba/F3 cells purchased from DSMZ were grown in RPMI+ 10% FBS+10 ng/mL IL-3 and infected with filtered retroviral supernatant at a 1:2 dilution. Polybrene was added to a concentration of 8 µg/mL, plates were spun for 90 min, and incubated overnight at 37° C. 2 µg/mL puromycin was added to the infected cells 24 h after infection and cells were continually grown in the presence of puromycin and 10 ng/mL IL-3. Following stably expressing Ba/F3 cell lines were generated: Ba/F3-EGFR-WT, Ba/F3-EGFR-insSVD.

For cell survival assays, Ba/F3 cells were grown to a density of 1-2 million cells per mL, spun down and resuspended in media without IL-3, and replated at a concentration 200,000-500,000 cells per mL. The cells ectopically expressing WT EGFR were plated with 10 ng/mL Millipore Culture grade EGF. The cells ectopically expressing EGFR-insSVD were plated without EGF.

24 hours later, cells were plated in 30 µL in a 384 well plate at a concentration of 3200 cells per well for cells assayed in the absence of IL-3. 100 nL of compound was added to each well using a 100 nL pin head, and plates were incubated at 37° C. for 48 h.

Cell viability was measured by adding 30 µL of Cell Titer-Glo Luminescent Cell Viability Reagent. Plates were sealed with Perkin Elmer Top-Seal, inverted several times to mix, and immediately centrifuged at 1000 rpm for 2 min. Plates were incubated in low light conditions for 8-10 min and luminescence was measured.

Table 10 shows the results of the inhibition in proliferation assays performed in BA/F3 (ins SVD) and BA/F3 (wild type) cell lines (IC$_{50}$ is the concentration for 50% of maximal inhibition of cell proliferation).

TABLE 10

| Example No. | BA/F3 (insSVD) IC$_{50}$ [mol/l] | BA/F3 (wild type) IC$_{50}$ [mol/l] |
|---|---|---|
| 1 | 2.74E-7 | 4.81E-7 |
| 2 | 8.81E-9 | 1.87E-6 |
|  | 7.48E-9 |  |
|  | <4.78E-9 |  |
|  | 6.80E-9 |  |
|  | 7.49E-9 |  |
| 3 | 5.87E-7 | 2.16E-6 |
| 4 | 3.29E-7 | 1.61E-6 |
| 5 | 5.67E-7 |  |
| 6 | 6.33E-8 | 3.94E-7 |
| 7 | 4.62E-7 | 2.70E-6 |
| 8 | 6.95E-8 | 6.23E-7 |
| 9 | 1.21E-7 | 3.76E-7 |
| 10 | 5.69E-8 | 3.52E-7 |
| 11 | 3.57E-7 | 1.78E-6 |
| 12 |  |  |
| 13 | 8.11E-7 | 4.01E-6 |
| 14 | 1.04E-6 | 2.53E-6 |
| 15 | 4.09E-7 | 2.87E-6 |
| 16 | 2.41E-8 | 4.54E-7 |
| 17 | 1.19E-8 | 3.97E-7 |
| 18 | 1.80E-7 | 2.45E-6 |
| 19 | 4.01E-8 | 8.70E-7 |
| 20 | 4.83E-8 | 6.25E-7 |
| 21 | 8.81E-9 | 2.51E-7 |
|  | 7.48E-9 |  |
|  | <4.78E-9 |  |
|  | 6.80E-9 |  |
|  | 7.49E-9 |  |
| 22 | 1.16E-7 | 1.56E-6 |
| 23 | 3.30E-8 | 3.88E-7 |
| 24 |  |  |
| 25 | 8.42E-7 | 2.28E-6 |
|  | 8.72E-7 |  |
|  | >2.00E-6 |  |
|  | 7.71E-7 |  |
|  | 7.41E-7 |  |
| 26 | 6.18E-7 | 2.00E-6 |
| 27 | 4.98E-7 | 2.50E-6 |
| 28 | 6.44E-7 | 3.67E-6 |
| 29 | 2.29E-7 | 2.36E-6 |
| 30 | 1.49E-7 | 1.86E-6 |
| 31 | 1.58E-7 | 1.71E-6 |
| 32 | 9.87E-9 | 2.99E-7 |
| 33 | 9.32E-9 | 4.76E-7 |
| 34 | 7.00E-9 | 2.78E-7 |
| 35 | 7.98E-9 | 4.28E-7 |

TABLE 10-continued

| Example No. | BA/F3 (insSVD) IC$_{50}$ [mol/l] | BA/F3 (wild type) IC$_{50}$ [mol/l] |
|---|---|---|
| 36 | 9.55E−9 | 5.29E−7 |
| 37 | 1.60E−8 | 5.83E−7 |
| 38 | 1.75E−8 | 4.66E−7 |
| 39 | 2.75E−8 | 6.61E−7 |
| 40 | 5.05E−8 | 1.45E−6 |
| 41 | 5.25E−8 | 7.95E−7 |
| 42 | 7.29E−8 | 6.25E−7 |
| 43 | 1.17E−7 | 1.88E−6 |
| 44 | 1.73E−7 | 2.45E−6 |
| 45 | 2.55E−7 | 2.49E−6 |
| 46 | 1.51E−8 | 3.64E−7 |
| 47 | 4.48E−7 | 3.24E−6 |
| 48 | 5.59E−9 | 2.76E−7 |
| 49 | 1.91E−8 | 9.19E−7 |
| 50 | 6.09E−8 | 2.10E−6 |
| 51 | 1.07E−7 | 3.29E−6 |
| 52 | 2.91E−8 | 8.34E−7 |
| 53 | 3.11E−8 | 8.04E−7 |
| 54 | 3.75E−8 | 1.30E−6 |
| 55 | 3.03E−7 | 2.83E−6 |
| 56 | 2.42E−7 | 1.90E−6 |
| 57 | 1.47E−8 | 5.35E−7 |
| 58 | 1.86E−8 | 5.61E−7 |
| 59 | 1.77E−8 | 5.42E−7 |
| 60 | 3.86E−8 | 1.75E−6 |
| 61 | 8.89E−8 | 1.46E−6 |
| 62 | 1.66E−7 | 2.76E−6 |
| 63 | 1.23E−8 | 4.85E−7 |
| 64 | 1.21E−7 | 1.89E−6 |
| 65 | 1.43E−7 | 2.26E−6 |
| 66 | 4.60E−9 | 1.53E−7 |
| 67 | 9.33E−9 | 2.84E−7 |
| 68 | 2.94E−9 | 1.09E−7 |
| 69 | 1.24E−8 | 2.90E−7 |
| 70 | 1.61E−8 | 2.97E−7 |
| 71 | 2.02E−8 | 7.81E−7 |
| 72 | 6.77E−8 | 1.01E−6 |
| 73 | 4.16E−7 | 2.52E−6 |
| 74 | 9.79E−8 | 4.07E−6 |
| 75 | 9.80E−8 | 2.36E−6 |
| 76 | 2.50E−7 | 2.09E−6 |
| 77 | 4.63E−8 | 1.48E−6 |
| 78 | 1.60E−8 | 5.83E−7 |
| 79 | 1.18E−7 | 1.81E−6 |
| 80 | 2.06E−7 | 1.46E−6 |
| 81 | 4.05E−7 | 4.19E−6 |
| 82 | 9.09E−7 | 8.61E−6 |
| 83 | 1.00E−7 | 2.29E−6 |
| 84 | 1.88E−7 | 2.21E−6 |
| 85 | 5.01E−7 | 6.57E−6 >2.00E−5 |
| 86 | 1.28E−8 | 3.77E−7 |
| 87 | 3.44E−8 | 1.06E−6 |
| 88 | 3.80E−8 | 3.88E−7 |
| 89 | 1.28E−8 | 2.52E−7 |
| 90 | 2.90E−8 | 2.66E−6 |
| 91 | 3.57E−8 | 1.10E−6 |
| 92 | 1.04E−8 | 3.09E−7 |
| 93 | 4.68E−7 | 3.68E−6 |
| 94 | 5.49E−8 | 4.62E−6 |
| 95 | 1.41E−7 | 2.37E−6 |
| 96 | 4.96E−8 | 1.47E−6 |

Compounds of the present invention may show additional advantageous properties, such as, more potent inhibition of mutant EGFR with exon 20 insertions than inhibition of wild-type EGFR, which may be useful to reduce potential toxicity arising from excessive inhibition of wild-type EGFR. Surprisingly, we found that the claimed compounds are biochemically highly potent and show a >5-fold selectivity on EGFR exon 20 insertions versus wild-type EGFR in anti-proliferative assays. This finding clearly supports improved feasibility of the here described compounds for a novel, efficacious and more tolerable therapy for EGFR exon 20 insertion patients.

In contrast to the claimed compounds of this invention the compounds claimed in the closest prior art WO2016/120196 do not show the advantageous combined properties described above. This can be seen in Table 11.

TABLE 11

| WO2016/120196 Example No. | mutEGFR (D770_N771insSVD) kinase assay IC$_{50}$ [mol/l] | BA/F3 (insSVD) IC$_{50}$ [mol/l] | BA/F3 (wild type) IC$_{50}$ [mol/l] |
|---|---|---|---|
| 38 | 2.24E−7 | >2.00E−6 | 5.91E−6 |
| 41 | 3.43E−8 | >2.00E−6 | 5.02E−6 |
| 45 | 1.28E−8 | >2.00E−6 | 4.04E−6 |

REFERENCES

Pao et al, 2010: Pao and Chmielecki, Nat Rev Cancer. 2010 November; 10(11):760-74

Paez et al, 2004: Paez et al., Science. 2004 Jun. 4; 304 (5676):1497-500

Mok et al, 2009: Mok et al., N Engl J Med. 2009 Sep. 3; 361(10):947-57

Sequist et al, 2013: Sequist et al., J Clin Oncol. 2013 Sep. 20; 31(27):3327-34

Pao et al, 2005: Pao et al., PLoS Med. 2005 March; 2(3):e73

Mok et al, 2017: Mok et al., N Engl J Med. 2017 Feb. 16; 376(7):629-640

Yasuda, 2013: Yasuda, Sci Transl Med. 2013 Dec. 18; 5(216):216ra177

Chen et al, 2016: Chen et al., Onco Targets Ther. 2016 Jul. 8; 9:4181-6

Yang et al, 2015: Yang et al., Lancet Oncol. 2015 July; 16(7):830-8

Hasako et al., 2018: Hasako et al., Mol Cancer Ther. 2018 August; 17(8): 1648-1658

Jang et al., 2018: Jang et al., Angew Chem Int Ed Engl. 2018 Sep. 3; 57(36)

Floc'h et al., 2018: Floc'h et al., Mol Cancer Ther. 2018 May 17(5): 885-896

Robichaux et al., 2018: Robichaux et al., Nat Med. 2018 May; 24(5):638-646

Doebele et al., 2018: Doebele et al., Poster 338, presented at the 54th Annual Meeting of the American Society of Clinical Oncology, Jun. 1-5, 2018, Chicago, Ill.

Oxnard et al, 2013: Oxnard et al., J Thorac Oncol. 2013 February; 8(2): 179-184

The invention claimed is:
1. A compound of formula (I)

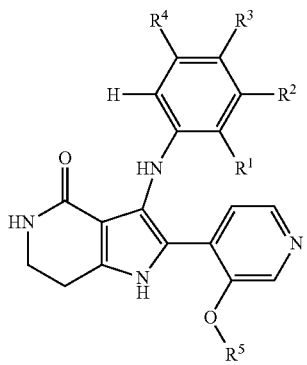

in which:
R¹ represents methyl, ethyl, trifluoromethyl, 2,2-difluoroethyl, cyano, bromo, methoxy, or difluoromethoxy, or with the proviso that when R¹ is chloro, then R² represents hydrogen or chloro and R³ and R⁴ represent hydrogen;
R² represents hydrogen, methyl, fluoro, chloro or bromo;
R³ represents hydrogen or fluoro;
R⁴ represents hydrogen or fluoro, wherein at least one of R³ and R⁴ represents hydrogen;
R⁵ represents C₂-C₅-alkyl, which is substituted once with hydroxy, C₁-C₄-alkoxy, R⁷R⁸N—, or phenyl, or R⁶—CH₂—,
wherein said phenyl groups are optionally substituted one or more times, independently of each other, with R;
R' represents, independently of each other, hydroxy, halogen, cyano, C₁-C₄-alkyl, C₁-C₄-alkoxy, C₁-C₄-haloalkyl or C₁-C₄-haloalkoxy;
R⁶ represents a group selected from the group:

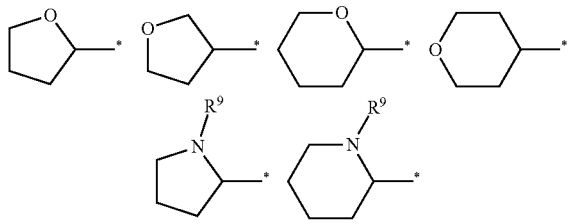

wherein * indicates the point of attachment of said group with the rest of the molecule;
R⁷, R⁸ represent, independently of each other, C₁-C₃-alkyl, C₁-C₃-haloalkyl or
R⁷ and R⁸ together with the nitrogen atom to which they are attached form a 5- to 6-membered nitrogen containing heterocyclic ring, optionally containing one additional heteroatom or heteroatom containing group selected from O and NR¹⁰;
R⁹ represents hydrogen, C₁-C₃-alkyl or C₁-C₃-haloalkyl;
R¹⁰ represents hydrogen or C₁-C₃-alkyl;
or an N-oxide, a salt, a tautomer or a stereoisomer of said compound, or a salt of said N-oxide, tautomer or stereoisomer.

2. The compound of formula (I) according to claim 1, wherein:
R¹ represents methyl, ethyl, trifluoromethyl, 2,2-difluoroethyl, cyano, bromo, methoxy, or difluoromethoxy, or with the proviso that when R¹ is chloro, then R² represents;
R² represents fluoro or chloro;
R³ represents hydrogen;
R⁴ represents hydrogen;
R⁵ represents C2-C₅-alkyl, which is substituted once with hydroxy, C₁-C₂-alkoxy or R⁷R⁸N—, or R⁶—CH₂—;
R⁶ represents a group selected from the group:

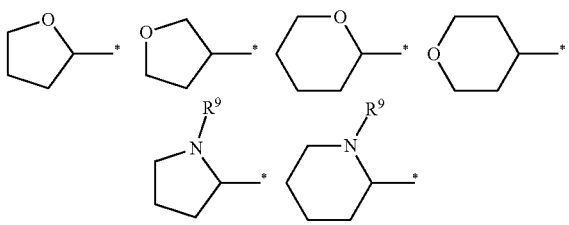

wherein * indicates the point of attachment of said group with the rest of the molecule;
R⁷, R⁸ represent, independently of each other, C₁-C₂-alkyl, or C₁-C₂-haloalkyl;
R⁹ represents hydrogen, C₁-C₂-alkyl or C₁-C₂-haloalkyl;
or an N-oxide, a salt, a tautomer or a stereoisomer of said compound, or a salt of said N-oxide, tautomer or stereoisomer.

3. The compound of formula (I) according to claim 1, wherein:
R¹ represents methyl, ethyl, trifluoromethyl, 2,2-difluoroethyl, cyano, bromo, methoxy, or difluoromethoxy, or with the proviso that when R¹ is chloro, then R² represents chloro;
R² represents fluoro or chloro;
R³ represents hydrogen;
R⁴ represents hydrogen;
R⁵ represents C₄-C₅-alkyl, which is substituted once with hydroxy, methoxy or R⁷R⁸N—, or R⁶—CH₂—;
R⁶ represents a group selected from the group:

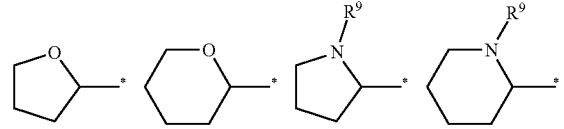

wherein * indicates the point of attachment of said group with the rest of the molecule;
R⁷, R⁸ represent, independently of each other, methyl, or C₁-C₂-fluoroalkyl;
R⁹ represents C₁-C₂-alkyl or C₁-C₂-fluoroalkyl;
or an N-oxide, a salt, a tautomer or a stereoisomer of said compound, or a salt of said N-oxide, tautomer or stereoisomer.

4. The compound of formula (I) according to claim 1, which is selected from the group consisting of:
3-{[2-(difluoromethoxy)phenyl]amino}-2-[3-(2-methoxyethoxy)pyridin-4-yl]-1,5,6,7-tetrahydro-4H-pyrrolo[3,2-c]pyridin-4-one 3-[(2-bromo-3-fluorophenyl)amino]-2-[3-(2-methoxyethoxy)pyridin-4-yl]-1,5,6,7-tetrahydro-4H-pyrrolo[3,2-c]pyridin-4-one 2-[3-(2-methoxyethoxy)pyridin-4-yl]-3-[(2-methoxyphenyl)amino]-1,5,6,7-tetrahydro-4H-pyrrolo[3,2-c]pyridin-4-one 3-{[2-(2,2-difluoroethyl)phenyl]amino}-2-[3-(2-methoxyethoxy)pyridin-4-yl]-1,5,6,7-tetrahydro-4H-pyrrolo[3,2-c]pyridin-4-one 3-(3-fluoro-2-methoxyanilino)-2-[3-(2-methoxyethoxy)pyridin-4-yl]-1,5,6,7-tetrahydro-4H-pyrrolo[3,2-c]pyridin-4-one 3-(3-fluoro-2-methoxyanilino)-2-[3-(2-methoxy-2-methylpropoxy)pyridin-4-yl]-1,5,6,7-tetrahydro-4H-pyrrolo[3,2-c]pyridin-4-one 3-[2-(difluoromethoxy)-3-fluoroanilino]-2-[3-(2-methoxyethoxy)pyridin-4-yl]-1,5,6,7-tetrahydro-4H-pyrrolo[3,2-c]pyridin-4-one 3-[2-(difluoromethoxy)-3-fluoroanilino]-2-[3-(2-methoxy-2-methylpropoxy)pyridin-4-yl]-1,5,6,7-tetrahydro-4H-pyrrolo[3,2-c]pyridin-4-one 3-[(3-fluoro-2-methylphenyl)amino]-2-[3-(2-methoxyethoxy)pyridin-4-yl]-1,5,6,7-tetrahydro-4H-pyrrolo[3,2-c]pyridin-4-one 3-(3-fluoro-2-methylanilino)-2-[3-(2-methoxy-2-methylpropoxy)pyridin-4-yl]-1,5,6,7-tetrahydro-4H-pyrrolo[3,2-c]pyridin-4-one 3-{[2-(2,2-difluoroethyl)-3-fluorophenyl]amino}-2-[3-(2-methoxyethoxy)pyridin-4-yl]-1,5,6,7-tetrahydro-4H-pyrrolo[3,2-c]pyridin-4-one 3-[2-(2,2-difluoroethyl)-3-fluoroanilino]-2-[3-(2-methoxy-2-methylpropoxy)pyridin-4-yl]-1,5,6,7-tetrahydro-4H-pyrrolo[3,2-c]pyridin-4-one 3-[(3,4-difluoro-2-methoxyphenyl)amino]-2-[3-(2-methoxyethoxy)pyridin-4-yl]-1,5,6,7-tetrahydro-4H-pyrrolo[3,2-c]pyridin-4-one 3-[(3,4-difluoro-2-methoxyphenyl)amino]-2-[3-(2-methoxy-2-methylpropoxy)pyridin-4-yl]-1,5,6,7-tetrahydro-4H-pyrrolo[3,2-c]pyridin-4-one 3-[(3,5-difluoro-2-methoxyphenyl)amino]-2-[3-(2-methoxyethoxy)pyridin-4-yl]-1,5,6,7-tetrahydro-4H-pyrrolo[3,2-c]pyridin-4-one 3-(3,5-difluoro-2-methoxyanilino)-2-[3-(2-methoxy-2-methylpropoxy)pyridin-4-yl]-1,5,6,7-tetrahydro-4H-pyrrolo[3,2-c]pyridin-4-one 3-(3-chloro-2-methoxyanilino)-2-[3-(2-methoxyethoxy)pyridin-4-yl]-1,5,6,7-tetrahydro-4H-pyrrolo[3,2-c]pyridin-4-one 3-(3-chloro-2-methoxyanilino)-2-[3-(2-methoxy-2-methylpropoxy)pyridin-4-yl]-1,5,6,7-tetrahydro-4H-pyrrolo[3,2-c]pyridin-4-one 3-(2,3-dichloroanilino)-2-[3-(2-methoxy-2-methylpropoxy)pyridin-4-yl]-1,5,6,7-tetrahydro-4H-pyrrolo[3,2-c]pyridin-4-one 3-(2-ethyl-3-fluoroanilino)-2-[3-(2-methoxy-2-methylpropoxy)pyridin-4-yl]-1,5,6,7-tetrahydro-4H-pyrrolo[3,2-c]pyridin-4-one 3-(3-chloro-2-methylanilino)-2-[3-(2-methoxy-2-methylpropoxy)pyridin-4-yl]-1,5,6,7-tetrahydro-4H-pyrrolo[3,2-c]pyridin-4-one 3-(2-bromo-3-fluoroanilino)-2-[3-(2-methoxy-2-methylpropoxy)pyridin-4-yl]-1,5,6,7-tetrahydro-4H-pyrrolo[3,2-c]pyridin-4-one 3-[3-chloro-2-(difluoromethoxy)anilino]-2-[3-(2-methoxy-2-methylpropoxy)pyridin-4-yl]-1,5,6,7-tetrahydro-4H-pyrrolo[3,2-c]pyridin-4-one 3-(2-chloroanilino)-2-[3-(2-methoxy-2-methylpropoxy)pyridin-4-yl]-1,5,6,7-tetrahydro-4H-pyrrolo[3,2-c]pyridin-4-one 3-(3,5-difluoro-2-methylanilino)-2-[3-(2-methoxy-2-methylpropoxy)pyridin-4-yl]-1,5,6,7-tetrahydro-4H-pyrrolo[3,2-c]pyridin-4-one 3-[3-fluoro-2-(trifluoromethyl)anilino]-2-[3-(2-methoxy-2-methylpropoxy)pyridin-4-yl]-1,5,6,7-tetrahydro-4H-pyrrolo[3,2-c]pyridin-4-one 2-[3-(2-methoxy-2-methylpropoxy)pyridin-4-yl]-3-[2-(trifluoromethyl)anilino]-1,5,6,7-tetrahydro-4H-pyrrolo[3,2-c]pyridin-4-one 3-[2-(difluoromethoxy)-3,5-difluoroanilino]-2-[3-(2-methoxy-2-methylpropoxy)pyridin-4-yl]-1,5,6,7-tetrahydro-4H-pyrrolo[3,2-c]pyridin-4-one 3-(3-chloro-4-fluoro-2-methoxyanilino)-2-[3-(2-methoxy-2-methylpropoxy)pyridin-4-yl]-1,5,6,7-tetrahydro-4H-pyrrolo[3,2-c]pyridin-4-one 3-(5-fluoro-2-methylanilino)-2-[3-(2-methoxy-2-methylpropoxy)pyridin-4-yl]-1,5,6,7-tetrahydro-4H-pyrrolo[3,2-c]pyridin-4-one 3-(2,3-dichloroanilino)-2-[3-(2-methoxyethoxy)pyridin-4-yl]-1,5,6,7-tetrahydro-4H-pyrrolo[3,2-c]pyridin-4-one 2-[3-(2-methoxy ethoxy)pyridin-4-yl]-3-[2-(trifluoromethyl)anilino]-1,5,6,7-tetrahydro-4H-pyrrolo[3,2-c]pyridin-4-one 3-(3-chloro-2-methoxyanilino)-2-(3-{[(2S)-1-methylpyrrolidin-2-yl]methoxy}pyridin-4-yl)-1,5,6,7-tetrahydro-4H-pyrrolo[3,2-c]pyridin-4-one 3-(3-fluoro-2-methylanilino)-2-(3-{[(2S)-1-methyl pyrrol i di n-2-yl]methoxy}pyridin-4-yl)-1,5,6,7-tetrahydro-4H-pyrrolo[3,2-c]pyridin-4-one 3-[3-chloro-2-(difluoromethoxy)anilino]-2-(3-{[(2S)-1-methylpyrrolidin-2-yl]methoxy}pyridin-4-yl)-1,5,6,7-tetrahydro-4H-pyrrolo[3,2-c]pyridin-4-one 3-(3,5-difluoro-2-methylanilino)-2-(3-{[(2S)-1-methyl pyrrol i di n-2-yl]methoxy}pyridin-4-yl)-1,5,6,7-tetrahydro-4H-pyrrolo[3,2-c]pyridin-4-one 3-(3-chloro-2-methylanilino)-2-{3-[2-(dimethylamino)ethoxy]pyridin-4-yl}-1,5,6,7-tetrahydro-4H-pyrrolo[3,2-c]pyridin-4-one 2-{3-[2-(dimethylamino)ethoxy]pyridin-4-yl}-3-(3-fluoro-2-methoxyanilino)-1,5,6,7-tetrahydro-4H-pyrrolo[3,2-c]pyridin-4-one 3-(3-chloro-2-methoxyanilino)-2-{3-[2-(dimethylamino)ethoxy]pyridin-4-yl}-1,5,6,7-tetrahydro-4H-pyrrolo[3,2-c]pyridin-4-one 3-(3,5-difluoro-2-methylanilino)-2-{3-[2-(dimethylamino)ethoxy]pyridin-4-yl}-1,5,6,7-tetrahydro-4H-pyrrolo[3,2-c]pyridin-4-one 2-{3-[2-(dimethylamino)ethoxy]pyridin-4-yl}-3-(3-fluoro-2-methylanilino)-1,5,6,7-tetrahydro-4H-pyrrolo[3,2-c]pyridin-4-one 3-(3-fluoro-2-methoxyanilino)-2-[3-(3-methoxy-3-methylbutoxy)pyridin-4-yl]-1,5,6,7-tetrahydro-4H-pyrrolo[3,2-c]pyridin-4-one 2-[3-(2-ethoxy-2-methylpropoxy)pyridin-4-yl]-3-(3-fluoro-2-methoxyanilino)-1,5,6,7-tetrahydro-4H-pyrrolo[3,2-c]pyridin-4-one 3-(3-chloro-2-methoxyanilino)-2-[3-(2-hydroxy-2-methylpropoxy)pyridin-4-yl]-1,5,6,7-tetrahydro-4H-pyrrolo[3,2-c]pyridin-4-one 3-(3-chloro-2-methylanilino)-2-{3-[2-(dimethylamino)-2-methylpropoxy]pyridin-4-yl}-1,5,6,7-tetrahydro-4H-pyrrolo[3,2-c]pyridin-4-one 2-{3-[2-(dimethylamino)-2-methylpropoxy]pyridin-4-yl}-3-(3-fluoro-2-methylanilino)-1,5,6,7-tetrahydro-4H-pyrrolo[3,2-c]pyridin-4-one 3-(3,5-difluoro-2-methylanilino)-2-{3-[2-(dimethylamino)-2-methylpropoxy]pyridin-4-yl}-1,5,6,7-tetrahydro-4H-pyrrolo[3,2-c]pyridin-4-one 3-(3-chloro-2-methoxyanilino)-2-(3-{[1-methylpiperidin-2-yl]methoxy}pyridin-4-yl)-1,5,6,7-tetrahydro-4H-pyrrolo[3,2-c]pyridin-4-one 3-[2-(difluoromethoxy)-3-fluoroanilino]-2-{3-[2-(dimethylamino)ethoxy]pyridin-4-yl}-1,5,6,7-tetrahydro-4H-pyrrolo[3,2-c]pyridin-4-one 3-(3-fluoro-2-methylanilino)-2-(3-{[oxolan-3-yl]methoxy}pyridin-4-yl)-1,5,6,7-tetrahydro-4H-pyrrolo[3,2-c]pyridin-4-one 3-(3-chloro-2-methoxyanilino)-2-(3-{[(2S)-oxolan-2-yl]methoxy}pyridin-4-yl)-1,5,6,7-tetrahydro-4H-pyrrolo[3,2-c]pyridin-4-one 3-(3-chloro-2-methoxyanilino)-2-(3-{[(2R)-oxolan-2-yl]methoxy}pyridin-4-yl)-1,5,6,7-tetrahydro-4H-pyrrolo[3,2-c]pyridin-4-one 3-(3-chloro-2-methoxy anilino)-2-{3-[(oxan-2-yl)methoxy]pyridin-4-yl}-1,5,6,7-tetrahydro-4H-pyrrolo[3,2-c]pyridin-4-one 3-(2,3-dichloroanilino)-2-{3-[(oxan-2-yl)methoxy]pyridin-4-yl}-1,5,6,7-tetrahydro-4H-pyrrolo[3,2-c]pyridin-4-one 3-(2,3-dichloroanilino)-2-(3-{[(2S)-oxolan-2-yl]methoxy}pyridin-4-yl)-1,5,6,7-tetrahydro-4H-pyrrolo[3,2-c]pyridin-4-one 3-(2,3-dichloroanilino)-2-(3-{[(2S)-1-methylpyrrolidin-2-yl]methoxy}pyridin-4-yl)-1,5,6,7-tetrahydro-4H-pyrrolo[3,2-c]pyridin-4-one 3-(3-fluoro-2-methoxyanilino)-2-[3-(2-hydroxy-2-methylpropoxy)pyridin-4-yl]-1,5,6,7-tetrahydro-4H-pyrrolo[3,2-c]pyridin-4-one 3-[2-(difluoromethoxy)-3-fluoroanilino]-2-[3-(2-hydroxy-2-methylpropoxy)pyridin-4-yl]-1,5,6,7-tetrahydro-4H-pyrrolo[3,2-c]pyridin-4-one 2-{3-[2-(dimethylamino)-2-methylpropoxy]pyridin-4-yl}-3-(3-fluoro-2-methoxy anilino)-1,5,6,7-tetrahydro-4H-pyrrolo[3,2-c]pyridin-4-one 3-(3-fluoro-2-methoxyanilino)-2-{3-[2-methyl-2-(morpholin-4-yl)propoxy]pyridin-4-yl}-1,5,6,7-tetrahydro-4H-pyrrolo[3,2-c]pyridin-4-one 3-[2-(difluoromethoxy)-3-fluoroanilino]-2-{3-[2-methyl-2-(morpholin-4-yl)propoxy]pyridin-4-yl}-1,5,6,7-tetrahydro-4H-pyrrolo[3,2-c]pyridin-4-one 3-(3-chloro-2-methylanilino)-2-(3-{[(2S)-1-methylpyrrolidin-2-yl]methoxy}pyridin-4-yl)-1,5,6,7-tetrahydro-4H-pyrrolo[3,2-c]pyridin-4-one 3-(2-bromo-3-chloroanilino)-2-[3-(2-methoxy-2-methylpropoxy)pyridin-4-yl]-1,5,6,7-tetrahydro-4H-pyrrolo[3,2-c]pyridin-4-one 3-[3-chloro-2-(difluoromethoxy)anilino]-2-{3-[(oxolan-3-yl)methoxy]pyridin-4-yl}-1,5,6,7-tetrahydro-4H-pyrrolo[3,2-c]pyridin-4-one 3-(3-chloro-2-methoxyanilino)-2-(3-{[(2S)-pyrrolidin-2-yl]methoxy}pyridin-4-yl)-1,5,6,7-tetrahydro-4H-pyrrolo[3,2-c]pyridin-4-one 3-[3-chloro-2-(difluoromethoxy)anilino]-2-{3-[2-(morpholin-4-yl)ethoxy]pyridin-4-yl}-1,5,6,7-tetrahydro-4H-pyrrolo[3,2-c]pyridin-4-one 3-[3-chloro-2-(difluoromethoxy)anilino]-2-{3-[(oxan-4-yl)methoxy]pyridin-4-yl}-1,5,6,7-tetrahydro-4H-pyrrolo[3,2-c]pyridin-4-one 3-{[2-(difluoromethoxy)-3-fluorophenyl]amino}-2-[3-(2-methoxy-2-methylpropoxy)pyridin-4-yl]-1,5,6,7-tetrahydro-4H-pyrrolo[3,2-c]pyridin-4-one hydrochloride 3-(3-fluoro-2-m ethoxy anilino)-2-{3-[2-(morpholin-4-yl)ethoxy]pyridin-4-yl}-1,5,6,7-tetrahydro-4H-pyrrolo[3,2-c]pyridin-4-one 2-{3-[2-(diethylamino)ethoxy]pyridin-4-yl}-3-(3-fluoro-2-methoxyanilino)-1,5,6,7-tetrahydro-4H-pyrrolo[3,2-c]pyridin-4-one 3-(3-fluoro-2-methoxyanilino)-2-{3-[(oxolan-2-yl)methoxy]pyridin-4-yl}-1,5,6,7-tetrahydro-4H-pyrrolo[3,2-c]pyridin-4-one 2-[3-(2-tert-butoxyethoxy)pyridin-4-yl]-3-(3-chloro-2-methoxyanilino)-1,5,6,7-tetrahydro-4H-pyrrolo[3,2-c]pyridin-4-one 3-(3-fluoro-2-m ethoxy anilino)-2-(3-{[(2S)-oxolan-2-yl]methoxy}pyridin-4-yl)-1,5,6,7-tetrahydro-4H-pyrrolo[3,2-c]pyridin-4-one 3-(3-fluoro-2-methoxyanilino)-2-(3-{[(2R)-oxolan-2-yl]methoxy}pyridin-4-yl)-1,5,6,7-tetrahydro-4H-pyrrolo[3,2-c]pyridin-4-one 3-(3-fluoro-2-m ethoxy anilino)-2-(3-{[1-methylpiperidin-2-yl]methoxy}pyridin-4-yl)-1,5,6,7-tetrahydro-4H-pyrrolo[3,2-c]pyridin-4-one 2-[3-(2-tert-butoxyethoxy)pyridin-4-yl]-3-(3-fluoro-2-methoxyanilino)-1,5,6,7-tetrahydro-4H-pyrrolo[3,2-c]pyridin-4-one 3-(3-fluoro-2-methoxyanilino)-2-{3-[(2R)-2-methoxypropoxy]pyridin-4-yl}-1,5,6,7-tetrahydro-4H-pyrrolo[3,2-c]pyridin-4-one 3-(3-fluoro-2-methoxyanilino)-2-(3-{[1-phenylpropan-2-yl]oxy}pyridin-4-yl)-1,5,6,7-tetrahydro-4H-pyrrolo[3,2-c]pyridin-4-one 2-fluoro-6-({2-[3-(2-methoxy-2-methylpropoxy)pyridin-4-yl]-4-oxo-4,5,6,7-tetrahydro-1H-pyrrolo[3,2-c]pyridin-3-yl}amino)benzonitrile 3-(3-chloro-2-methoxyanilino)-2-(3-{[(2S)-1-(2,2,2-trifluoroethyl)pyrrolidin-2-yl]methoxy}pyridin-4-yl)-1,5,6,7-tetrahydro-4H-pyrrolo[3,2-c]pyridin-4-one 3-(3-chloro-4-fluoro-2-methoxyanilino)-2-(3-{2-[methyl(2,2,2-trifluoroethyl)amino]ethoxy}pyridin-4-yl)-1,5,6,7-tetrahydro-4H-pyrrolo[3,2-c]pyridin-4-one or an N-oxide, a salt, a tautomer or a stereoisomer of said compound, or a salt of said N-oxide, tautomer or stereoisomer.

5. A pharmaceutical composition comprising at least one compound of general formula (I) according to claim 1, together with at least one pharmaceutically acceptable auxiliary.

6. The composition according to claim 5 for the treatment of haematological tumours, solid tumours and/or metastases thereof.

7. A combination comprising one or more first active ingredients selected from a compound of general formula (I) according to claim 1, and one or more chemotherapeutic anti-cancer agents.

8. A method for the treatment or prophylaxis of disease of a subject comprising administration of a compound of general formula (I) according to claim 1 to the subject:
wherein the disease comprises uncontrolled cell growth, proliferation, and/or survival, inappropriate cellular immune responses, or inappropriate inflammatory responses mediated by an EGF-receptor having a mutation in exon 20.

9. A method of inhibiting EGF-receptor kinase activity in a cancer cell comprising an EGF-receptor having a mutation in exon 20, the method comprising contacting the cancer cell with a compound of general formula (I) according to claim 1.

10. A method of reducing the survival of a cancer cell or inducing death in a cancer cell, the method comprising contacting a cancer cell comprising an EGF-receptor having a mutation in exon 20 with a compound of general formula (I) according to claim 1.

11. A method of enhancing the efficacy of an anti-EGF-receptor therapy, the method comprising administering to the subject an anti-EGF receptor therapy in combination with a compound of general formula (I) according to claim 1.

12. A method of treating cancer in a subject, wherein the cancer is or has acquired resistance to an anti-EGF receptor therapy, the method comprising administering to the subject an effective amount of a compound of general formula (I) according to claim 1.

13. A method for treating a patient with cancer, the method comprising administering to the subject an anti-EGF receptor therapy in combination with a compound of general formula (I) according to claim 1, wherein the subject is selected for therapy by detecting the presence of a mutation in exon 20 of the EGF-receptor in a biological sample of the subject.

14. A method of treating cancer comprising an EGF-receptor having a mutation in exon 20 in a subject, the method comprising administering to the subject an effective amount of a compound of general formula (I) according to claim 1.

15. The method of claim 14, wherein the cancer is selected from the group consisting of leukemia, myelodysplastic syndrome, malignant lymphoma, head and neck tumours, tumours of the thorax, gastrointestinal tumours, endocrine tumours, mammary and other gynaecological tumours, urological tumours, skin tumours, and sarcomas.

16. The method of claim 15, wherein the cancer is selected from the group consisting of inverted sinonasal papilloma or inverted sinonasal papilloma associated sinanonasal squamous cell carcinoma.

17. The method of claim 14, wherein the EGF-receptor comprises an insertion in exon 20.

18. The method of claim 17, wherein the EGF-receptor comprises an insertion between amino acids V769-D770 and/or between amino acids D770-N771.

19. The method of claim 15, wherein the tumour of the thorax is non-small cell lung cancer.

\* \* \* \* \*

SEQUENCE LISTING

<160> NUMBER OF SEQ ID NOS: 9

<210> SEQ ID NO 1
<211> LENGTH: 788

```
<212> TYPE: PRT
<213> ORGANISM: Artificial Sequence
<220> FEATURE:
<223> OTHER INFORMATION: Description of Artificial Sequence: Synthetic
      modified polypeptide

<400> SEQUENCE: 1

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Pro Ile Thr Ser
    210                 215                 220

Leu Tyr Lys Lys Ala Gly Ser Asp Tyr Asp Ile Pro Thr Thr Thr Glu
225                 230                 235                 240

Asn Leu Tyr Phe Gln Gly Arg Arg His Ile Val Arg Lys Arg Thr
                245                 250                 255

Leu Arg Arg Leu Leu Gln Glu Arg Glu Leu Val Glu Pro Leu Thr Pro
            260                 265                 270

Ser Gly Glu Ala Pro Asn Gln Ala Leu Leu Arg Ile Leu Lys Glu Thr
        275                 280                 285

Glu Phe Lys Lys Ile Lys Val Leu Gly Ser Gly Ala Phe Gly Thr Val
    290                 295                 300

Tyr Lys Gly Leu Trp Ile Pro Glu Gly Glu Lys Val Lys Ile Pro Val
305                 310                 315                 320

Ala Ile Lys Glu Leu Arg Glu Ala Thr Ser Pro Lys Ala Asn Lys Glu
                325                 330                 335

Ile Leu Asp Glu Ala Tyr Val Met Ala Ser Val Asp Asn Pro His Val
            340                 345                 350

Cys Arg Leu Leu Gly Ile Cys Leu Thr Ser Thr Val Gln Leu Ile Thr
        355                 360                 365

Gln Leu Met Pro Phe Gly Cys Leu Leu Asp Tyr Val Arg Glu His Lys
    370                 375                 380
```

```
Asp Asn Ile Gly Ser Gln Tyr Leu Leu Asn Trp Cys Val Gln Ile Ala
385                 390                 395                 400

Lys Gly Met Asn Tyr Leu Glu Asp Arg Arg Leu Val His Arg Asp Leu
            405                 410                 415

Ala Ala Arg Asn Val Leu Val Lys Thr Pro Gln His Val Lys Ile Thr
            420                 425                 430

Asp Phe Gly Leu Ala Lys Leu Leu Gly Ala Glu Glu Lys Glu Tyr His
            435                 440                 445

Ala Glu Gly Gly Lys Val Pro Ile Lys Trp Met Ala Leu Glu Ser Ile
        450                 455                 460

Leu His Arg Ile Tyr Thr His Gln Ser Asp Val Trp Ser Tyr Gly Val
465                 470                 475                 480

Thr Val Trp Glu Leu Met Thr Phe Gly Ser Lys Pro Tyr Asp Gly Ile
                485                 490                 495

Pro Ala Ser Glu Ile Ser Ser Ile Leu Glu Lys Gly Glu Arg Leu Pro
            500                 505                 510

Gln Pro Pro Ile Cys Thr Ile Asp Val Tyr Met Ile Met Val Lys Cys
            515                 520                 525

Trp Met Ile Asp Ala Asp Ser Arg Pro Lys Phe Arg Glu Leu Ile Ile
530                 535                 540

Glu Phe Ser Lys Met Ala Arg Asp Pro Gln Arg Tyr Leu Val Ile Gln
545                 550                 555                 560

Gly Asp Glu Arg Met His Leu Pro Ser Pro Thr Asp Ser Asn Phe Tyr
                565                 570                 575

Arg Ala Leu Met Asp Glu Glu Asp Met Asp Asp Val Val Asp Ala Asp
                580                 585                 590

Glu Tyr Leu Ile Pro Gln Gln Gly Phe Phe Ser Ser Pro Ser Thr Ser
                595                 600                 605

Arg Thr Pro Leu Leu Ser Ser Leu Ser Ala Thr Ser Asn Asn Ser Thr
            610                 615                 620

Val Ala Cys Ile Asp Arg Asn Gly Leu Gln Ser Cys Pro Ile Lys Glu
625                 630                 635                 640

Asp Ser Phe Leu Gln Arg Tyr Ser Ser Asp Pro Thr Gly Ala Leu Thr
                645                 650                 655

Glu Asp Ser Ile Asp Asp Thr Phe Leu Pro Val Pro Glu Tyr Ile Asn
            660                 665                 670

Gln Ser Val Pro Lys Arg Pro Ala Gly Ser Val Gln Asn Pro Val Tyr
            675                 680                 685

His Asn Gln Pro Leu Asn Pro Ala Pro Ser Arg Asp Pro His Tyr Gln
            690                 695                 700

Asp Pro His Ser Thr Ala Val Gly Asn Pro Glu Tyr Leu Asn Thr Val
705                 710                 715                 720

Gln Pro Thr Cys Val Asn Ser Thr Phe Asp Ser Pro Ala His Trp Ala
                725                 730                 735

Gln Lys Gly Ser His Gln Ile Ser Leu Asp Asn Pro Asp Tyr Gln Gln
                740                 745                 750

Asp Phe Phe Pro Lys Glu Ala Lys Pro Asn Gly Ile Phe Lys Gly Ser
            755                 760                 765

Thr Ala Glu Asn Ala Glu Tyr Leu Arg Val Ala Pro Gln Ser Ser Glu
            770                 775                 780

Phe Ile Gly Ala
785
```

<210> SEQ ID NO 2
<211> LENGTH: 791
<212> TYPE: PRT
<213> ORGANISM: Artificial Sequence
<220> FEATURE:
<223> OTHER INFORMATION: Description of Artificial Sequence: Synthetic modified polypeptide

<400> SEQUENCE: 2

```
Met Ser Pro Ile Leu Gly Tyr Trp Lys Ile Lys Gly Leu Val Gln Pro
1               5                  10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Pro Ile Thr Ser
    210                 215                 220

Leu Tyr Lys Lys Ala Gly Ser Asp Tyr Asp Ile Pro Thr Thr Thr Glu
225                 230                 235                 240

Asn Leu Tyr Phe Gln Gly Arg Arg His Ile Val Arg Lys Arg Thr
                245                 250                 255

Leu Arg Arg Leu Leu Gln Glu Arg Glu Leu Val Glu Pro Leu Thr Pro
            260                 265                 270

Ser Gly Glu Ala Pro Asn Gln Ala Leu Leu Arg Ile Leu Lys Glu Thr
        275                 280                 285

Glu Phe Lys Lys Ile Lys Val Leu Gly Ser Gly Ala Phe Gly Thr Val
    290                 295                 300

Tyr Lys Gly Leu Trp Ile Pro Glu Gly Glu Lys Val Lys Ile Pro Val
305                 310                 315                 320

Ala Ile Lys Glu Leu Arg Glu Ala Thr Ser Pro Lys Ala Asn Lys Glu
                325                 330                 335

Ile Leu Asp Glu Ala Tyr Val Met Ala Ser Val Asp Ala Ser Val Asn
            340                 345                 350

Pro His Val Cys Arg Leu Leu Gly Ile Cys Leu Thr Ser Thr Val Gln
        355                 360                 365
```

-continued

```
Leu Ile Thr Gln Leu Met Pro Phe Gly Cys Leu Leu Asp Tyr Val Arg
        370             375                 380
Glu His Lys Asp Asn Ile Gly Ser Gln Tyr Leu Leu Asn Trp Cys Val
385             390                 395                 400
Gln Ile Ala Lys Gly Met Asn Tyr Leu Glu Asp Arg Arg Leu Val His
            405                 410                 415
Arg Asp Leu Ala Ala Arg Asn Val Leu Val Lys Thr Pro Gln His Val
            420                 425                 430
Lys Ile Thr Asp Phe Gly Leu Ala Lys Leu Leu Gly Ala Glu Glu Lys
        435                 440                 445
Glu Tyr His Ala Glu Gly Gly Lys Val Pro Ile Lys Trp Met Ala Leu
    450                 455                 460
Glu Ser Ile Leu His Arg Ile Tyr Thr His Gln Ser Asp Val Trp Ser
465                 470                 475                 480
Tyr Gly Val Thr Val Trp Glu Leu Met Thr Phe Gly Ser Lys Pro Tyr
                485                 490                 495
Asp Gly Ile Pro Ala Ser Glu Ile Ser Ser Ile Leu Glu Lys Gly Glu
            500                 505                 510
Arg Leu Pro Gln Pro Pro Ile Cys Thr Ile Asp Val Tyr Met Ile Met
        515                 520                 525
Val Lys Cys Trp Met Ile Asp Ala Asp Ser Arg Pro Lys Phe Arg Glu
    530                 535                 540
Leu Ile Ile Glu Phe Ser Lys Met Ala Arg Asp Pro Gln Arg Tyr Leu
545                 550                 555                 560
Val Ile Gln Gly Asp Glu Arg Met His Leu Pro Ser Pro Thr Asp Ser
                565                 570                 575
Asn Phe Tyr Arg Ala Leu Met Asp Glu Glu Asp Met Asp Asp Val Val
            580                 585                 590
Asp Ala Asp Glu Tyr Leu Ile Pro Gln Gln Gly Phe Phe Ser Ser Pro
        595                 600                 605
Ser Thr Ser Arg Thr Pro Leu Leu Ser Ser Leu Ser Ala Thr Ser Asn
    610                 615                 620
Asn Ser Thr Val Ala Cys Ile Asp Arg Asn Gly Leu Gln Ser Cys Pro
625                 630                 635                 640
Ile Lys Glu Asp Ser Phe Leu Gln Arg Tyr Ser Ser Asp Pro Thr Gly
                645                 650                 655
Ala Leu Thr Glu Asp Ser Ile Asp Asp Thr Phe Leu Pro Val Pro Glu
            660                 665                 670
Tyr Ile Asn Gln Ser Val Pro Lys Arg Pro Ala Gly Ser Val Gln Asn
        675                 680                 685
Pro Val Tyr His Asn Gln Pro Leu Asn Pro Ala Pro Ser Arg Asp Pro
    690                 695                 700
His Tyr Gln Asp Pro His Ser Thr Ala Val Gly Asn Pro Glu Tyr Leu
705                 710                 715                 720
Asn Thr Val Gln Pro Thr Cys Val Asn Ser Thr Phe Asp Ser Pro Ala
                725                 730                 735
His Trp Ala Gln Lys Gly Ser His Gln Ile Ser Leu Asp Asn Pro Asp
            740                 745                 750
Tyr Gln Gln Asp Phe Phe Pro Lys Glu Ala Lys Pro Asn Gly Ile Phe
        755                 760                 765
Lys Gly Ser Thr Ala Glu Asn Ala Glu Tyr Leu Arg Val Ala Pro Gln
    770                 775                 780
```

Ser Ser Glu Phe Ile Gly Ala
785                 790

<210> SEQ ID NO 3
<211> LENGTH: 791
<212> TYPE: PRT
<213> ORGANISM: Artificial Sequence
<220> FEATURE:
<223> OTHER INFORMATION: Description of Artificial Sequence: Synthetic
      modified polypeptide

<400> SEQUENCE: 3

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Pro Ile Thr Ser
    210                 215                 220

Leu Tyr Lys Lys Ala Gly Ser Asp Tyr Asp Ile Pro Thr Thr Thr Glu
225                 230                 235                 240

Asn Leu Tyr Phe Gln Gly Arg Arg His Ile Val Arg Lys Arg Thr
                245                 250                 255

Leu Arg Arg Leu Leu Gln Glu Arg Glu Leu Val Glu Pro Leu Thr Pro
            260                 265                 270

Ser Gly Glu Ala Pro Asn Gln Ala Leu Leu Arg Ile Leu Lys Glu Thr
        275                 280                 285

Glu Phe Lys Lys Ile Lys Val Leu Gly Ser Gly Ala Phe Gly Thr Val
    290                 295                 300

Tyr Lys Gly Leu Trp Ile Pro Glu Gly Glu Lys Val Lys Ile Pro Val
305                 310                 315                 320

Ala Ile Lys Glu Leu Arg Glu Ala Thr Ser Pro Lys Ala Asn Lys Glu
                325                 330                 335

Ile Leu Asp Glu Ala Tyr Val Met Ala Ser Val Asp Ser Val Asp Asn
            340                 345                 350

```
Pro His Val Cys Arg Leu Leu Gly Ile Cys Leu Thr Ser Thr Val Gln
        355                 360                 365

Leu Ile Thr Gln Leu Met Pro Phe Gly Cys Leu Leu Asp Tyr Val Arg
370                 375                 380

Glu His Lys Asp Asn Ile Gly Ser Gln Tyr Leu Leu Asn Trp Cys Val
385                 390                 395                 400

Gln Ile Ala Lys Gly Met Asn Tyr Leu Glu Asp Arg Arg Leu Val His
                405                 410                 415

Arg Asp Leu Ala Ala Arg Asn Val Leu Val Lys Thr Pro Gln His Val
                420                 425                 430

Lys Ile Thr Asp Phe Gly Leu Ala Lys Leu Leu Gly Ala Glu Glu Lys
                435                 440                 445

Glu Tyr His Ala Glu Gly Gly Lys Val Pro Ile Lys Trp Met Ala Leu
                450                 455                 460

Glu Ser Ile Leu His Arg Ile Tyr Thr His Gln Ser Asp Val Trp Ser
465                 470                 475                 480

Tyr Gly Val Thr Val Trp Glu Leu Met Thr Phe Gly Ser Lys Pro Tyr
                485                 490                 495

Asp Gly Ile Pro Ala Ser Glu Ile Ser Ser Ile Leu Glu Lys Gly Glu
                500                 505                 510

Arg Leu Pro Gln Pro Pro Ile Cys Thr Ile Asp Val Tyr Met Ile Met
                515                 520                 525

Val Lys Cys Trp Met Ile Asp Ala Asp Ser Arg Pro Lys Phe Arg Glu
                530                 535                 540

Leu Ile Ile Glu Phe Ser Lys Met Ala Arg Asp Pro Gln Arg Tyr Leu
545                 550                 555                 560

Val Ile Gln Gly Asp Glu Arg Met His Leu Pro Ser Pro Thr Asp Ser
                565                 570                 575

Asn Phe Tyr Arg Ala Leu Met Asp Glu Glu Asp Met Asp Asp Val Val
                580                 585                 590

Asp Ala Asp Glu Tyr Leu Ile Pro Gln Gln Gly Phe Phe Ser Ser Pro
                595                 600                 605

Ser Thr Ser Arg Thr Pro Leu Leu Ser Ser Leu Ser Ala Thr Ser Asn
                610                 615                 620

Asn Ser Thr Val Ala Cys Ile Asp Arg Asn Gly Leu Gln Ser Cys Pro
625                 630                 635                 640

Ile Lys Glu Asp Ser Phe Leu Gln Arg Tyr Ser Ser Asp Pro Thr Gly
                645                 650                 655

Ala Leu Thr Glu Asp Ser Ile Asp Asp Thr Phe Leu Pro Val Pro Glu
                660                 665                 670

Tyr Ile Asn Gln Ser Val Pro Lys Arg Pro Ala Gly Ser Val Gln Asn
                675                 680                 685

Pro Val Tyr His Asn Gln Pro Leu Asn Pro Ala Pro Ser Arg Asp Pro
690                 695                 700

His Tyr Gln Asp Pro His Ser Thr Ala Val Gly Asn Pro Glu Tyr Leu
705                 710                 715                 720

Asn Thr Val Gln Pro Thr Cys Val Asn Ser Thr Phe Asp Ser Pro Ala
                725                 730                 735

His Trp Ala Gln Lys Gly Ser His Gln Ile Ser Leu Asp Asn Pro Asp
                740                 745                 750

Tyr Gln Gln Asp Phe Phe Pro Lys Glu Ala Lys Pro Asn Gly Ile Phe
                755                 760                 765
```

```
Lys Gly Ser Thr Ala Glu Asn Ala Glu Tyr Leu Arg Val Ala Pro Gln
    770                 775                 780

Ser Ser Glu Phe Ile Gly Ala
785                 790

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (1)..(1)
<223> OTHER INFORMATION: Biotin-Ahx
<220> FEATURE:
<221> NAME/KEY: MOD_RES
<222> LOCATION: (15)..(15)
<223> OTHER INFORMATION: Amidation

<400> SEQUENCE: 4

Xaa Ala Glu Glu Glu Glu Tyr Phe Glu Leu Val Ala Lys Lys Lys
1               5                   10                  15

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (1)..(1)
<223> OTHER INFORMATION: Biotin-Ahx
<220> FEATURE:
<221> NAME/KEY: MOD_RES
<222> LOCATION: (13)..(13)
<223> OTHER INFORMATION: Amidation

<400> SEQUENCE: 5

Xaa Val Leu Leu Pro Lys Lys Ser Phe Ala Glu Pro Gly
1               5                   10

<210> SEQ ID NO 6
<211> LENGTH: 1210
<212> TYPE: PRT
<213> ORGANISM: Homo sapiens

<400> SEQUENCE: 6

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110
```

```
Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
            165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
            245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
            290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
                435                 440                 445

Gly Leu Arg Ser Leu Lys Glu Ile Ser Asp Gly Asp Val Ile Ile Ser
            450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
```

```
                530                  535                  540
Glu Pro Arg Glu Phe Val Glu Asn Ser Glu Cys Ile Gln Cys His Pro
545                  550                  555                  560

Glu Cys Leu Pro Gln Ala Met Asn Ile Thr Cys Thr Gly Arg Gly Pro
                565                  570                  575

Asp Asn Cys Ile Gln Cys Ala His Tyr Ile Asp Gly Pro His Cys Val
                580                  585                  590

Lys Thr Cys Pro Ala Gly Val Met Gly Glu Asn Asn Thr Leu Val Trp
                595                  600                  605

Lys Tyr Ala Asp Ala Gly His Val Cys His Leu Cys His Pro Asn Cys
                610                  615                  620

Thr Tyr Gly Cys Thr Gly Pro Gly Leu Glu Gly Cys Pro Thr Asn Gly
625                  630                  635                  640

Pro Lys Ile Pro Ser Ile Ala Thr Gly Met Val Gly Ala Leu Leu Leu
                645                  650                  655

Leu Leu Val Val Ala Leu Gly Ile Gly Leu Phe Met Arg Arg Arg His
                660                  665                  670

Ile Val Arg Lys Arg Thr Leu Arg Arg Leu Leu Gln Glu Arg Glu Leu
                675                  680                  685

Val Glu Pro Leu Thr Pro Ser Gly Glu Ala Pro Asn Gln Ala Leu Leu
690                  695                  700

Arg Ile Leu Lys Glu Thr Glu Phe Lys Lys Ile Lys Val Leu Gly Ser
705                  710                  715                  720

Gly Ala Phe Gly Thr Val Tyr Lys Gly Leu Trp Ile Pro Glu Gly Glu
                725                  730                  735

Lys Val Lys Ile Pro Val Ala Ile Lys Glu Leu Arg Glu Ala Thr Ser
                740                  745                  750

Pro Lys Ala Asn Lys Glu Ile Leu Asp Glu Ala Tyr Val Met Ala Ser
                755                  760                  765

Val Asp Asn Pro His Val Cys Arg Leu Leu Gly Ile Cys Leu Thr Ser
                770                  775                  780

Thr Val Gln Leu Ile Thr Gln Leu Met Pro Phe Gly Cys Leu Leu Asp
785                  790                  795                  800

Tyr Val Arg Glu His Lys Asp Asn Ile Gly Ser Gln Tyr Leu Leu Asn
                805                  810                  815

Trp Cys Val Gln Ile Ala Lys Gly Met Asn Tyr Leu Glu Asp Arg Arg
                820                  825                  830

Leu Val His Arg Asp Leu Ala Ala Arg Asn Val Leu Val Lys Thr Pro
                835                  840                  845

Gln His Val Lys Ile Thr Asp Phe Gly Leu Ala Lys Leu Leu Gly Ala
850                  855                  860

Glu Glu Lys Glu Tyr His Ala Glu Gly Gly Lys Val Pro Ile Lys Trp
865                  870                  875                  880

Met Ala Leu Glu Ser Ile Leu His Arg Ile Tyr Thr His Gln Ser Asp
                885                  890                  895

Val Trp Ser Tyr Gly Val Thr Val Trp Glu Leu Met Thr Phe Gly Ser
                900                  905                  910

Lys Pro Tyr Asp Gly Ile Pro Ala Ser Glu Ile Ser Ser Ile Leu Glu
                915                  920                  925

Lys Gly Glu Arg Leu Pro Gln Pro Pro Ile Cys Thr Ile Asp Val Tyr
930                  935                  940

Met Ile Met Val Lys Cys Trp Met Ile Asp Ala Asp Ser Arg Pro Lys
945                  950                  955                  960
```

```
Phe Arg Glu Leu Ile Ile Glu Phe Ser Lys Met Ala Arg Asp Pro Gln
            965                 970                 975
Arg Tyr Leu Val Ile Gln Gly Asp Glu Arg Met His Leu Pro Ser Pro
            980                 985                 990
Thr Asp Ser Asn Phe Tyr Arg Ala  Leu Met Asp Glu Glu  Asp Met Asp
            995                 1000                1005
Asp Val  Val Asp Ala Asp Glu  Tyr Leu Ile Pro Gln  Gln Gly Phe
    1010                 1015                1020
Phe Ser  Ser Pro Ser Thr Ser  Arg Thr Pro Leu Leu  Ser Ser Leu
    1025                 1030                1035
Ser Ala  Thr Ser Asn Asn Ser  Thr Val Ala Cys Ile  Asp Arg Asn
    1040                 1045                1050
Gly Leu  Gln Ser Cys Pro Ile  Lys Glu Asp Ser Phe  Leu Gln Arg
    1055                 1060                1065
Tyr Ser  Ser Asp Pro Thr Gly  Ala Leu Thr Glu Asp  Ser Ile Asp
    1070                 1075                1080
Asp Thr  Phe Leu Pro Val Pro  Glu Tyr Ile Asn Gln  Ser Val Pro
    1085                 1090                1095
Lys Arg  Pro Ala Gly Ser Val  Gln Asn Pro Val Tyr  His Asn Gln
    1100                 1105                1110
Pro Leu  Asn Pro Ala Pro Ser  Arg Asp Pro His Tyr  Gln Asp Pro
    1115                 1120                1125
His Ser  Thr Ala Val Gly Asn  Pro Glu Tyr Leu Asn  Thr Val Gln
    1130                 1135                1140
Pro Thr  Cys Val Asn Ser Thr  Phe Asp Ser Pro Ala  His Trp Ala
    1145                 1150                1155
Gln Lys  Gly Ser His Gln Ile  Ser Leu Asp Asn Pro  Asp Tyr Gln
    1160                 1165                1170
Gln Asp  Phe Phe Pro Lys Glu  Ala Lys Pro Asn Gly  Ile Phe Lys
    1175                 1180                1185
Gly Ser  Thr Ala Glu Asn Ala  Glu Tyr Leu Arg Val  Ala Pro Gln
    1190                 1195                1200
Ser Ser  Glu Phe Ile Gly Ala
    1205                 1210

<210> SEQ ID NO 7
<211> LENGTH: 3859
<212> TYPE: DNA
<213> ORGANISM: Homo sapiens

<400> SEQUENCE: 7
gtccgggcag cccccggcgc agcgcggccg cagcagcctc cgccccccgc acggtgtgag     60
cgcccgacgc ggccgaggcg ccggagtccc gagctagcc ccggcggccg ccgccgccca    120
gaccggacga caggccacct cgtcggcgtc cgcccgagtc cccgcctcgc cgccaacgcc    180
acaaccaccg cgcacggccc cctgactccg tccagtattg atcgggagag ccggagcgag    240
ctcttcgggg agcagcgatg cgaccctccg ggacggccgg ggcagcgctc ctggcgctgc    300
tggctgcgct ctgcccggcg agtcgggctc tggaggaaaa gaaagtttgc caaggcacga    360
gtaacaagct cacgcagttg ggcactttg aagatcattt tctcagcctc cagaggatgt    420
tcaataactg tgaggtggtc cttgggaatt tggaaattac ctatgtgcag aggaattatg    480
atctttcctt cttaaagacc atccaggagg tggctggtta tgtcctcatt gccctcaaca    540
cagtggagcg aattcctttg gaaaacctgc agatcatcag aggaaatatg tactacgaaa    600
```

```
attcctatgc cttagcagtc ttatctaact atgatgcaaa taaaaccgga ctgaaggagc    660
tgcccatgag aaatttacag ggccaaaagt gtgatccaag ctgtcccaat gggagctgct    720
ggggtgcagg agaggagaac tgccagaaac tgaccaaaat catctgtgcc cagcagtgct    780
ccgggcgctg ccgtggcaag tcccccagtg actgctgcca caaccagtgt gctgcaggct    840
gcacaggccc ccgggagagc gactgcctgg tctgccgcaa attccgagac gaagccacgt    900
gcaaggacac ctgcccccca ctcatgctct acaaccccac cacgtaccag atggatgtga    960
accccgaggg caaatacagc tttggtgcca cctgcgtgaa gaagtgtccc cgtaattatg   1020
tggtgacaga tcacggctcg tgcgtccgag cctgtggggc cgacagctat gagatggagg   1080
aagacggcgt ccgcaagtgt aagaagtgcg aagggccttg ccgcaaagtg tgtaacggaa   1140
taggtattgg tgaatttaaa gactcactct ccataaatgc tacgaatatt aaacacttca   1200
aaaactgcac ctccatcagt ggcgatctcc acatcctgcc ggtggcattt aggggtgact   1260
ccttcacaca tactcctcct ctggatccac aggaactgga tattctgaaa accgtaaagg   1320
aaatcacagg gttttgctg attcaggctt ggcctgaaaa caggacggac ctccatgcct   1380
ttgagaacct agaaatcata cgcggcagga ccaagcaaca tggtcagttt tctcttgcag   1440
tcgtcagcct gaacataaca tccttgggat tacgctccct caaggagata agtgatggag   1500
atgtgataat ttcaggaaac aaaaatttgt gctatgcaaa tacaataaac tggaaaaaac   1560
tgtttgggac ctccggtcag aaaaccaaaa ttataagcaa cagaggtgaa acagctgca   1620 aggccacagg ccaggtctgc catgccttgt gctcccccga gggctgctgg gcccggagc   1680 ccagggactg cgtctcttgc cggaatgtca gccgaggcag ggaatgcgtg acaagtgca   1740 accttctgga gggtgagcca agggagtttg tggagaactc tgagtgcata cagtgccacc   1800
cagagtgcct gcctcaggcc atgaacatca cctgcacagg acggggacca gacaactgta   1860
tccagtgtgc ccactacatt gacgccccc actgcgtcaa gacctgcccg gcaggagtca   1920
tgggagaaaa caacaccctg gtctggaagt acgcagacgc cggccatgtg tgccacctgt   1980
gccatccaaa ctgcacctac ggatgcactg ggccaggtct tgaaggctgt ccaacgaatg   2040
ggcctaagat cccgtccatc gccactggga tggtggggc cctcctcttg ctgctggtgg   2100
tggccctggg gatcggcctc ttcatgcgaa ggcgccacat cgttcggaag cgcacgctgc   2160
ggaggctgct gcaggagagg gagcttgtgg agcctcttac acccagtgga gaagctccca   2220
accaagctct cttgaggatc ttgaaggaaa ctgaattcaa aaagatcaaa gtgctgggct   2280
ccggtgcgtt cggcacggtg tataagggac tctggatccc agaaggtgag aaagttaaaa   2340
ttcccgtcgc tatcaaggaa ttaagagaag caacatctcc gaaagccaac aaggaaatcc   2400
tcgatgaagc ctacgtgatg gccagcgtgg acaacccca cgtgtgccgc ctgctgggca   2460
tctgcctcac ctccaccgtg cagctcatca cgcagctcat gcccttcggc tgcctcctgg   2520
actatgtccg ggaacacaaa gacaatattg gctcccagta cctgctcaac tggtgtgtgc   2580
agatcgcaaa gggcatgaac tacttggagg accgtcgctt ggtgcaccgc gacctggcag   2640
ccaggaacgt actggtgaaa acaccgcagc atgtcaagat cacagatttt gggctggcca   2700
aactgctggg tgcggaagag aaagaatacc atgcagaagg aggcaaagtg cctatcaagt   2760
ggatggcatt ggaatcaatt ttacacagaa tctataccca ccagagtgat gtctggagct   2820
acggggtgac tgtttgggag ttgatgacct ttggatccaa gccatatgac ggaatccctg   2880
ccagcgagat ctcctccatc ctggagaaag gagaacgcct ccctcagcca cccatatgta   2940
```

```
ccatcgatgt ctacatgatc atggtcaagt gctggatgat agacgcagat agtcgcccaa    3000
agttccgtga gttgatcatc gaattctcca aaatggcccg agaccccag cgctaccttg     3060 tcattcaggg ggatgaaaga atgcatttgc caagtcctac agactccaac ttctaccgtg    3120
ccctgatgga tgaagaagac atggacgacg tggtggatgc cgacgagtac ctcatcccac    3180
agcagggctt cttcagcagc ccctccacgt cacggactcc cctcctgagc tctctgagtg    3240
caaccagcaa caattccacc gtggcttgca ttgatagaaa tgggctgcaa agctgtccca    3300
tcaaggaaga cagcttcttg cagcgataca gctcagaccc cacaggcgcc ttgactgagg    3360
acagcataga cgacaccttc ctcccagtgc ctggtgagtg gcttgtctgg aaacagtcct    3420
gctcctcaac ctcctcgacc cactcagcag cagccagtct ccagtgtcca agccaggtgc    3480
tccctccagc atctccagag ggggaaacag tggcagattt gcagacacag tgaagggcgt    3540
aaggagcaga taaacacatg accgagcctg cacaagctct tgttgtgtc tggttgtttg     3600 ctgtacctct gttgtaagaa tgaatctgca aaatttctag cttatgaagc aaatcacgga    3660
catacacatc tgtgtgtgtg agtgttcatg atgtgtgtac atctgtgtat gtgtgtgtgt    3720
gtatgtgtgt gtttgtgaca gatttgatcc ctgttctctc tgctggctct atcttgacct    3780
gtgaaacgta tatttaacta attaaatatt agttaatatt aataaatttt aagctttatc    3840
cagaaaaaaa aaaaaaaaa                                                 3859
```

<210> SEQ ID NO 8
<211> LENGTH: 14
<212> TYPE: PRT
<213> ORGANISM: Tobacco etch virus

<400> SEQUENCE: 8

Asp Tyr Asp Ile Pro Thr Thr Glu Asn Leu Tyr Phe Gln Gly
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5